United States Patent
Itoi et al.

(10) Patent No.: US 9,590,186 B2
(45) Date of Patent: Mar. 7, 2017

(54) MATERIAL FOR ORGANIC ELECTROLUMINESCENT DEVICE AND ORGANIC ELECTROLUMINESCENT DEVICE INCLUDING THE SAME

(71) Applicant: SAMSUNG DISPLAY CO., LTD., Yongin-si, Gyeonggi-do (KR)

(72) Inventors: Hiroaki Itoi, Yokohama (JP); Ichinori Takada, Yokohama (JP); Koushin Matsuoka, Yokohama (JP); Masatsugu Ueno, Yokohama (JP); Naoya Sakamoto, Yokohama (JP); Hiromi Nakano, Yokohama (JP); Nobutaka Akashi, Yokohama (JP); Hideo Miyake, Yokohama (JP); Xiulan Jin, Yokohama (JP); Asami Sakamoto, Yokohama (JP); Junta Fuchiwaki, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 0 days.

(21) Appl. No.: 14/924,574

(22) Filed: Oct. 27, 2015

(65) Prior Publication Data

US 2016/0118597 A1    Apr. 28, 2016

(30) Foreign Application Priority Data

Oct. 28, 2014 (JP) ................. 2014-219497
Apr. 28, 2015 (JP) ................. 2015-092410

(51) Int. Cl.
*H01L 51/00* (2006.01)
*C09K 11/02* (2006.01)
(Continued)

(52) U.S. Cl.
CPC ........ *H01L 51/0061* (2013.01); *C07D 307/91* (2013.01); *C07D 333/76* (2013.01);
(Continued)

(58) Field of Classification Search
None
See application file for complete search history.

(56) References Cited

U.S. PATENT DOCUMENTS

2003/0165715 A1* 9/2003 Yoon ............... C07D 235/08
                                                   428/690
2014/0061630 A1 3/2014 Yabunouchi
(Continued)

FOREIGN PATENT DOCUMENTS

CN    101432272 A    5/2009
CN    103936749 A    7/2014
(Continued)

OTHER PUBLICATIONS

EPO Search Report dated Mar. 1, 2016, for corresponding European Patent application 15191755.6, (13 pages).
(Continued)

*Primary Examiner* — J. L. Yang
(74) *Attorney, Agent, or Firm* — Lewis Roca Rothgerber Christie LLP

(57) ABSTRACT

A material for an organic electroluminescent device having high emission efficiency and long life and an organic electroluminescent device including the same. The material for an organic electroluminescent device is represented by the following Formula 5.

Formula 5

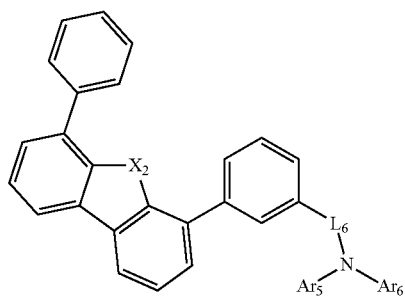

(5)

5 Claims, 2 Drawing Sheets

(51) Int. Cl.
*C07D 333/76* (2006.01)
*C07D 307/91* (2006.01)
*C09K 11/06* (2006.01)
*H01L 51/50* (2006.01)

(52) U.S. Cl.
CPC ............ *C09K 11/025* (2013.01); *C09K 11/06* (2013.01); *H01L 51/006* (2013.01); *H01L 51/0058* (2013.01); *H01L 51/0059* (2013.01); *H01L 51/0072* (2013.01); *H01L 51/0073* (2013.01); *H01L 51/0074* (2013.01); *H01L 51/0052* (2013.01); *H01L 51/5004* (2013.01); *H01L 51/5012* (2013.01); *H01L 51/5056* (2013.01); *H01L 51/5064* (2013.01); *H01L 2251/552* (2013.01)

(56) References Cited

U.S. PATENT DOCUMENTS

| | | |
|---|---|---|
| 2014/0231774 A1 | 8/2014 | Huh et al. |
| 2015/0179951 A1 | 6/2015 | Fuchiwaki |
| 2015/0295181 A1 | 10/2015 | Mujica-Fernaud et al. |
| 2015/0322337 A1 | 11/2015 | Hattori et al. |

FOREIGN PATENT DOCUMENTS

| | | |
|---|---|---|
| EP | 2 372 803 A1 | 10/2011 |
| EP | 2 502 908 A1 | 9/2012 |
| EP | 2 755 252 A2 | 7/2014 |
| EP | 2 755 253 A2 | 7/2014 |
| EP | 2 755 254 A2 | 7/2014 |
| JP | 2006-287218 A | 10/2006 |
| JP | 2008-060379 A | 3/2008 |
| JP | 2009-029726 A | 2/2009 |
| JP | 2009-267255 A | 11/2009 |
| JP | 2010-254635 A | 11/2010 |
| JP | 2011-051936 A | 3/2011 |
| JP | 2012-248534 A | 12/2012 |
| JP | 2012-248852 A | 12/2012 |
| JP | 2013-045812 A | 3/2013 |
| JP | 5193295 B2 | 5/2013 |
| JP | 5476034 B2 | 4/2014 |
| JP | 2014-527066 A | 10/2014 |
| KR | 10-2008-0112325 | 12/2008 |
| KR | 10-2012-0009984 | 2/2012 |
| KR | 10-2014-0074228 | 6/2014 |
| KR | 10-2015-0024804 | 3/2015 |
| KR | 10-2015-0102734 | 9/2015 |
| TW | 200812994 A | 3/2008 |
| WO | WO 2010/061824 A1 | 6/2010 |
| WO | WO 2012/011756 A1 | 1/2012 |
| WO | WO 2012/091471 A2 | 7/2012 |
| WO | WO 2012/148127 A2 | 11/2012 |
| WO | WO 2014/042420 A1 | 3/2014 |
| WO | WO 2014/067614 A1 | 5/2014 |
| WO | WO 2014/072017 A1 | 5/2014 |
| WO | WO 2014/091958 A1 | 6/2014 |
| WO | WO 2014/104515 A1 | 7/2014 |
| WO | WO 2015/014434 A1 | 2/2015 |
| WO | WO 2015/041492 A1 | 3/2015 |

OTHER PUBLICATIONS

Online Database: Kim, Y.G., et al., *Aromatic hole injecting or transporting material for organic electroluminescent device*, (KR 10-2012-009984), Retrieved Feb. 17, 2016, XP002754489, (3 pages).

Online Database: Hong, S.G., et al., *Aryl-amine compounds as organic light-emitting device materials*, (KR 10-2015-024804), Retrieved Feb. 18, 2016, XP002754490, (4 pages).

Online Database: Lee, S.C., *Carbazoles and related compounds as organic electroluminescent device materials*, (KR 10-2015-102734), Retrieved Feb. 18, 2016, XP002754491, (7 pages).

Japanese Office Action mailed Jun. 23, 2015 of the corresponding Japanese Patent Application No. 2015-092410, with English translation (8 pages).

Office Action dated Jul. 22, 2016, with English Machine translation, issued in Japanese Patent Application No. JP 2015-230011 (7 pages).

* cited by examiner

MATERIAL FOR ORGANIC ELECTROLUMINESCENT DEVICE AND ORGANIC ELECTROLUMINESCENT DEVICE INCLUDING THE SAME

CROSS-REFERENCE TO RELATED APPLICATION

This patent application claims priority to and the benefit of Japanese Patent Application Nos. 2014-219497, filed on Oct. 28, 2014, and 2015-092410, filed on Apr. 28, 2015, the entire contents of both are incorporated herein by reference.

BACKGROUND

The present disclosure herein relates to a material for an organic electroluminescent device and an organic electroluminescent device including the same. For example, the present disclosure herein relates to a material for an organic electroluminescent device having high emission efficiency and long life, and an organic electroluminescent device including the same.

Recently, the developments of organic electroluminescent (EL) displays as one type of image displays are being actively conducted. Organic EL devices are so-called self luminescent displays and are different from liquid crystal displays. The organic EL devices display images by emitting light from a luminescent material (including an organic material) in its emission layer via recombination of holes and electrons injected from an anode and a cathode in the emission layer.

As an organic EL device, an organic device may include, for example, an anode, a hole transport layer disposed on the anode, an emission layer disposed on the hole transport layer, an electron transport layer disposed on the emission layer and a cathode disposed on the electron transport layer. Holes are injected from the anode, and the injected holes move via the hole transport layer and are injected into the emission layer. Electrons are injected from the cathode, and the injected electrons move via the electron transport layer and are injected into the emission layer. The injected holes and electrons recombine to generate excitons in the emission layer. The organic EL device emits light utilizing light generated by the radiation deactivation of the excitons. The configuration of the organic EL device is not limited thereto, however, and various modifications may be possible.

When organic EL devices are applied to display apparatuses, the high efficiency and long life of the organic EL devices are required. However, in an organic EL device—particularly in a blue emission region when compared to a green emission region and a red emission region, the driving voltage is high and the emission efficiency is insufficient. To realize the high efficiency and long life of an organic EL device, ways of increasing the normalization, stabilization and durability of the hole transport layer have been examined.

As a hole transport material utilized in a hole transport layer, various compounds such as an aromatic amine compound have been utilized. However, issues related to resolving the short life of the device remain. As a useful material for increasing the life of the organic EL device, for example, an amine derivative substituted with an aryl group or a heteroaryl group has been suggested. However, an organic EL device utilizing the above-mentioned material has insufficient emission life. Thus, an organic EL device having higher efficiency and long emission life is desired at present.

SUMMARY

According to an embodiment of the disclosure, a material for an organic EL device is represented by Formula 1.

Formula 1

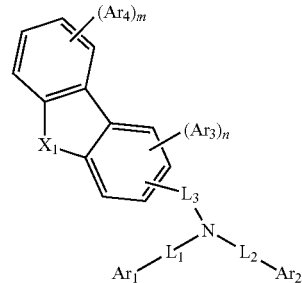

(1)

In Formula 1, $X_1$ is O or S; $Ar_1$ and $Ar_2$ are each independently a substituted or unsubstituted aryl group having 6 to 30 carbon atoms for forming a ring, a silyl group, a halogen atom, a deuterium atom, a hydrogen atom, or a substituted or unsubstituted dibenzoheterole group having 10 to 30 carbon atoms for forming a ring and including an oxygen atom or a sulfur atom; $Ar_3$ and $Ar_4$ are each independently a silyl group, or a substituted or unsubstituted aryl group having 6 to 30 carbon atoms for forming a ring; $L_1$ and $L_2$ are each independently a direct linkage, or a divalent group selected from a silyl group and a substituted or unsubstituted arylene group having 6 to 30 carbon atoms for forming a ring; $L_3$ is a divalent group selected from a silyl group and a substituted or unsubstituted arylene group having 6 to 30 carbon atoms for forming a ring; n is an integer from 0 to 3; m is an integer from 0 to 4; and $n+m \geq 1$.

In the material for an organic EL device according to an embodiment, a substituted dibenzoheterole group with high electron tolerance is introduced in (e.g., linked to) an amine group (or an amine compound), and the life of a layer utilizing the material for an organic EL device may increase, and the life of an organic EL device may increase. Since the dibenzoheterole group includes a substituent, the amorphous properties of the material may be improved (e.g., the crystallinity of the material may be decreased), charge mobility may increase, and high emission efficiency may be realized.

In an embodiment, a compound represented by Formula 1 may be a compound represented by Formula 2 or Formula 3.

Formula 2

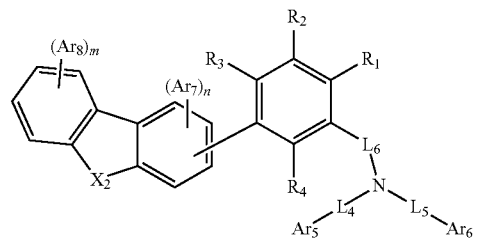

(2)

Formula 3

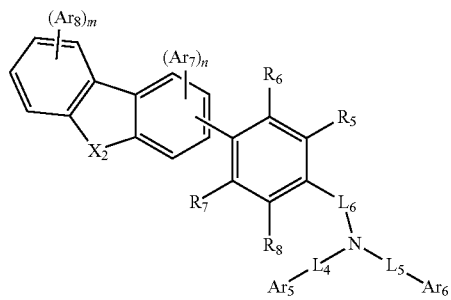

In Formulae 2 and 3, $X_2$ is O or S; $Ar_5$ and $Ar_6$ are each independently a substituted or unsubstituted aryl group having 6 to 30 carbon atoms for forming a ring, a silyl group, a halogen atom, a deuterium atom, a hydrogen atom, or a substituted or unsubstituted dibenzoheterole group having 10 to 30 carbon atoms for forming a ring and including an oxygen atom or a sulfur atom; $Ar_7$ and $Ar_8$ are each independently a silyl group, or a substituted or unsubstituted aryl group having 6 to 30 carbon atoms for forming a ring; $L_4$ and $L_5$ are each independently a direct linkage, or a divalent group selected from a silyl group and a substituted or unsubstituted arylene group having 6 to 30 carbon atoms for forming a ring; $L_6$ is a direct linkage or a divalent group selected from a substituted or unsubstituted aryl group having 6 to 24 carbon atoms for forming a ring and a silyl group; $R_1$ to $R_8$ are each independently an aryl group having 6 to 30 carbon atoms for forming a ring, a heteroaryl group having 5 to 30 carbon atoms for forming a ring, an alkyl group having 1 to 15 carbon atoms, a silyl group, a halogen atom, a hydrogen atom or a deuterium atom; n is an integer from 0 to 3; m is an integer from 0 to 4; and n+m≥1.

In the material for an organic EL device according to an embodiment, in Formula 1, $L_3$ includes an m-phenylene group or a p-phenylene group, and a dibenzoheterole group is linked at the meta position or para position of a phenylene group that is linked to an amine group. The dibenzoheterole group is combined via a direct linkage or $L_6$ to the phenylene group. The molecular symmetry of the material may be broken, the amorphous properties of the material may be improved further, and charge mobility may increase, thereby realizing the long life and high emission efficiency of an organic EL device.

In an embodiment, the compound represented by Formula 2 may be a compound represented by Formula 4.

Formula 4

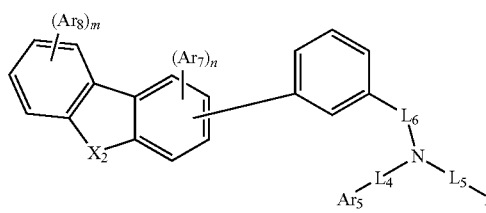

In the material for an organic EL device according to an embodiment, in Formula 2, $R_1$ to $R_4$ are each independently a hydrogen atom, and the long life and high efficiency of an organic EL device may be realized.

In an embodiment, the compound represented by Formula 4 may be a compound represented by Formula 5.

Formula 5

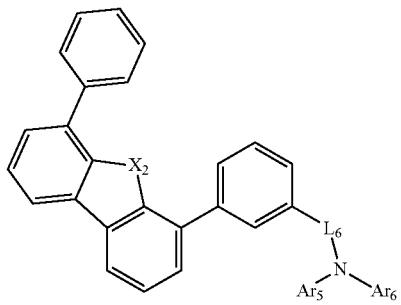

In the material for an organic EL device according to an embodiment, in Formula 4, $L_4$ and $L_5$ are each independently a direct linkage, $Ar_8$ is a phenyl group, m is 1, n is 0, and a dibenzoheterole group makes a bond with an m-phenylene group at position 4. Since a part with high electron density of the dibenzoheterole group is substituted, the material may be stabilized, and the long life and high efficiency of an organic EL device may be realized.

In an embodiment, the compound represented by Formula 3 may be a compound represented by Formula 6.

Formula 6

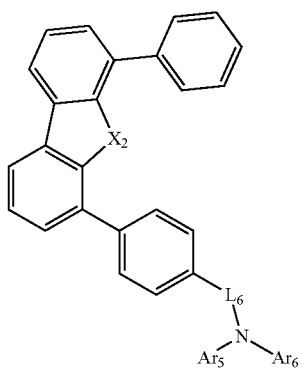

In the material for an organic EL device according to an embodiment, in Formula 3, since each of $R_5$ to $R_8$ is a hydrogen atom, the long life and high efficiency of an organic EL device may be realized.

In an embodiment, the compound represented by Formula 6 may be a compound represented by Formula 7.

Formula 7

In the material for an organic EL device according to an embodiment, in Formula 6, each of $L_4$ and $L_5$ is a direct linkage, $Ar_8$ is a phenyl group, m is 1, n is 0, the dibenzoheterole group is combined with (e.g., bonded to) a p-phenylene group at position 4, and a part with high electron density of the dibenzoheterole group is substituted. Thus, the material may be stabilized, and the long life and high efficiency of an organic EL device may be realized.

According to an embodiment of the disclosure, an organic EL device includes the material for an organic EL device in at least one layer of a plurality of stacking layers between an emission layer and an anode.

In an embodiment, a first layer including the material for an organic EL device may be adjacent to the emission layer.

Since the first layer is disposed adjacent to the emission layer in the organic EL device according to an embodiment, a hole transport layer disposed between the first layer and the anode may be passivated from electrons not consumed in the emission layer, the diffusion of energy with an excited state generated in the emission layer into the hole transport layer may be prevented, and the charge balance of a whole device may be controlled. Thus, the increase of emission efficiency and long life may be realized.

In an embodiment, the plurality of stacking layers may include a second layer including an electron accepting compound having a lowest unoccupied molecular orbital (LUMO) level within a range from about −9.0 eV to about −4.0 eV, and the second layer may be between the anode and the first layer.

Since the organic EL device according to an embodiment includes the second layer, hole injection properties from the anode may be improved, and emission efficiency may be improved.

In an embodiment, the plurality of stacking layers may include a third layer including an amine derivative represented by Formula 8, and the third layer may be between the first layer and the second layer.

Formula 8

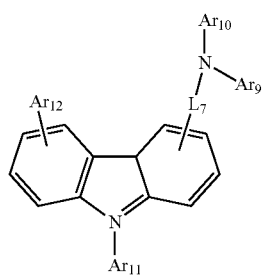

In Formula 8, $Ar_9$, $Ar_{10}$ and $Ar_{11}$ are each independently a substituted or unsubstituted aryl group having 6 to 50 carbon atoms for forming a ring, or a substituted or unsubstituted heteroaryl group having 5 to 50 carbon atoms for forming a ring; $Ar_{12}$ is a substituted or unsubstituted aryl group having 6 to 50 carbon atoms for forming a ring, a substituted or unsubstituted heteroaryl group having 5 to 50 carbon atoms for forming a ring, or a substituted or unsubstituted alkyl group having 1 to 50 carbon atoms; $L_7$ is a direct linkage, a substituted or unsubstituted arylene group having 6 to 18 carbon atoms for forming a ring, or a substituted or unsubstituted heteroarylene group having 5 to 15 carbon atoms for forming a ring.

Since the organic EL device according to an embodiment includes a compound having a carbazolyl group in a hole transport layer, hole transport properties and current flow durability may be improved, and emission efficiency and life may increase.

Since the organic EL device according to an embodiment utilizes the material for an organic EL device in at least one layer of a plurality of stacking layers disposed between the emission layer and the anode, high emission efficiency and long life may be realized. For example, remarkable effects may be obtainable in from a green emission region to a blue emission region.

BRIEF DESCRIPTION OF THE FIGURES

The accompanying drawings are included to provide a further understanding of the disclosure, and are incorporated in and constitute a part of this specification. The drawings illustrate example embodiments of the disclosure and, together with the description, serve to explain principles of the disclosure. In the drawings.

DETAILED DESCRIPTION

Figure 1:
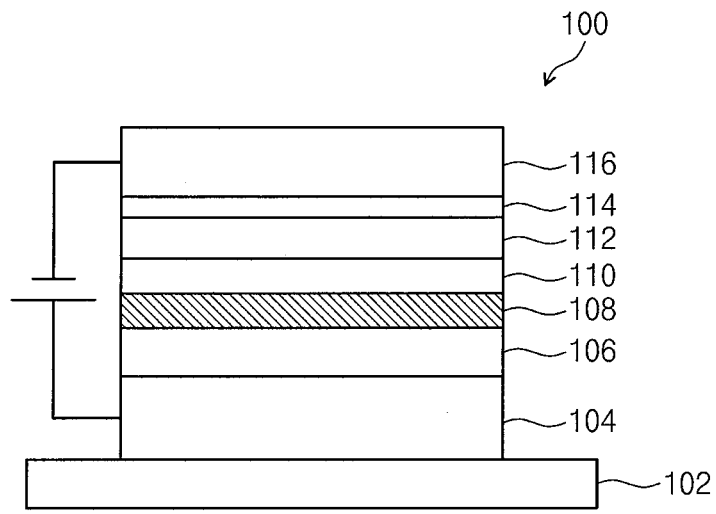
FIG. 1 is a schematic diagram illustrating an organic EL device 100 according to an embodiment.

The inventors of the present disclosure thoroughly examined to solve the above-described defects and found that high efficiency and long life may be realized for a layer utilizing a material for an organic EL device, in which a substituted dibenzoheterole group with high electron tolerance is introduced in an amine group, thereby obtaining an organic EL device having high efficiency and long life.

Hereinafter, the material for an organic EL device and the organic EL device including the same according to an embodiment of the disclosure will be described with reference to the accompanying drawings. The material for an organic EL device and the organic EL device including the same according to an embodiment may, however, be embodied in different forms and should not be construed as limited to the embodiments set forth herein. In the drawings, like reference numerals refer to like elements or elements having like functions throughout, and repeated explanation thereof will not be provided again.

The material for an organic EL device according to an embodiment is an amine compound including a substituted dibenzoheterole group represented by the following Formula 1.

Formula 1

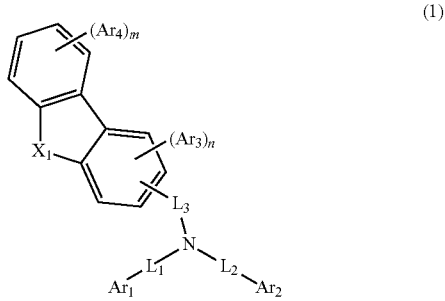

In the material for an organic EL device of Formula 1 according to an embodiment, $X_1$ is O or S; $Ar_1$ and $Ar_2$ are each independently a substituted or unsubstituted aryl group having 6 to 30 carbon atoms for forming a ring, a silyl group, a halogen atom, a deuterium atom, a hydrogen atom, or a substituted or unsubstituted dibenzoheterole group having 10 to 30 carbon atoms for forming a ring and including an oxygen atom or a sulfur atom; $Ar_3$ and $Ar_4$ are each independently a silyl group, or a substituted or unsubstituted aryl group having 6 to 30 carbon atoms for forming a ring; $L_1$ and $L_2$ are each independently a direct linkage, or a divalent group selected from a silyl group and a substituted or unsubstituted arylene group having 6 to 30 carbon atoms for forming a ring; $L_3$ is a divalent group selected from a silyl group and a substituted or unsubstituted arylene group having 6 to 30 carbon atoms for forming a ring; n is an integer from 0 to 3; m is an integer from 0 to 4; and n+m≥1.

In the present disclosure, the term "substituted or unsubstituted" may correspond to an unsubstituted group; a group substituted with at least one substituent selected from a deuterium atom, a halogen atom, a nitrile group, a nitro group, an amino group, a phosphine oxide group, an alkoxy group, an aryloxy group, an alkylthioxy group, an arylthioxy group, an alkylsulfoxy group, an arylsulfoxy group, a silyl group, a boron group, an alkyl group, a cycloalkyl group, an alkenyl group, an aryl group, an aralkyl group, an aralkenyl group, an alkylaryl group, an alkylamine group, a heteroarylamine group, an arylamine group and a heterocyclic group; or a group substituted with a substituent obtained by connecting two or more substituents described above. For example, "a substituent obtained by connecting two or more substituents" may be a biphenyl group. For example, the biphenyl group may be interpreted as the aryl group or a substitutent obtained by connecting two or more phenyl groups.

In Formula 1, the aryl group having 6 to 30 carbon atoms for forming a ring utilized as $Ar_1$ and $Ar_2$ may include a phenyl group, a naphthyl group, an anthracenyl group, a phenanthryl group, a biphenyl group, a terphenyl group, a quaterphenyl group, a fluorenyl group, a triphenylene group, a biphenylene group, a pyrenyl group, a benzofluoranthenyl group, a chrysenyl group, a phenylnaphthyl group, a naphthylphenyl group, etc., without being limited thereto.

The dibenzoheterole group having 10 to 30 carbon atoms for forming a ring and including an oxygen atom or a sulfur atom utilized as $Ar_1$ and $Ar_2$ may include a dibenzofuryl group, a dibenzothienyl group, etc.

The silyl group utilized as $Ar_1$ and $Ar_2$ may include a trialkylsilyl group, a triarylsilyl group, a monoalkyldiarylsilyl group and a dialkylmonoarylsilyl group, and may include, for example, a trimethylsilyl group, a triphenylsilyl group, etc.

The halogen atoms utilized as $Ar_1$ and $Ar_2$ may include a fluorine atom (F), a chlorine atom (Cl) and a bromine atom (Br).

In one embodiment, in Formula 1, an aryl group having 6 to 30 carbon atoms for forming a ring or a hydrogen atom may be utilized as $Ar_1$ and/or $Ar_2$.

In Formula 1, the aryl group having 6 to 30 carbon atoms for forming a ring utilized as $Ar_3$ and $Ar_4$ may be the same as the aryl group utilized as $Ar_1$ and $Ar_2$. In addition, the silyl group utilized as $Ar_3$ and $Ar_4$ may be the same as the silyl group utilized as $Ar_1$ and $Ar_2$.

In Formula 1, the arylene group having 6 to 30 carbon atoms for forming a ring among the divalent groups utilized as $L_1$ to $L_3$ may include a phenylene group, a biphenylene group, a terphenylene group, a naphthylene group, an anthracenyl group, a fluorenyl group, a triphenylene group, etc., without being limited thereto.

The divalent silyl group among the divalent groups utilized as $L_1$ to $L_3$ may include a dimethylsilyl group and a diphenylsilylene group.

The substituents of the aryl group, the dibenzoheterole group including an oxygen atom or a sulfur atom or the silyl group utilized as $Ar_1$ and $Ar_2$, of the aryl group and the silyl group utilized as $Ar_3$ and $Ar_4$, and of the arylene group utilized as $L_1$ to $L_3$ may include a phenyl group, a naphthyl group, an anthracenyl group, a phenanthryl group, a biphenyl group, a terphenyl group, a quaterphenyl group, a fluorenyl group, a triphenylene group, a biphenylene group, a pyrenyl group, a benzofluoranthenyl group, a chrysenyl group, a phenylnaphthyl group, a naphthylphenyl group, a trimethylsilyl group, a triphenylsilyl group, a dibenzofuranyl group and a dibenzothiophenyl group. In one embodiment, the phenyl group, the naphthyl group, the biphenyl group, the phenylnaphthyl group, the naphthylphenyl group, the trimethylsilyl group and the triphenylsilyl group may be utilized.

In the material for an organic EL device according to an embodiment, a substituted dibenzoheterole group combined with (e.g., bonded to) the nitrogen atom (N) of the amine via $L_3$ is introduced. Since the substituted dibenzoheterole has high electron tolerance, the deterioration of a material due to electrons not consumed in an emission layer may be restrained (e.g., reduced or prevented). In addition, since the dibenzoheterole group has a substituent, the amorphous properties of the material may be improved, and the mobility of charges may increase. Thus, the long life and high efficiency of the organic EL device may be realized.

In the material for an organic EL device according to an embodiment, an m-phenylene group or a p-phenylene group may be included in $L_3$ in Formula 1. The material for an organic EL device according to an embodiment may be an amine compound represented by the following Formula 2 or Formula 3.

Formula 2

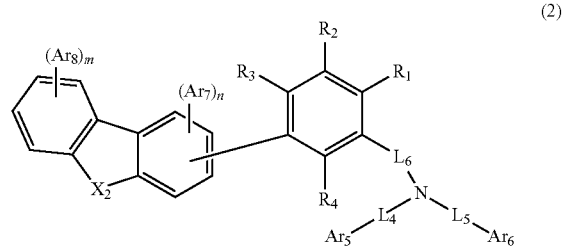

(2)

Formula 3

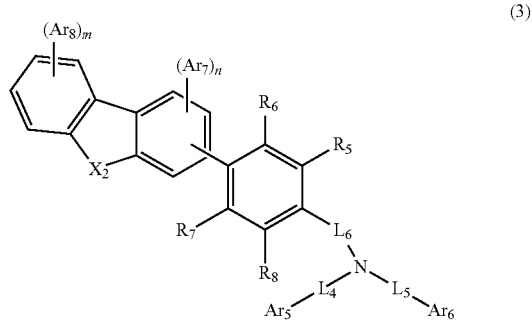

(3)

In the material for an organic EL device of Formula 2 and Formula 3 according to an embodiment, $X_2$ is O or S; $Ar_5$ and $Ar_6$ are each independently a substituted or unsubstituted aryl group having 6 to 30 carbon atoms for forming a ring, a substituted or unsubstituted dibenzoheterole group having 10 to 30 carbon atoms for forming a ring and including an oxygen atom or a sulfur atom, a silyl group, a halogen atom, a deuterium atom or a hydrogen atom; $Ar_7$ and $Ar_8$ are each independently a silyl group, or a substituted or unsubstituted aryl group having 6 to 30 carbon atoms for forming a ring; $L_4$ and $L_5$ are each independently a direct linkage, or a divalent group selected from a silyl group and a substituted or unsubstituted arylene group having 6 to 30 carbon atoms for forming a ring; $L_6$ is a direct linkage or a divalent group selected from a substituted or unsubstituted aryl group having 6 to 24 carbon atoms for forming a ring and a silyl group, $R_1$ to $R_8$ are each independently a substituted or unsubstituted aryl group having 6 to 30 carbon atoms for forming a ring, a substituted or unsubstituted heteroaryl group having 5 to 30 carbon atoms for forming a ring, an alkyl group having 1 to 15 carbon atoms, a silyl group, a halogen atom, a hydrogen atom or a deuterium atom; n is an integer from 0 to 3; m is an integer from 0 to 4; and n+m≥1.

In Formulae 2 and 3, the aryl group having 6 to 30 carbon atoms for forming a ring, the dibenzoheterole group having 10 to 30 carbon atoms for forming a ring and including an oxygen atom or a sulfur atom, the silyl group and the halogen atom utilized as $Ar_5$ and $Ar_6$ may be the same as the aryl group having 6 to 30 carbon atoms for forming a ring, the dibenzoheterole group having 10 to 30 carbon atoms for forming a ring and including an oxygen atom or a sulfur atom, the silyl group and the halogen atom utilized as $Ar_1$ and $Ar_2$ in the compound represented by Formula 1.

In Formulae 2 and 3, $Ar_5$ and $Ar_6$ may be each independently an aryl group having 6 to 30 carbon atoms for forming a ring or a hydrogen atom.

In Formulae 2 and 3, the aryl group having 6 to 30 carbon atoms for forming a ring utilized as $Ar_7$ and $Ar_8$ may be the same as the aryl group utilized as $Ar_1$ and $Ar_2$ in the compound represented by Formula 1. In addition, the silyl group utilized as $Ar_3$ and $Ar_4$ may be the same as the silyl group utilized as $Ar_1$ and $Ar_2$ in the compound represented by Formula 1.

In Formulae 2 and 3, the divalent group of the arylene group having 6 to 30 carbon atoms for forming a ring and the silyl group utilized as $L_4$ and $L_5$ may be the same as the divalent group of the arylene group and the silyl group utilized as $L_1$ to $L_3$ in the compound represented by Formula 1.

In Formulae 2 and 3, the arylene group having 6 to 24 carbon atoms for forming a ring utilized as $L_6$ may include a phenylene group, a biphenylene group, a terphenylene group, a naphthylene group, an anthracenyl group, a fluorenylene group, a triphenylene group, etc., without being limited thereto.

The divalent silyl group utilized as $L_6$ may be the same as the divalent silyl group utilized as $L_1$ to $L_3$ in the compound represented by Formula 1.

The aryl group having 6 to 30 carbon atoms for forming a ring utilized as $R_1$ to $R_8$ in Formulae 2 and 3 may include a phenyl group, a naphthyl group, an anthracenyl group, a phenanthryl group, a biphenyl group, a terphenyl group, a quaterphenyl group, a fluorenyl group, a triphenylene group, a biphenylene group, a pyrenyl group, a benzofluoranthenyl group, a chrysenyl group, a phenylnaphthyl group, a naphthylphenyl group, etc., without being limited thereto.

In addition, the heteroaryl group having 5 to 30 carbon atoms for forming a ring utilized as $R_1$ to $R_8$ may include a pyridyl group, a quinolyl group, an isoquinolyl group, a benzofuryl group, a benzothienyl group, an indolyl group, a benzoxazolyl group, a benzothiazolyl group, a quinoxalyl group, a benzoimidazolyl group, a dibenzofuryl group, a dibenzothienyl group, a carbazolyl group, etc., without being limited thereto.

The alkyl group having 1 to 15 carbon atoms utilized as $R_1$ to $R_8$ may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, etc.

In addition, the silyl group utilized as $R_1$ to $R_8$ may include a trialkylsilyl group, a triarylsilyl group, a monoalkyldiarylsilyl group, a dialkylmonoarylsilyl group, a trimethylsilyl group, a triphenylsilyl group, etc.

In addition, the halogen atom utilized as $R_1$ to $R_8$ may include a fluorine atom (F), a chlorine atom (Cl), a bromine atom (Br), etc.

In the material for an organic EL device according to an embodiment, an m-phenylene group or a p-phenylene group may be included in $L_3$ in Formula 1. Into the material for an organic EL device according to an embodiment represented by Formula 2 or 3, a dibenzoheterole group is introduced at the meta position or the para position of a phenylene group combined with (e.g., bonded to) an amine group directly or via $L_6$. Thus, the symmetry of a molecule may be broken, and the amorphous properties of the material may be improved further. Therefore, the mobility of charges may increase, and the long life and high efficiency of the organic EL device may be realized.

In the material for an organic EL device according to an embodiment, each of $R_1$ to $R_4$ in Formula 2 may be a hydrogen atom. That is, the material for an organic EL device according to an embodiment may be an amine compound represented by the following Formula 4.

Formula 4

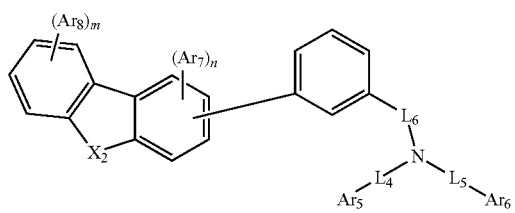

(4)

By utilizing the a hydrogen atom atom for each of $R_1$ to $R_4$ in Formula 2 of the material for an organic EL device according to an embodiment, the long life and high efficiency of the organic EL device may be realized.

In the material for an organic EL device according to an embodiment, in Formula 4, $L_4$ and $L_5$ are each independently a direct linkage, $Ar_8$ is a phenyl group, m is 1, n is 0, and the dibenzoheterole group is combined with (e.g., bonded to) the m-phenylene group at position 4. The material for an organic EL device according to an embodiment may be an amine compound represented by the following Formula 5.

Formula 5

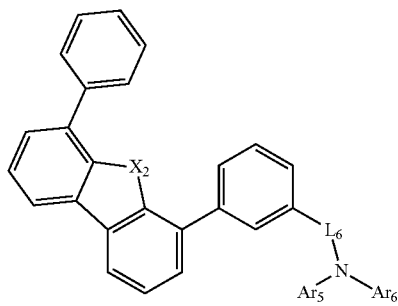

(5)

In the material for an organic EL device according to an embodiment, in Formula 4, $L_4$ and $L_5$ are each independently a direct linkage, $Ar_8$ is a phenyl group, m is 1, n is 0, and the dibenzoheterole group is combined with (e.g., bonded to) the m-phenylene group at position 4. The position 4 of the dibenzoheterole group is a part with high electron density and high reactivity. The compound may be stabilized by the substitution of the dibenzoheterole group at position 4 with high reactivity. Thus, the long life of a layer utilizing the material for an organic EL device according to an embodiment may be realized, and the life of the organic EL device may increase further.

In the material for an organic EL device according to an embodiment, each of $R_5$ to $R_8$ in Formula 3 may be a hydrogen atom. The material for an organic EL device according to an embodiment may be an amine compound represented by the following Formula 6.

Formula 6

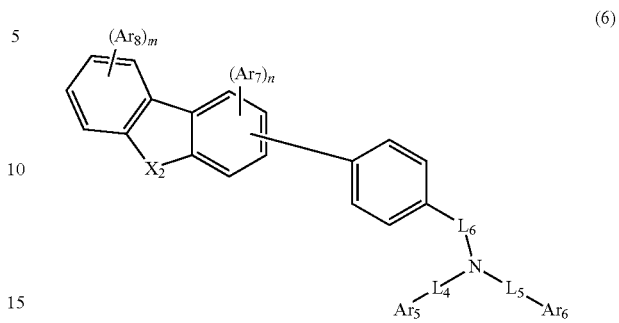

(6)

In the material for an organic EL device according to an embodiment, in Formula 3, each of $R_5$ to $R_8$ is a hydrogen atom, and the long life and high efficiency of the organic EL device may be realized.

In the material for an organic EL device according to an embodiment, in Formula 6, $L_4$ and $L_5$ are each independently a direct linkage, $Ar_8$ is a phenyl group, m is 1, n is 0, and the dibenzoheterole group is combined with (e.g., bonded to) the p-phenylene group at position 4. The material for an organic EL device according to an embodiment may be an amine compound represented by the following Formula 7.

Formula 7

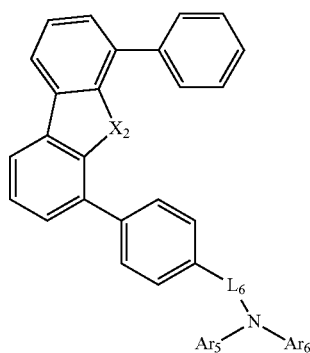

(7)

According to an embodiment, the material for an organic EL device represented by Formula 6 may be stabilized if $L_4$ and $L_5$ are each independently a direct linkage, $Ar_8$ is a phenyl group, m is 1, n is 0, and the dibenzoheterole group is combined with (e.g., bonded to) the p-phenylene group at position 4. Thus, the long life of a layer utilizing the material for an organic EL device according to an embodiment may be realized, and the increase of the life of the organic EL device may be realized.

The material for an organic EL device according to an embodiment may include at least one of compounds in Compounds group 1 (including compounds 1 to 269 and 300 to 311) below.

Compounds group 1
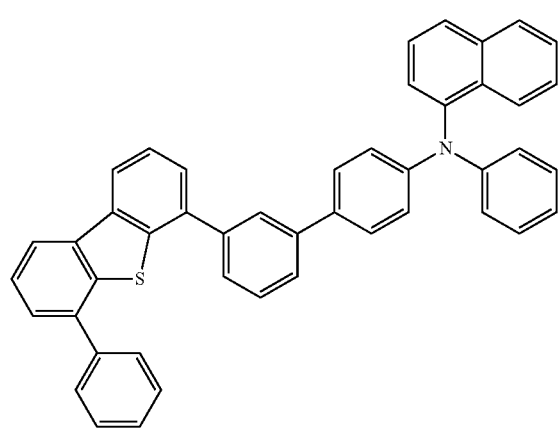
1
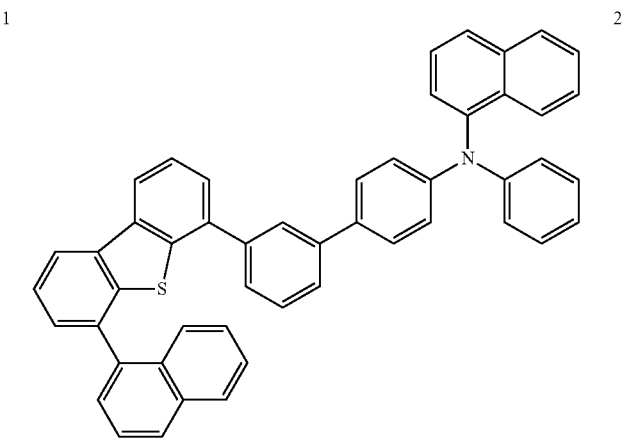
2
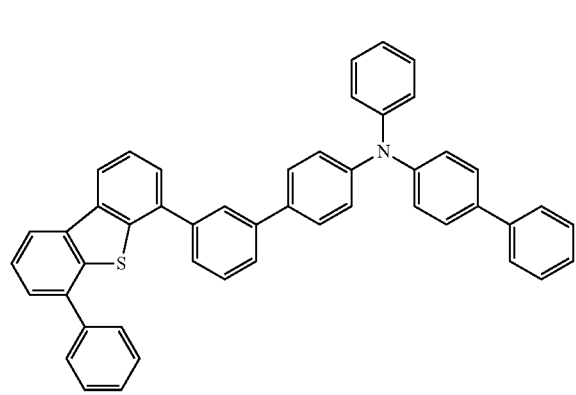
3
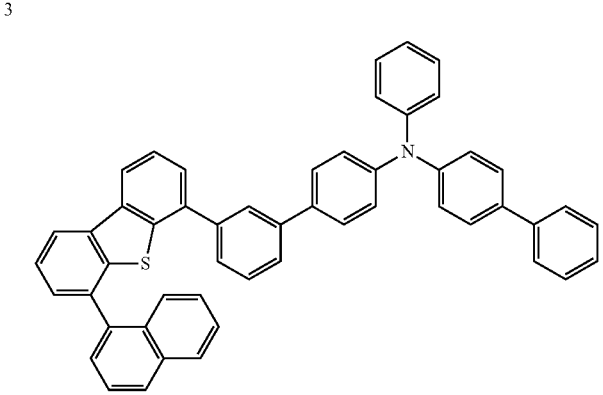
4
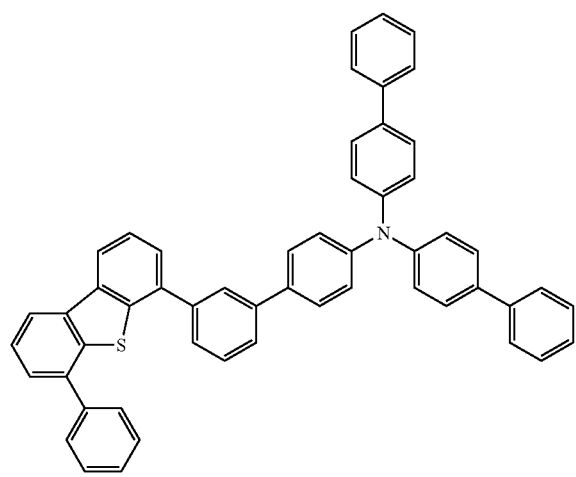
5
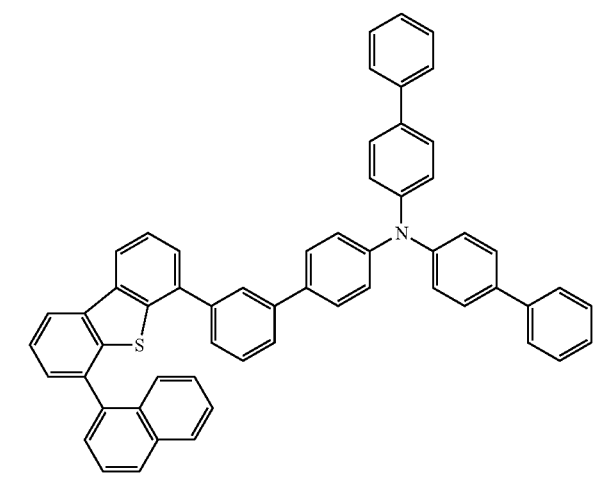
6

-continued
7
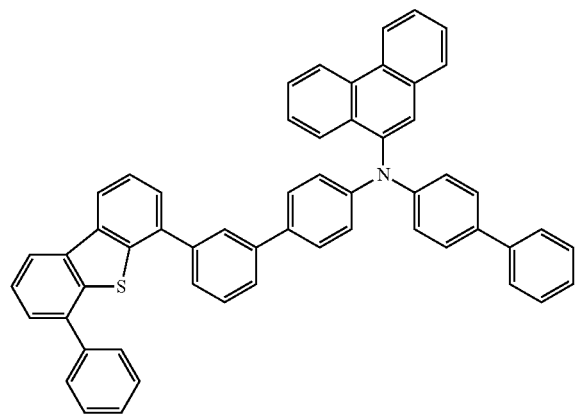
8
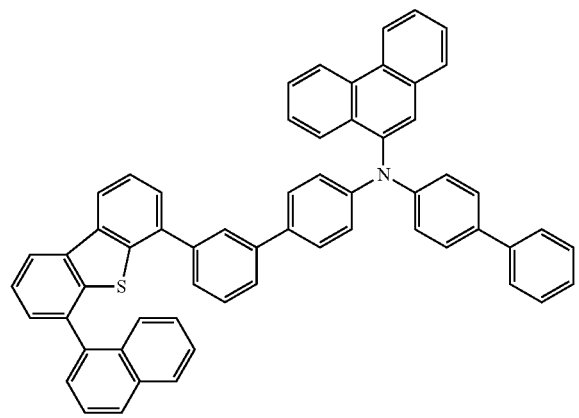
9
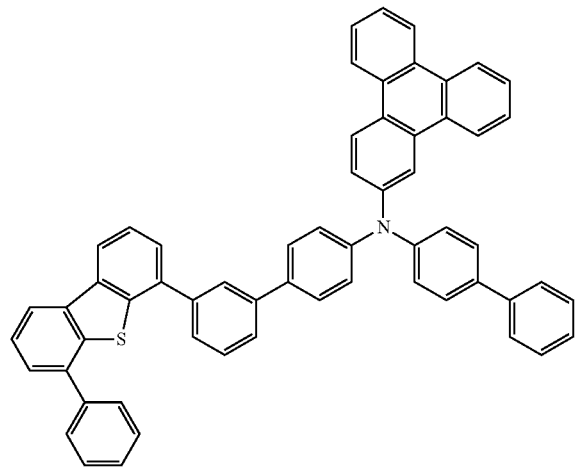
10
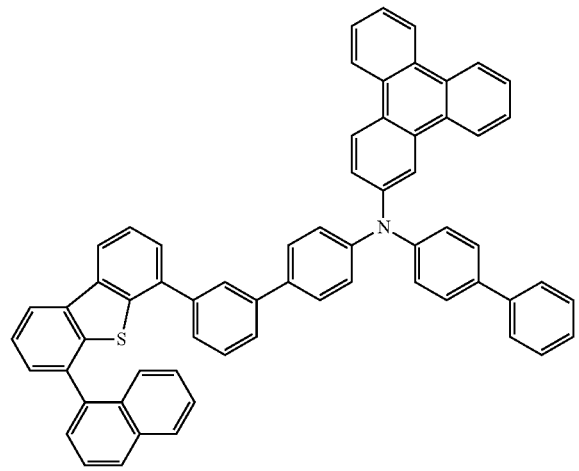
11
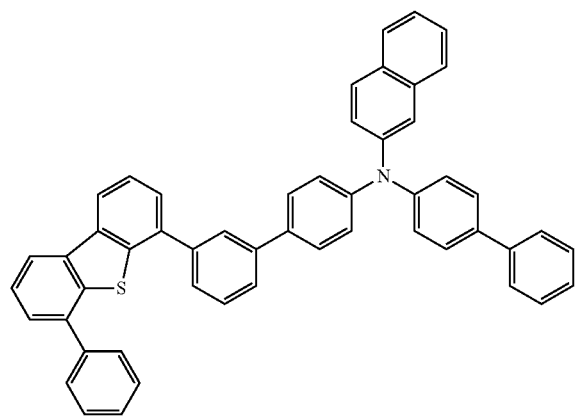
12
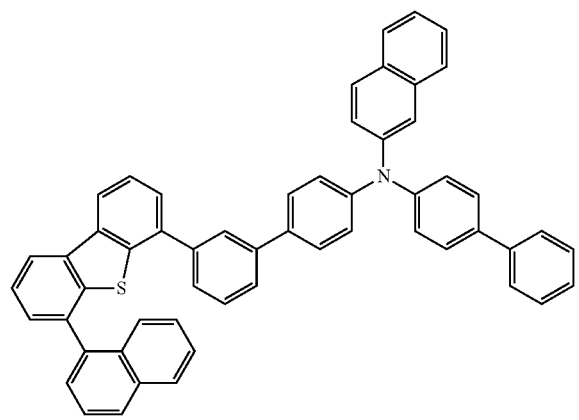

-continued
13
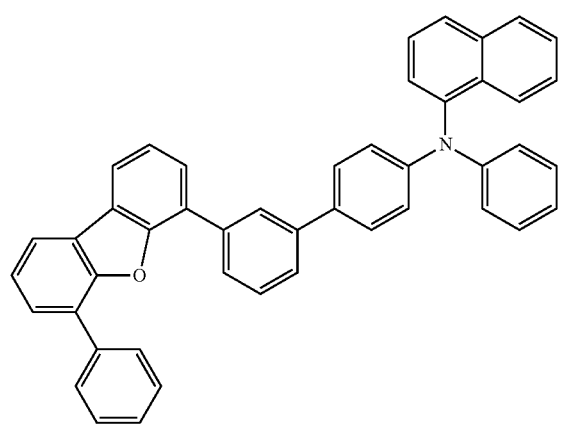
14
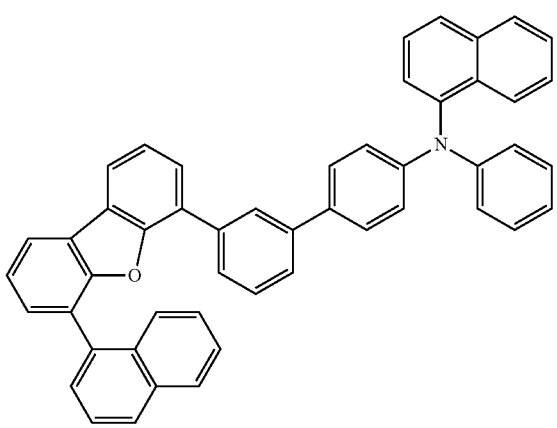
15
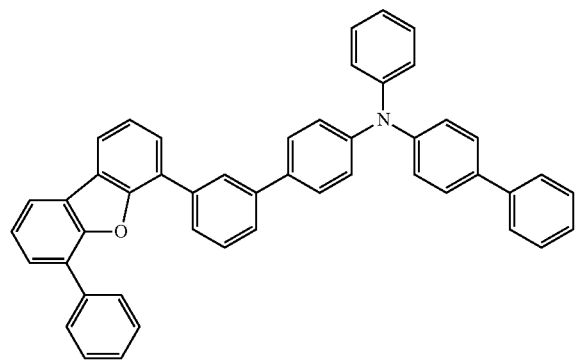
16
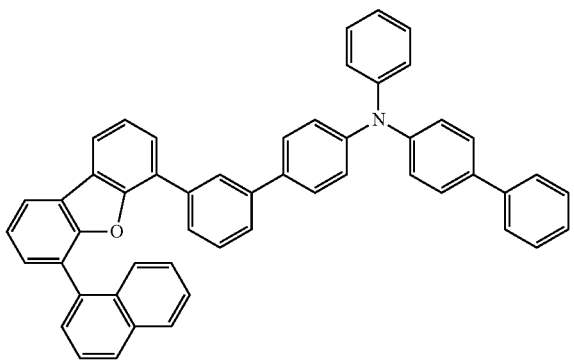
17
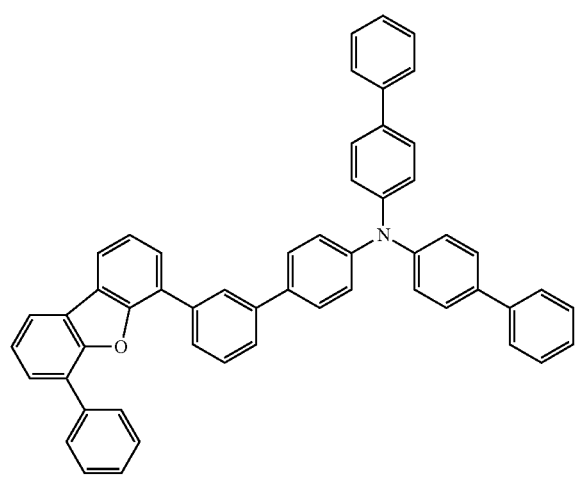
18
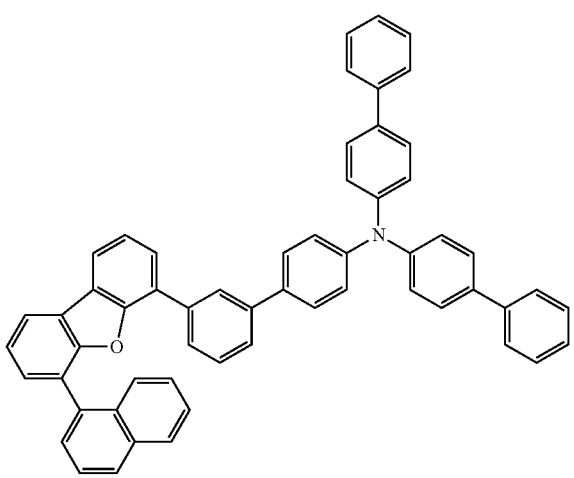

-continued
19
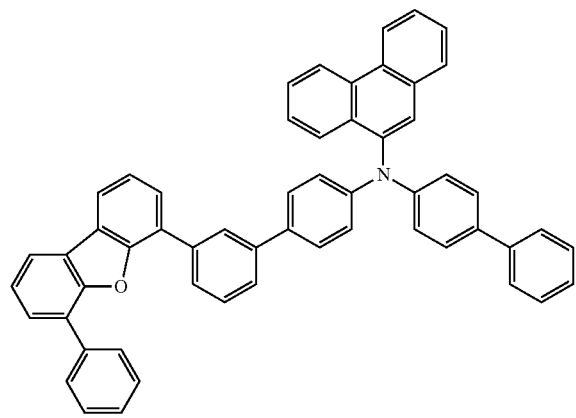
20
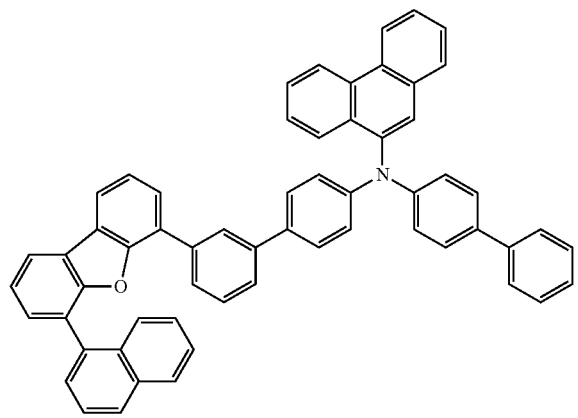
21
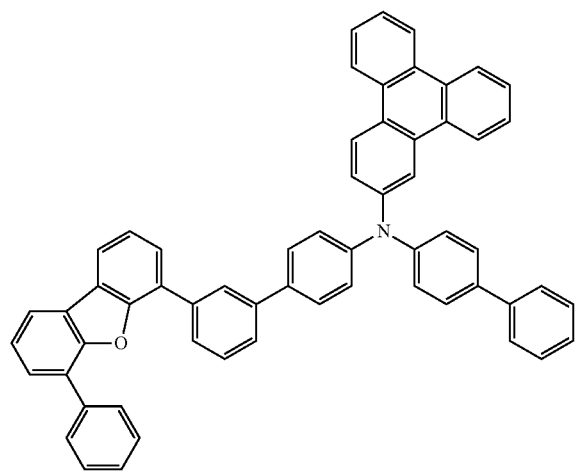
22
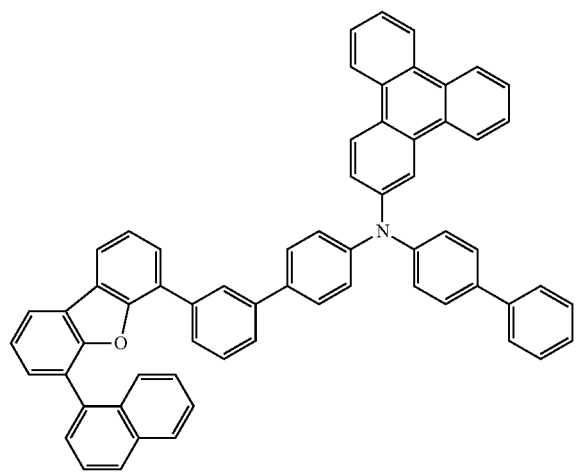
23
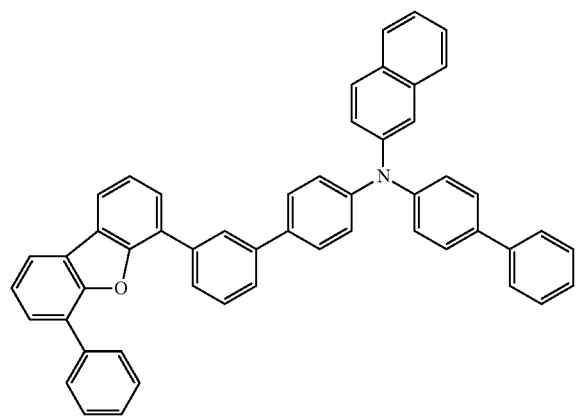
24
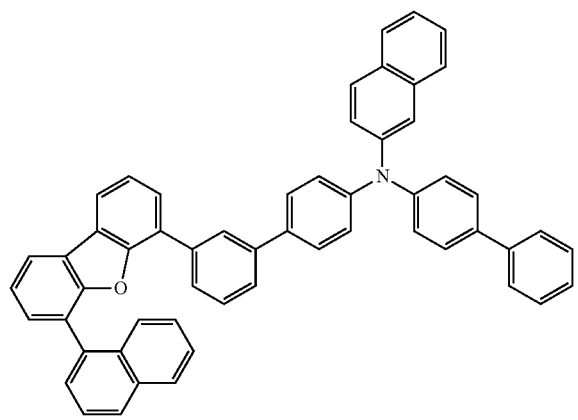

-continued
25
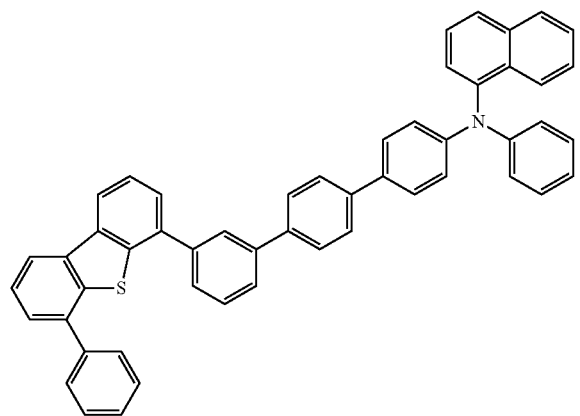
26
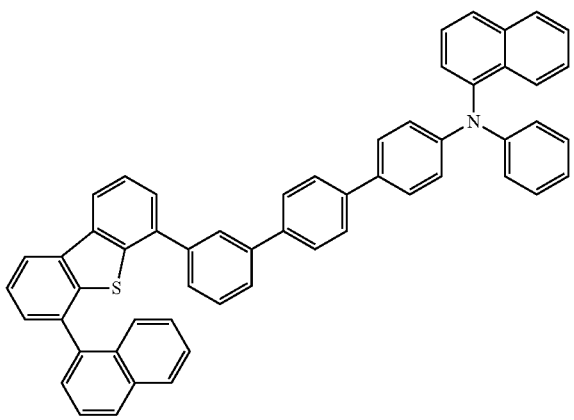
27
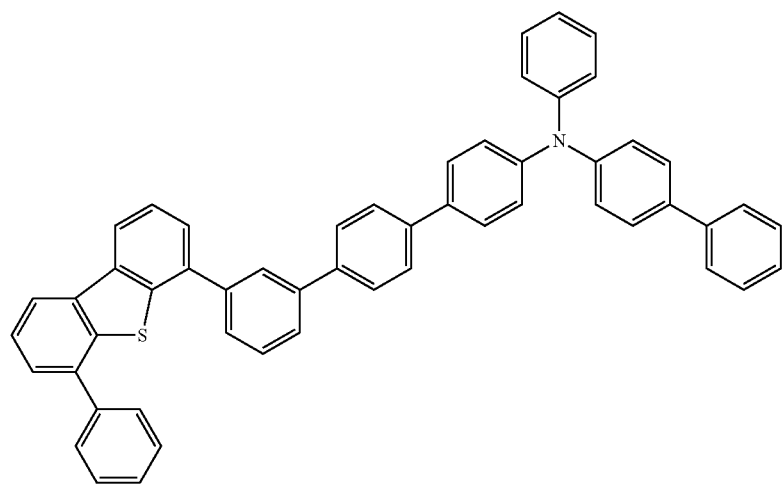
28
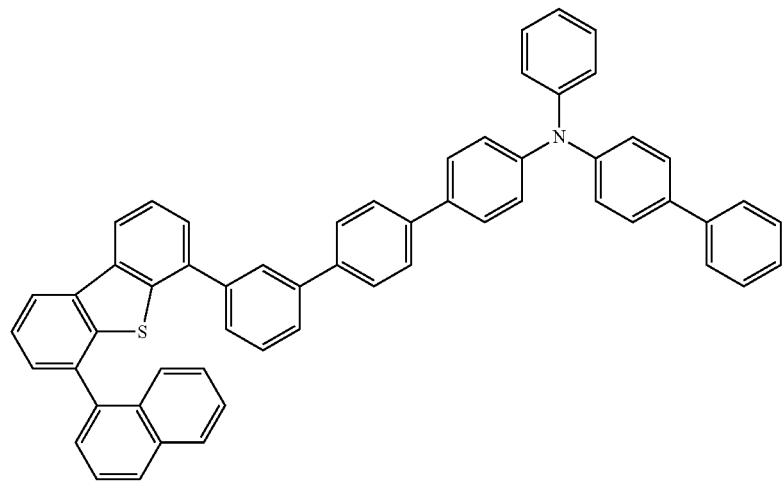

-continued
29
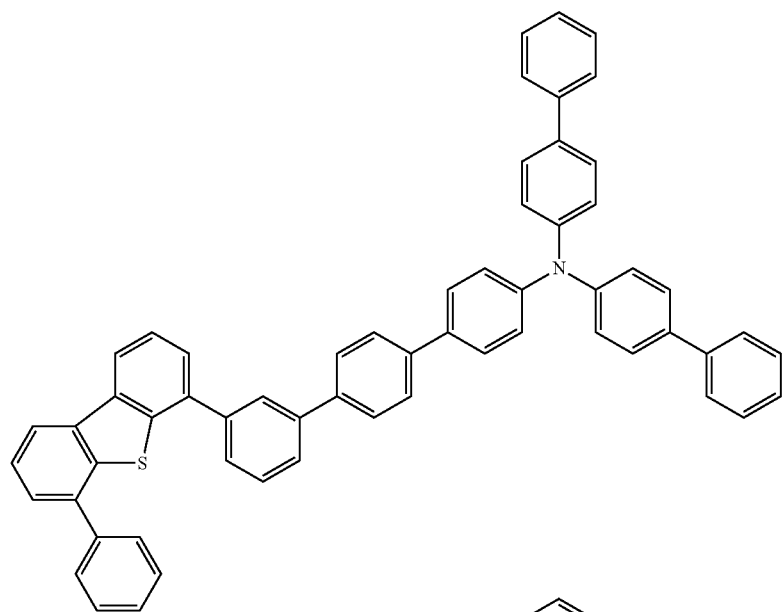
30
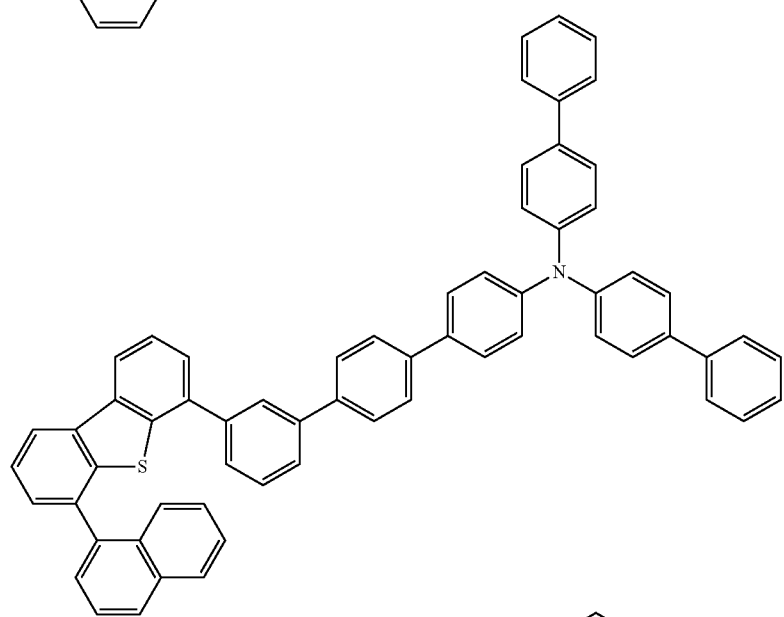
31
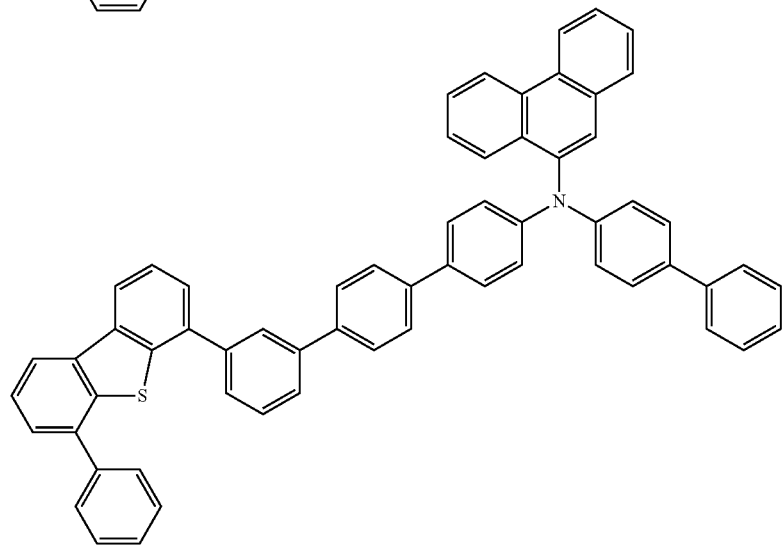

-continued
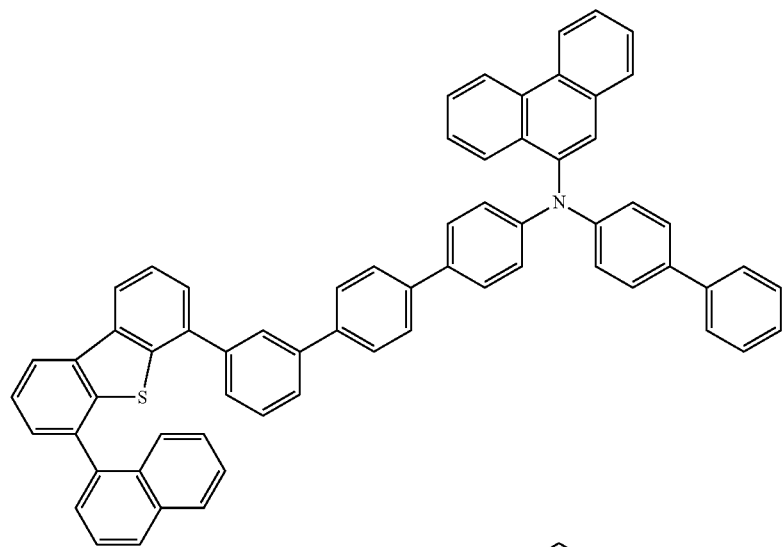
32
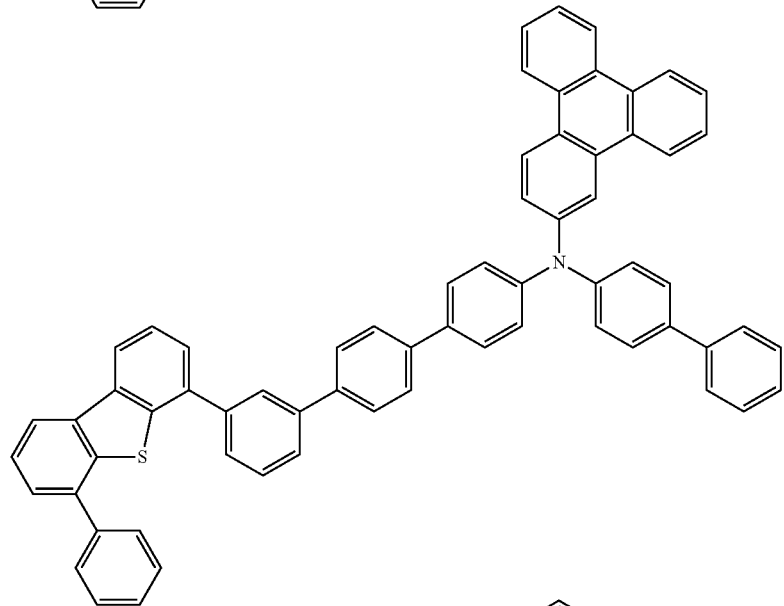
33
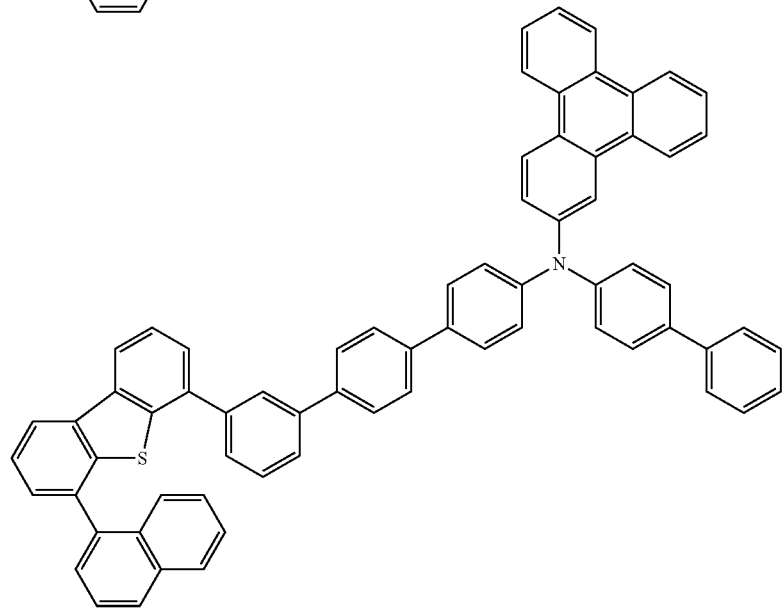
34

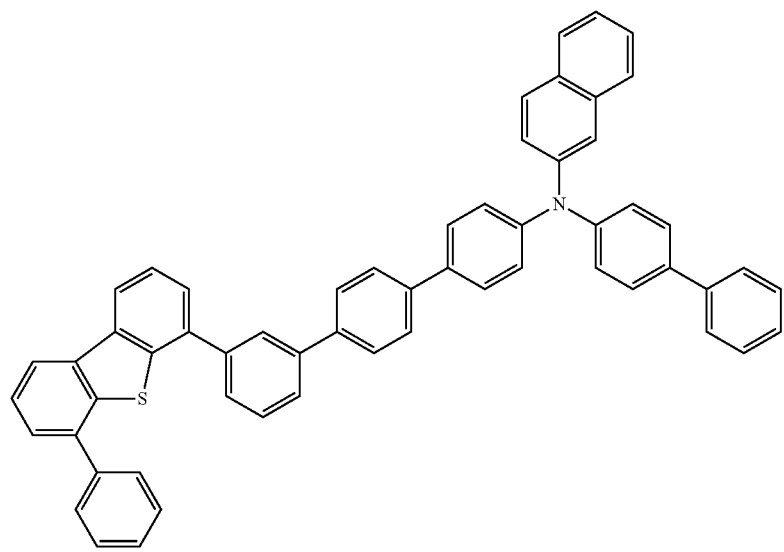
35
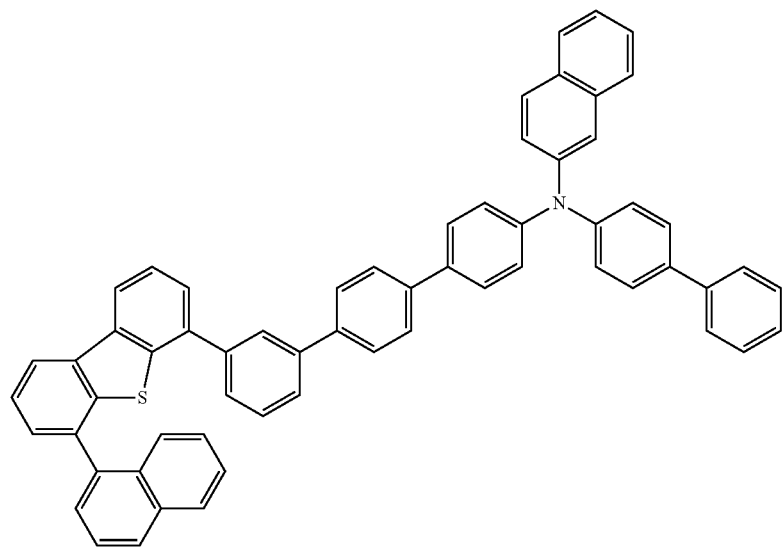
36
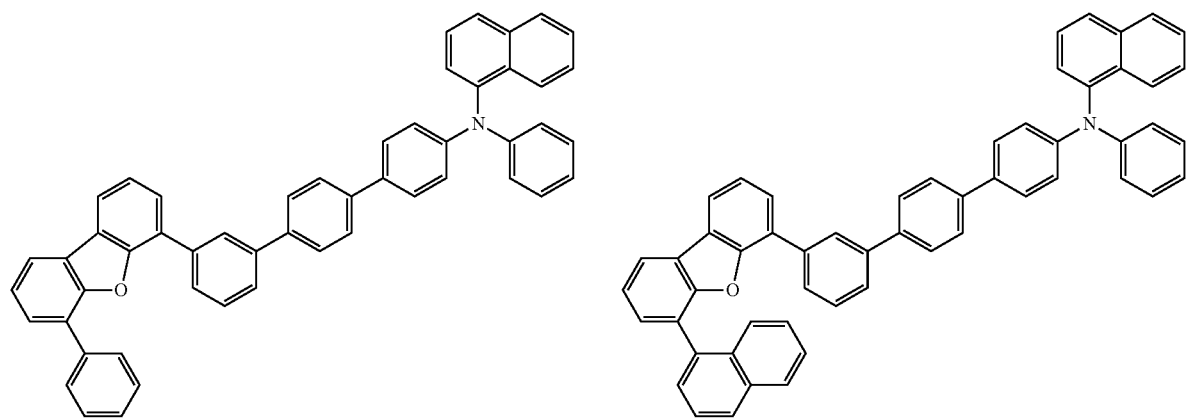

39
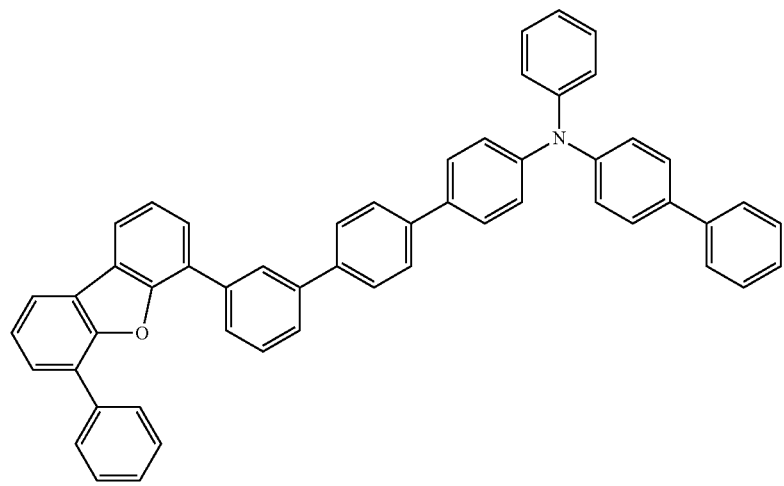
40
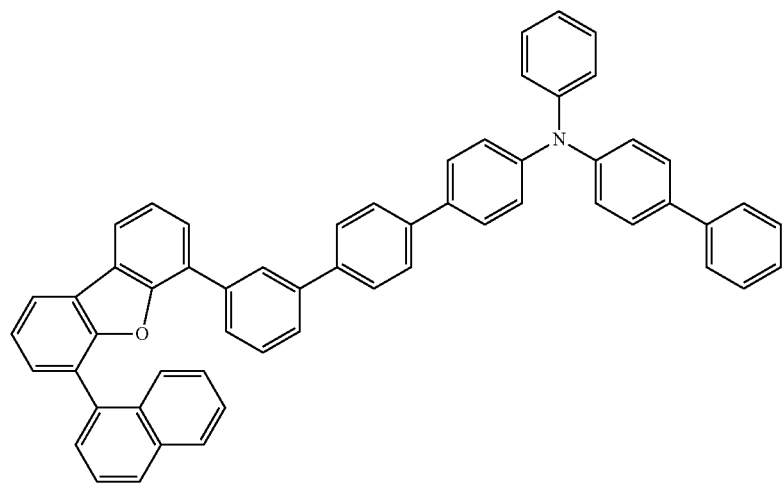
41
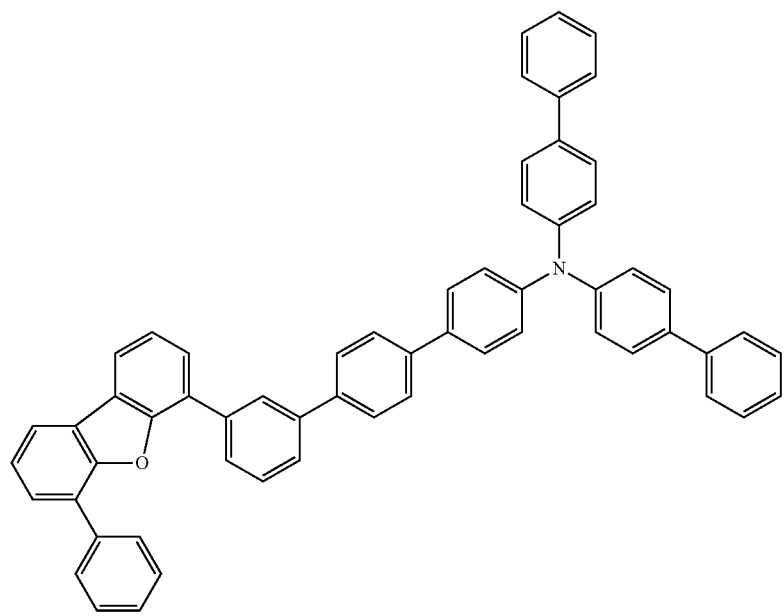

42
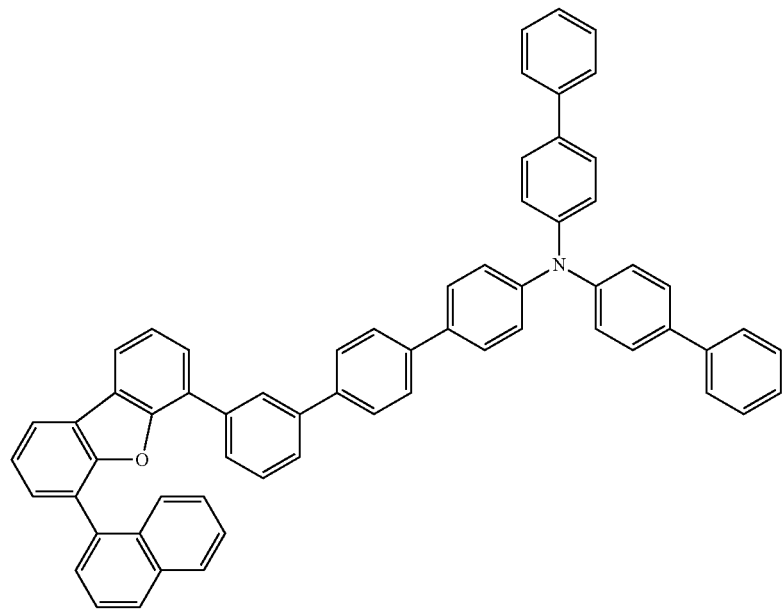
43
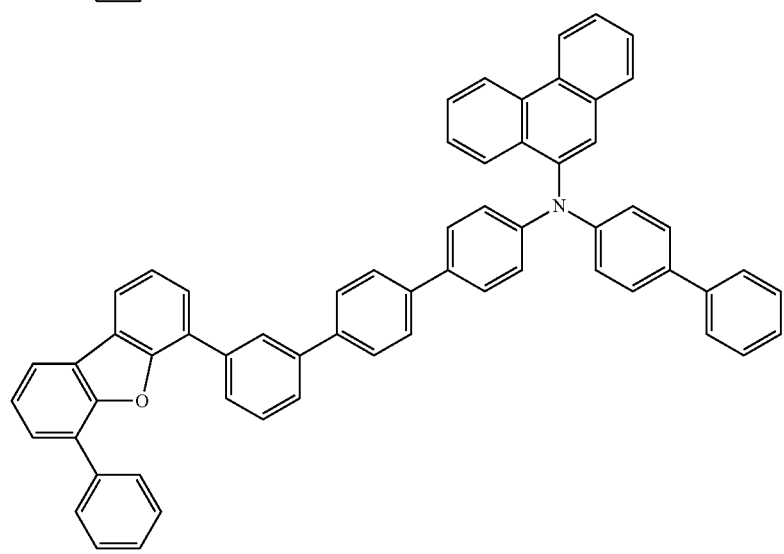
44
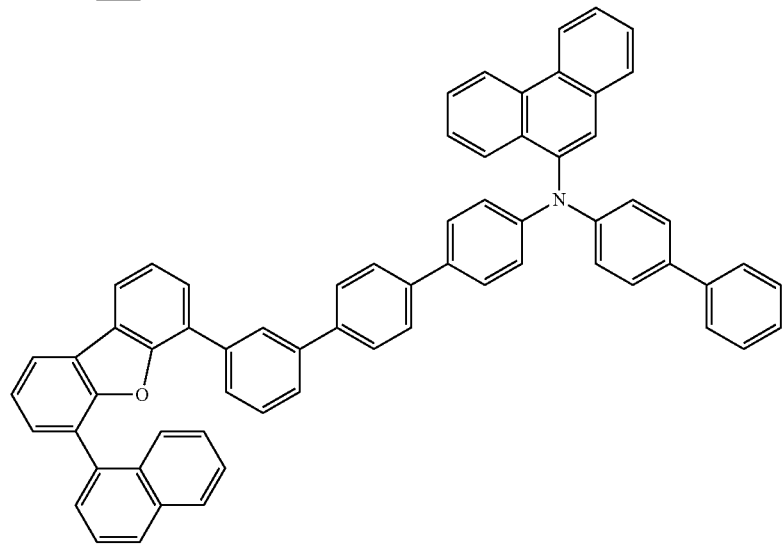

-continued
45
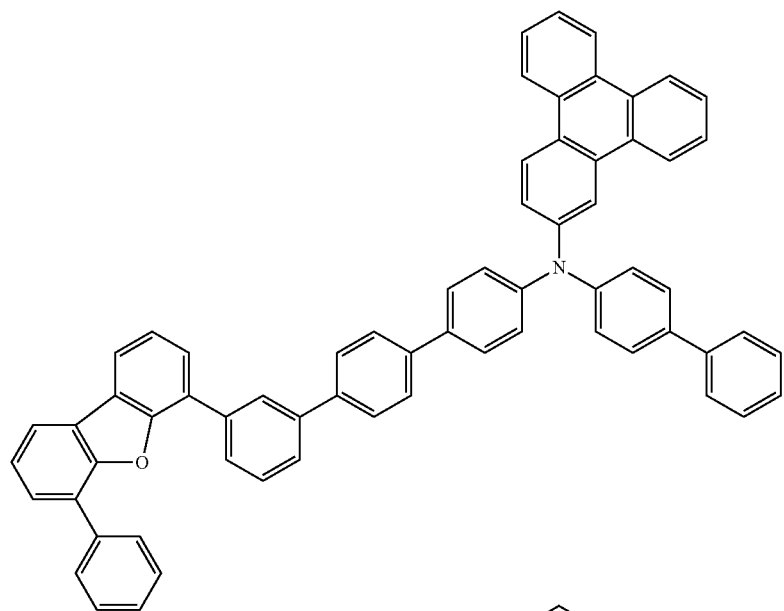
46
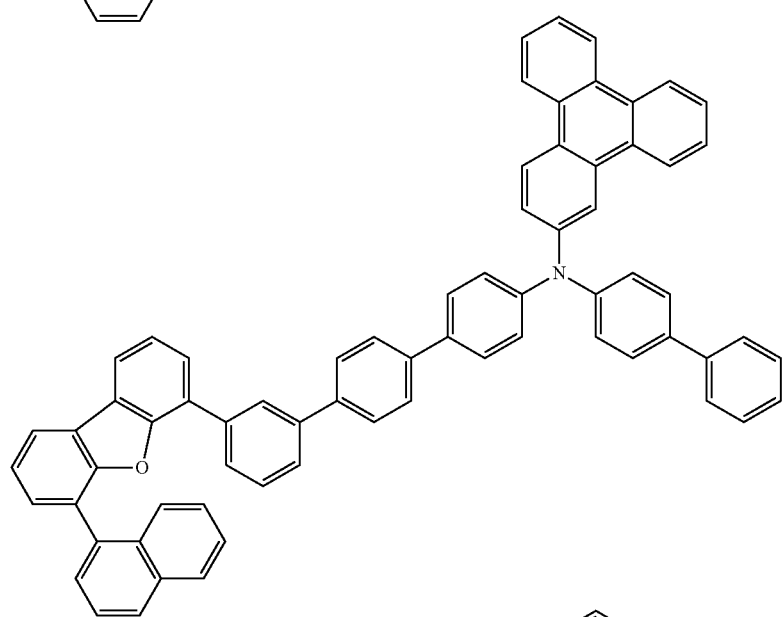
47
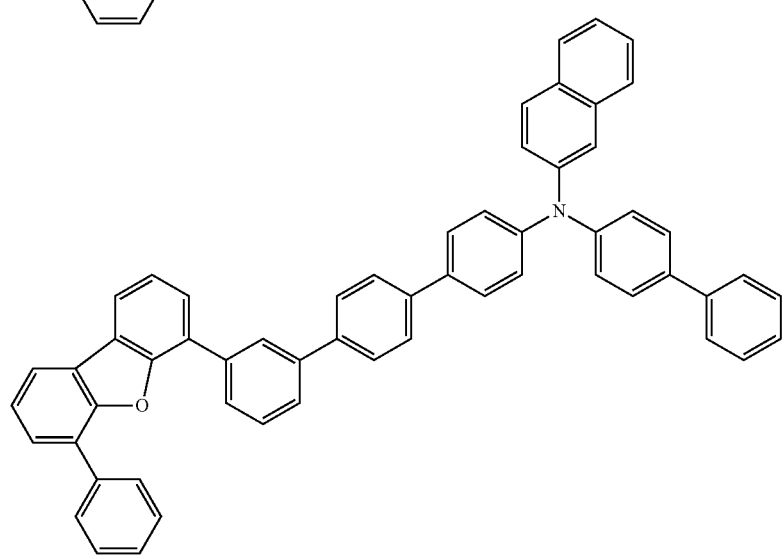

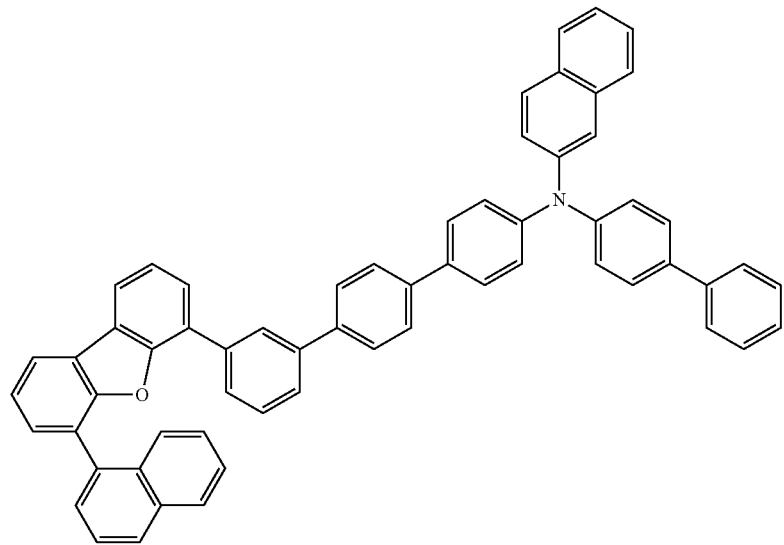
48
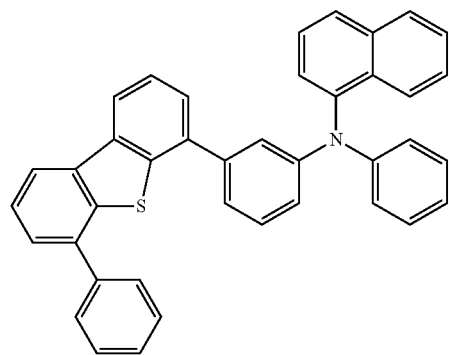
49
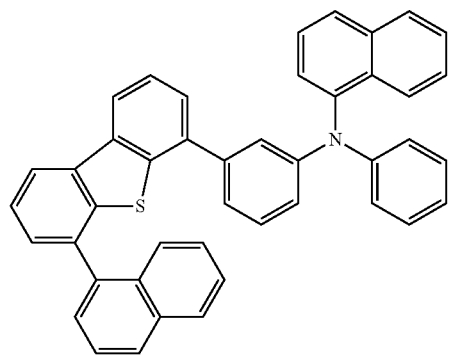
50
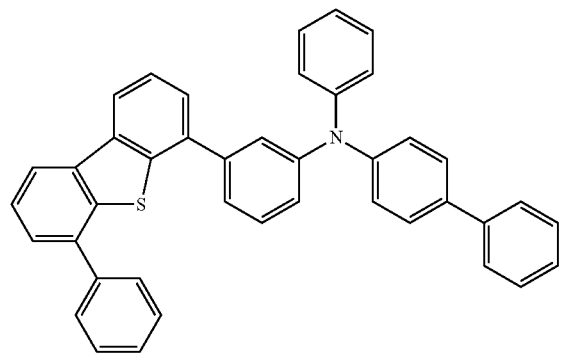
51
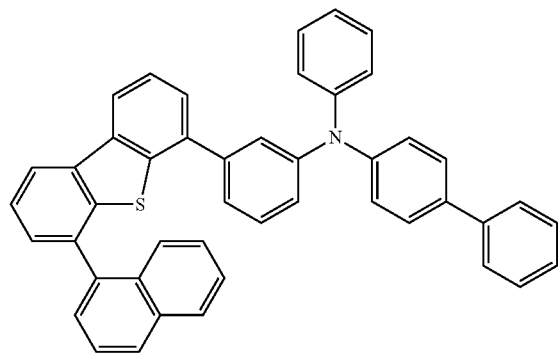
52

-continued
53
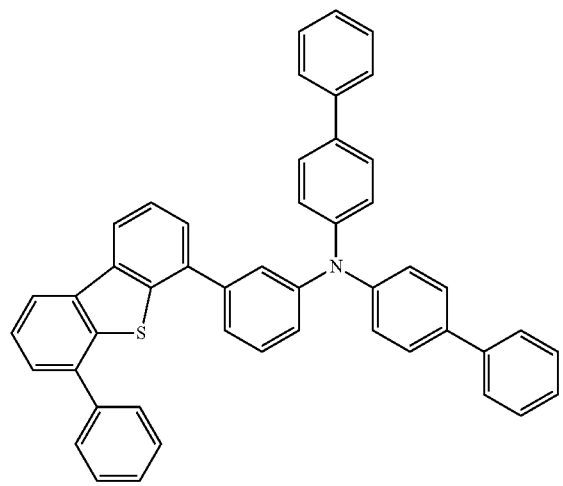
54
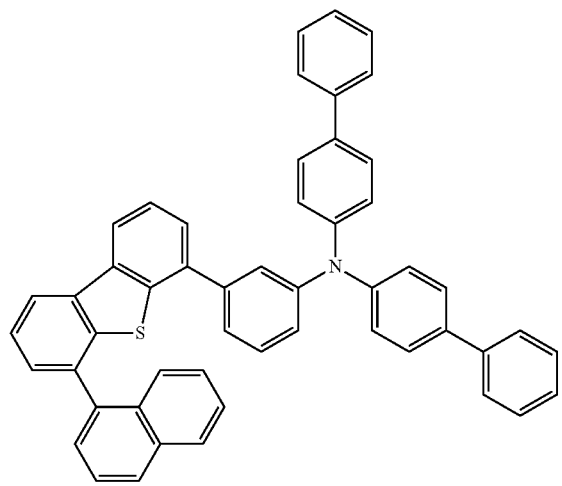
55
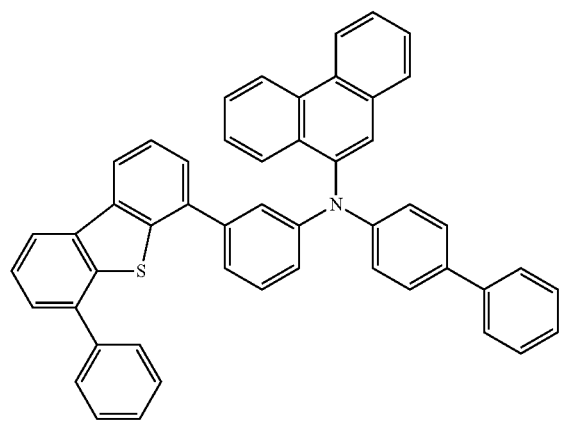
56
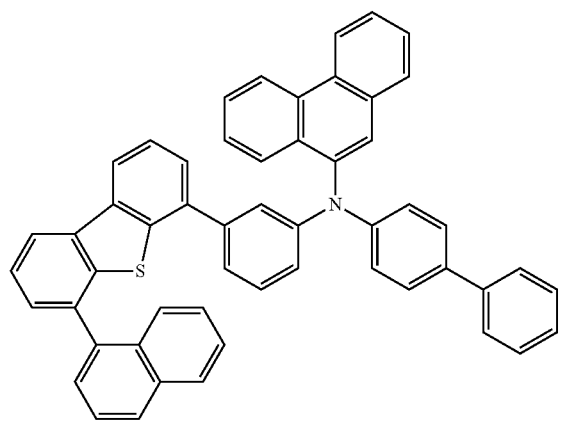
57
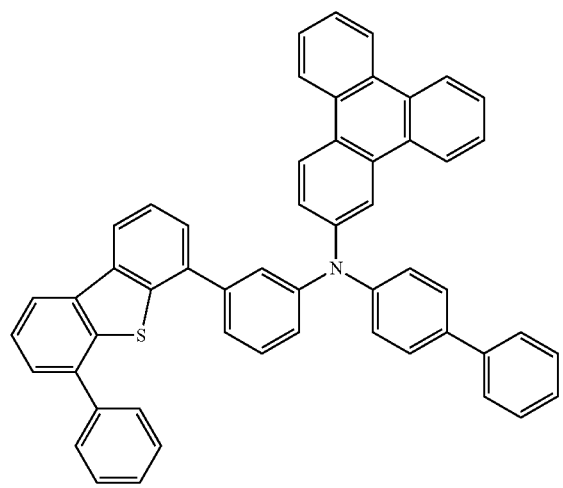
58
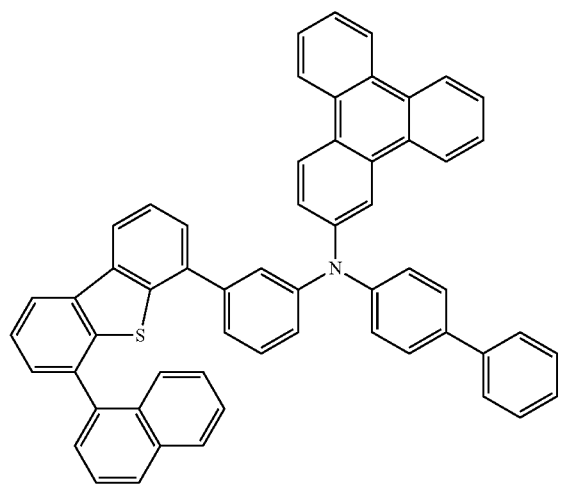

-continued
59
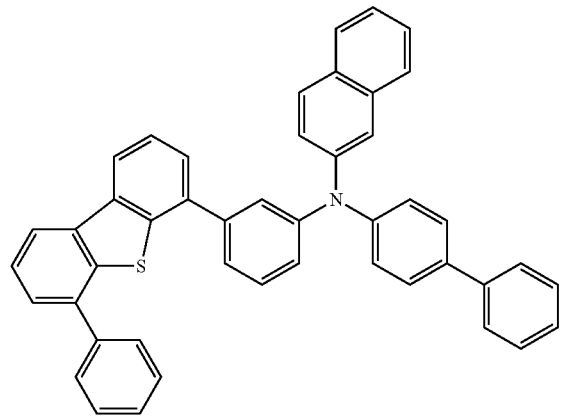
60
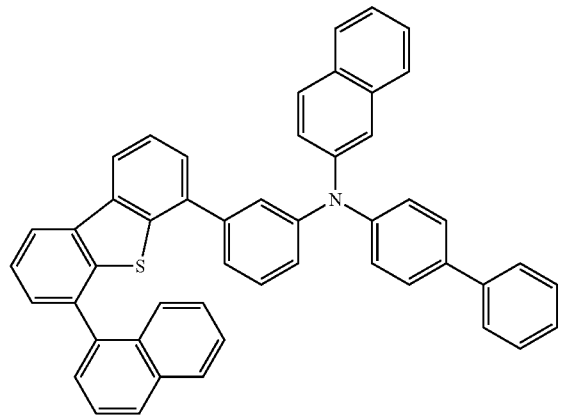
61
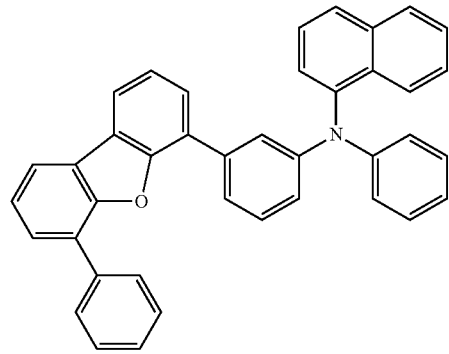
62
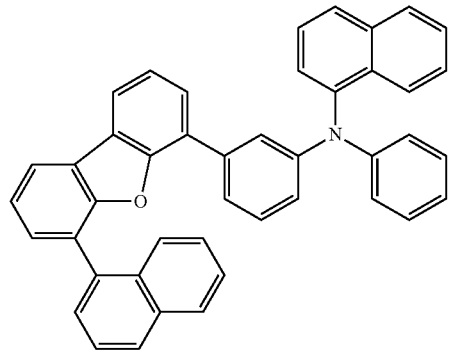
63
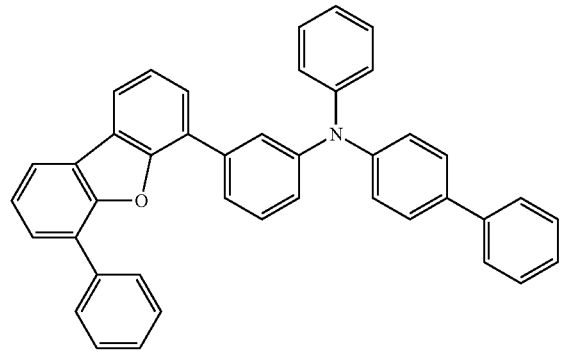
64
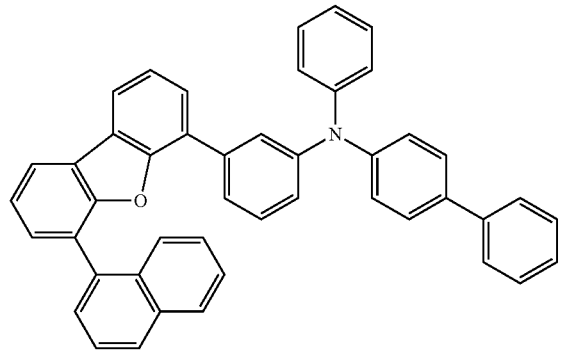
65
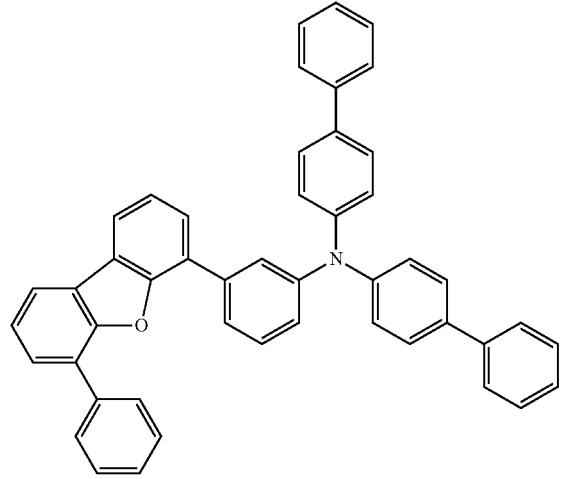
66
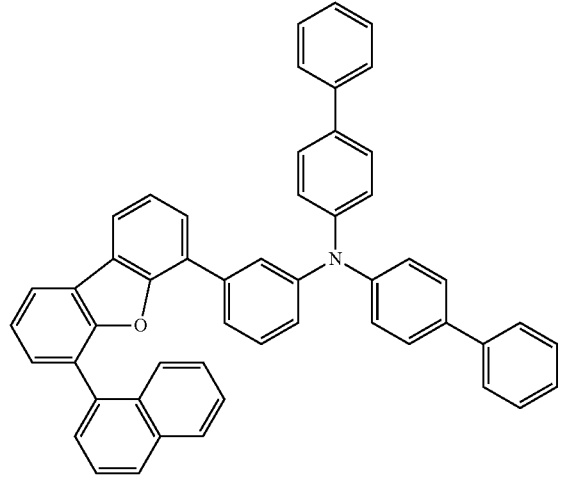

67
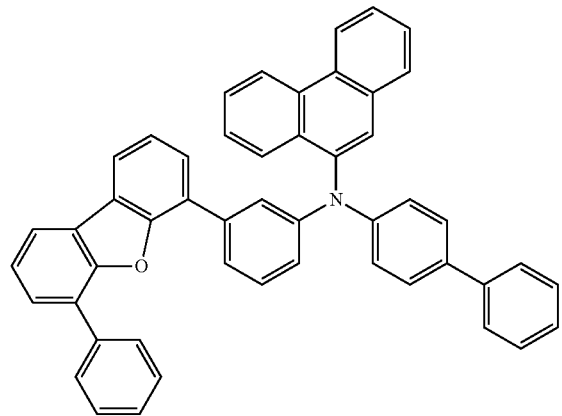
68
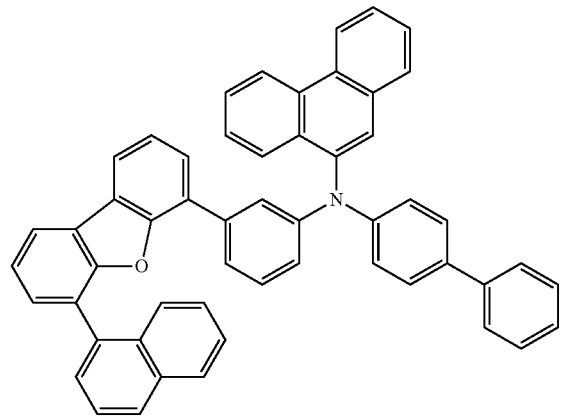
69
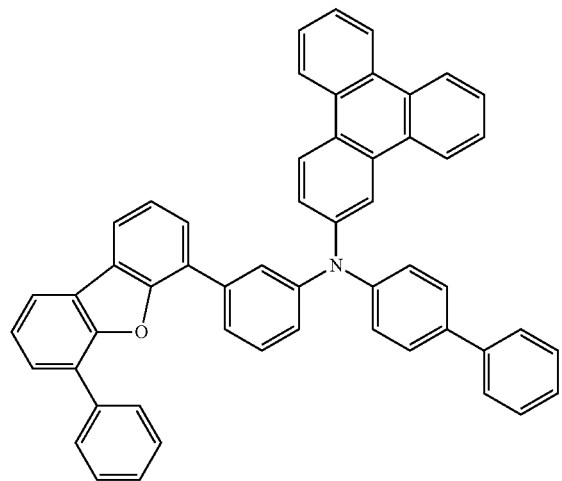
70
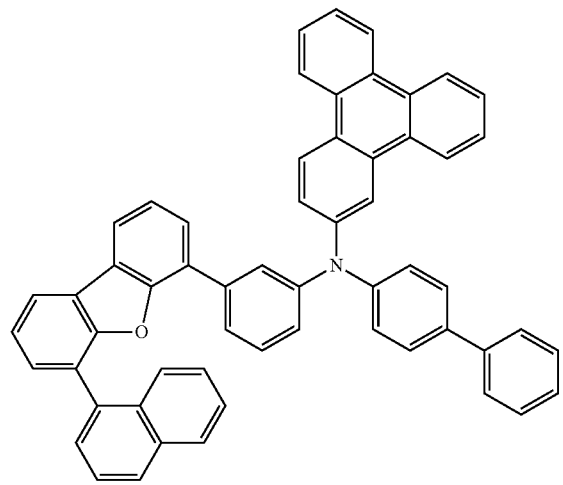
71
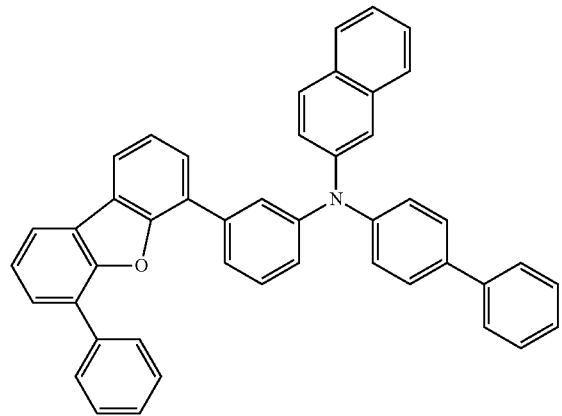
72
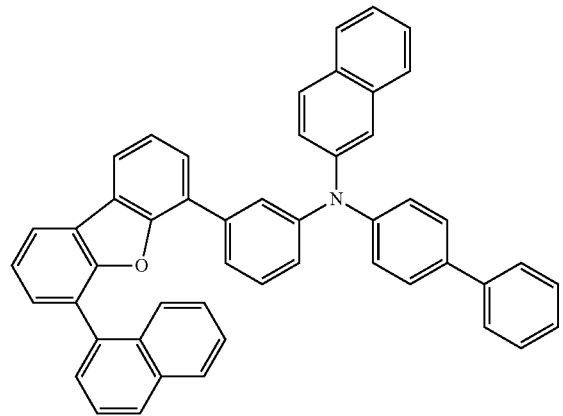

-continued
73
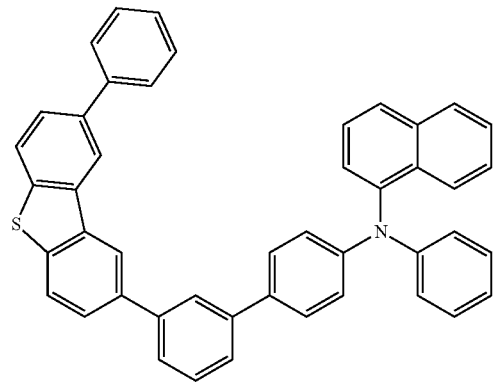
74
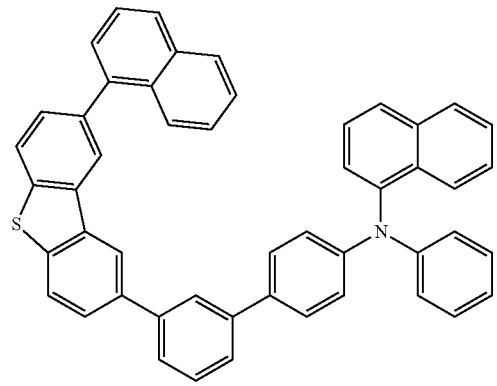
75
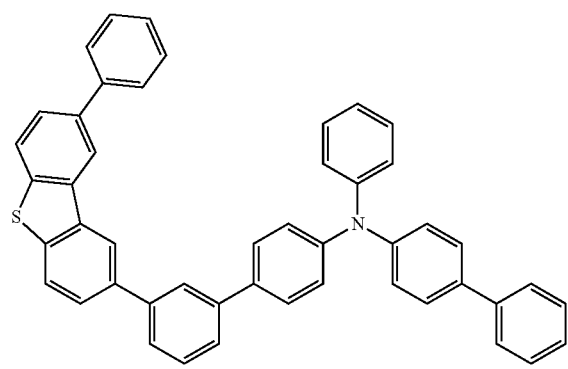
76
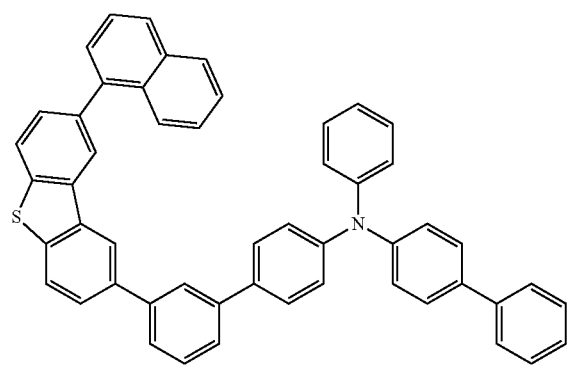
77
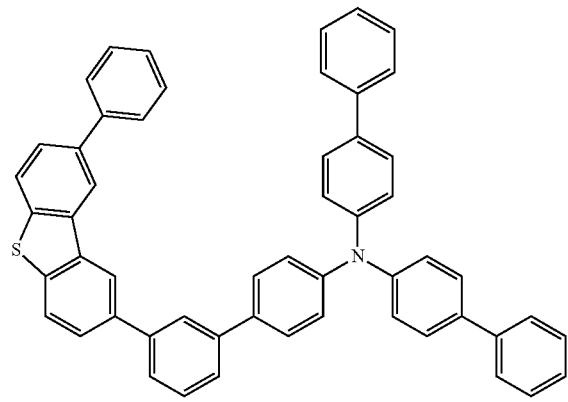
78
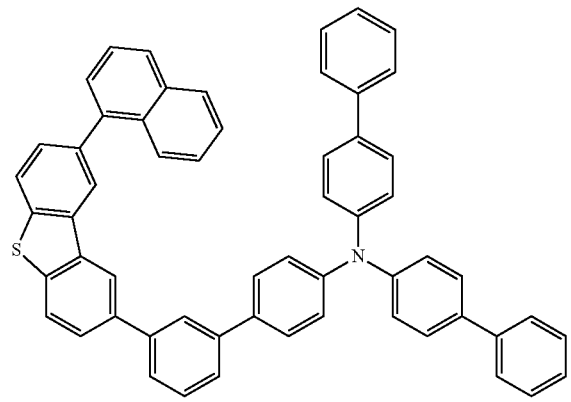
79
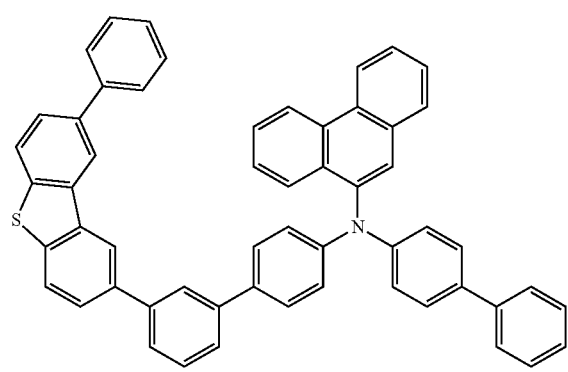
80
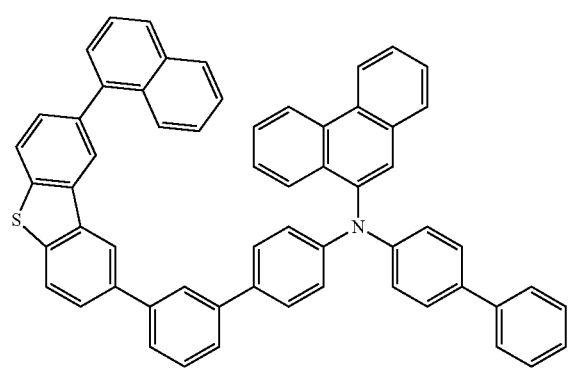

-continued
81
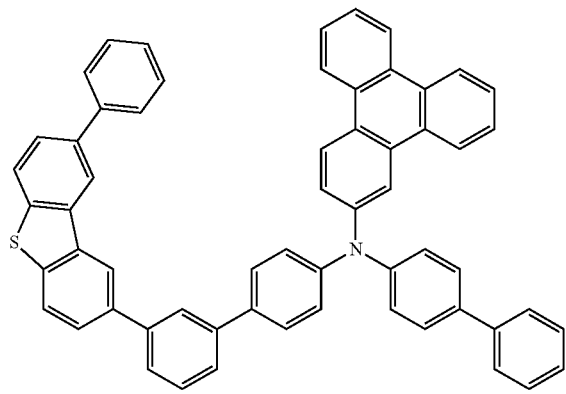
82
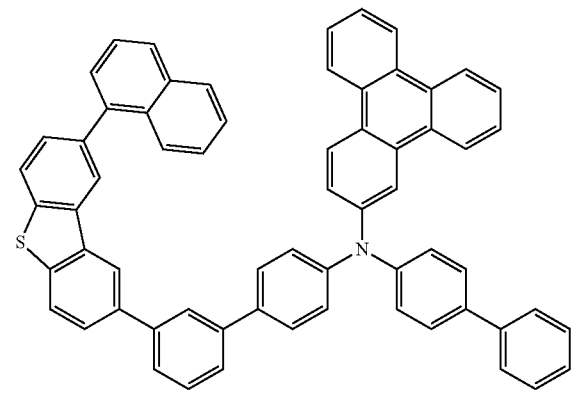
83
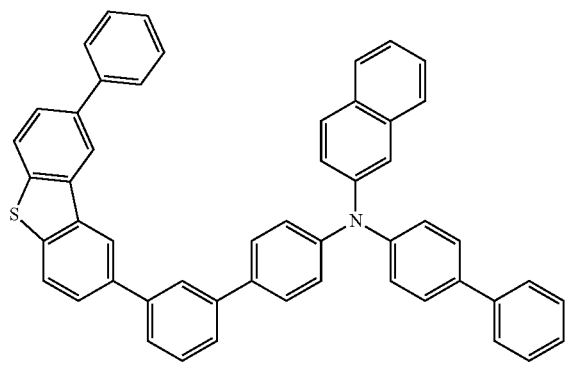
84
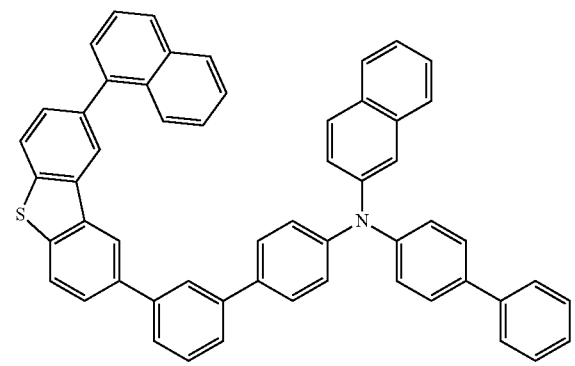
85
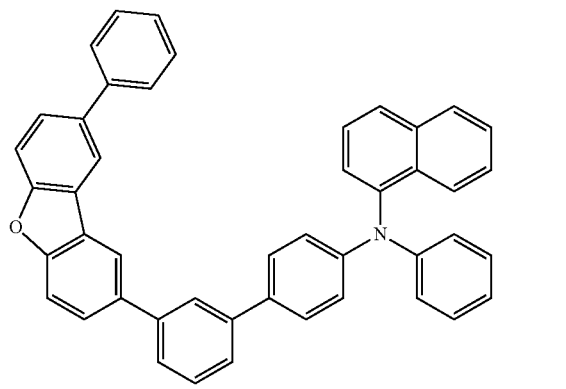
86
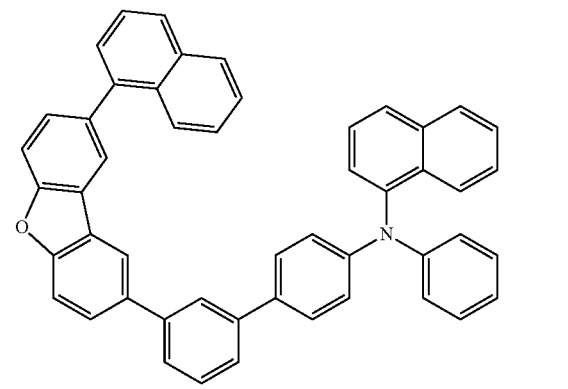
87
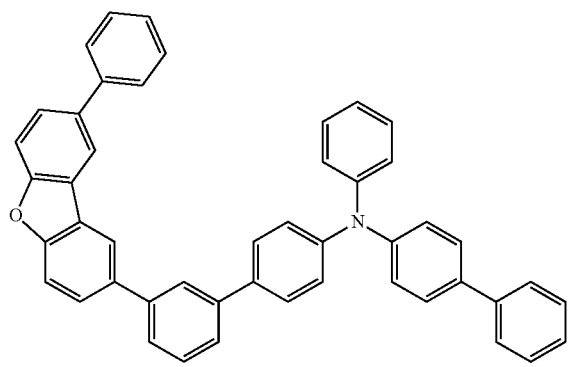
88
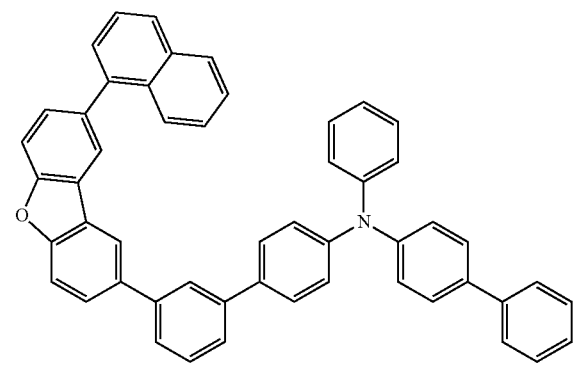

-continued
89
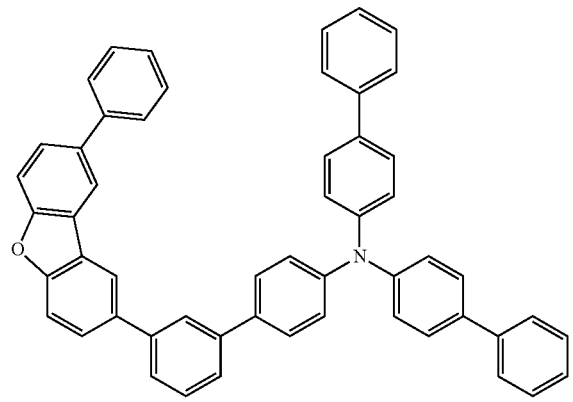
90
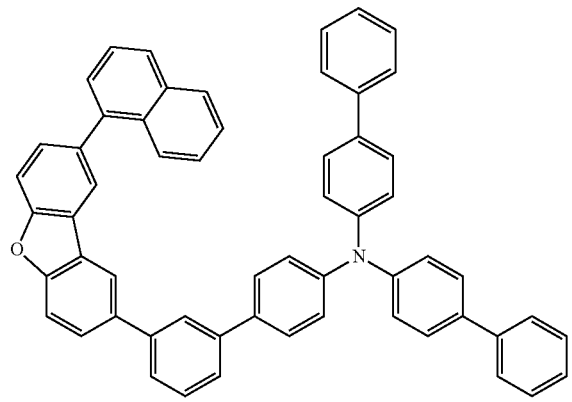
91
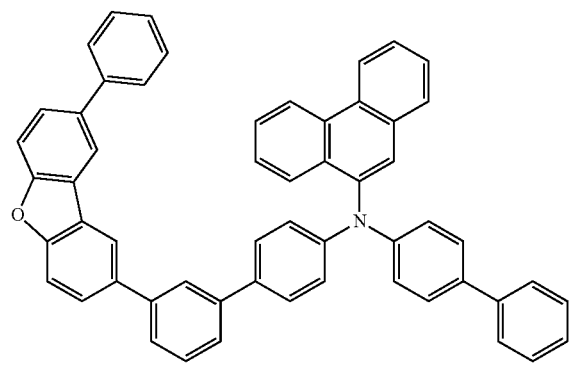
92
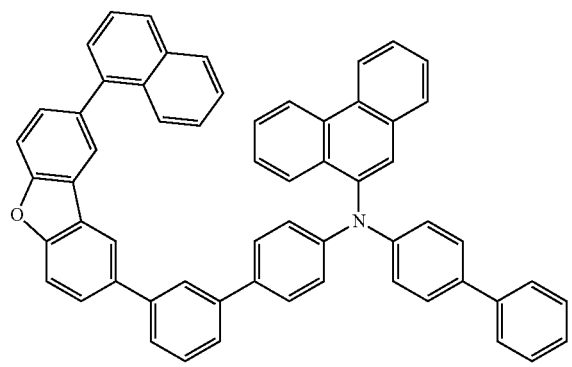
93
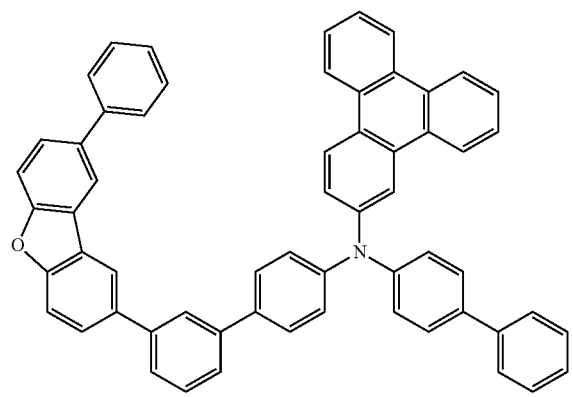
94
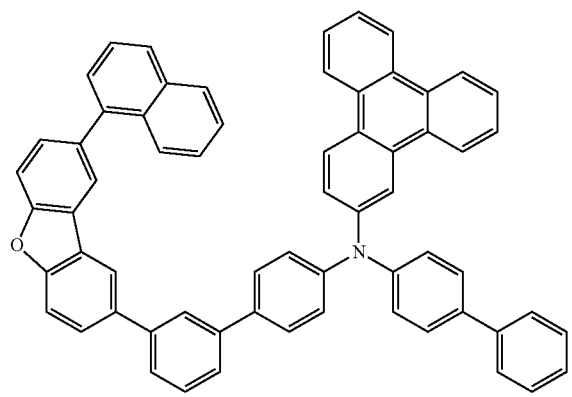
95
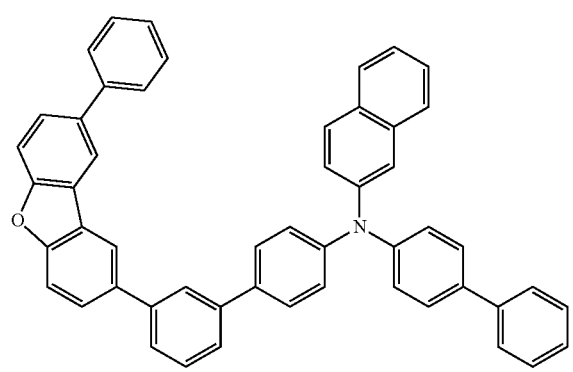
96
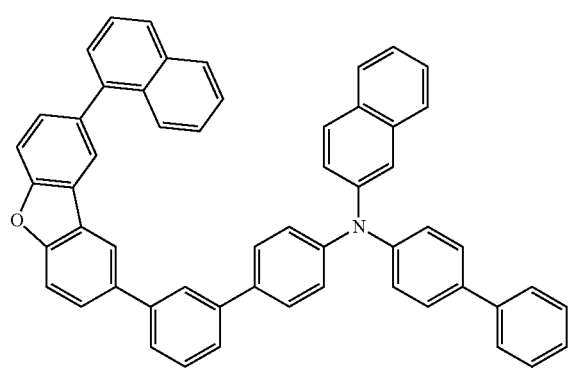

-continued
97
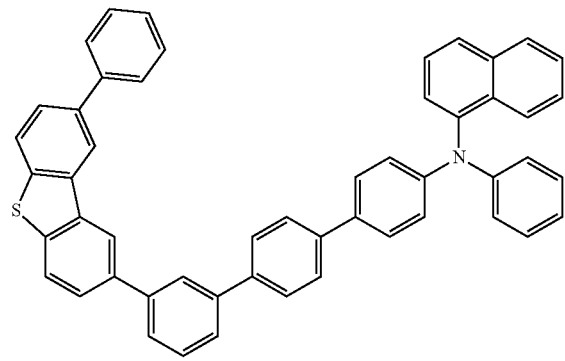
98
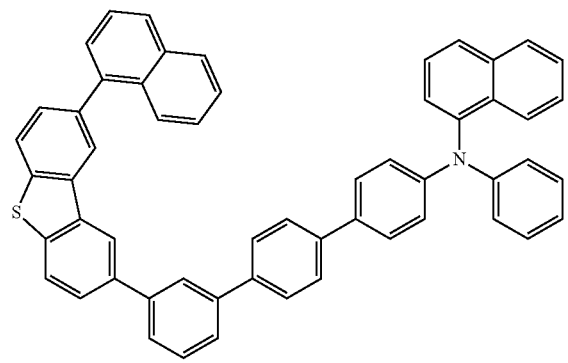
99
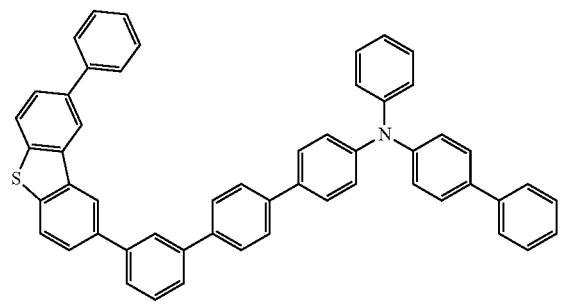
100
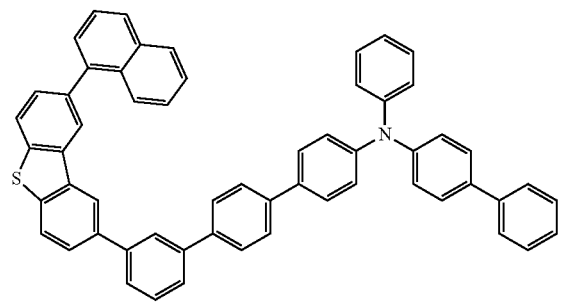
101
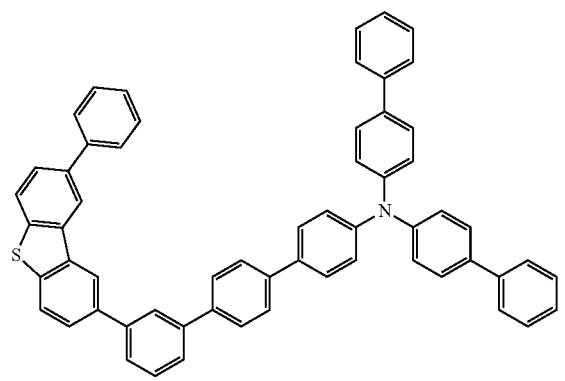
102
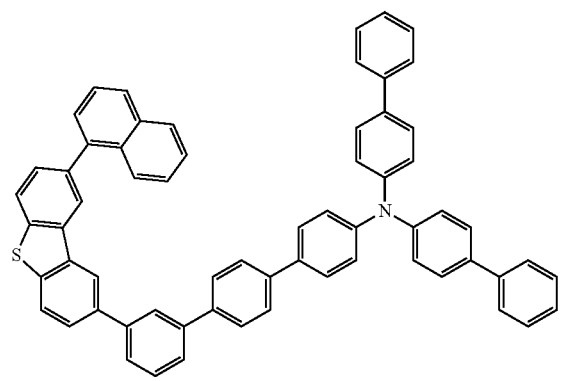
103
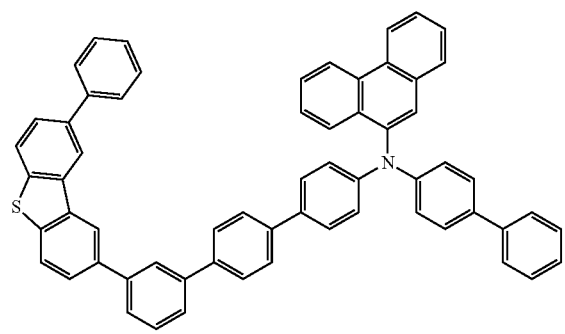
104
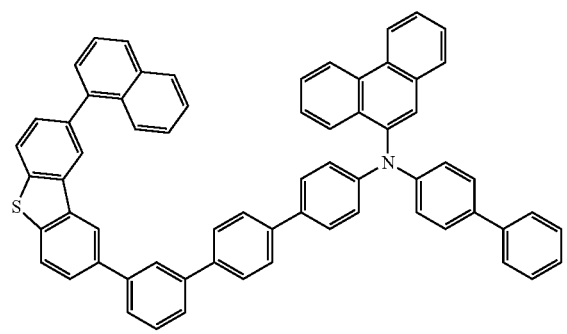

-continued
105
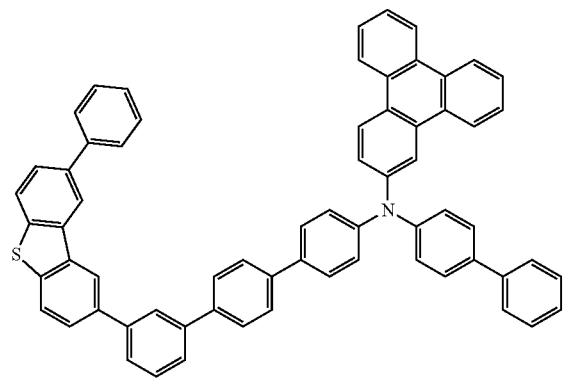
106
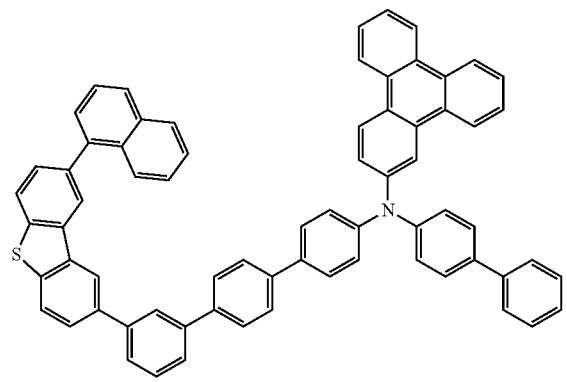
107
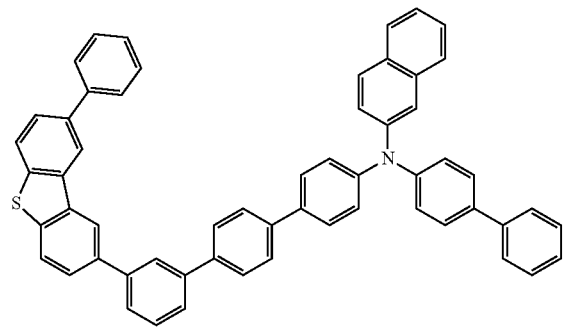
108
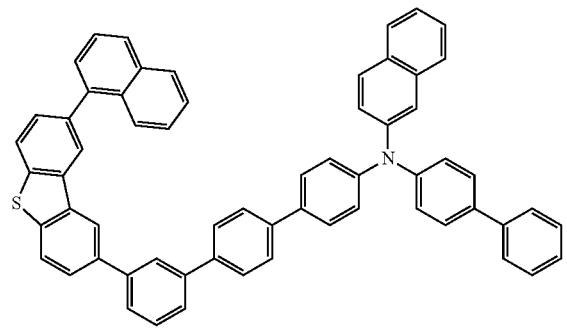
109
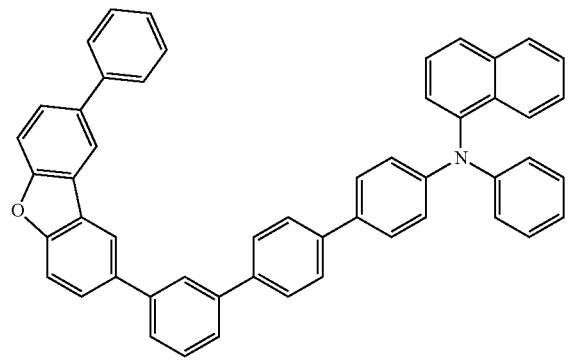
110
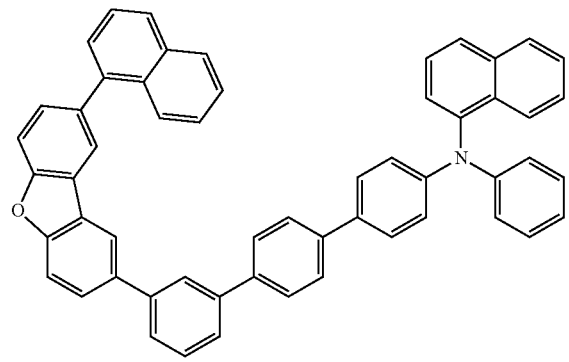
111
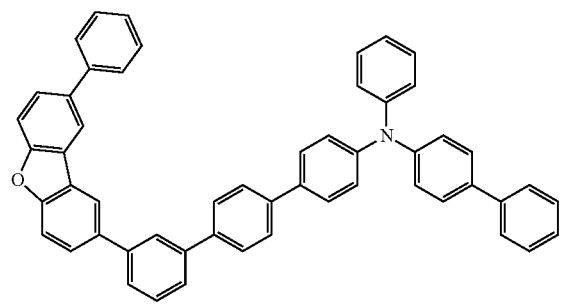
112
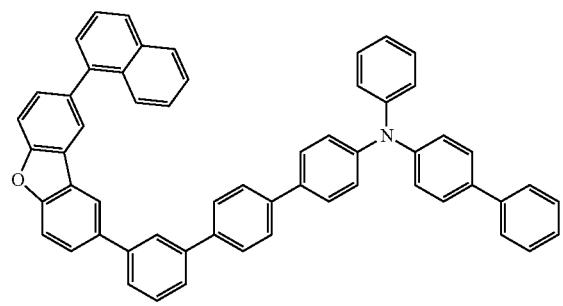

-continued
113
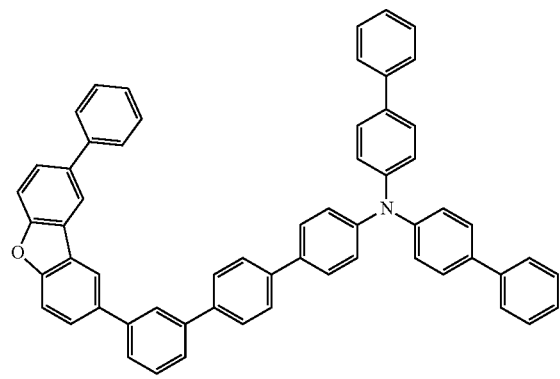
114
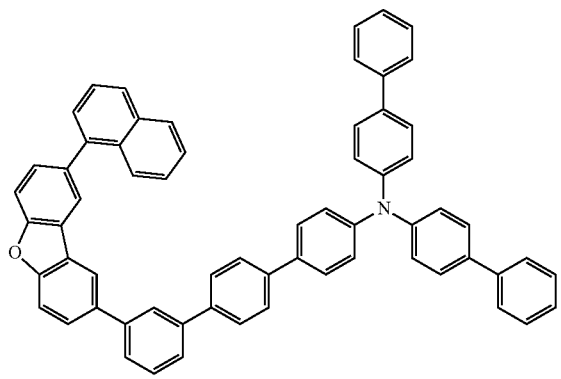
115
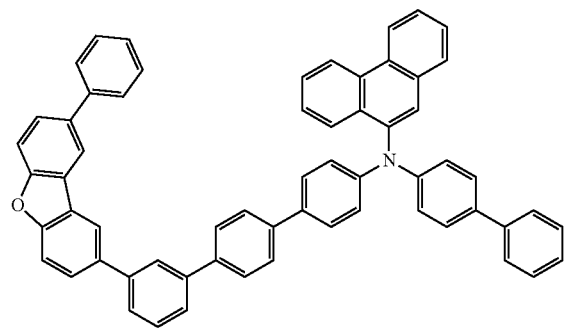
116
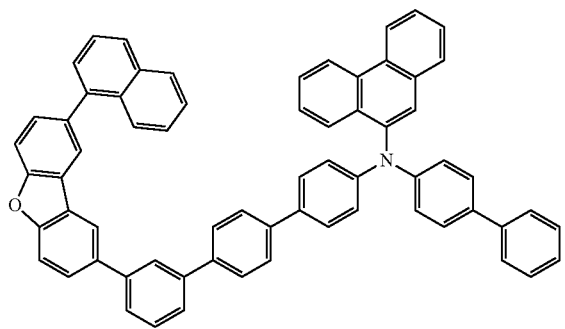
117
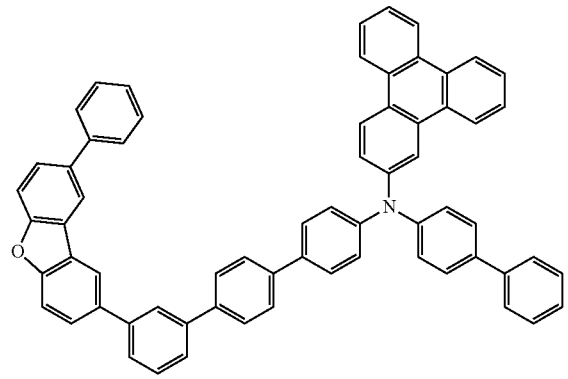
118
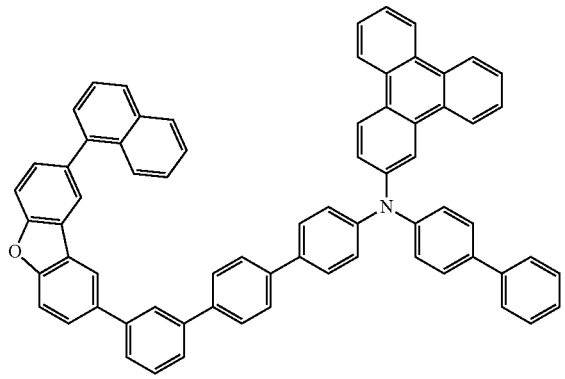
119
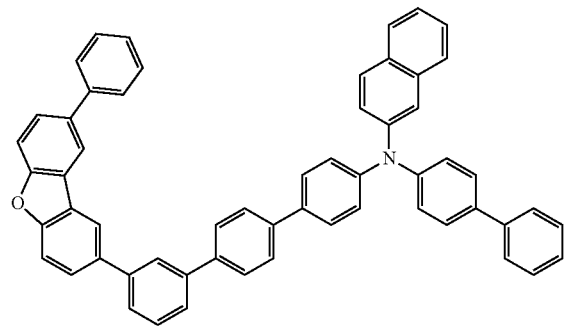
120
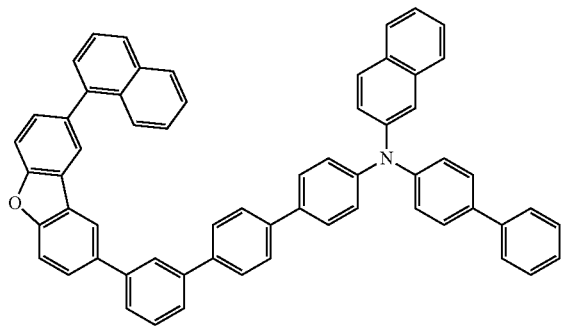

-continued
121 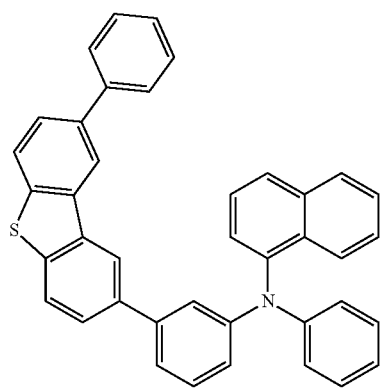
122 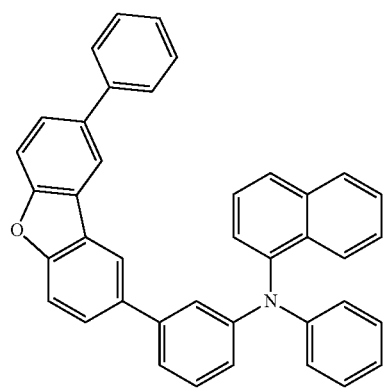
123 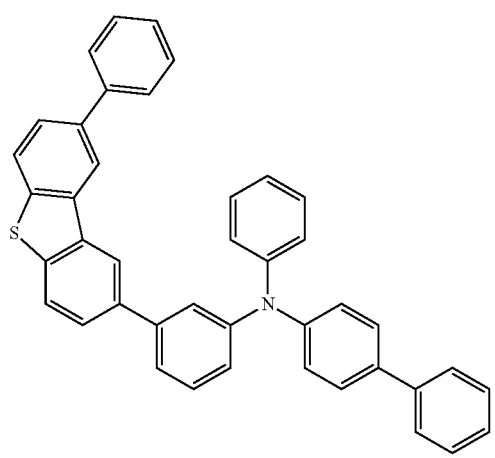
124 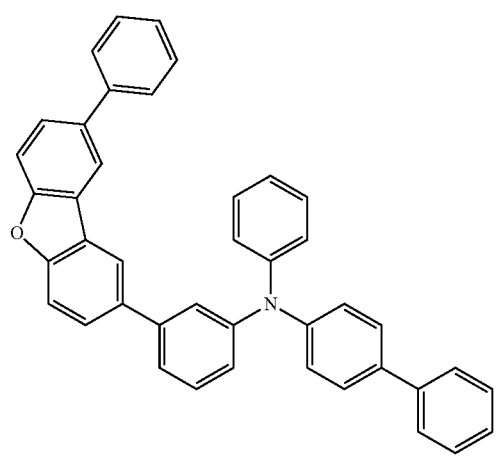
125 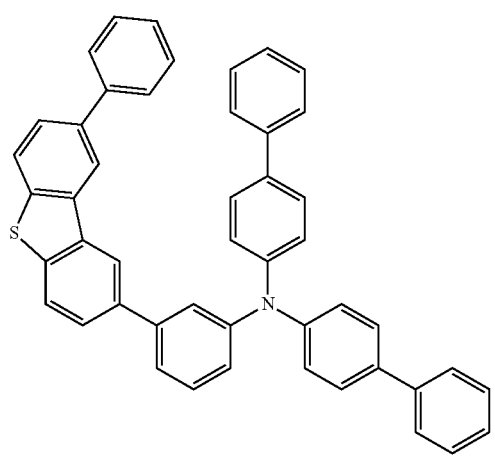
126 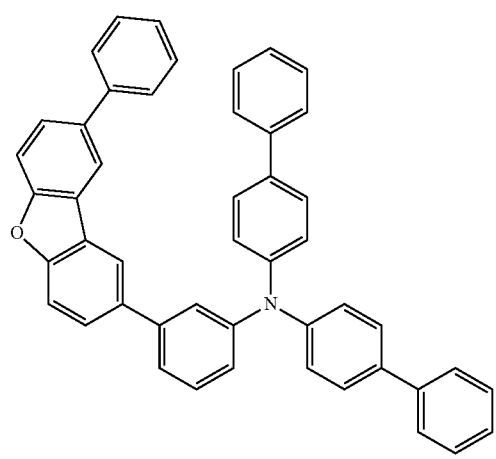

-continued
127
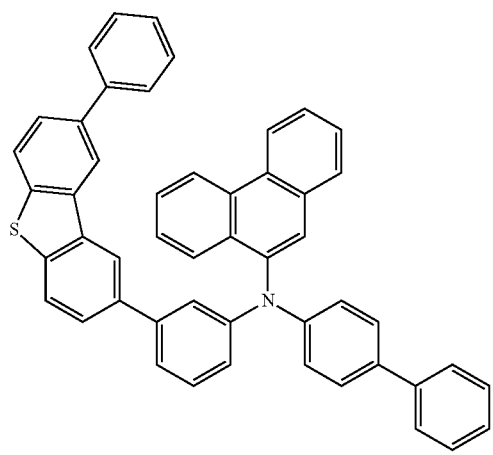
128
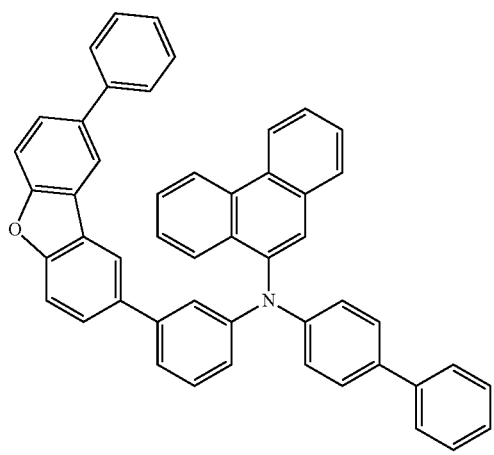
129
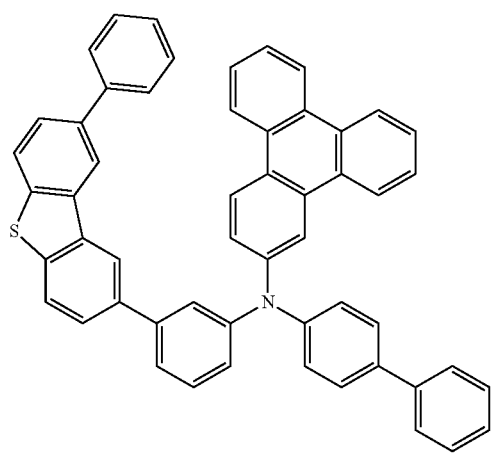
130
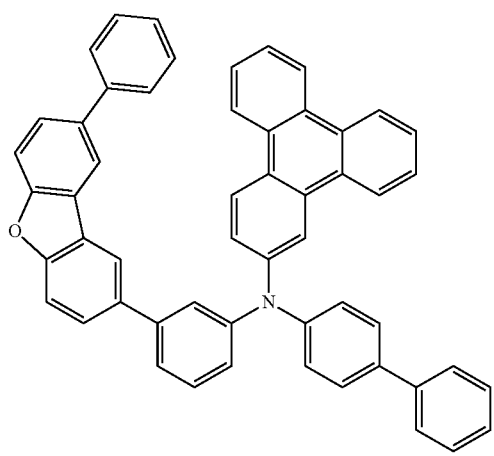
131
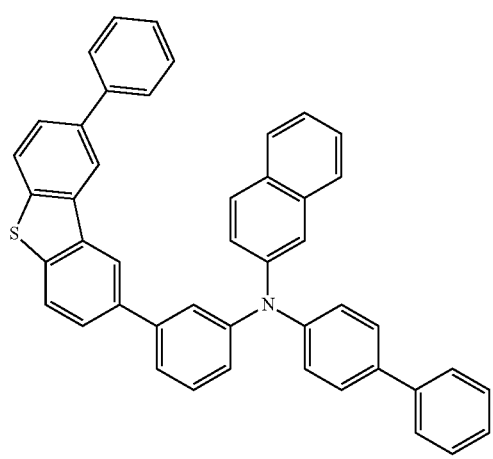
132
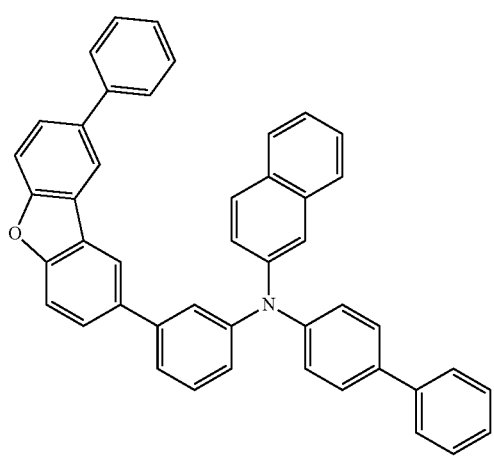

133
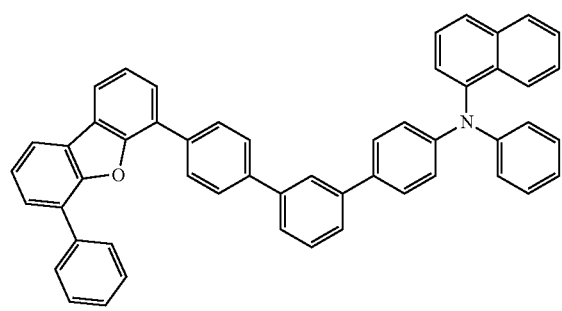
134
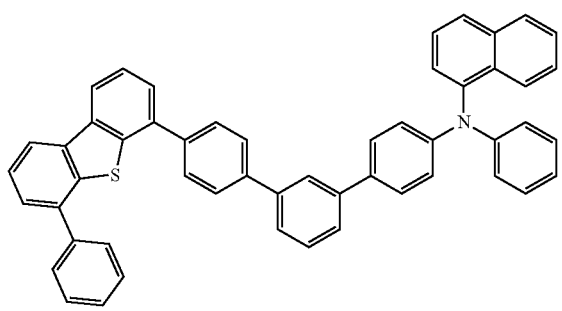
135
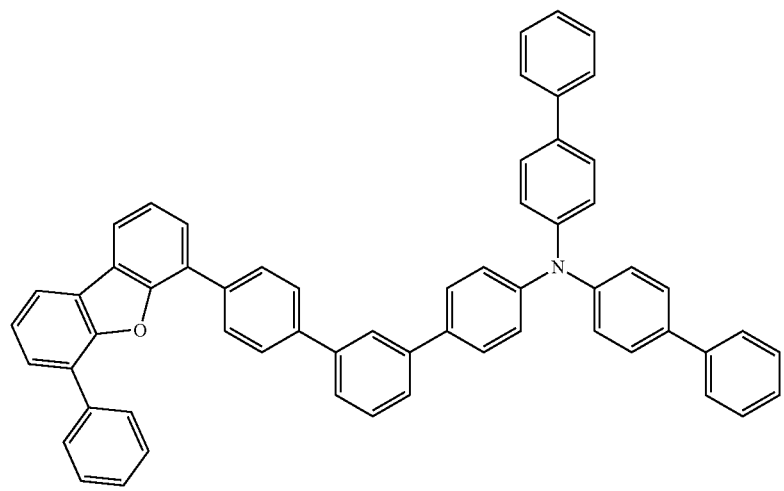
136
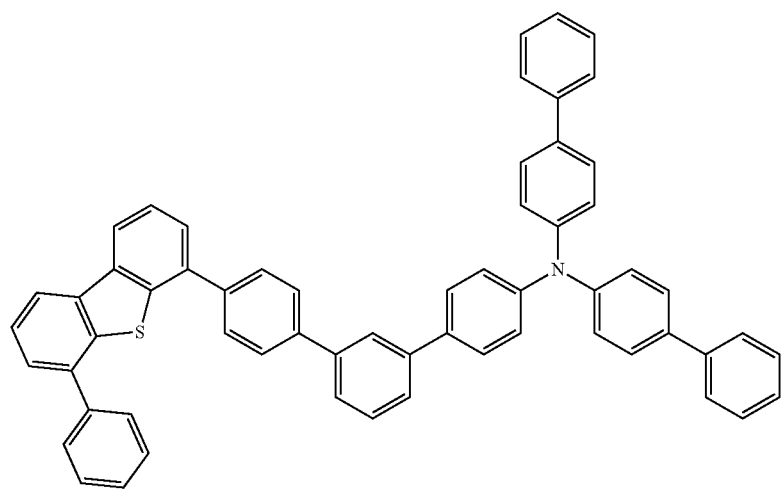

-continued
137
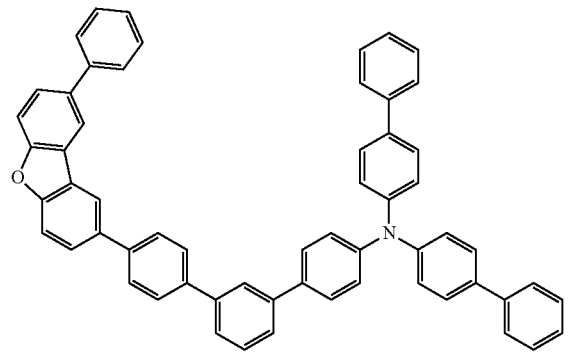
138
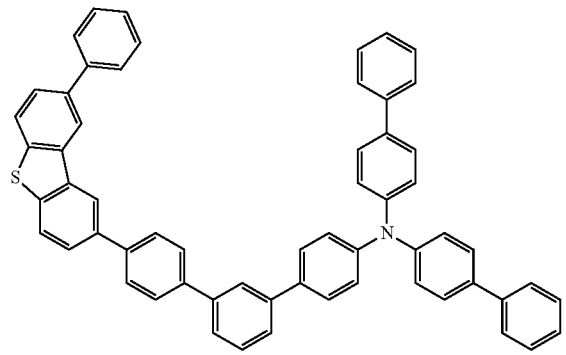
139
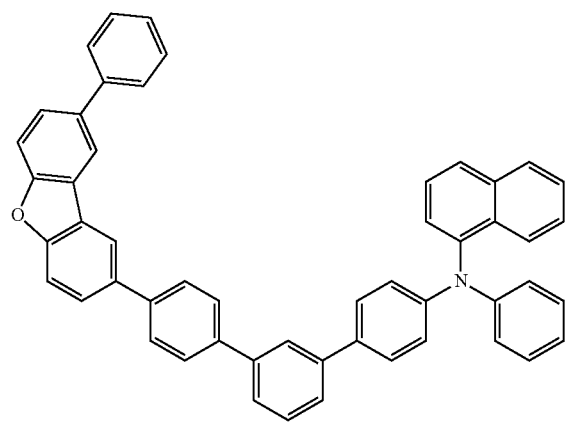
140
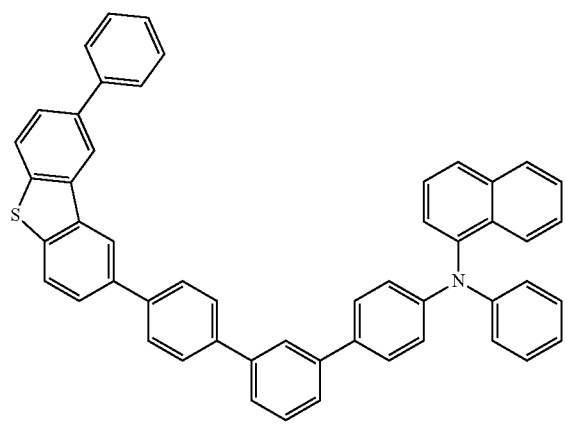
141
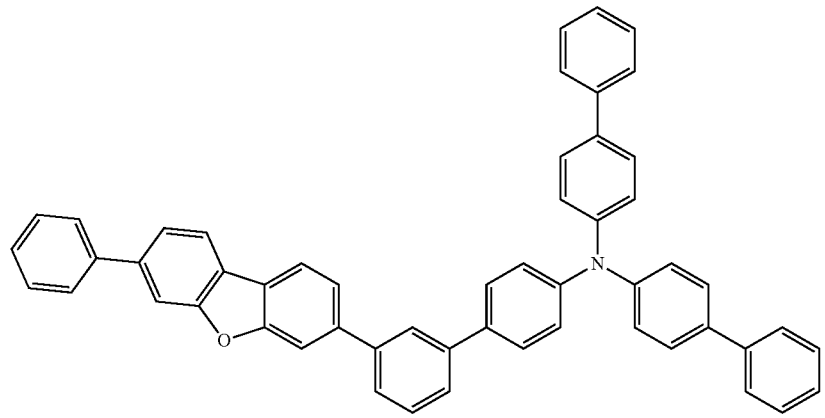
142
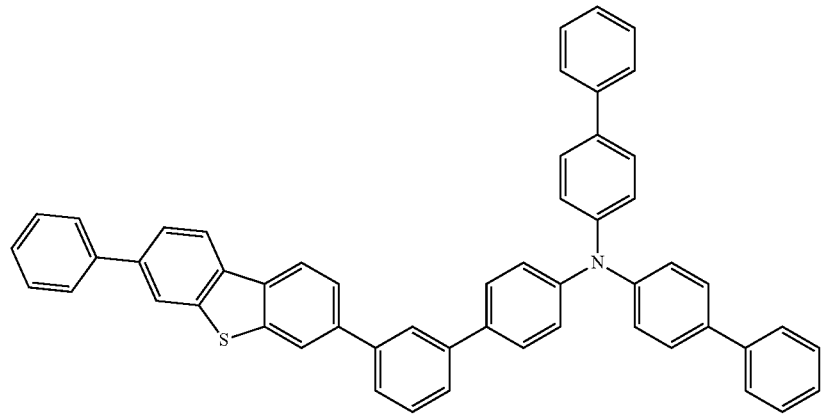

-continued
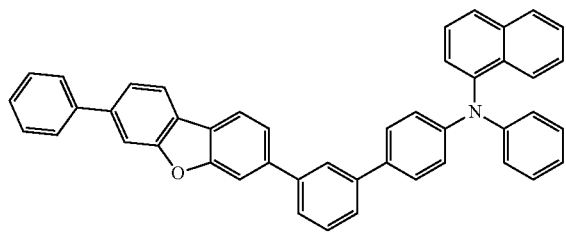
143
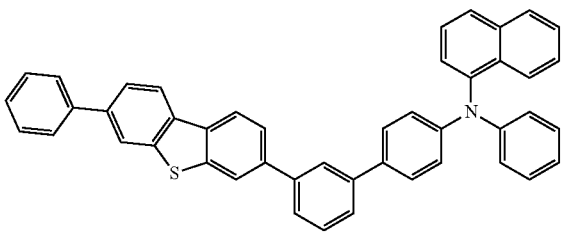
144
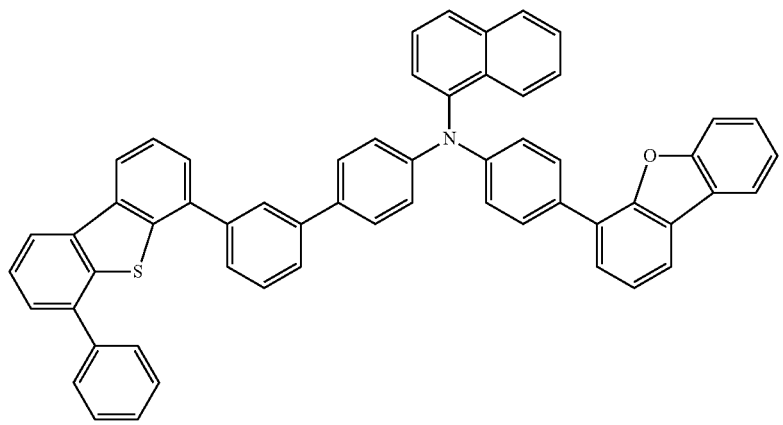
145
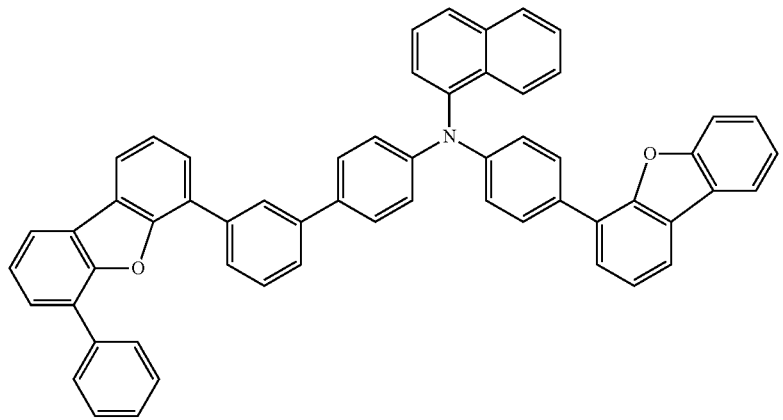
146
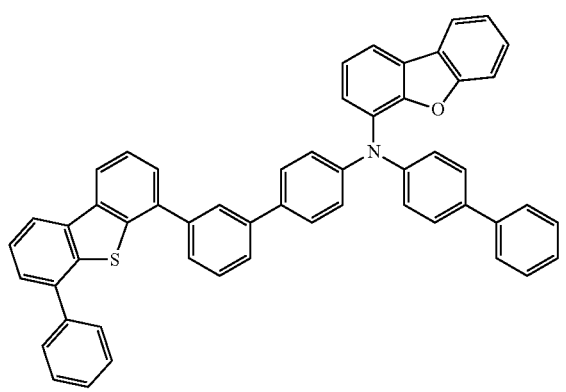
147
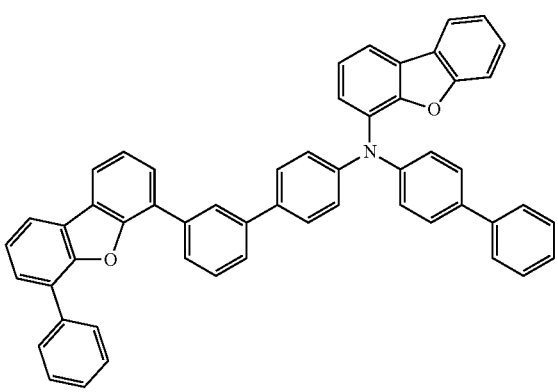
148

149
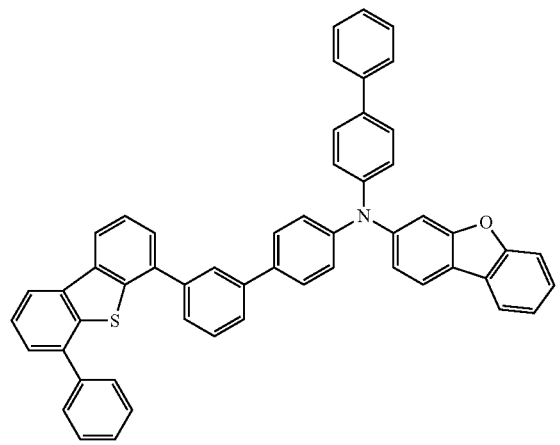
150
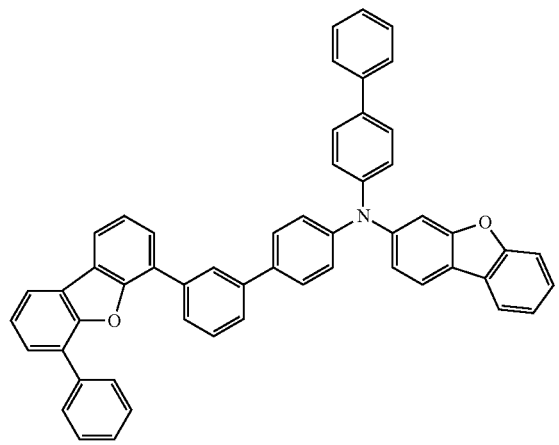
151
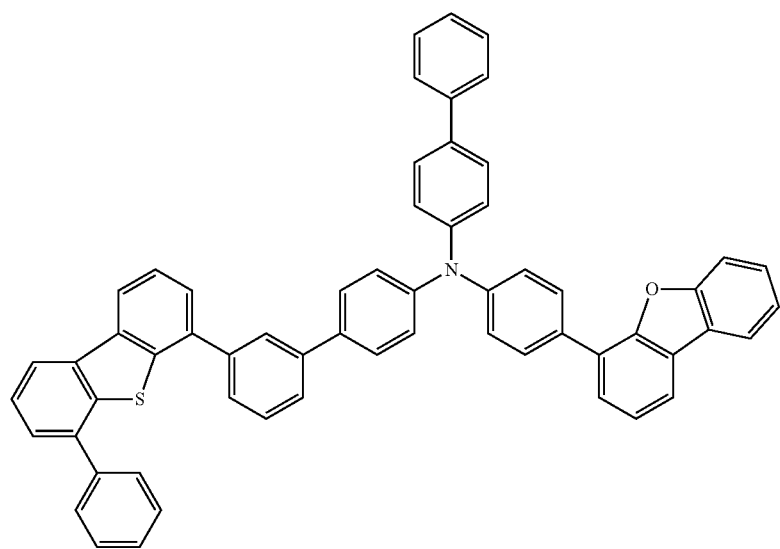
152
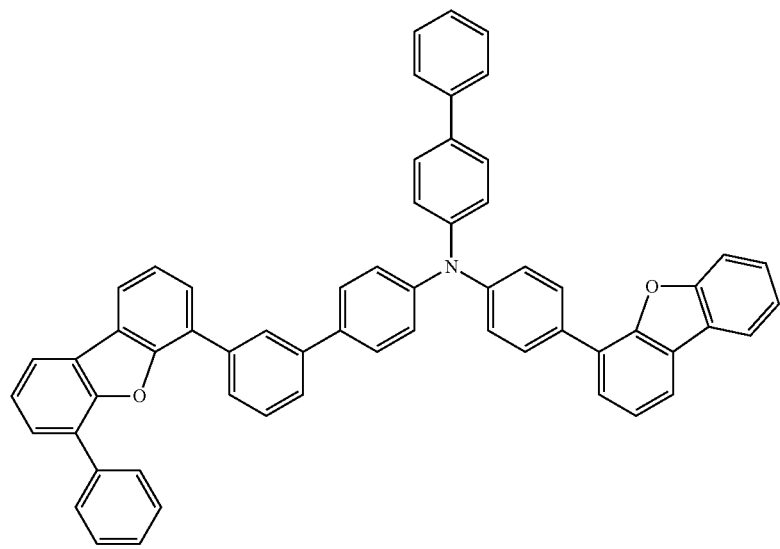

-continued
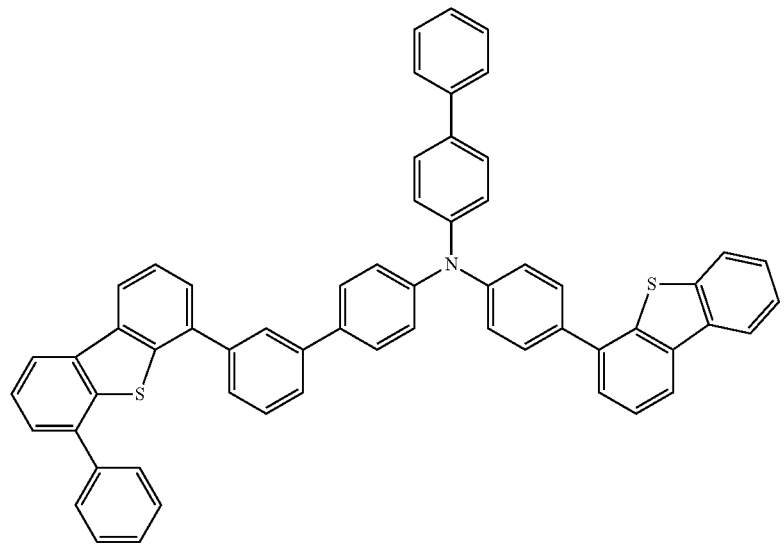
153
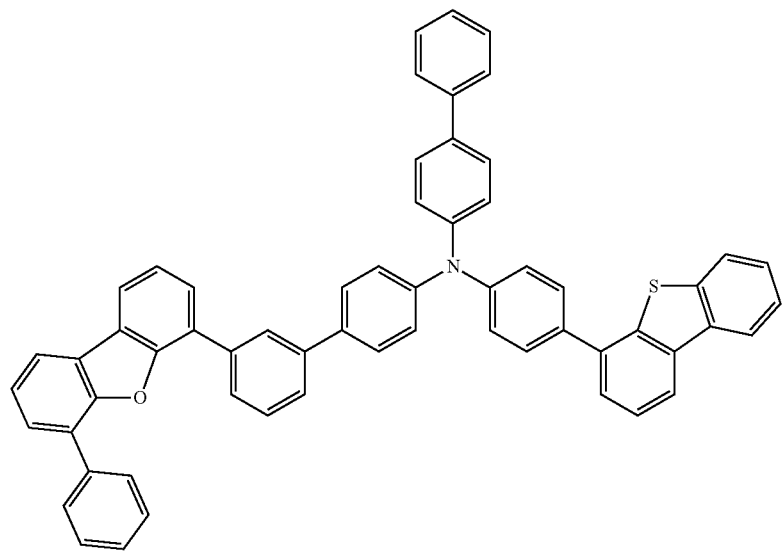
154
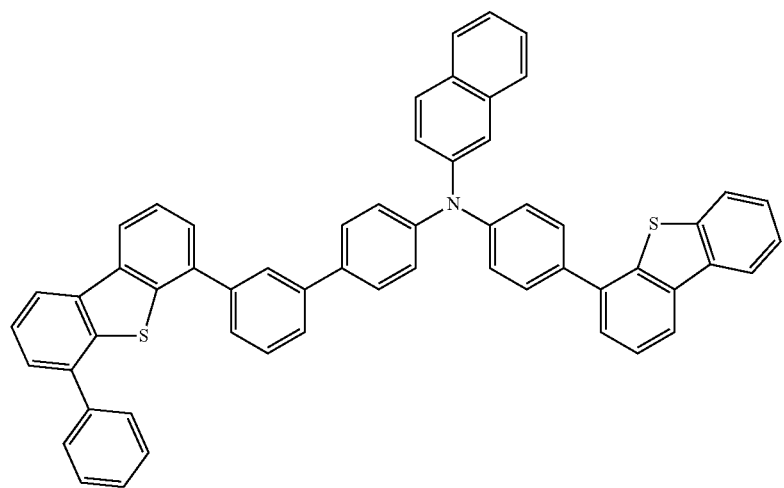
155

156
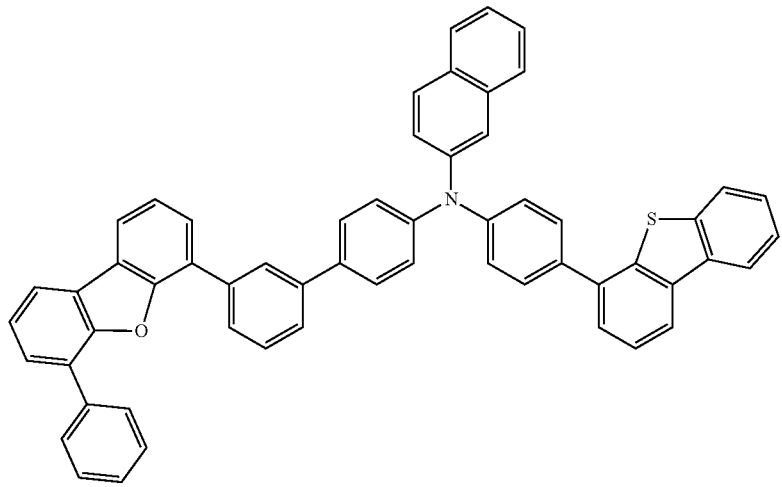
157
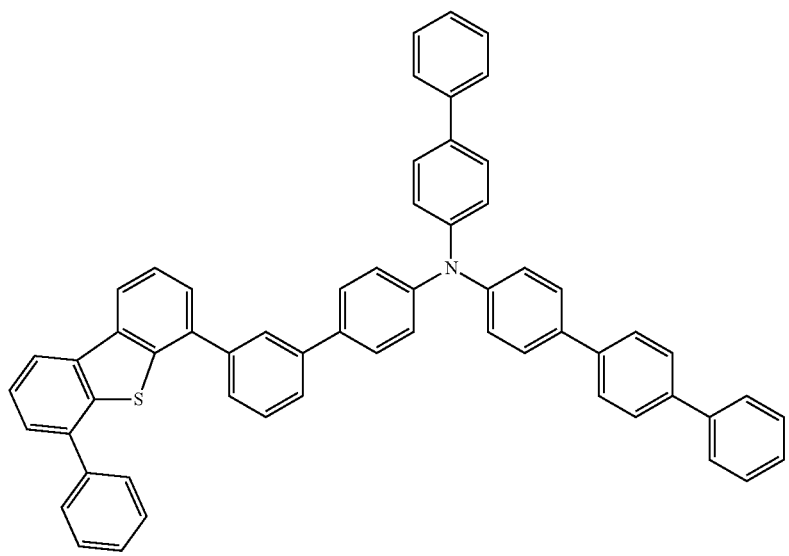
158
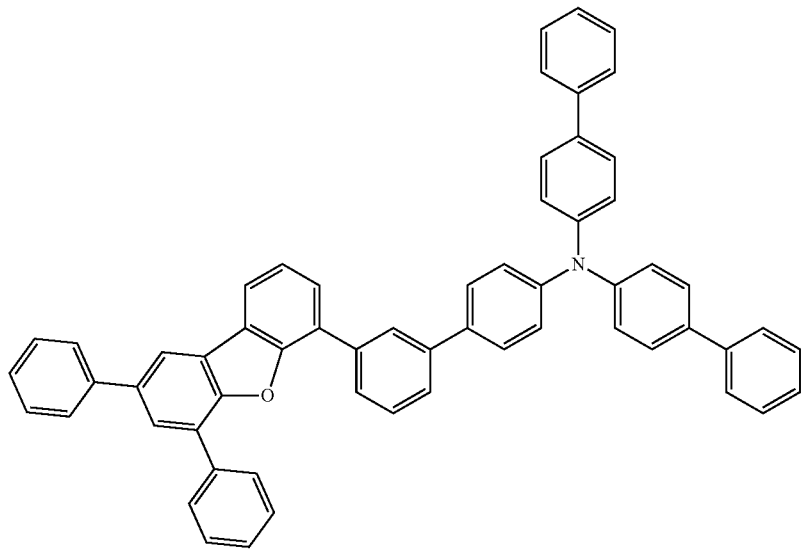

-continued
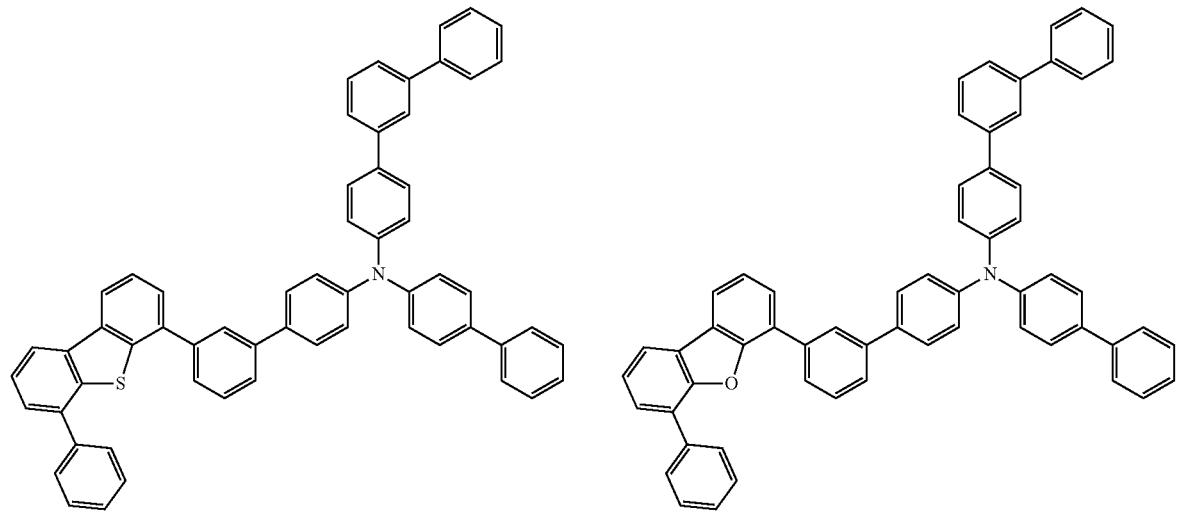
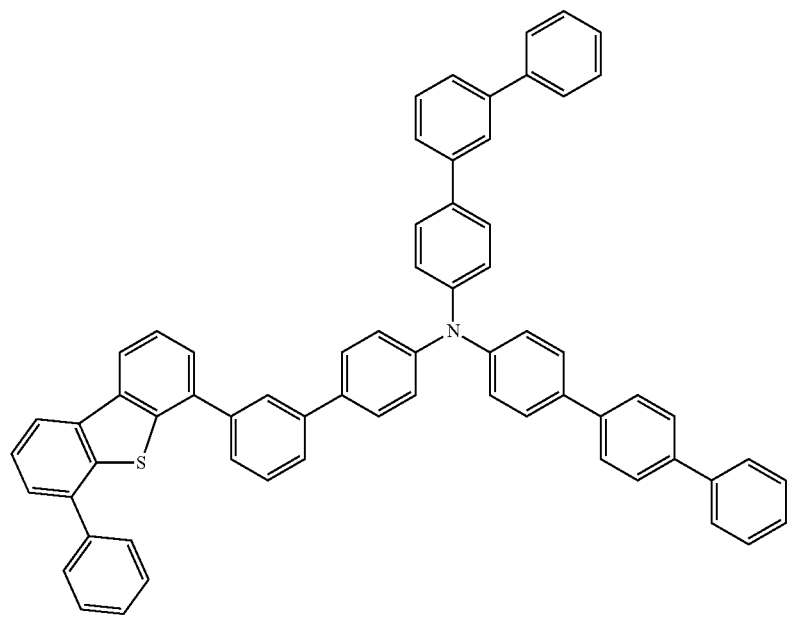
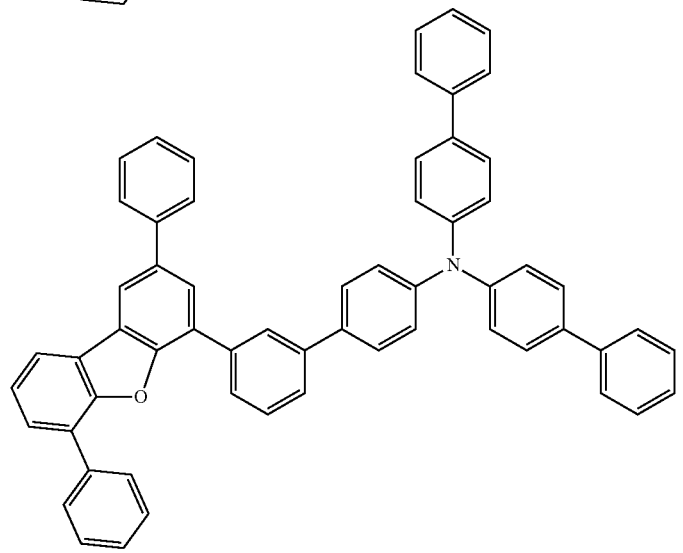

163
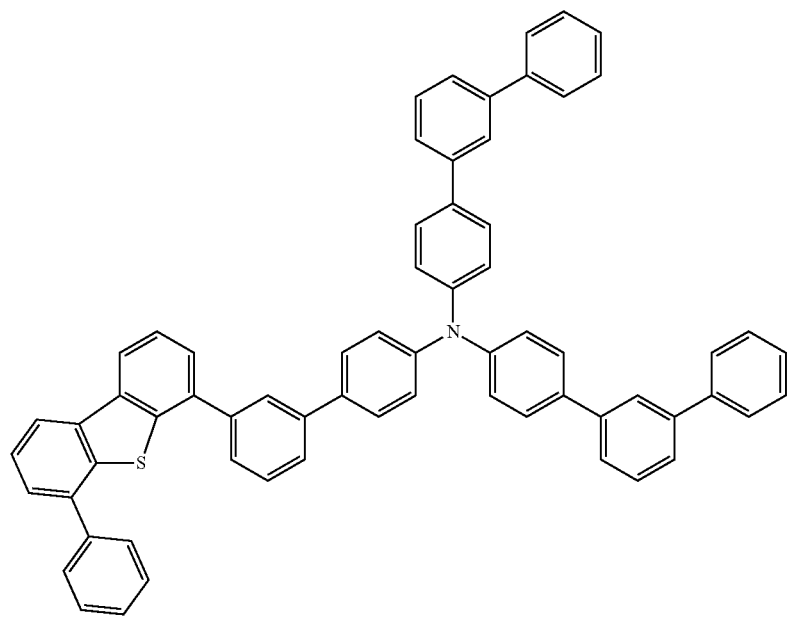
164
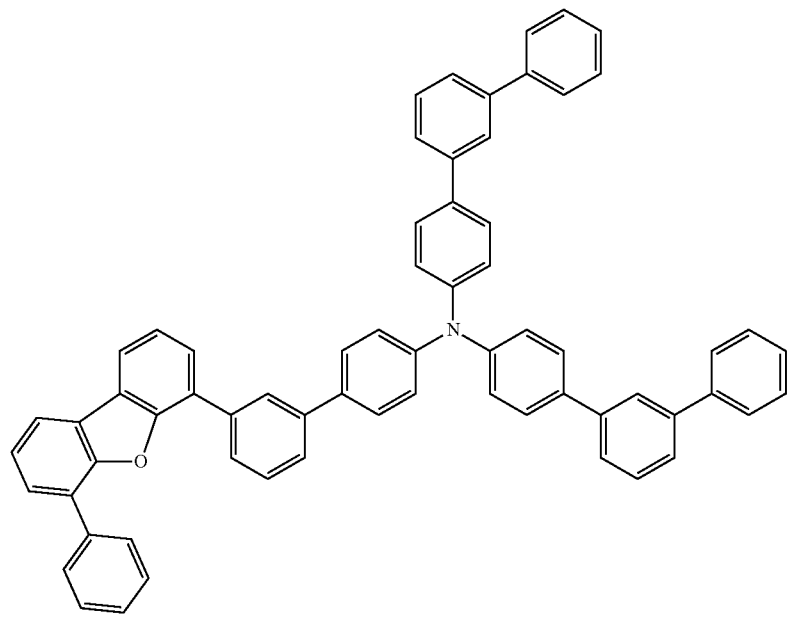
165 166
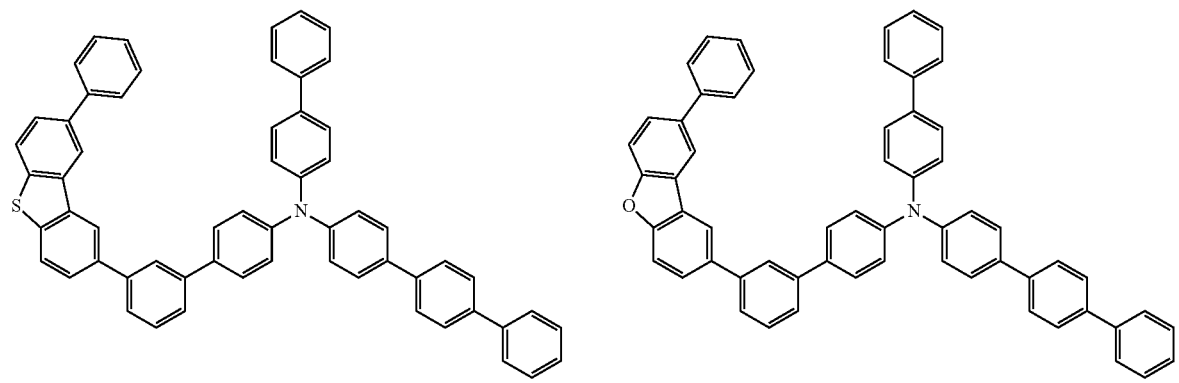

167
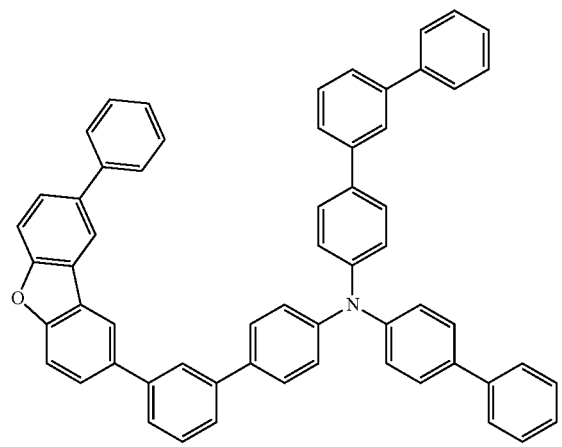
168
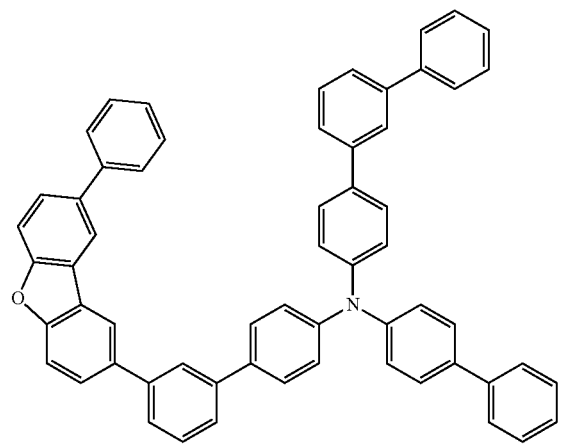
169
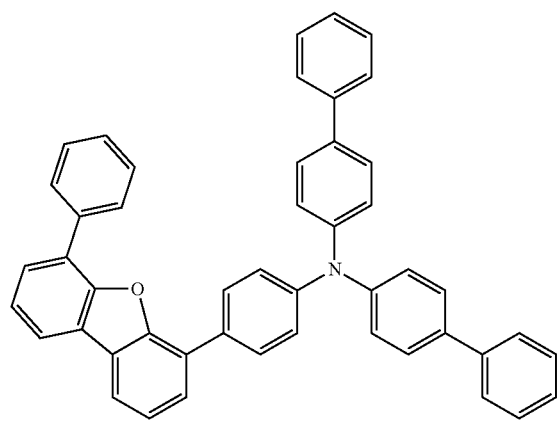
170
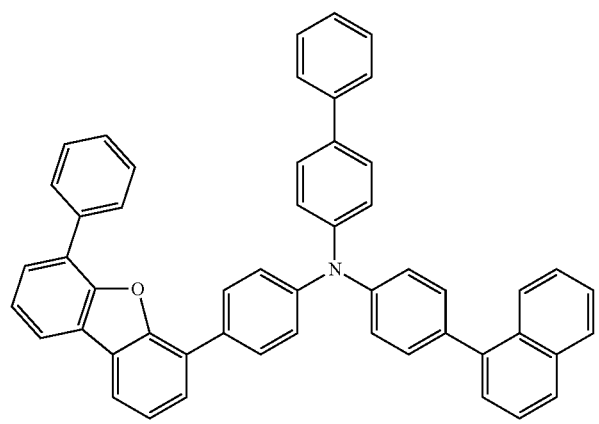
171
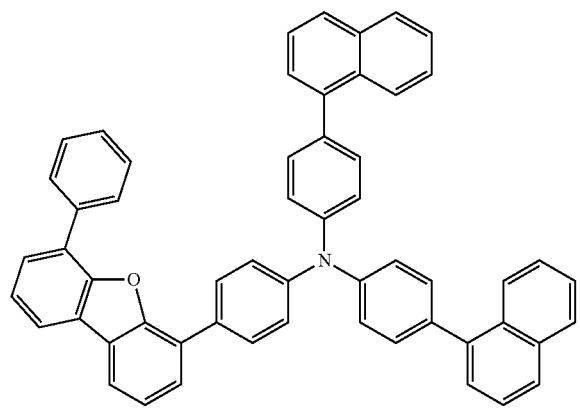
172
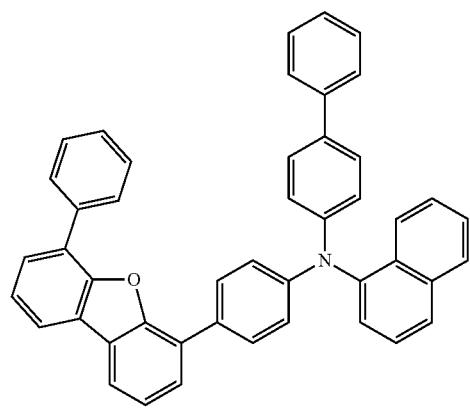

-continued
173
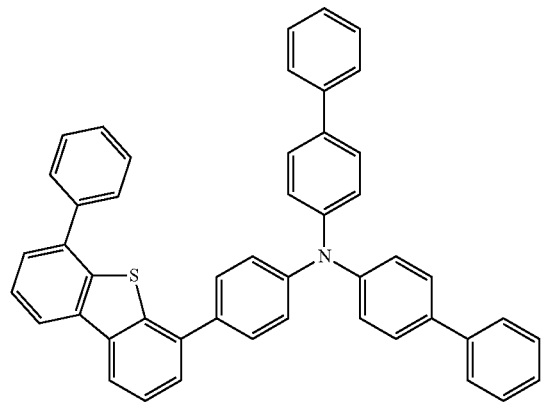
174
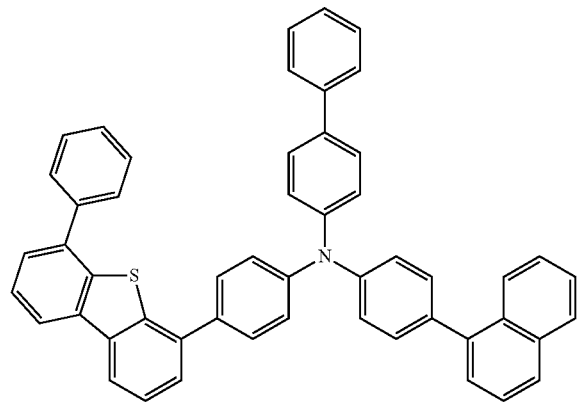
175
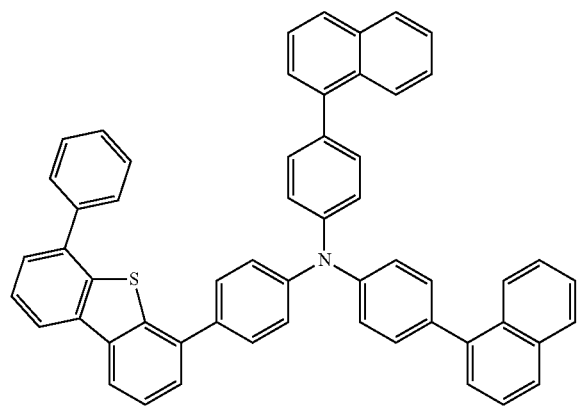
176
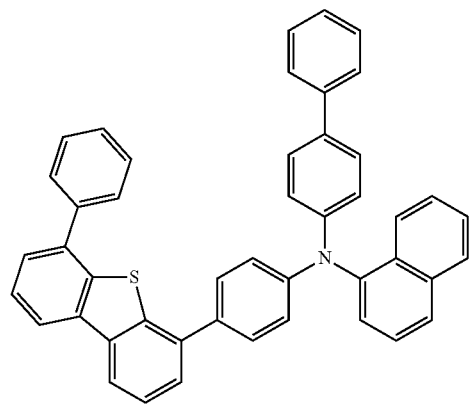
177
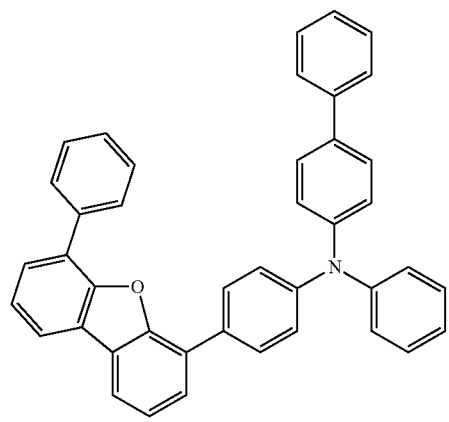
178
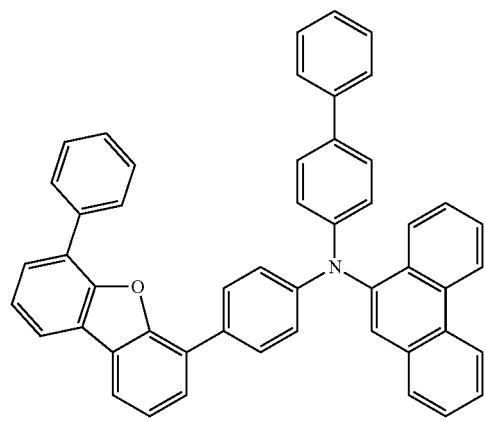

179
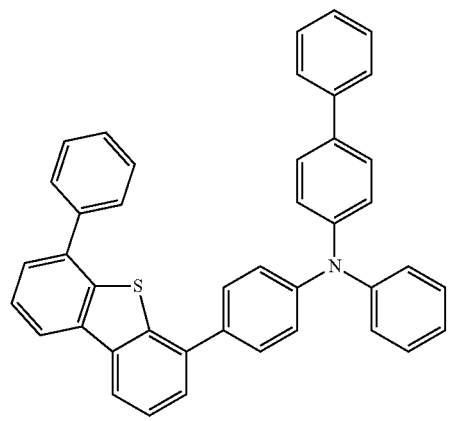
180
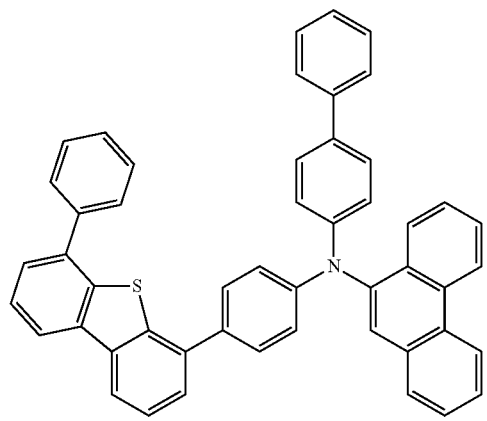
181
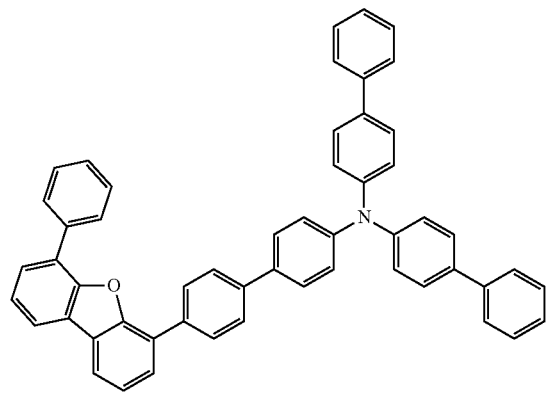
182
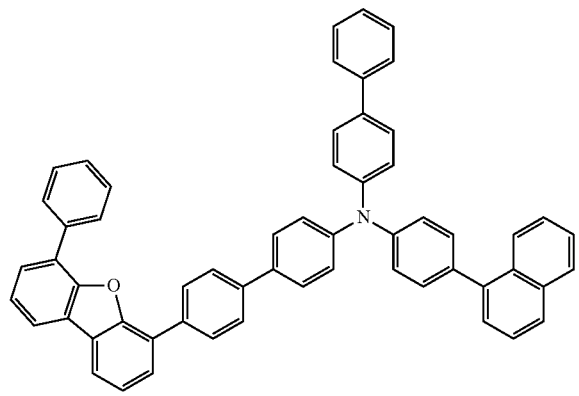
183
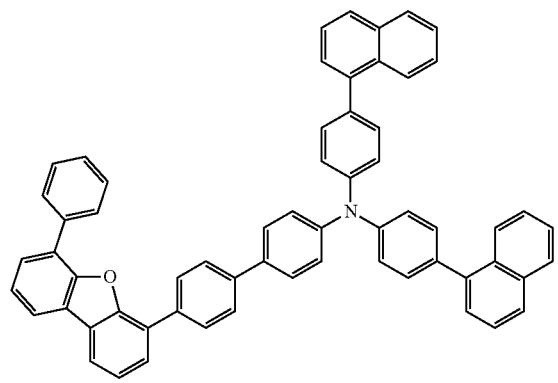
184
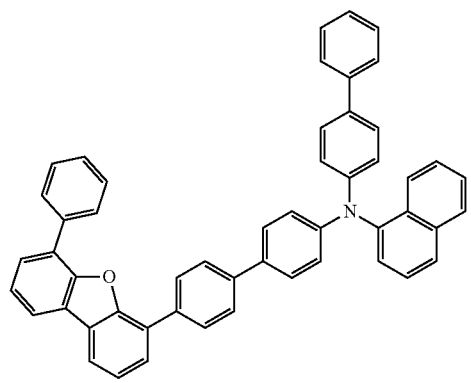
185
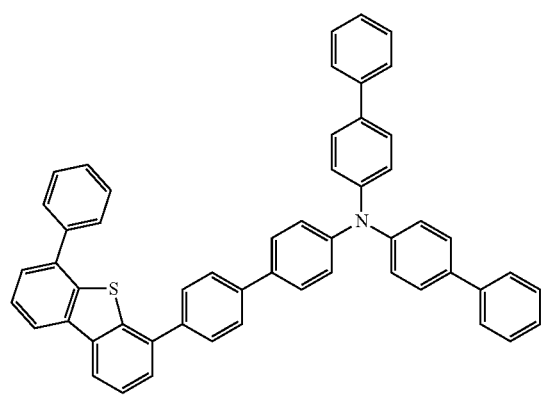
186
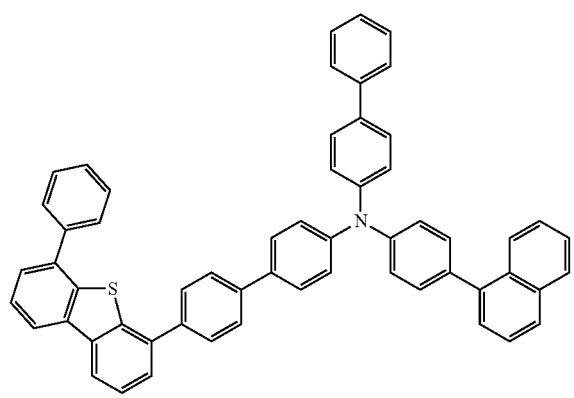

-continued
187
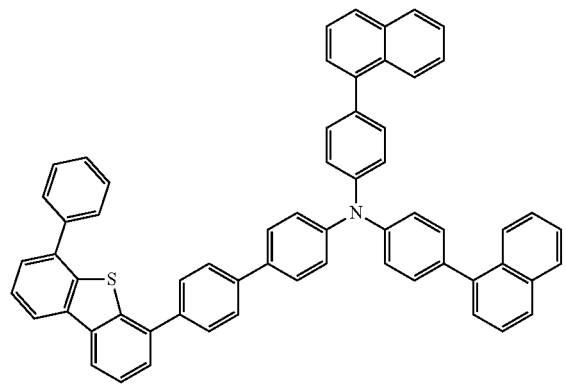
188
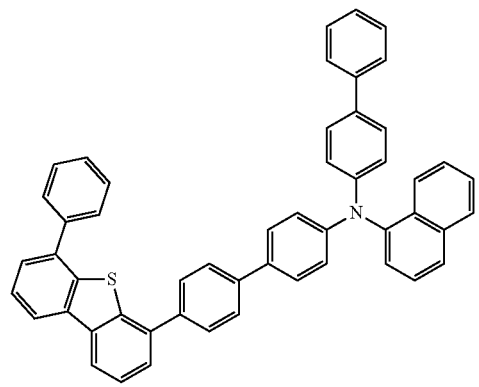
189
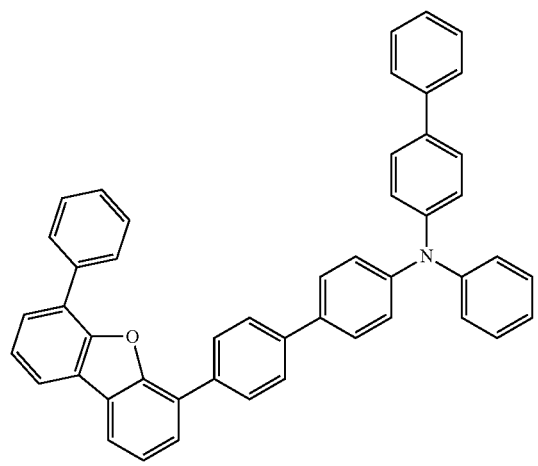
190
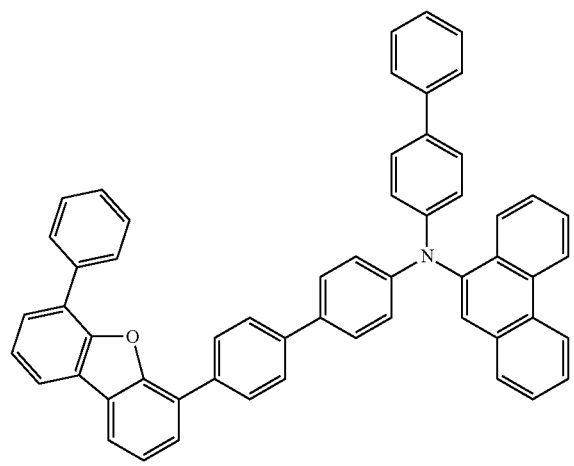
191
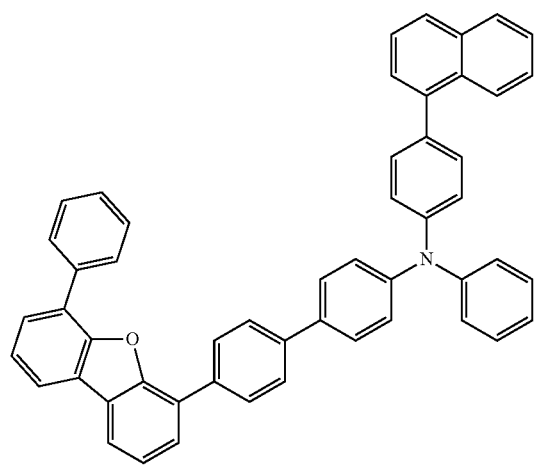
192
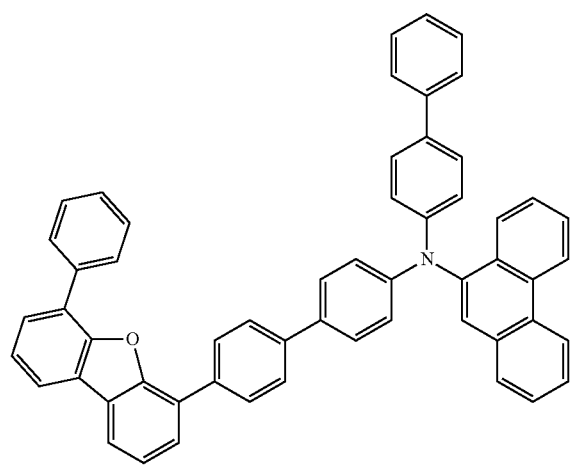

-continued
193
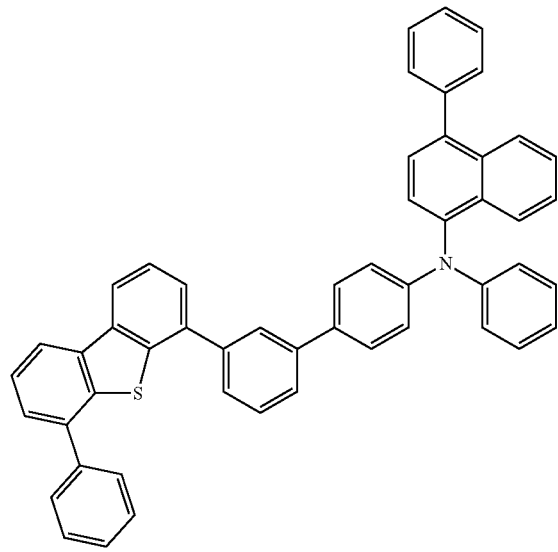
194
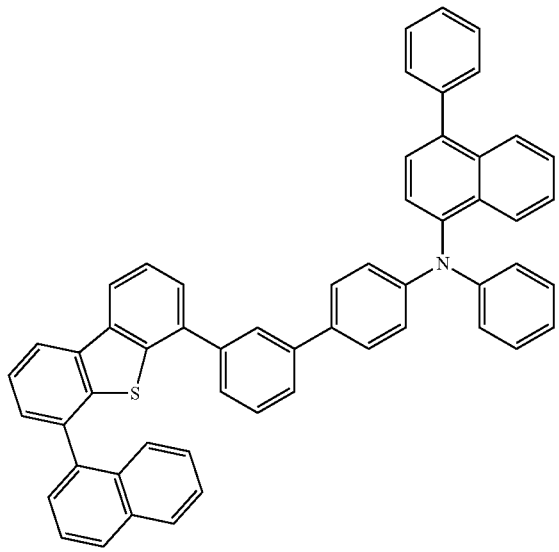
195
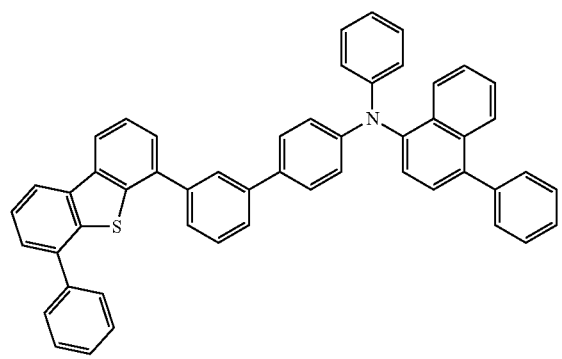
196
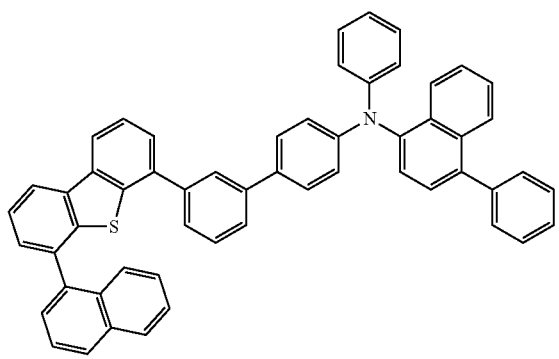
197
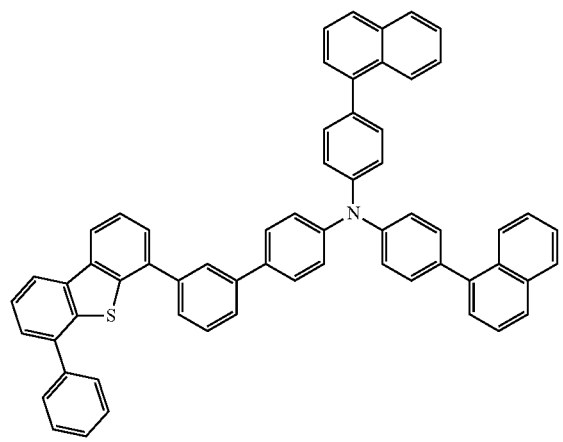
198
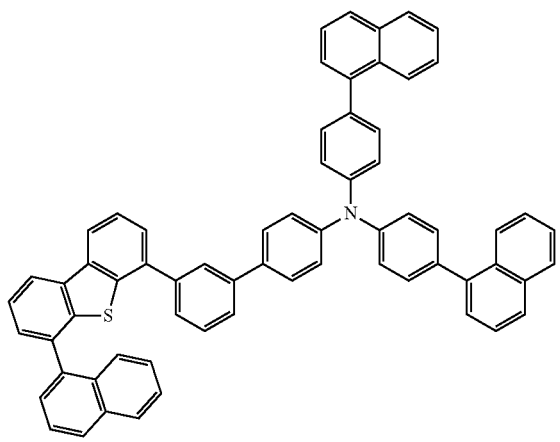

-continued
199
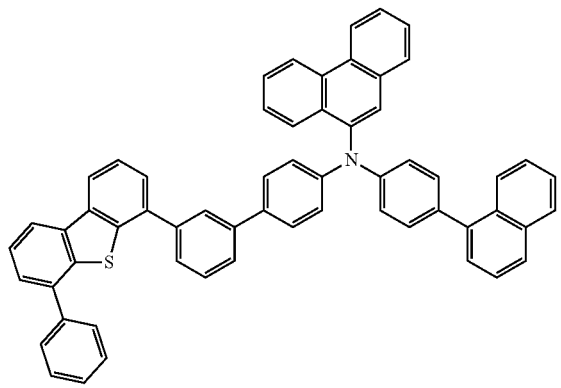
200
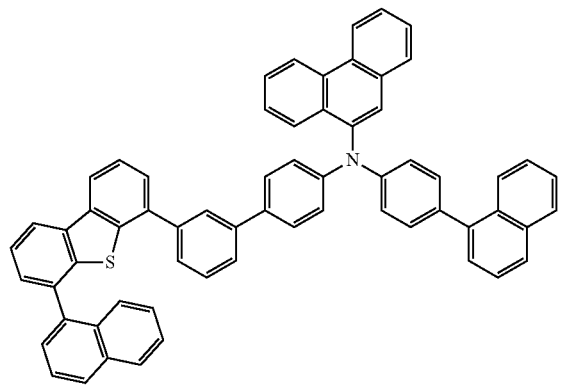
201
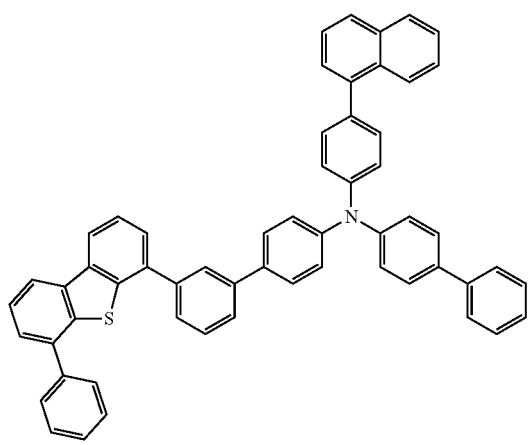
202
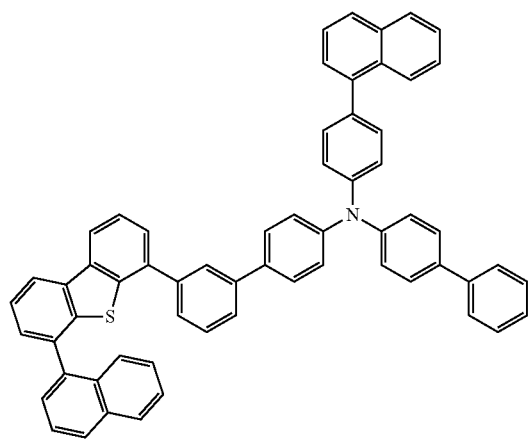
203
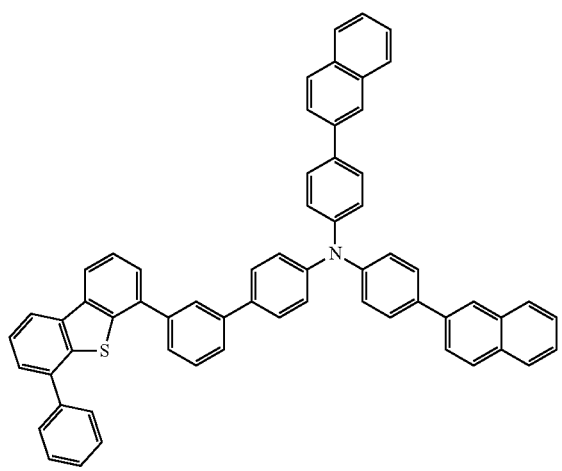
204
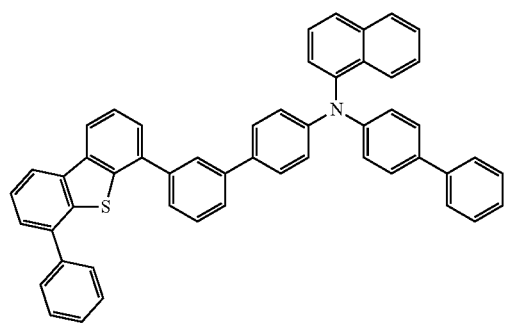

-continued
205
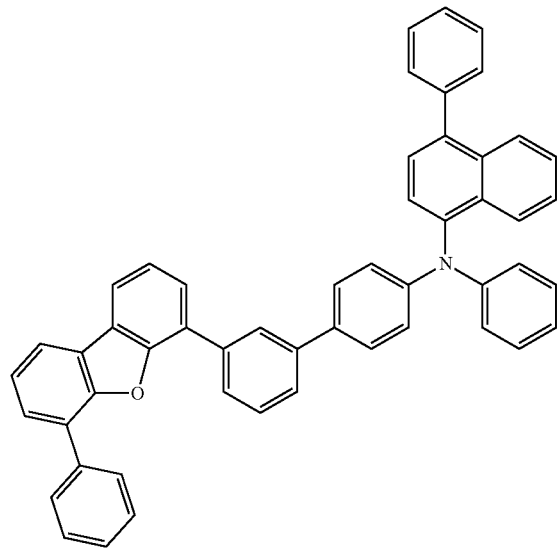
206
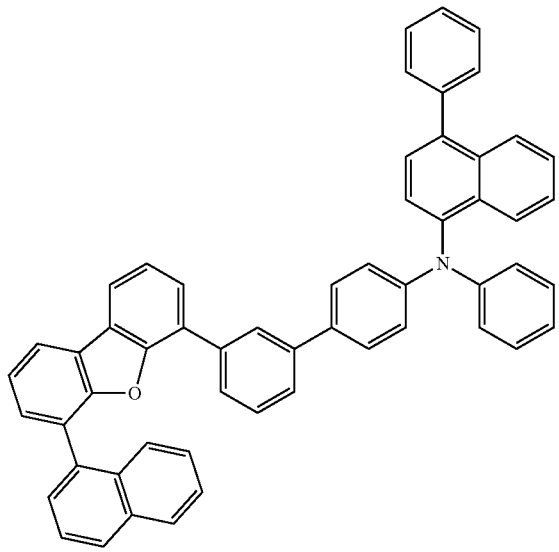
207
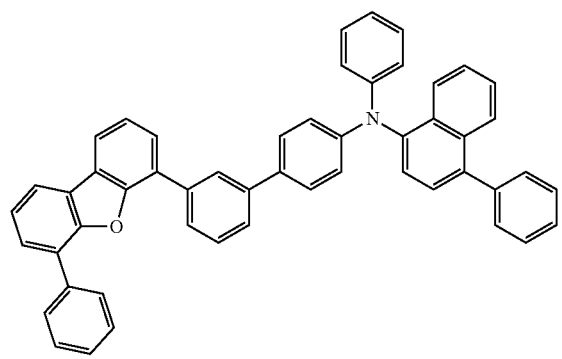
208
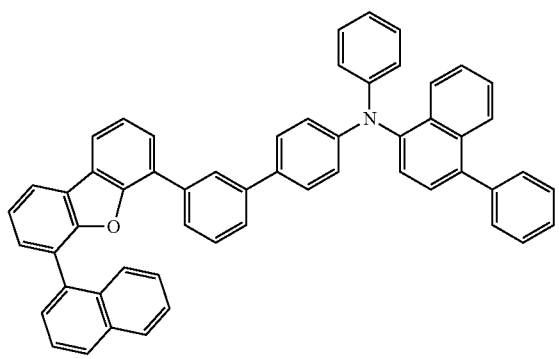
209
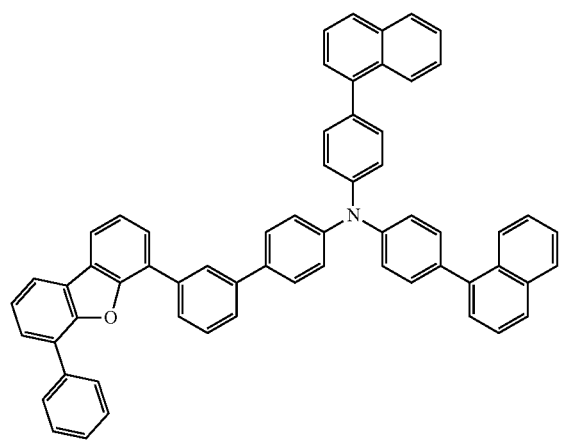
210
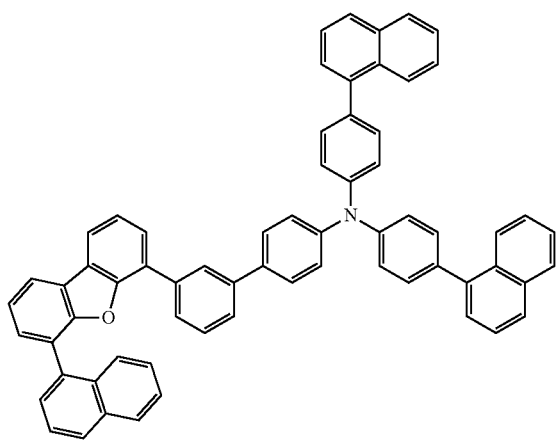

-continued
211
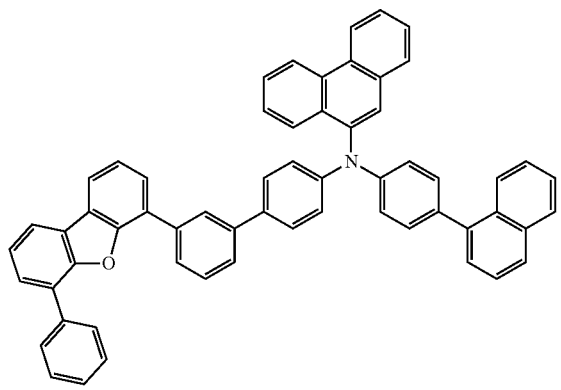
212
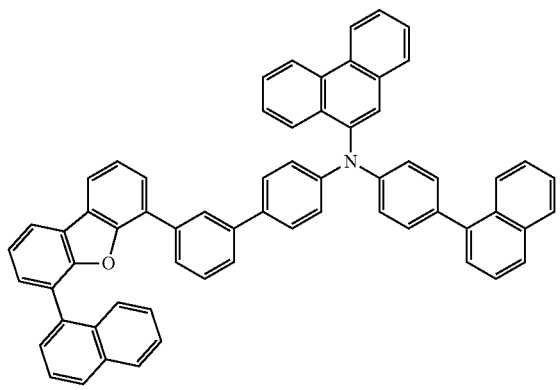
213
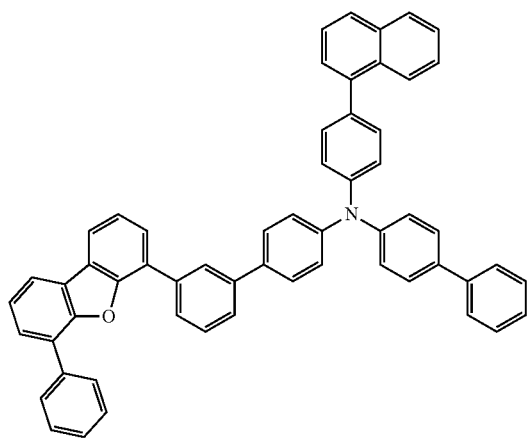
214
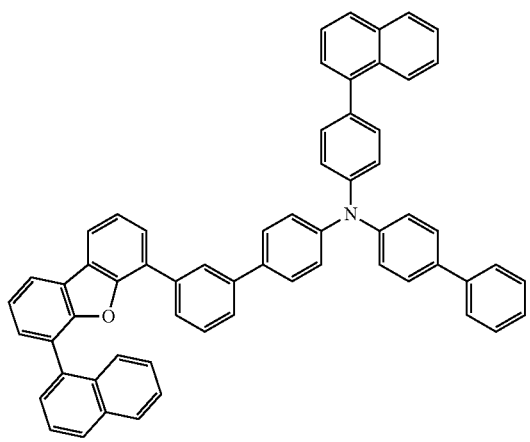
215
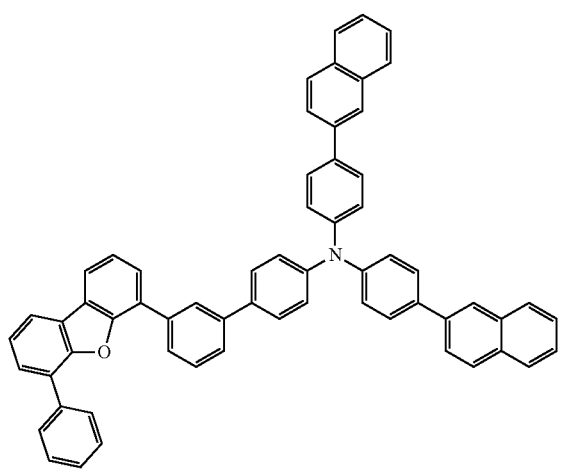
216
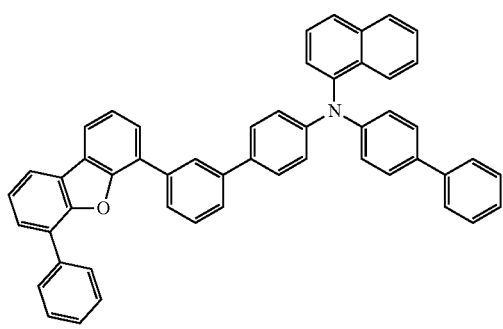

-continued
217
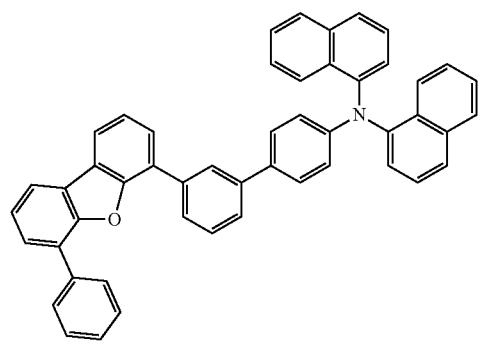
218
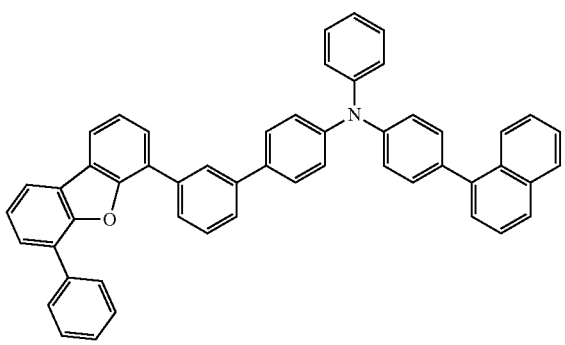
219
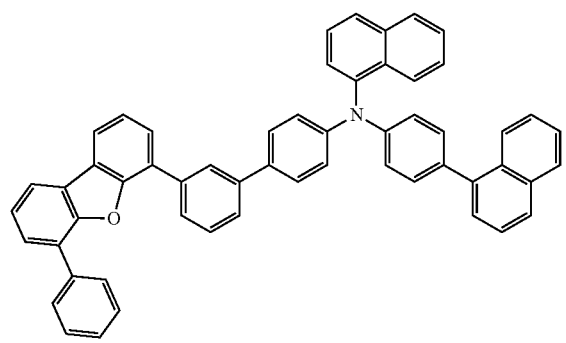
220
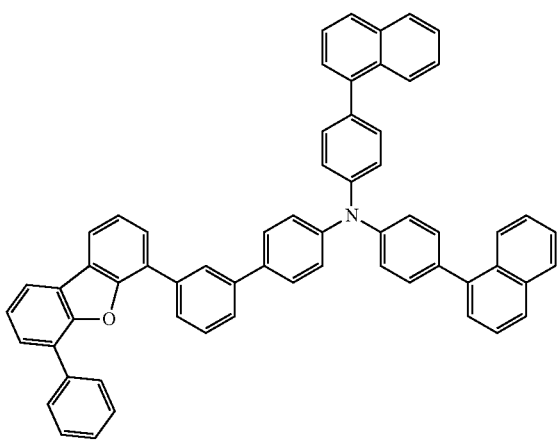
221
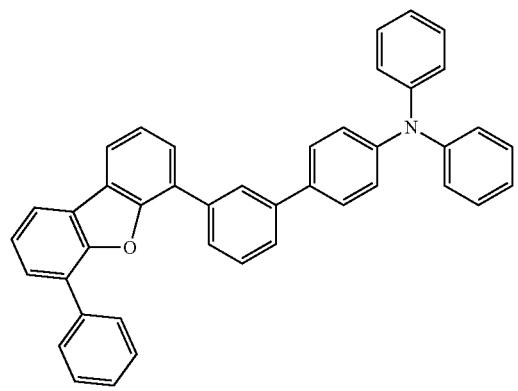
222
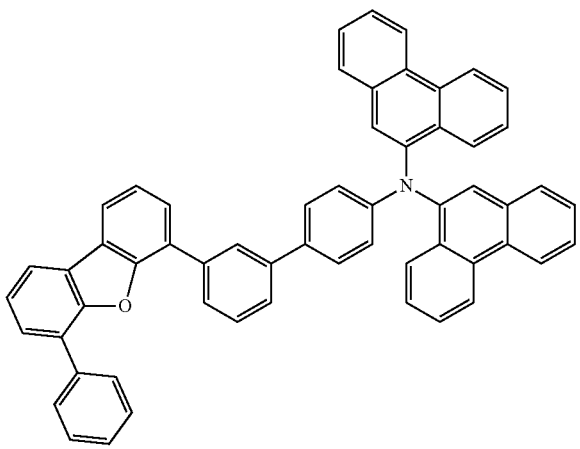
223
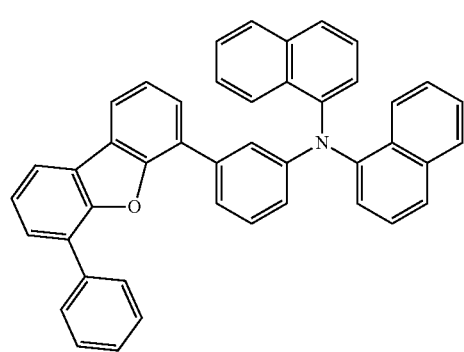
224
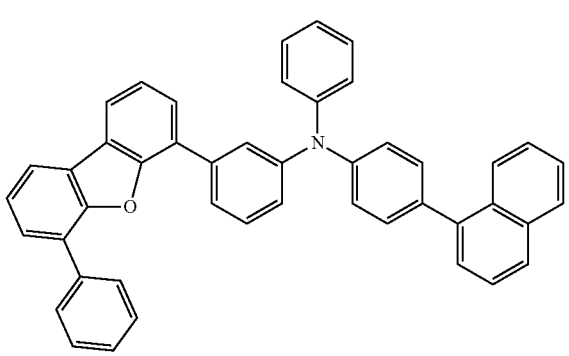

-continued
225 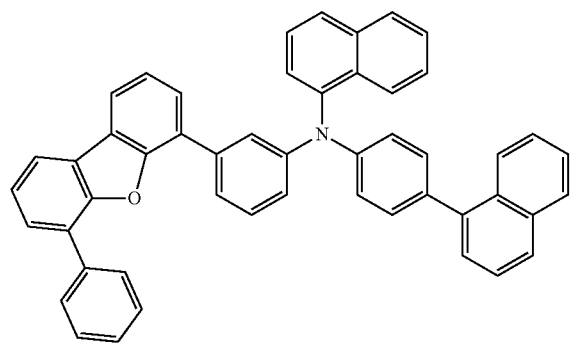
226 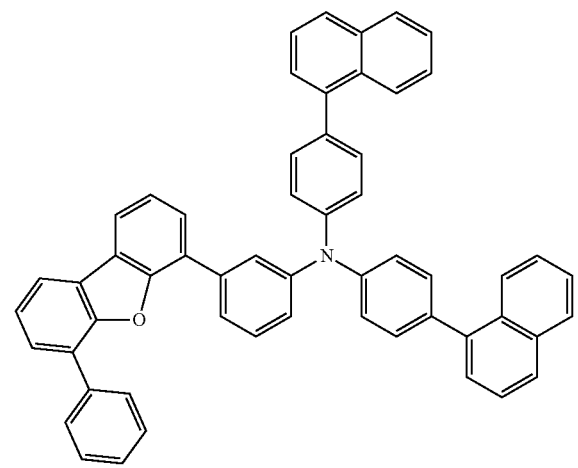
227 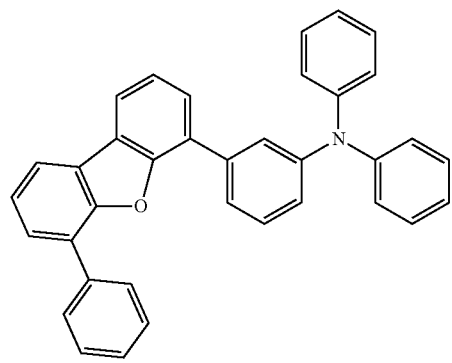
228 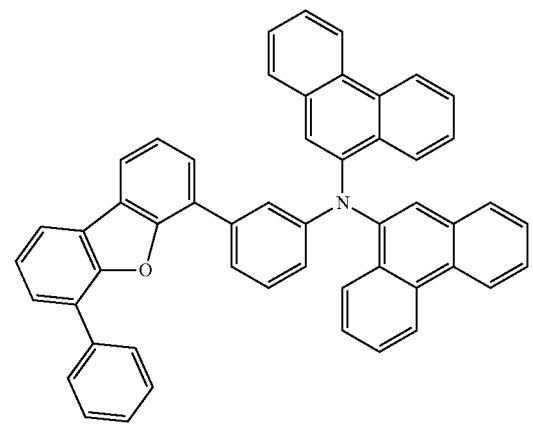
229 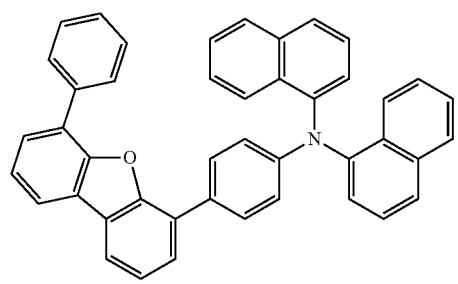
230 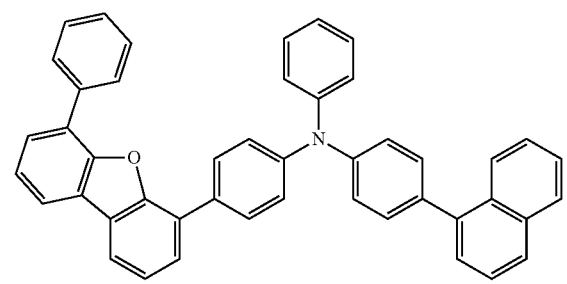
231 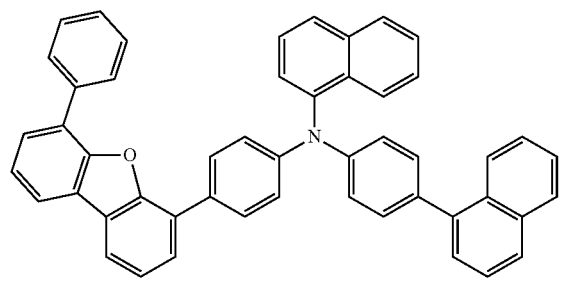
232 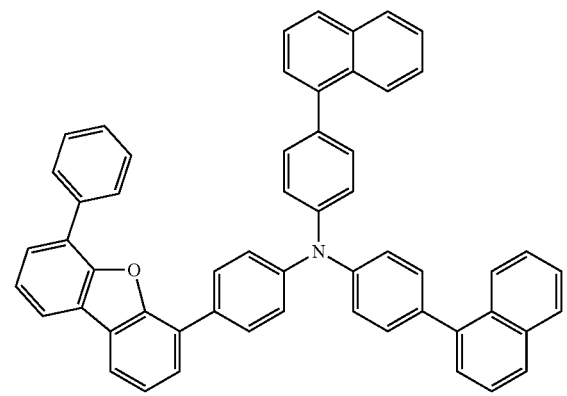

233 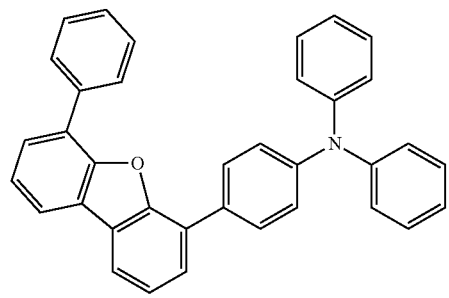
234 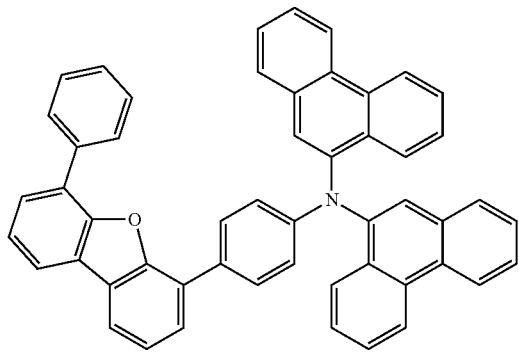
235 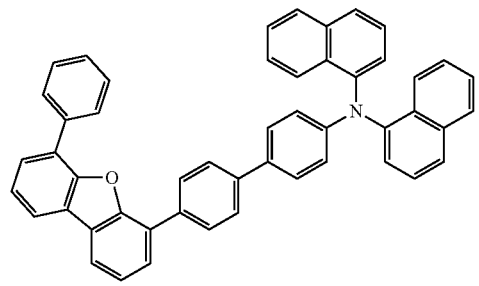
236 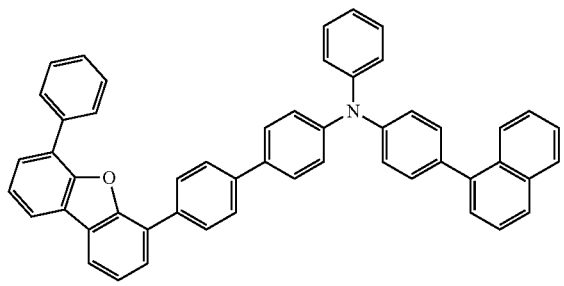
237 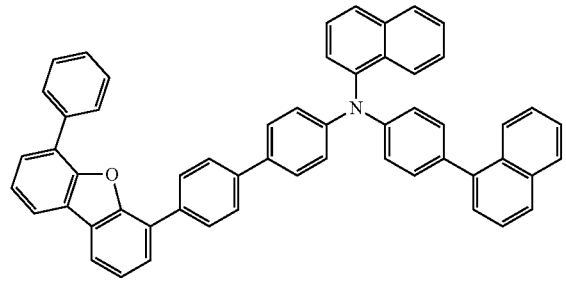
238 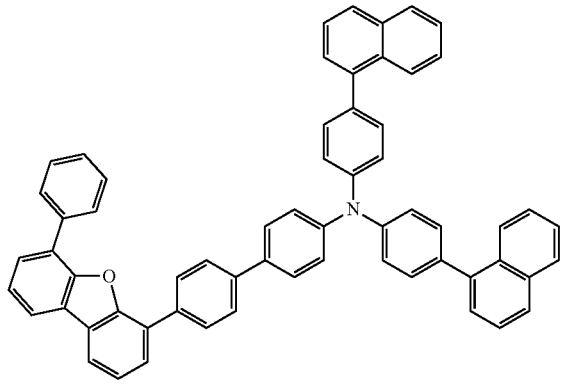
239 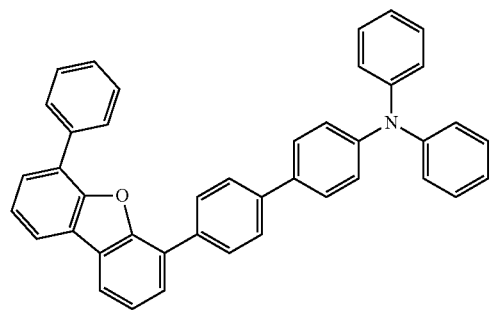
240 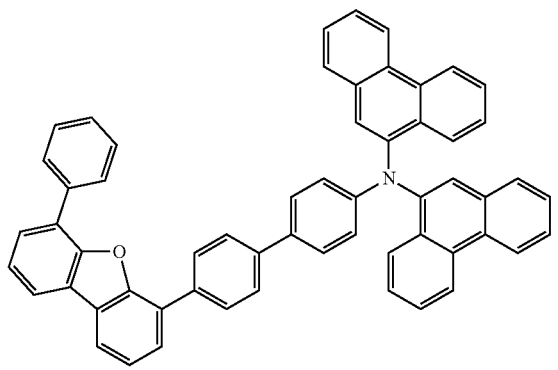

241
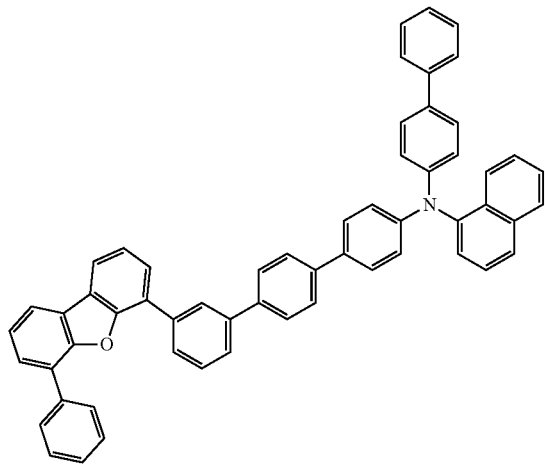
242
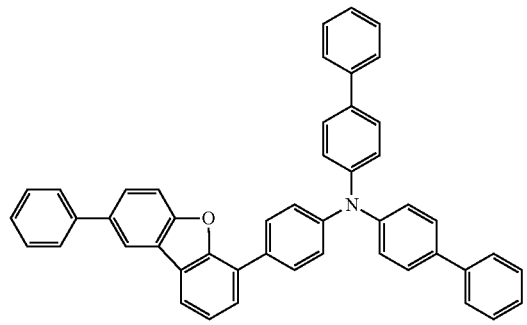
243
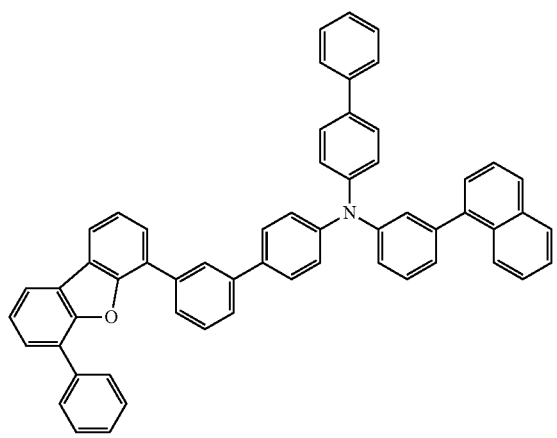
244
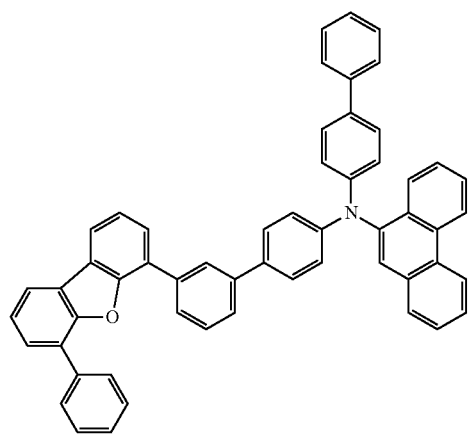
245
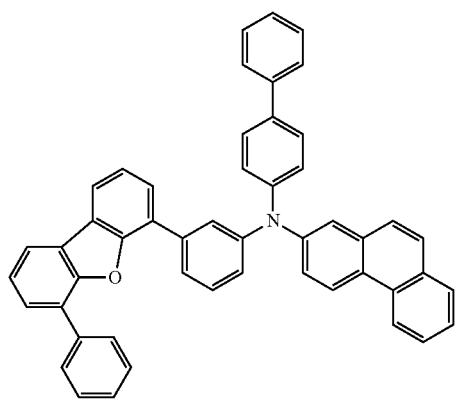
246
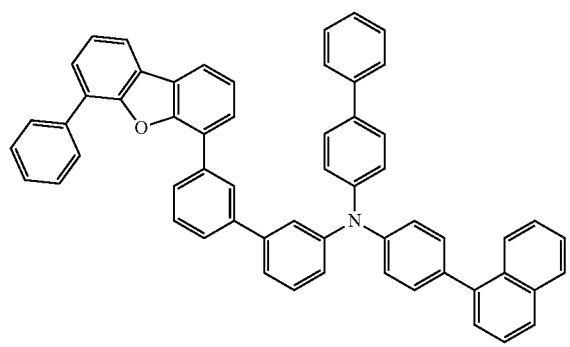

247
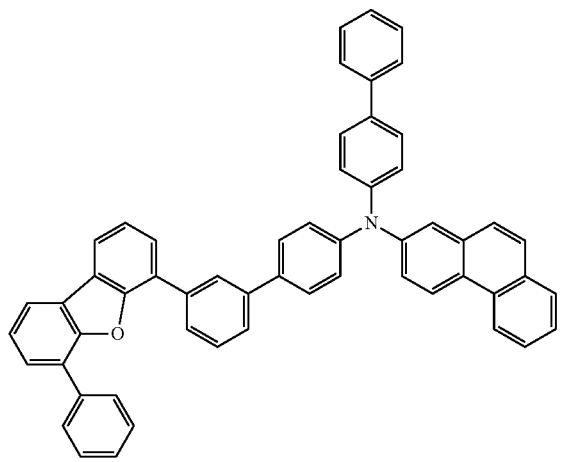
248
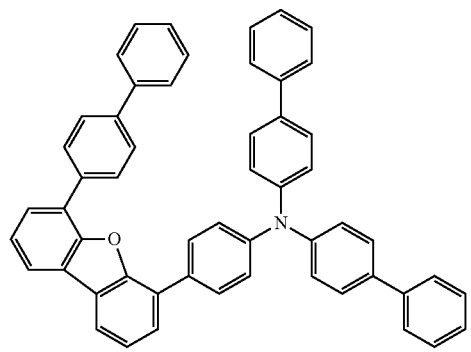
249
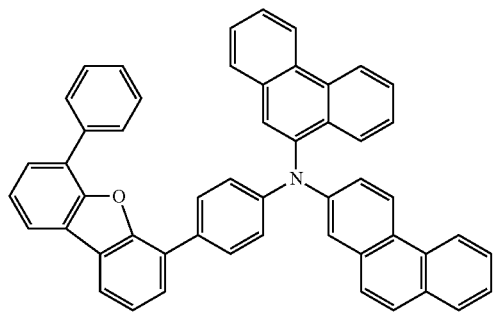
250
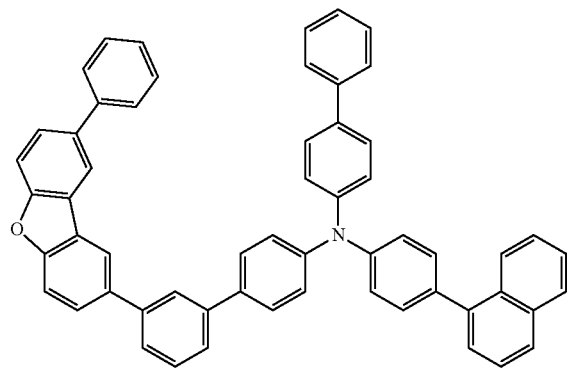
251
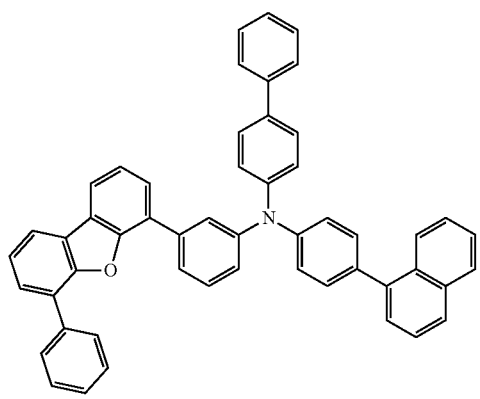
252
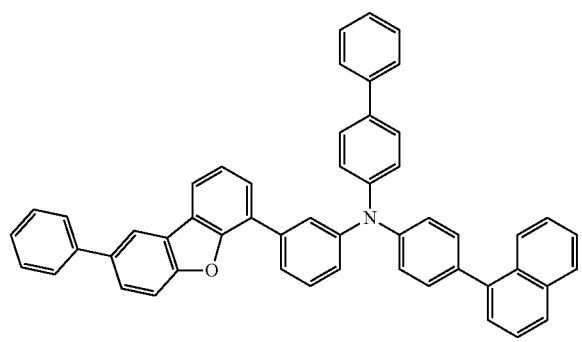

-continued
253
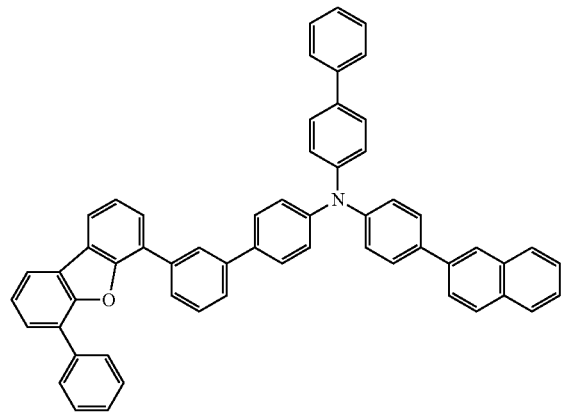
254
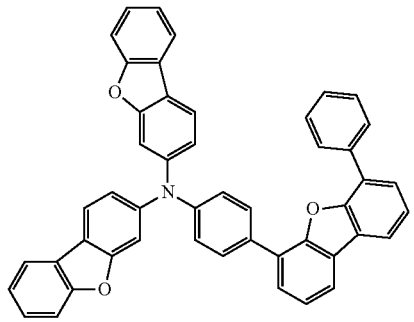
255
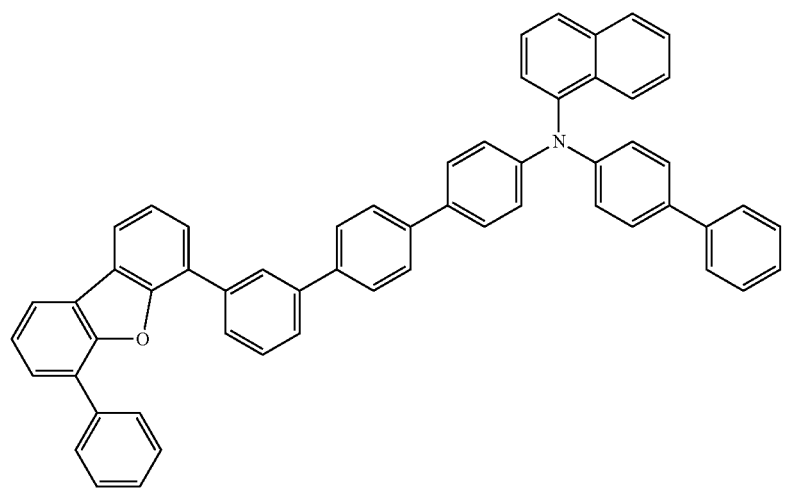
256
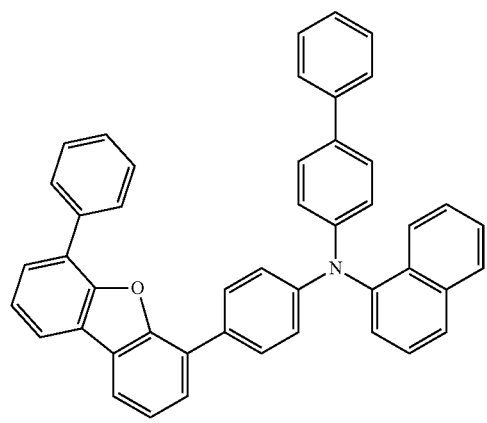
257
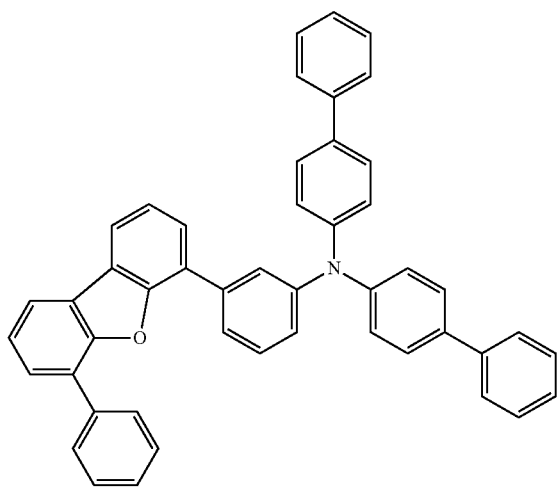

-continued
258
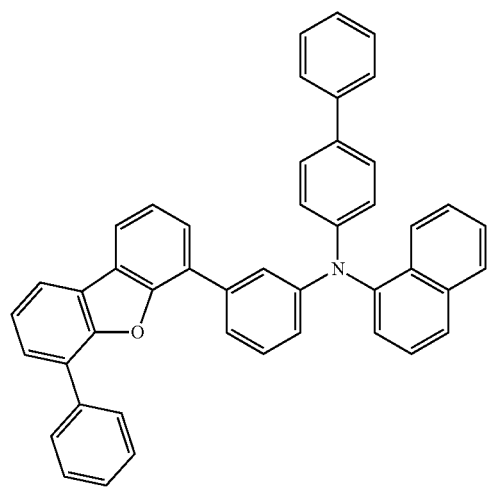
259
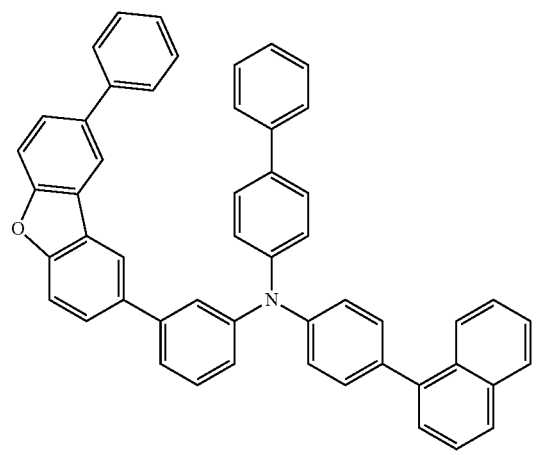
260
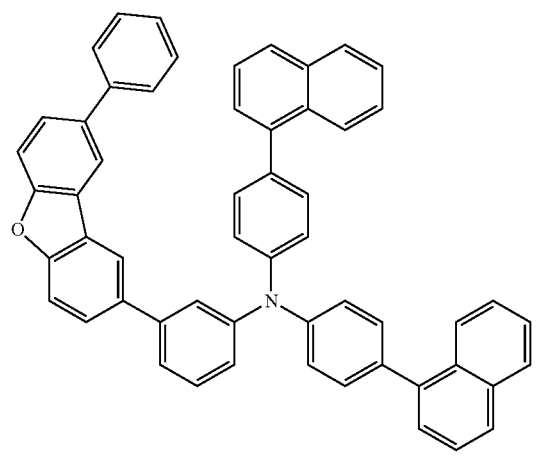
261
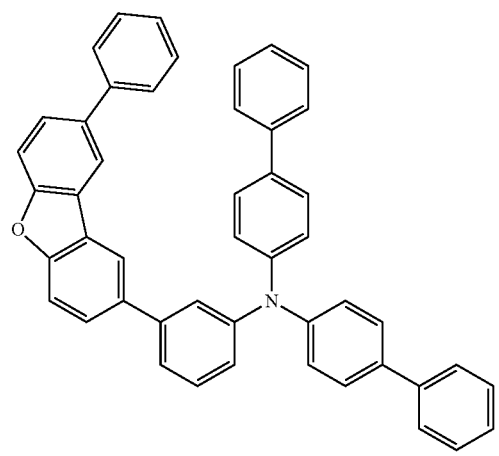
262
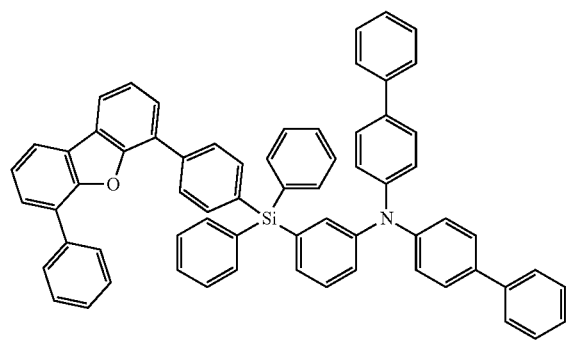
263
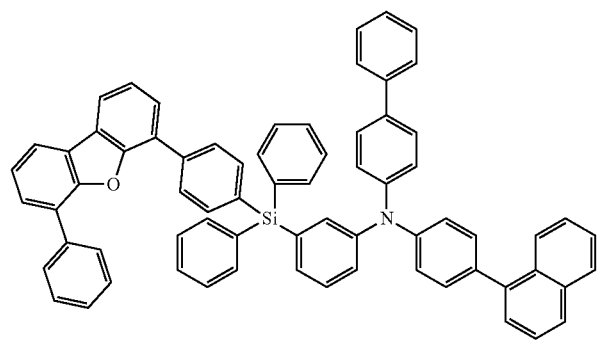

-continued
264
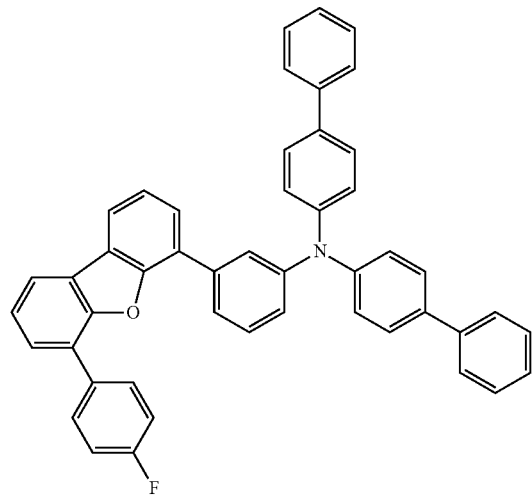
265
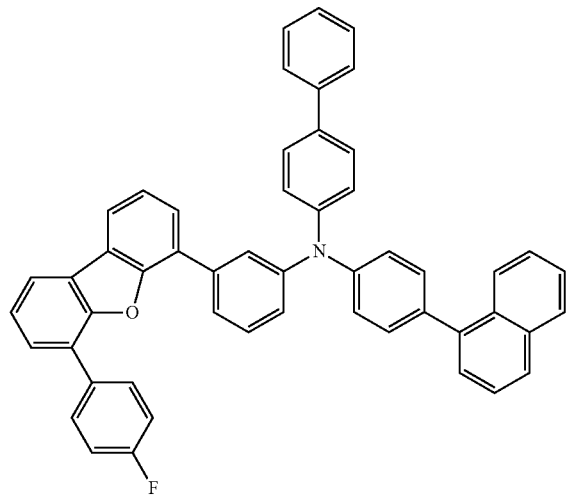
266
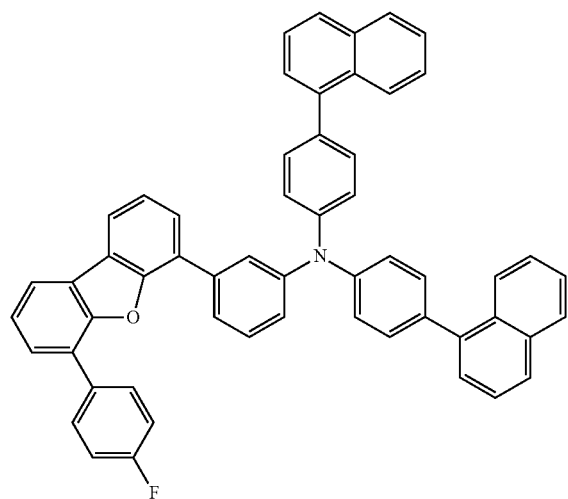
267
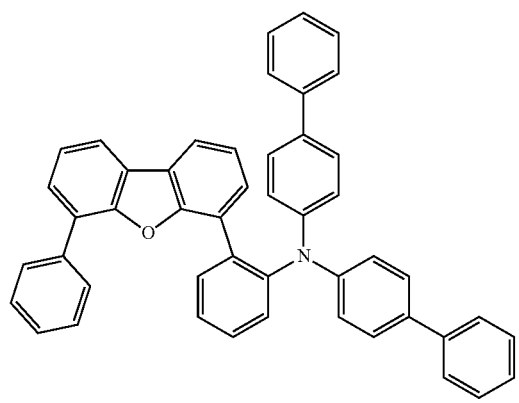
268
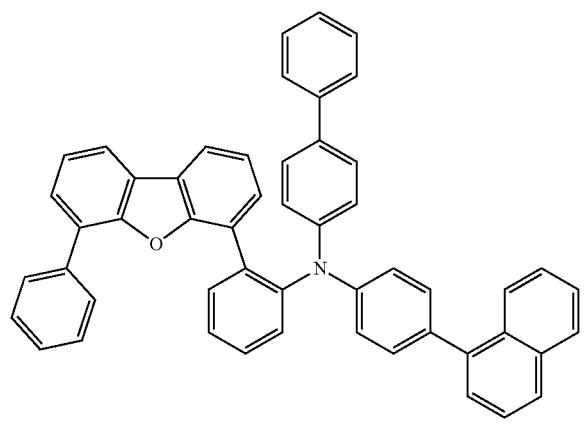
269
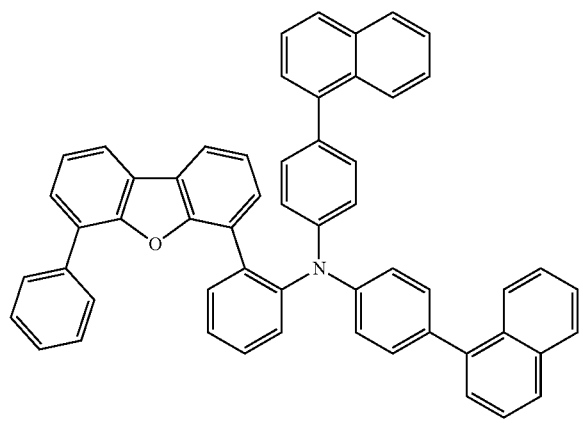

-continued
300
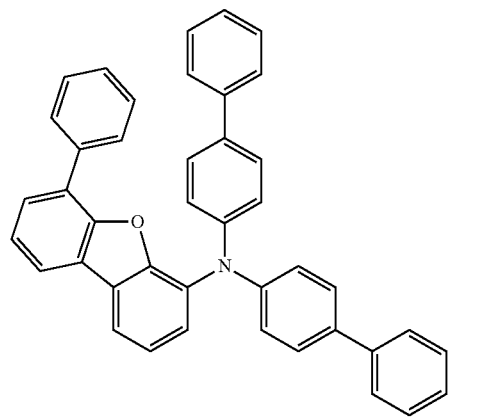
301
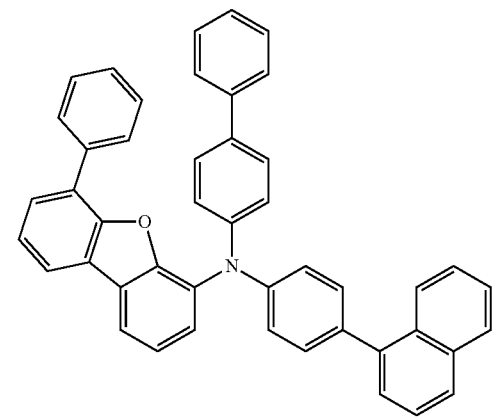
302
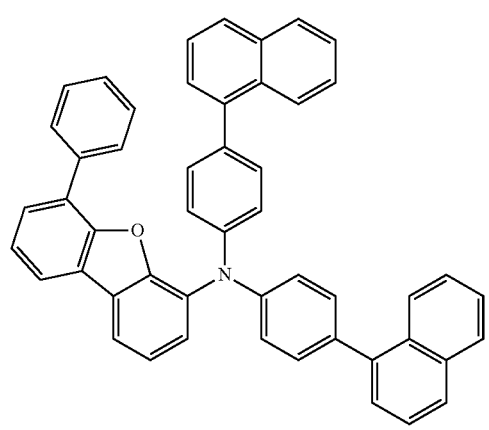
303
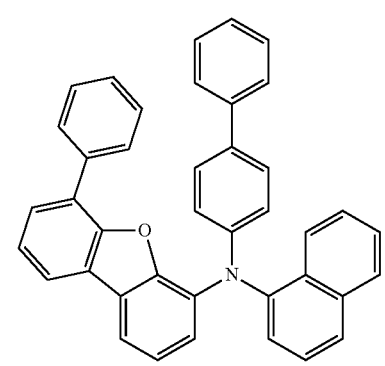
304
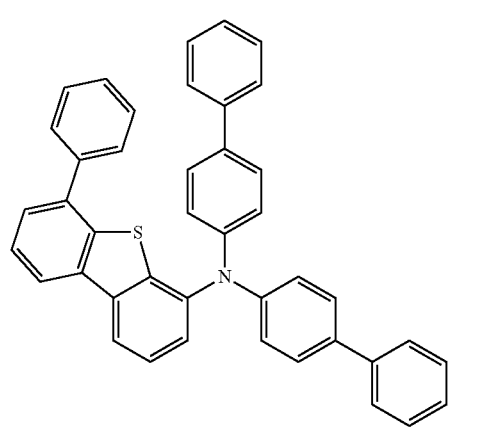
305
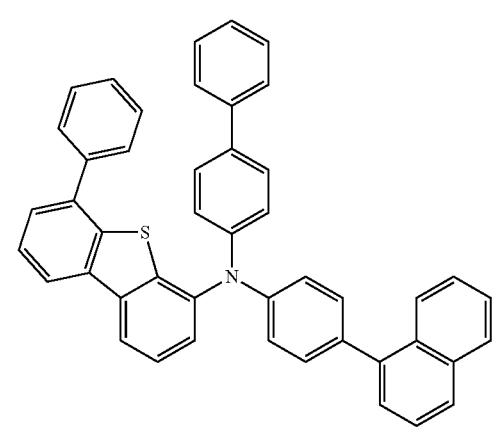
306
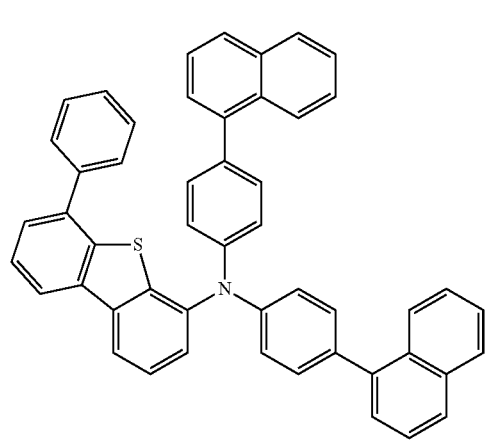
307
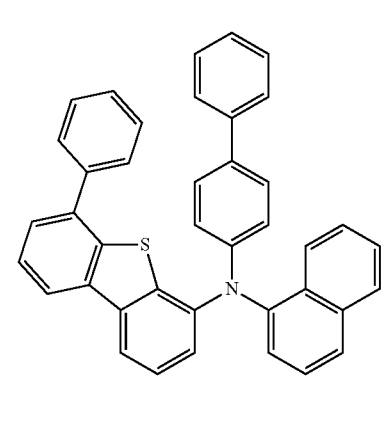

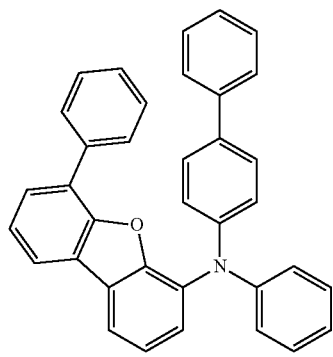

308

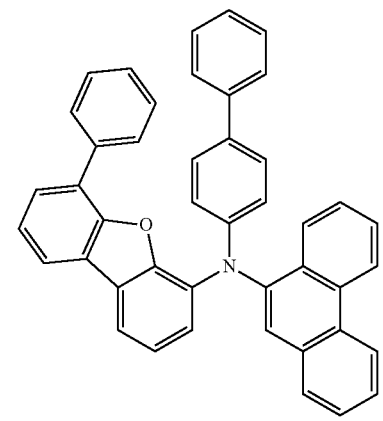

309

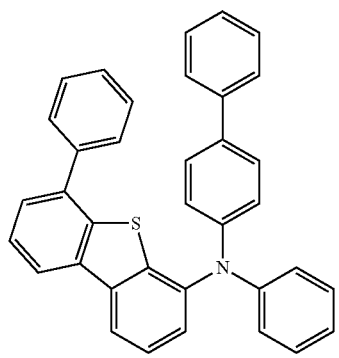

310

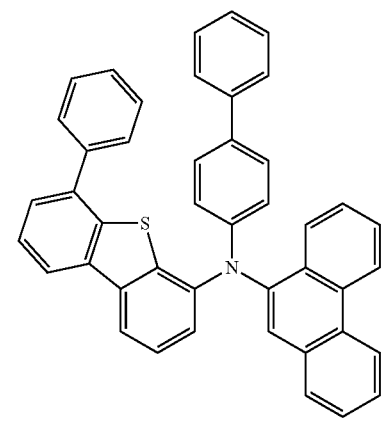

311

The material for an organic EL device according to an embodiment may be utilized in at least one layer of stacking layers (e.g., utilized in at least one layer of a plurality of layers stacked over one another) disposed between an emission layer and an anode of an organic EL device. As described above, in the material for an organic EL device according to an embodiment, a substituted dibenzoheterole group with high electron tolerance is introduced in (e.g., linked to) the nitrogen atom (N) of an amine group via a linker. Thus, the electron tolerance of a layer utilizing the material for an organic EL device according to an embodiment may be improved, the durability thereof may be improved, and the long life of the organic EL device may be realized. Since the dibenzoheterole group includes a substituent, the amorphous properties of the material may be improved, the mobility of charges may increase, and high emission efficiency may be realized.

The layer including the material for an organic EL device according to an embodiment may be a layer disposed adjacent to the emission layer among stacking layers disposed between the emission layer and the anode of the organic EL device. Since the layer including the material for an organic EL device according to an embodiment is disposed adjacent to the emission layer, the deterioration of the layer disposed between the layer including the material for an organic EL device according to an embodiment and the anode due to electrons may be restrained (e.g., reduced or prevented).

(Organic EL Device 1)

An organic EL device utilizing a material for an organic EL device according to an embodiment of the disclosure will be explained. FIG. 1 is a schematic diagram illustrating an organic EL device 100 according to an embodiment of the disclosure. The organic EL device 100 may include, for example, a substrate 102, an anode 104, a hole injection layer 106, a hole transport layer 108, an emission layer 110, an electron transport layer 112, an electron injection layer 114 and a cathode 116. In an embodiment, the material for an organic EL device according to an embodiment of the disclosure may be utilized in at least one layer of stacking layers disposed between the emission layer and the anode.

A case that the material for an organic EL device according to the disclosure is utilized in the hole transport layer 108 will be explained as an embodiment.

The substrate 102 may be a transparent glass substrate, a semiconductor substrate formed utilizing silicon, or a flexible substrate of a resin, etc.

The anode 104 may be disposed on the substrate 102 and may be formed utilizing indium tin oxide (ITO), indium zinc oxide (IZO), etc.

The hole injection layer (HIL) 106 may be formed utilizing a suitable material to a thickness within a range from about 10 nm to about 150 nm. For example, triphenylamine-containing poly ether ketone (TPAPEK), 4-isopropyl-4'-methyldiphenyliodoniumtetrakis(pentafluorophenyl)borate (PPBI), N,N'-diphenyl-N,N'-bis-[4-(phenyl-m-trile-amino)-phenyl]-biphenyl-4,4'-diamine (DNTPD), a phthalocyanine compound (such as copper phthalocyanine) suitable, 4,4',4"-tris(3-methylphenylphenylamino)triphenylamine (m-MTDATA), N,N'-di(1-naphthyl)-N,N'-diphenylbenzidine (NPB), 4,4',4"-tris{N,N- diphenylamino}triphenylamine (TDATA), 4,4',4''-tris(N,N-2-naphthylphenylamino)triphenylamine (2-TNATA), polyaniline/dodecylbenzenesulfonic acid (PANI/DBSA), poly(3,4-ethylenedioxythiophene)/poly(4-styrenesulfonate (PEDOT/PSS), polyaniline/camphorsulfonic acid (PANI/CSA), polyaniline/poly(4-styrenesulfonate) (PANI/PSS), etc., may be included.

The hole transport layer (HTL) 108 may be formed on the hole injection layer 106 utilizing the material for an organic EL device according to the disclosure to a thickness within a range from about 10 nm to about 150 nm. The hole transport layer 108 including the material for an organic EL device according to the disclosure may be formed by a vacuum evaporation method.

The emission layer (EL) 110 may be formed on the hole transport layer 108 utilizing a suitable host material to a thickness within a range from about 10 nm to about 60 nm. The suitable host material utilized in the emission layer 110 may include, for example, tris(8-quinolinolato)aluminum (Alq3), 4,4'-N,N'-dicarbazole-biphenyl (CBP), poly(n-vinylcarbazole) (PVK), 9,10-di(naphthalene-2-yl)anthracene (ADN), 4,4',4''-tris(N-carbazolyl)triphenylamine (TCTA), 1,3,5-tris(N-phenylbenzimidazole-2-yl)benzene (TPBI), 3-tert-butyl-9,10-di(naphtho-2-yl)anthracene (TBADN), distyrylarylene (DSA), 4,4'-bis(9-carbazole)-2,2'-dimethyl-biphenyl (dmCBP), etc.

The host material utilized in the emission layer 110 may be selected from an anthracene derivative, a pyrene derivative, a fluoranthene derivative, a chrysene derivative, a benzoanthracene derivative and a triphenylene derivative. In one embodiment, the emission layer 110 may include the anthracene derivative or the pyrene derivative. As the anthracene derivative utilized in the emission layer 110, a compound represented by the following Formula 9 may be utilized.

Formula 9

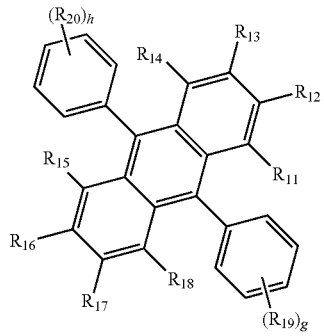

In Formula 9, $R_{11}$ to $R_{20}$ are each independently a substituted or unsubstituted aryl group having 6 to 30 carbon atoms for forming a ring, a substituted or unsubstituted heteroaryl group having 1 to 30 carbon atoms for forming a ring, an alkyl group having 1 to 15 carbon atoms, a silyl group, a halogen atom, a hydrogen atom or a deuterium atom. In addition, g and h are each independently an integer from 0 to 5. A plurality of adjacent $R_{11}$ to $R_{20}$ may make a bond to form a saturated or unsaturated ring.

The substituted or unsubstituted heteroaryl group having 1 to 30 carbon atoms for forming a ring utilized as $R_{11}$ to $R_{20}$ may include a benzothiazolyl group, a thiophenyl group, a thienothiophenyl group, a thienothienothiophenyl group, a benzothiophenyl group, a benzofuryl group, a dibenzothiophenyl group, a dibenzofuryl group, an N-aryl carbazolyl group, an N-heteroarylcarbazolyl group, an N-alkylcarbazolyl group, a phenoxazinyl group, a phenothiazyl group, a pyridyl group, a pyrimidyl group, a triazile group, a quinolinyl group, a quinoxalyl group, etc., without being limited thereto.

The substituted or unsubstituted heteroaryl group having 1 to 30 carbon atoms for forming a ring utilized as $R_{11}$ to $R_{20}$ may include a benzothiazolyl group, a thiophenyl group, a thienothiophenyl group, a thienothienothiophenyl group, a benzothiophenyl group, a benzofuryl group, a dibenzothiophenyl group, a dibenzofuryl group, an N-aryl carbazolyl group, an N-heteroarylcarbazolyl group, an N-alkylcarbazolyl group, a phenoxazinyl group, a phenothiazyl group, a pyridyl group, a pyrimidyl group, a triazile group, a quinolinyl group, a quinoxalyl group, etc., without being limited thereto.

The alkyl group having 1 to 15 carbon atoms utilized as $R_{11}$ to $R_{20}$ may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, etc., without being limited thereto.

The anthracene derivative utilized in the emission layer 110 of the organic EL device according to an embodiment may include at least one of compounds a-1 to a-12 below.

a-1

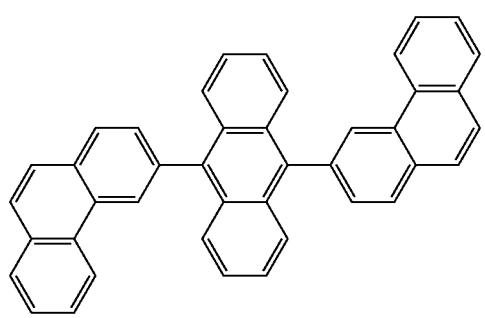

-continued
a-2
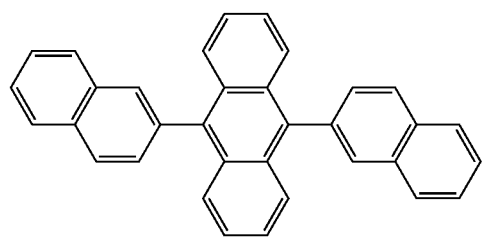
a-3
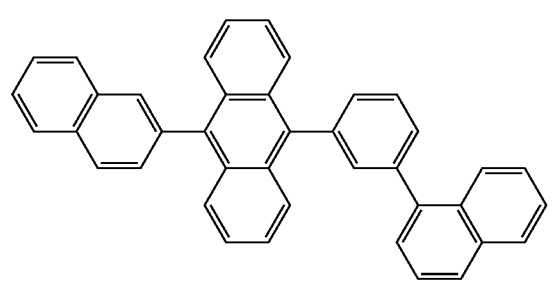
a-4
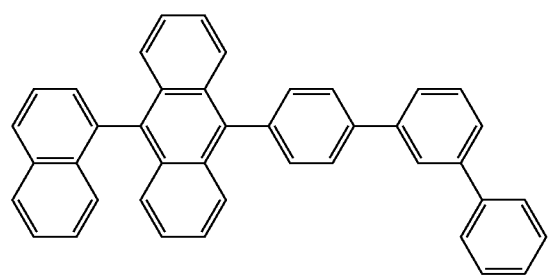
a-5
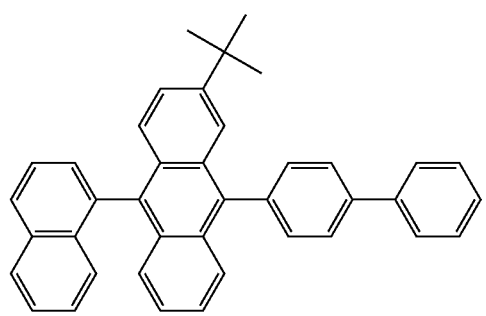
a-6
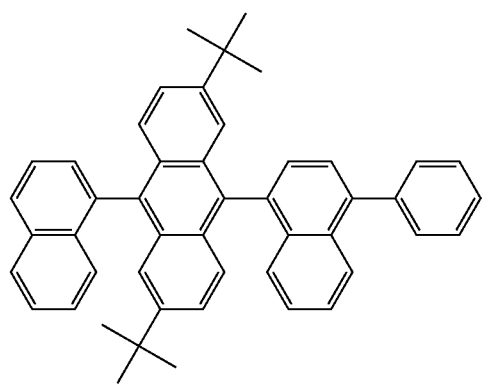
-continued
a-7
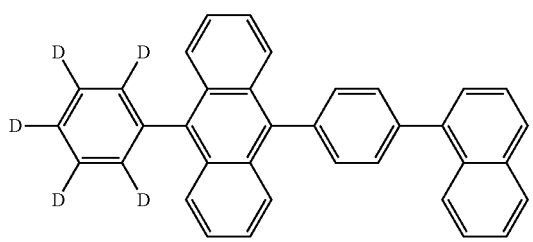
a-8
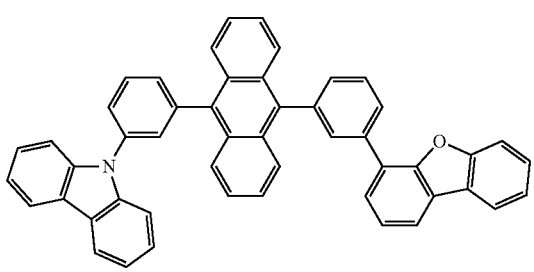
a-9
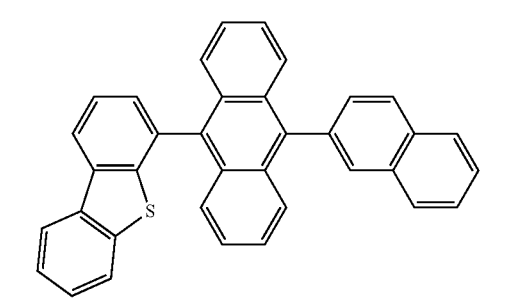
a-10
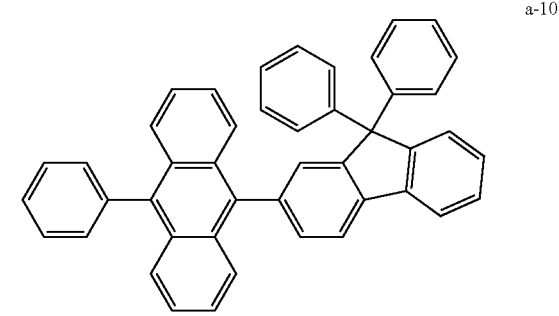
a-11
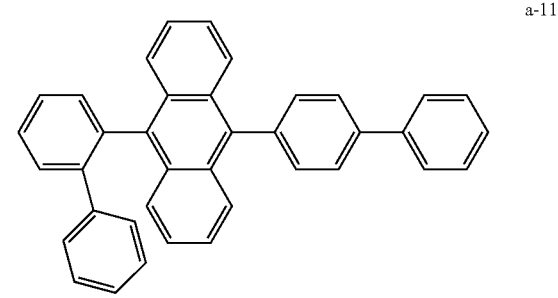

a-12

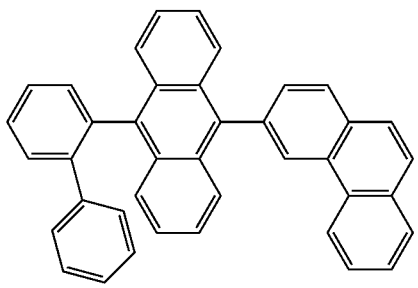

The emission layer 110 may include, as a dopant material, styryl derivatives (such as 1,4-bis[2-(3-N-ethylcarbazolyl) vinyl]benzene (BCzVB), 4-(di-p-tolylamino)-4'-[(di-p-tolylamino)styryl]stilbene (DPAVB), or N-(4-((E)-2-(6-((E)-4-(diphenylamino)styryl)naphthalene-2-yl)vinyl)phenyl-N-phenylbenzeneamine (N-BDAVBI)), perylene and the derivatives thereof (such as 2,5,8,11-tetra-t-butylperylene (TBPe)), pyrene and the derivatives thereof (such as 1,1-dipyrene, 1,4-dipyrenylbenzene, or 1,4-bis(N,N-diphenylamino)pyrene), etc., without being limited thereto.

The electron transport layer (ETL) 112 may be formed on the emission layer 110 to a thickness within a range from about 15 nm to about 50 nm utilizing tris(8-hydroxyquinolinato)aluminum (Alq3) or a material having a nitrogen-containing aromatic ring (for example, a material including a pyridine ring such as 1,3,5-tri[(3-pyridyl)-phen-3-yl]benzene, a material including a triazine ring such as 2,4,6-tris (3'-(pyridine-3-yl)biphenyl-3-yl)1,3,5-triazine, and a material including an imidazole derivative such as 2-(4-N-phenylbenzoimidazolyl-1-ylphenyl)-9,10-dinaphthylanthracene).

The electron injection layer (EIL) 114 may be formed on the electron transport layer 112 to a thickness within a range from about 0.3 nm to about 9 nm utilizing a material including, for example, lithium fluoride (LiF), lithium-8-quinolinato (Liq), etc.

The cathode 116 may be disposed on the electron injection layer 114 and may be formed utilizing a metal (such as aluminum (Al), silver (Ag), lithium (Li), magnesium (Mg), calcium (Ca), or a mixture thereof) and a transparent material (such as ITO or IZO).

Each electrode and each layer constituting the organic EL device according to the disclosure as described above may be formed by selecting an appropriate layer forming method depending on a material utilized, such as a vacuum evaporation method, a sputtering method, or various suitable coating methods. The hole transport layer 108 formed utilizing the material for an organic EL device according to the disclosure may be formed by the vacuum evaporation method.

In the organic EL device 100 according to the disclosure, a hole transport layer capable of realizing long life and high efficiency may be formed utilizing the material for an organic EL device according to the disclosure.

In the organic EL device 100 according to the disclosure, the material for an organic EL device according to the disclosure may be utilized as the material of the hole injection layer. As described above, an organic EL device with long life and high efficiency may be manufactured by utilizing the material for an organic EL device according to the disclosure in at least one layer of stacking layers disposed between the emission layer and the anode.

(Organic EL Device 2)

Figure 2:
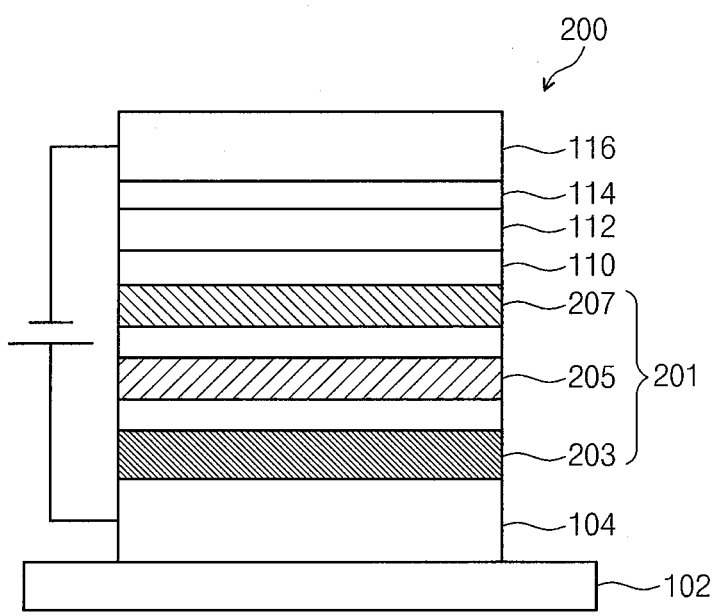
FIG. 2 is a schematic diagram illustrating an organic EL device 200 according to another embodiment.

Another organic EL device utilizing a material for an organic EL device according to an embodiment of the disclosure will be explained. FIG. 2 is a schematic diagram illustrating an organic EL device 200 according to another embodiment of the disclosure. In FIG. 2, the same reference numerals may be designated to the same parts or parts having substantially the same function as those in the organic EL device 100 shown in FIG. 1, and repeated explanation thereof will not be provided again.

The organic EL device 200 may include a substrate 102, an anode 104, a hole transport band 201, an emission layer 110, an electron transport layer 112, an electron injection layer 114 and a cathode 116. The hole transport band 201 may include a first layer 203 disposed at the anode-side and a second layer 207 disposed between the first layer 203 and the emission layer 110. In the hole transport band 201, a third layer 205 may be disposed between the anode 104 and the second layer 207. The position of the third layer 205 is not specifically limited, however, and it may be disposed between the first layer 203 and the second layer 207. In the hole transport band 201, another hole transport layer may be disposed between the first layer 203 and the third layer 205, and between the third layer 205 and the second layer 207. In the organic EL device 200, the material for an organic EL device may be appropriately utilized in the second layer 207 adjacent to the emission layer 110.

The first layer 203 disposed at the anode side of the hole transport band 201 may include an electron accepting compound having a LUMO level within a range from about −9.0 eV to about −4.0 eV. The first layer 203 may be formed utilizing a hole transport compound doped with the electron accepting compound or may be formed utilizing only the electron accepting compound. Examples of the electron accepting compound may be at least one of compounds ac1 to ac14. However, the electron accepting compound according to the disclosure is not limited thereto.

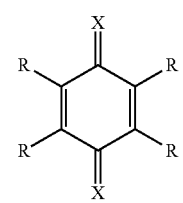

ac1

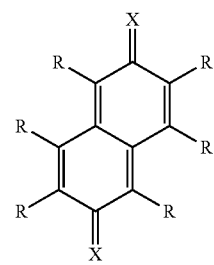

ac2 ac3 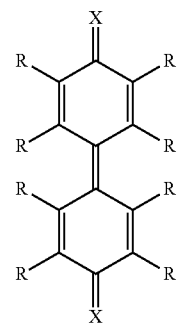

ac4 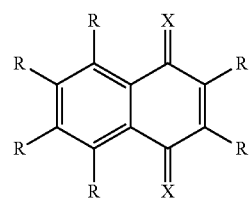

ac5 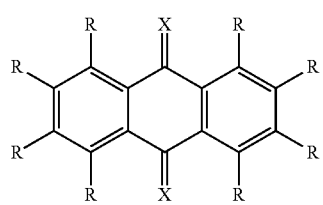

ac6 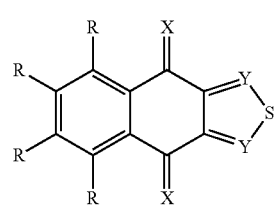

ac7 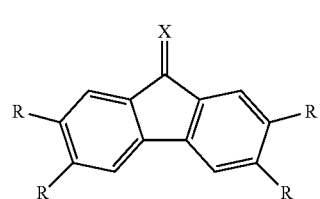

ac8 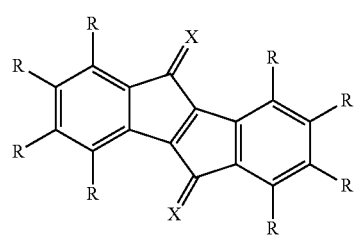

ac9 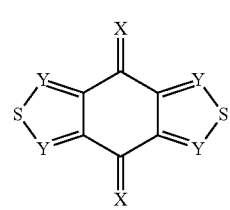

ac10 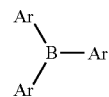

ac11 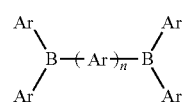

ac12 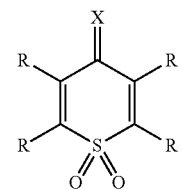

ac13 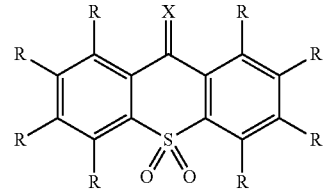

ac14 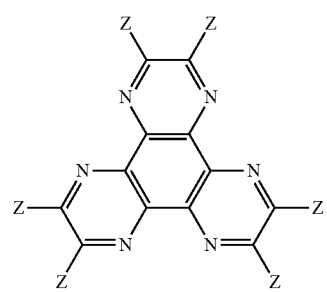

In the electron accepting Compounds ad to ac14, R is a hydrogen atom, a deuterium atom, a halogen atom, a fluoroalkyl group having 1 to 10 carbon atoms, a cyano group, an alkoxy group having 1 to 10 carbon atoms, an alkyl group having 1 to 10 carbon atoms, or a substituted or unsubstituted aryl group having 6 to 30 carbon atoms for forming a ring. However, all Rs may not be (e.g., at least one of the Rs is not) a hydrogen atom, a deuterium atom or fluorine in a molecule. Ar is each independently a substituted aryl group with an electron withdrawing group or an unsubstituted aryl group having 6 to 30 carbon atoms for forming a ring, or a substituted or unsubstituted heteroaryl group having 3 to 30 carbon atoms for forming a ring; Y is a methine group (—CH═) or a nitrogen atom (—N═); Z is a pseudohalogen atom or a sulfur (S) atom; and X is one of the substituents represented by the following formulae $X_1$ to $X_7$.

x1 x2 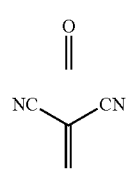

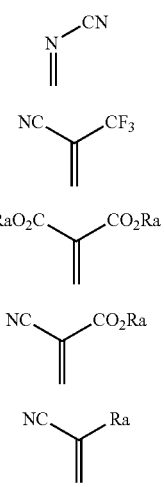

In Formulae X5 to X7, Ra is a hydrogen atom, a deuterium atom, a halogen atom, a fluoroalkyl group having 1 to 10 carbon atoms, a cyano group, an alkoxy group having 1 to 10 carbon atoms, an alkyl group having 1 to 10 carbon atoms, a substituted or unsubstituted aryl group having 6 to 30 carbon atoms for forming a ring or a substituted or unsubstituted heteroaryl group having 3 to 30 carbon atoms for forming a ring.

Examples of the substituted or unsubstituted aryl group having 6 to 30 carbon atoms for forming a ring, or the substituted or unsubstituted heteroaryl group having 3 to 30 carbon atoms for forming a ring, represented by R, Ar and Ra, may include a phenyl group, a 1-naphthyl group, a 2-naphthyl group, a 1-anthryl group, a 2-anthryl group, a 9-anthryl group, a 1-phenanthryl group, a 2-phenanthryl group, a 3-phenanthryl group, a 4-phenanthryl group, a 9-phenanthryl group, a 1-naphthacenyl group, a 2-naphthacenyl group, a 9-naphthacenyl group, a 1-pyrenyl group, a 2-pyrenyl group, a 4-pyrenyl group, a 2-biphenylyl group, a 3-biphenylyl group, a 4-biphenylyl group, a p-terphenyl-4-yl group, a p-terphenyl-3-yl group, a p-terphenyl-2-yl group, an m-terphenyl-4-yl group, an m-terphenyl-3-yl group, an m-terphenyl-2-yl group, an o-tolyl group, an m-tolyl group, a p-tolyl group, a p-t-butylphenyl group, a p-(2-phenylpropyl)phenyl group, a 3-methyl-2-naphthyl group, a 4-methyl-1-naphthyl group, a 4-methyl-1-anthryl group, a 4'-methylbiphenylyl group, a 4"-t-butyl-p-terphenyl-4-yl group, a fluoranthenyl group, a fluorenyl group, a 1-pyrrolyl group, a 2-pyrrolyl group, a 3-pyrrolyl group, a pyridinyl group, a 2-pyridinyl group, a 3-pyridinyl group, a 4-pyridinyl group, a 1-indolyl group, a 2-indolyl group, a 3-indolyl group, a 4-indolyl group, a 5-indolyl group, a 6-indolyl group, a 7-indolyl group, a 1-isoindolyl group, a 2-isoindolyl group, a 3-isoindolyl group, a 4-isoindolyl group, a 5-isoindolyl group, a 6-isoindolyl group, a 7-isoindolyl group, a 2-furyl group, a 3-furyl group, a 2-benzofuranyl group, a 3-benzofuranyl group, a 4-benzofuranyl group, a 5-benzofuranyl group, a 6-benzofuranyl group, a 7-benzofuranyl group, a 1-isobenzofuranyl group, a 3-isobenzofuranyl group, a 4-isobenzofuranyl group, a 5-isobenzofuranyl group, a 6-isobenzofuranyl group, a 7-isobenzofuranyl group, a quinolyl group, a 3-quinolyl group, a 4-quinolyl group, a 5-quinolyl group, a 6-quinolyl group, a 7-quinolyl group, an 8-quinolyl group, a 1-isoquinolyl group, a 3-isoquinolyl group, a 4-isoquinolyl group, a 5-isoquinolyl group, a 6-isoquinolyl group, a 7-isoquinolyl group, an 8-isoquinolyl group, a 2-quinoxalinyl group, a 5-quinoxalinyl group, a 6-quinoxalinyl group, a 1-carbazolyl group, a 2-carbazolyl group, a 3-carbazolyl group, a 4-carbazolyl group, a 9-carbazolyl group, a 1-phenanthridinyl group, a 2-phenanthridinyl group, a 3-phenanthridinyl group, a 4-phenanthridinyl group, a 6-phenanthridinyl group, a 7-phenanthridinyl group, an 8-phenanthridinyl group, a 9-phenanthridinyl group, a 10-phenanthridinyl group, a 1-acridinyl group, a 2-acridinyl group, a 3-acridinyl group, a 4-acridinyl group, a 9-acridinyl group, a 1,7-phenanthroline-2-yl group, a 1,7-phenanthroline-3-yl group, a 1,7-phenanthroline-4-yl group, a 1,7-phenanthroline-5-yl group, a 1,7-phenanthroline-6-yl group, a 1,7-phenanthroline-8-yl group, a 1,7-phenanthroline-9-yl group, a 1,7-phenanthroline-10-yl group, a 1,8-phenanthroline-2-yl group, a 1,8-phenanthroline-3-yl group, a 1,8-phenanthroline-4-yl group, a 1,8-phenanthroline-5-yl group, a 1,8-phenanthroline-6-yl group, a 1,8-phenanthroline-7-yl group, a 1,8-phenanthroline-9-yl group, a 1,8-phenanthroline-10-yl group, a 1,9-phenanthroline-2-yl group, a 1,9-phenanthroline-3-yl group, a 1,9-phenanthroline-4-yl group, a 1,9-phenanthroline-5-yl group, a 1,9-phenanthroline-6-yl group, a 1,9-phenanthroline-7-yl group, a 1,9-phenanthroline-8-yl group, a 1,9-phenanthroline-10-yl group, a 1,10-phenanthroline-2-yl group, a 1,10-phenanthroline-3-yl group, a 1,10-phenanthroline-4-yl group, a 1,10-phenanthroline-5-yl group, a 2,9-phenanthroline-1-yl group, a 2,9-phenanthroline-3-yl group, a 2,9-phenanthroline-4-yl group, a 2,9-phenanthroline-5-yl group, a 2,9-phenanthroline-6-yl group, a 2,9-phenanthroline-7-yl group, a 2,9-phenanthroline-8-yl group, a 2,9-phenanthroline-10-yl group, a 2,8-phenanthroline-1-yl group, a 2,8-phenanthroline-3-yl group, a 2,8-phenanthroline-4-yl group, a 2,8-phenanthroline-5-yl group, a 2,8-phenanthroline-6-yl group, a 2,8-phenanthroline-7-yl group, a 2,8-phenanthroline-9-yl group, a 2,8-phenanthroline-10-yl group, a 2,7-phenanthroline-1-yl group, a 2,7-phenanthroline-3-yl group, a 2,7-phenanthroline-4-yl group, a 2,7-phenanthroline-5-yl group, a 2,7-phenanthroline-6-yl group, a 2,7-phenanthroline-8-yl group, a 2,7-phenanthroline-9-yl group, a 2,7-phenanthroline-10-yl group, a 1-phenazinyl group, a 2-phenazinyl group, a 1-phenothiazinyl group, a 2-phenothiazinyl group, a 3-phenothiazinyl group, a 4-phenothiazinyl group, a 10-phenothiazinyl group, a 1-phenoxaziny group, a 2-phenoxazinyl group, a 3-phenoxazinyl group, a 4-phenoxazinyl group, a 10-phenoxazinyl group, a 2-oxazolyl group, a 4-oxazolyl group, a 5-oxazolyl group, a 2-oxadiazolyl group, a 5-oxadiazolyl group, a 3-furazanyl group, a 2-thienyl group, a 3-thienyl group, a 2-methylpyrrole-1-yl group, a 2-methylpyrrole-3-yl group, a 2-methylpyrrole-4-yl group, a 2-methylpyrrole-5-yl group, a 3-methylpyrrole-1-yl group, a 3-methylpyrrole-2-yl group, a 3-methylpyrrole-4-yl group, a 3-methylpyrrole-5-yl group, a 2-t-butylpyrrole-4-yl group, a 3-(2-phenylpropyl)pyrrole-1-yl group, a 2-methyl-1-indolyl group, a 4-methyl-1-indolyl group, a 2-methyl-3-indolyl group, a 4-methyl-3-indolyl group, a 2-t-butyl-1-indolyl group, a 4-t-butyl-1-indolyl group, a 2-t-butyl-3-indolyl group, a 4-t-butyl-3-indolyl group, etc.

Examples of the fluoroalkyl group having 1 to 10 carbon atoms represented by R and Ra may include a perfluoroalkyl group (such as a trifluoromethyl group, a pentafluoroethyl group, a heptafluoropropyl group or a heptadecafluorooctane group), a monofluoromethyl group, a difluoromethyl group, a trifluoroethyl group, a tetrafluoropropyl group, an octafluoropentyl group, etc.

Examples of the alkyl group having 1 to 10 carbon atoms represented by R and Ra may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, a cyclopropyl group, a cyclobutyl group, a cyclopentyl group, a cyclohexyl group, a 4-methylcyclohexyl group, a 1-adamantyl group, a 2-adamantyl group, a 1-norbornyl group, a 2-norbornyl group, etc.

The alkoxy group having 1 to 10 carbon atoms represented by R and Ra may be a group represented by —OY. Examples of Y may include a methyl group, an ethyl group, a propyl group, an isopropyl group, an n-butyl group, an s-butyl group, an isobutyl group, a t-butyl group, an n-pentyl group, an n-hexyl group, an n-heptyl group, an n-octyl group, a hydroxymethyl group, a 1-hydroxyethyl group, a 2-hydroxyethyl group, a 2-hydroxyisobutyl group, a 1,2-dihydroxyethyl group, a 1,3-dihydroxyisopropyl group, a 2,3-dihydroxy-t-butyl group, a 1,2,3-trihydroxypropyl group, a chloromethyl group, a 1-chloroethyl group, a 2-chloroethyl group, a 2-chloroisobutyl group, a 1,2-dichloroethyl group, a 1,3-dichloroisopropyl group, a 2,3-dichloro-t-butyl group, a 1,2,3-trichloropropyl group, a bromomethyl group, a 1-bromoethyl group, a 2-bromoethyl group, a 2-bromoisobutyl group, a 1,2-dibromoethyl group, a 1,3-dibromoisopropyl group, a 2,3-dibromo-t-butyl group, a 1,2,3-tribromopropyl group, an iodomethyl group, a 1-iodoethyl group, a 2-iodoethyl group, a 2-iodoisobutyl group, a 1,2-diiodoethyl group, a 1,3-diiodoisopropyl group, a 2,3-diiodo-t-butyl group, a 1,2,3-triiodopropyl group, an aminomethyl group, a 1-aminoethyl group, a 2-aminoethyl group, a 2-aminoisobutyl group, a 1,2-diaminoethyl group, a 1,3-diaminoisopropyl group, a 2,3-diamino-t-butyl group, a 1,2,3-triaminopropyl group, a cyanomethyl group, a 1-cyanoethyl group, a 2-cyanoethyl group, a 2-cyanoisobutyl group, a 1,2-dicyanoethyl group, a 1,3-dicyanoisopropyl group, a 2,3-dicyano-t-butyl group, a 1,2,3-tricyanopropyl group, a nitromethyl group, a 1-nitroethyl group, a 2-nitroethyl group, a 2-nitroisobutyl group, a 1,2-dinitroethyl group, a 1,3-dinitroisopropyl group, a 2,3-dinitro-t-butyl group, a 1,2,3-trinitropropyl group, etc.

Examples of the halogen atom represented by R and Ra may include fluorine, chlorine, bromine and iodine.

In the case that the electron accepting compound is doped in another hole transport compound, a suitable hole transport compound may be utilized as the hole transport compound included in the first layer 203. As the suitable hole transport compound, a compound having a carbazolyl group may be utilized, without being limited thereto. The hole transport compound having the carbazolyl group may be, for example, an amine derivative represented by the following Formula 8.

Formula 8

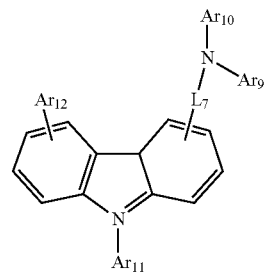

In Formula 8, $Ar_9$, $Ar_{10}$ and $Ar_{11}$ are each independently a substituted or unsubstituted aryl group having 6 to 50 carbon atoms for forming a ring, or a substituted or unsubstituted heteroaryl group having 5 to 50 carbon atoms for forming a ring; $Ar_{12}$ is a substituted or unsubstituted aryl group having 6 to 50 carbon atoms for forming a ring, a substituted or unsubstituted heteroaryl group having 5 to 50 carbon atoms for forming a ring, or a substituted or unsubstituted alkyl group having 1 to 50 carbon atoms; and $L_7$ is a direct linkage, a substituted or unsubstituted arylene group having 6 to 18 carbon atoms for forming a ring, or a substituted or unsubstituted heteroarylene group having 5 to 15 carbon atoms for forming a ring.

In one embodiment, $Ar_9$ to $Ar_{11}$ may be each independently a phenyl group, a biphenyl group, a terphenyl group, a naphthyl group, an anthryl group, a phenanthryl group, a fluorenyl group, an indenyl group, a pyranyl group, an acetonaphthenyl group, a fluoranthenyl group, a triphenylenyl group, a pyridyl group, a pyranyl group, a quinolyl group, an isoquinolyl group, a benzofuranyl group, a benzothienyl group, an indolyl group, a carbazolyl group, a benzoxazolyl group, a benzothiazolyl group, a quinoxalyl group, a benzoimidazolyl group, a dibenzofuranyl group, a dibenzothienyl group, etc. For example, the phenyl group, the biphenyl group, the terphenyl group, the fluorenyl group, the carbazolyl group, the dibenzofuranyl group, etc. may be utilized.

As $Ar_{12}$, the aryl group and the heteroaryl group may be the same as the functional groups exemplified as $Ar_9$ to $Ar_{11}$, and the alkyl group may be, for example, a methyl group or an ethyl group.

$L_7$ may include, other than the direct linkage, a phenylene group, a biphenylylene group, a terphenylylene group, a naphthylene group, an anthrylene group, a phenanthrylene group, a fluorelene group, an indandiyl group, a pyrenediyl group, an acenaphthenediyl group, a fluoranthenediyl group, a triphenylenediyl group, a pyridinediyl group, a pyranediyl group, a quinolinediyl group, an isoquinolinediyl group, a benzofurandiyl group, a benzothiophenediyl group, an indolediyl group, a carbazolediyl group, a benzoxazolediyl group, a benzothiazolediyl group, a quinoxalinediyl group, a benzoimidazolediyl group, a dibenzofuranediyl group, etc. For example, the phenylene group, the terphenylene group, the fluorenediyl group, the carbazolediyl group, the dibenzofuranediyl, etc. may be utilized.
The compound represented by Formula 8 may include at least one of the compounds 270 to 285.
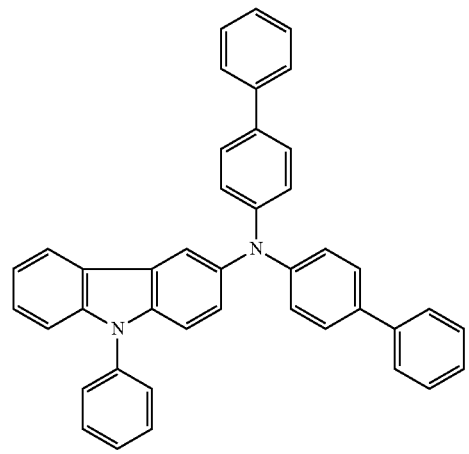
270
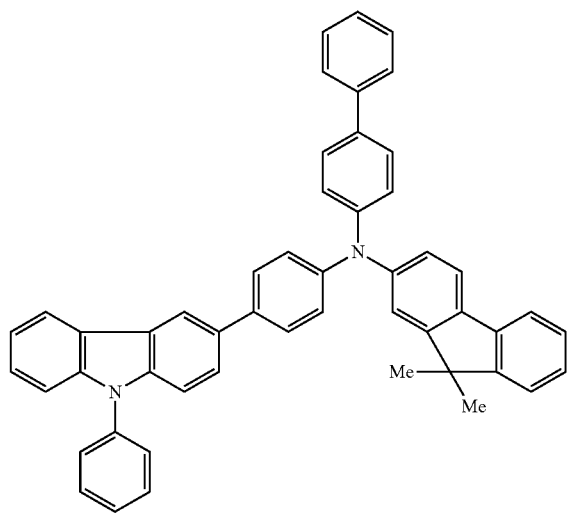
271
272
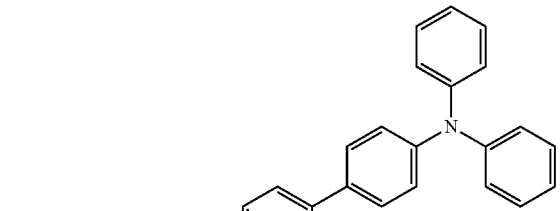
273
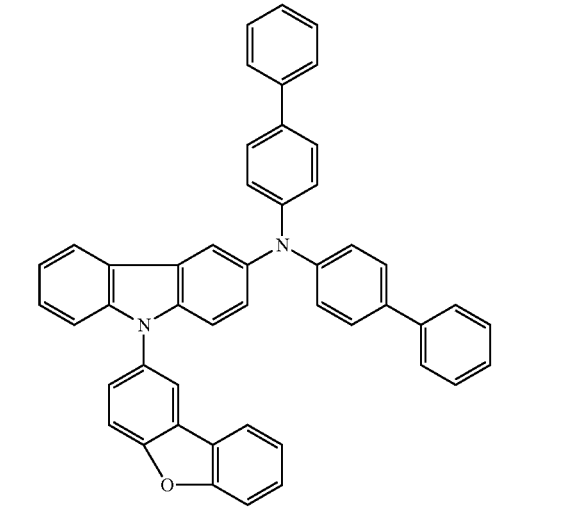
274
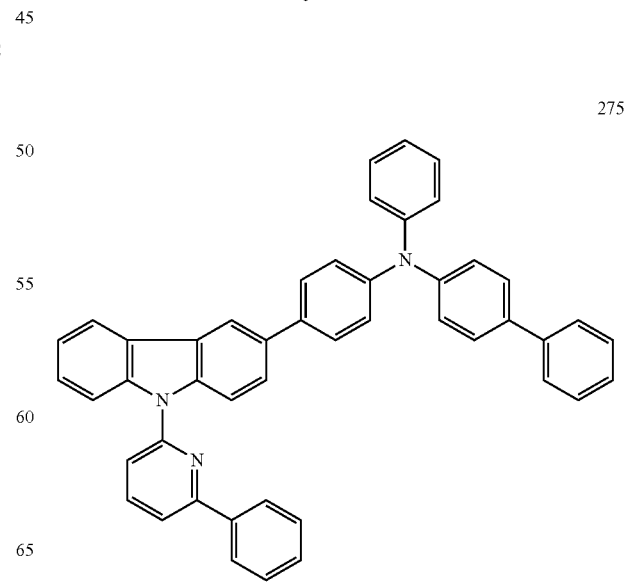
275

276
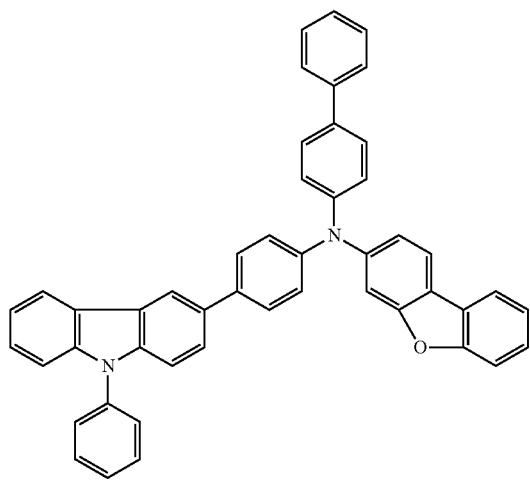
277
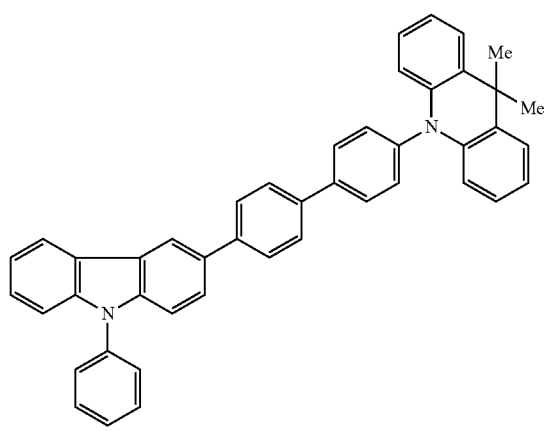
278
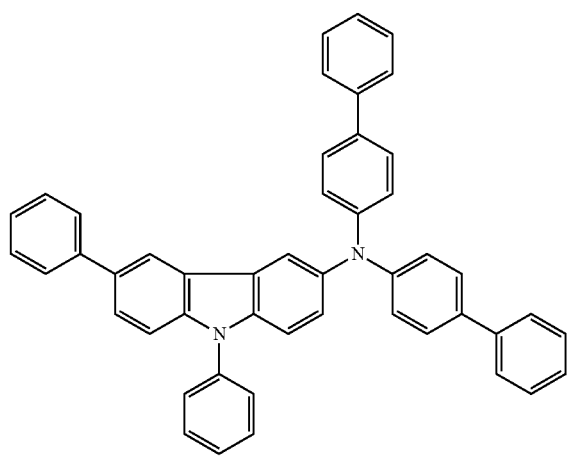
279
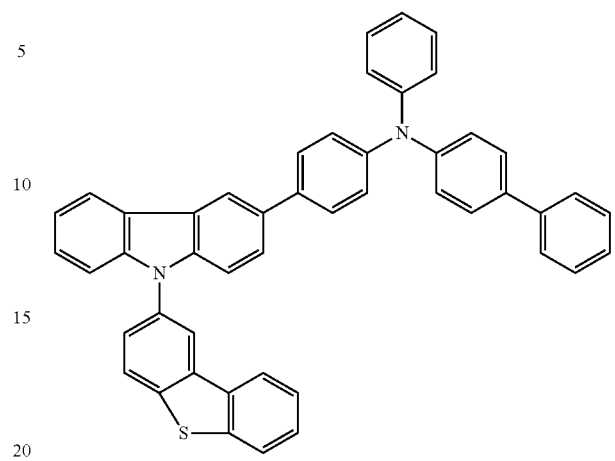
280
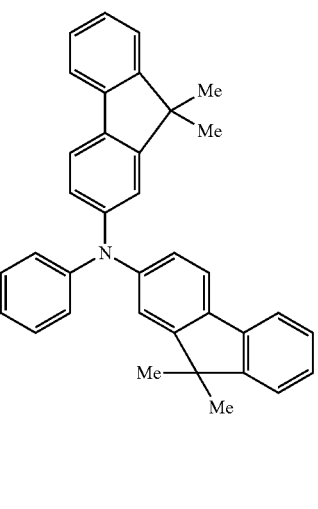
281
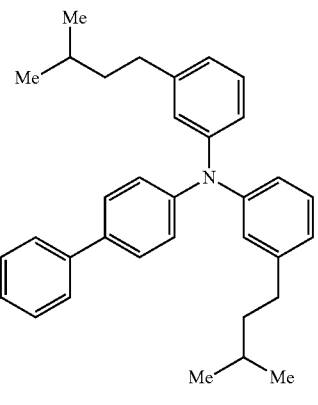

282

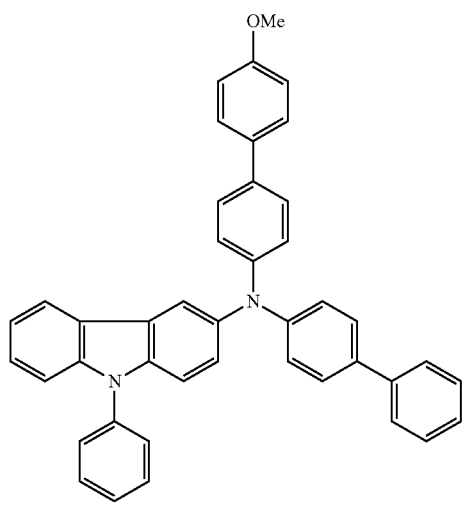

283

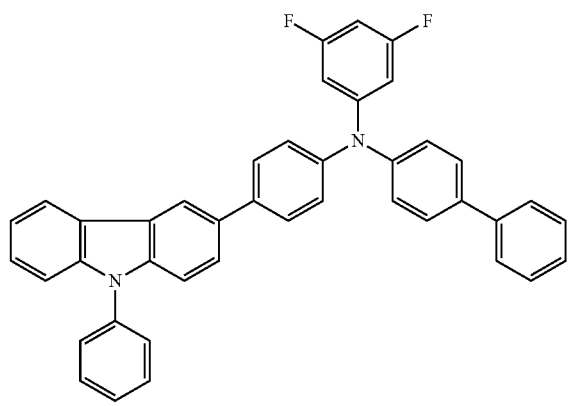

284

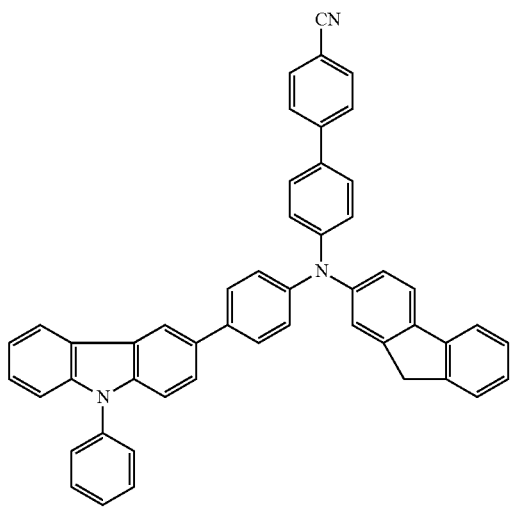

285

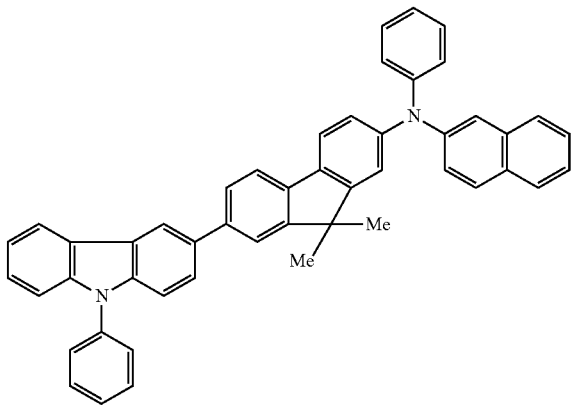

In the hole transport band 201, the third layer 205 may include a compound represented by Formula 8. The compound represented by Formula 8 and included in the third layer 205 may be Compounds 270 to 285.

Each electrode and each layer constituting the organic EL device 200 according to the disclosure as described above may be formed by selecting an appropriate layer forming method depending on materials utilized, such as a vacuum evaporation method, a sputtering method or various suitable coating methods. In addition, the second layer 207 formed utilizing the material for an organic EL device according to the disclosure may be formed by the vacuum evaporation method.

In the hole transport band 201 in the organic EL device 200, at least one of the first layer 203 including an electron accepting compound having a LUMO level within a range from about −9.0 eV to about −4.0 eV is disposed adjacent to the anode 104, and at least one of the second layer 207 including the material for an organic EL device according to an embodiment is disposed adjacent to the emission layer 110. The organic EL device 200 according to an embodiment includes the material for an organic EL device according to an embodiment with high electron tolerance and improved amorphous properties in the hole transport second layer 207 disposed adjacent to the emission layer 110 in the hole transport band 201, and the hole transport layer between the anode 104 and the second layer 207 may be passivated from electrons not consumed in the emission layer 110. In addition, the diffusion of energy with an excited state generated in the emission layer 110 into the hole transport layer between the anode 104 and the second layer 207 may be reduced or prevented, and the charge balance of the whole organic EL device 200 may be adjusted. By disposing the second layer 207 including the material for an organic EL device adjacent to the emission layer 110, the diffusion of the electron accepting compound included in the first layer 203 into the emission layer 110 may be restrained.

According to an embodiment, as the material for an organic EL device included in the second layer 207, a compound of Formula 1, in which a dibenzoheterole group is dibenzofuran, $L_3$ includes an m-phenylene group or a p-phenylene group, and an amine group includes a substituent of a naphthyl group, a biphenyl group or a naphthyl phenyl group, is utilized. According to another embodiment, as the material for an organic EL device included in the second layer 207, a compound represented by Formula 4 or 6 and includes an amine group having a substituent of a naphthyl group, a biphenyl group or a naphthyl phenyl group may be utilized.

In the organic EL device 200, the first layer 203 including the electron accepting compound may be disposed near the anode 104, for example, adjacent to (e.g., in contact with) the anode 104. By disposing a layer including the electron accepting compound adjacent to the anode 104, the hole injection properties from the anode 104 may be improved. In the case that a hole transport compound having a carbazolyl group, represented by Formula 8, is included in the first layer 203, charge transport properties and current flow durability may be improved.

In the organic EL device 200, the third layer 205 including a compound having a carbazolyl group and represented by Formula 8 may be disposed nearer to the emission layer 110 than to the first layer 203. By including the compound having the carbazolyl group in the hole transport band 201, charge transport properties and current flow durability may be improved. In addition, since the third layer 205 includes the compound represented by Formula 8, the hole transport layer between the anode 104 and the third layer 205 may be passivated from electrons not consumed in the emission layer 110, and the diffusion of energy with an excited state generated in the emission layer 110 into the hole transport layer between the anode 104 and the third layer 205 may be reduced or prevented. In addition, the compound represented by Formula 8, which is an amine derivative having a carbazolyl group may restrain (e.g., reduce or prevent) the diffusion of the electron accepting compound included in the first layer 203 into the emission layer 110.

In the organic EL device 200 according to an embodiment, the material for an organic EL device according to an embodiment may be utilized as the material of the second layer 207 adjacent to the emission layer 110, the first layer 203 including the electron accepting compound may be disposed adjacent to the anode 104, and the third layer 205 including the compound represented by Formula 8 may be disposed between the first layer 203 and the second layer 207. Thus, the high efficiency and long life of the organic EL device may be realized.

The material for an organic EL device according to an embodiment may be applied in an organic EL display of an active matrix type utilizing a thin film transistor (TFT).

(Manufacturing Method)

The material for an organic EL device according to an embodiment may be synthesized, for example, as follows.

Synthetic Method of Compound 17

Synthesis of Compound A in Formula 14

First, the following Compound A was synthesized. Under an Ar atmosphere, 53.8 g of N-[1,1'-biphenyl]-4-yl-N-(4-bromophenyl)-[1,1'-biphenyl]-4-amine, 6.46 g of Pd(dppf)Cl$_2$·CH$_2$Cl$_2$, 33.3 g of KOAc and 33.0 g of bis(pinacolato)diboron were added to a 2 L flask, followed by degassing under vacuum in a dioxane solvent and stirring at about 100° C. for about 12 hours. After that, the solvent was distilled, CH$_2$Cl$_2$ and water were added thereto, an organic phase was separated, magnesium sulfate and activated clay were added thereto (e.g, added to the organic phase), filtering with suction was performed, and the solvents were distilled. The crude product thus obtained was separated by silica gel column chromatography (utilizing a mixture solvent of dichloromethane and hexane) to produce 56.8 g of Compound A as a white solid (Yield 98%). The molecular weight of Compound A measured by FAB-MS was 523.

Formula 14

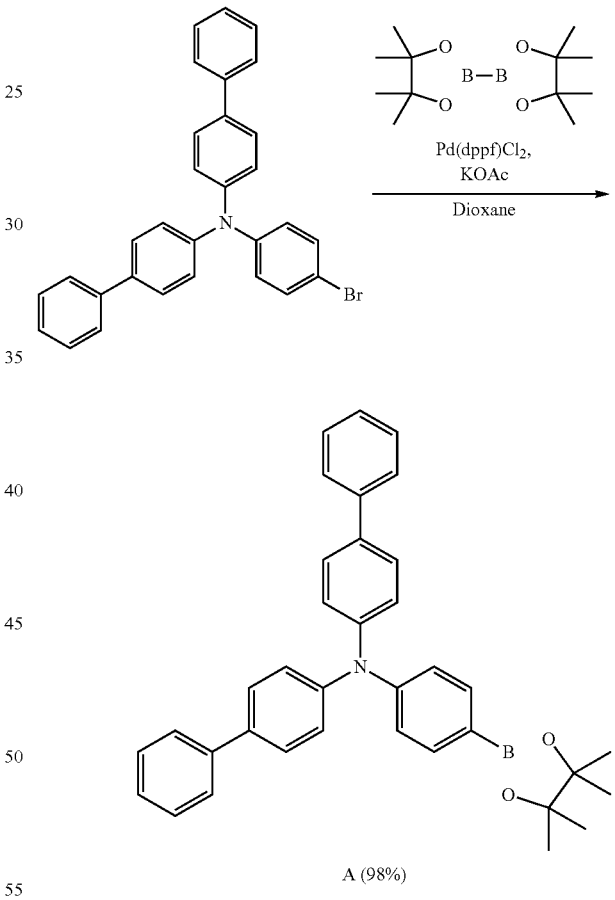

A (98%)

Synthesis of Compound B in Formula 15

Then, the following Compound B was synthesized. Under an Ar atmosphere, 10.0 g of Compound A, 6.00 g of 1-iodo-3-bromobenzene, 1.54 g of Pd(PPh$_3$)$_4$ and 5.25 g of potassium carbonate were added to a 300 ml, three necked flask, followed by heating and stirring in a mixture solvent of 450 mL of toluene and 60 mL of water at about 90° C. for about 8 hours. After air cooling, water was added, an organic layer was separated, and the solvents were distilled. The crude product thus obtained was separated by silica gel column chromatography (utilizing a mixture solvent of dichloromethane and hexane) and recrystallized utilizing a mixture solvent of toluene and hexane to produce 9.29 g of Compound B as a white solid (Yield 87%). The molecular weight of Compound B measured by FAB-MS was 553.

Formula 15

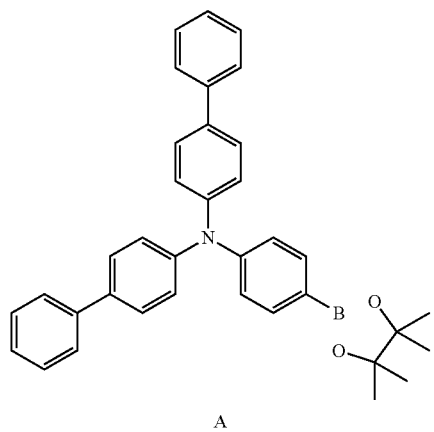
A

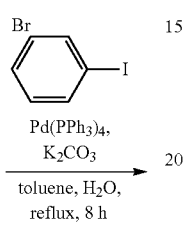

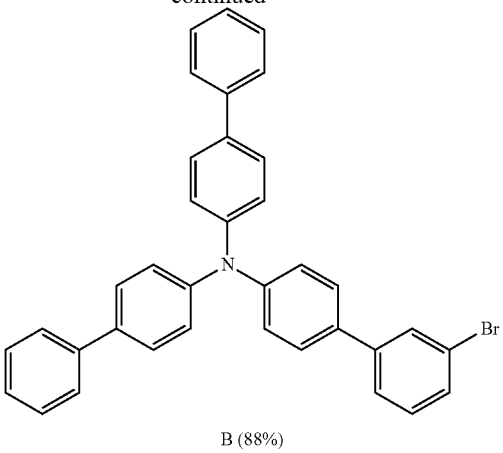
B (88%)

Synthesis of Compound C in Formula 16

Then, the following Compound C was synthesized. Substantially the same procedure as that of the method for synthesizing Compound A was conducted except for utilizing 4.00 g of Compound B instead of N-[1,1'-biphenyl]-4-yl-N-(4-bromophenyl)-[1,1'-biphenyl]-4-amine to produce 4.12 g of Compound C as a pale yellow solid (Yield 95%). The molecular weight of Compound C measured by FAB-MS was 599.

Formula 16

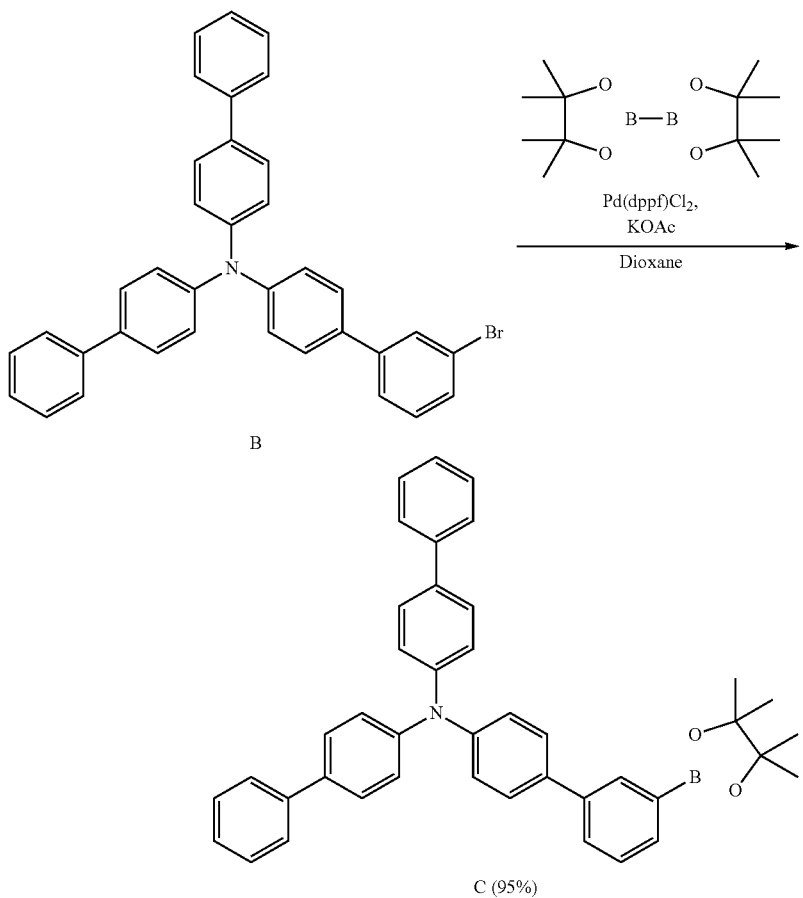

Synthesis of Compound D in Formula 17

The following Compound D was synthesized. Under an Ar atmosphere, 2.70 g of Compound C, 3.70 g of 4,6-dibromodibenzofuran, 0.34 g of Pd(PPh$_3$)$_4$ and 1.25 g of potassium carbonate were added to a 300 ml, three necked flask, followed by heating and stirring in a mixture solvent of 50 mL of toluene and 20 mL of water at about 90° C. for about 8 hours. After air cooling, water was added, an organic layer was separated, and the solvents were distilled. The crude product thus obtained was separated by silica gel column chromatography (utilizing a mixture solvent of dichloromethane and hexane) and recrystallized utilizing a mixture solvent of toluene and hexane to produce 1.78 g of Compound D as a white solid (Yield 55%). The molecular weight of Compound D measured by FAB-MS was 686.

Formula 17

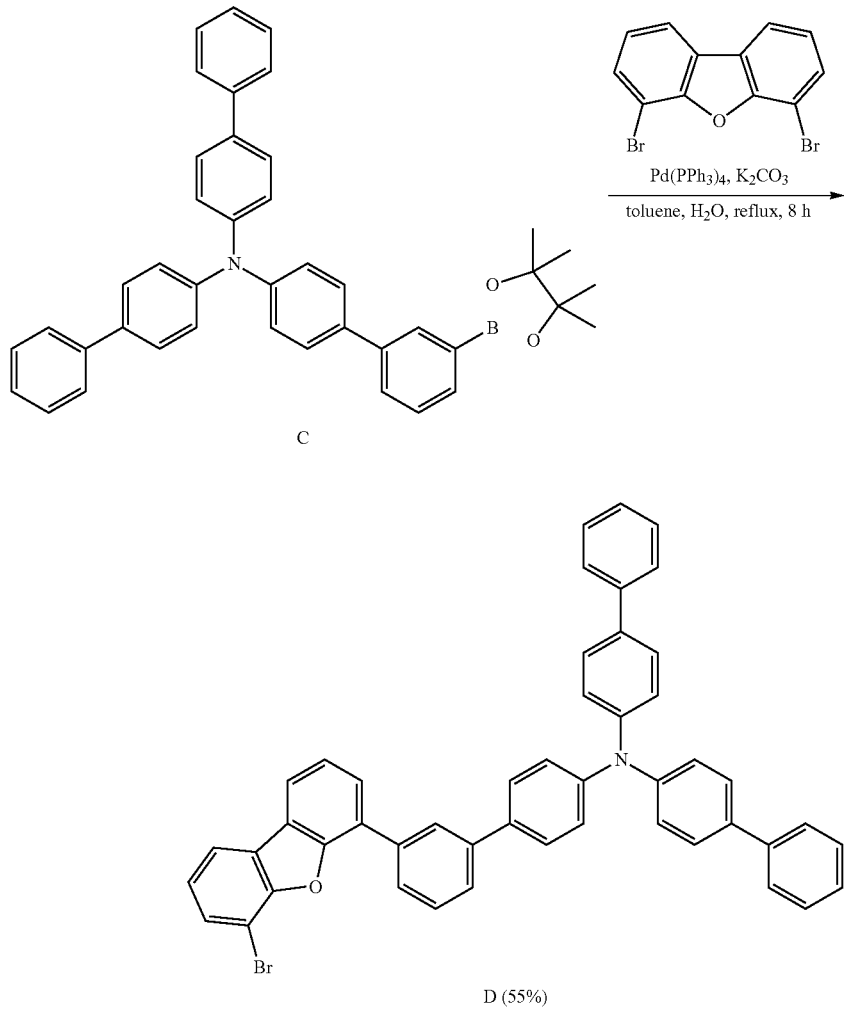

Synthesis of Compound 17 in Formula 18

Under an Ar atmosphere, 7.18 g of Compound D, 2.10 g of phenylboronic acid, 1.14 g of Pd(PPh$_3$)$_4$ and 3.55 g of potassium carbonate were added to a 300 ml, three necked flask, followed by heating and stirring in a mixture solvent of 150 mL of toluene and 60 mL of water at about 90° C. for about 8 hours. After air cooling, water was added, an organic layer was separated, and the solvents were distilled. The crude product thus obtained was separated by silica gel column chromatography (utilizing a mixture solvent of dichloromethane and hexane) and recrystallized utilizing a mixture solvent of toluene and hexane to produce 6.79 g of Compound 17 as a white solid (Yield 95%).

Formula 18

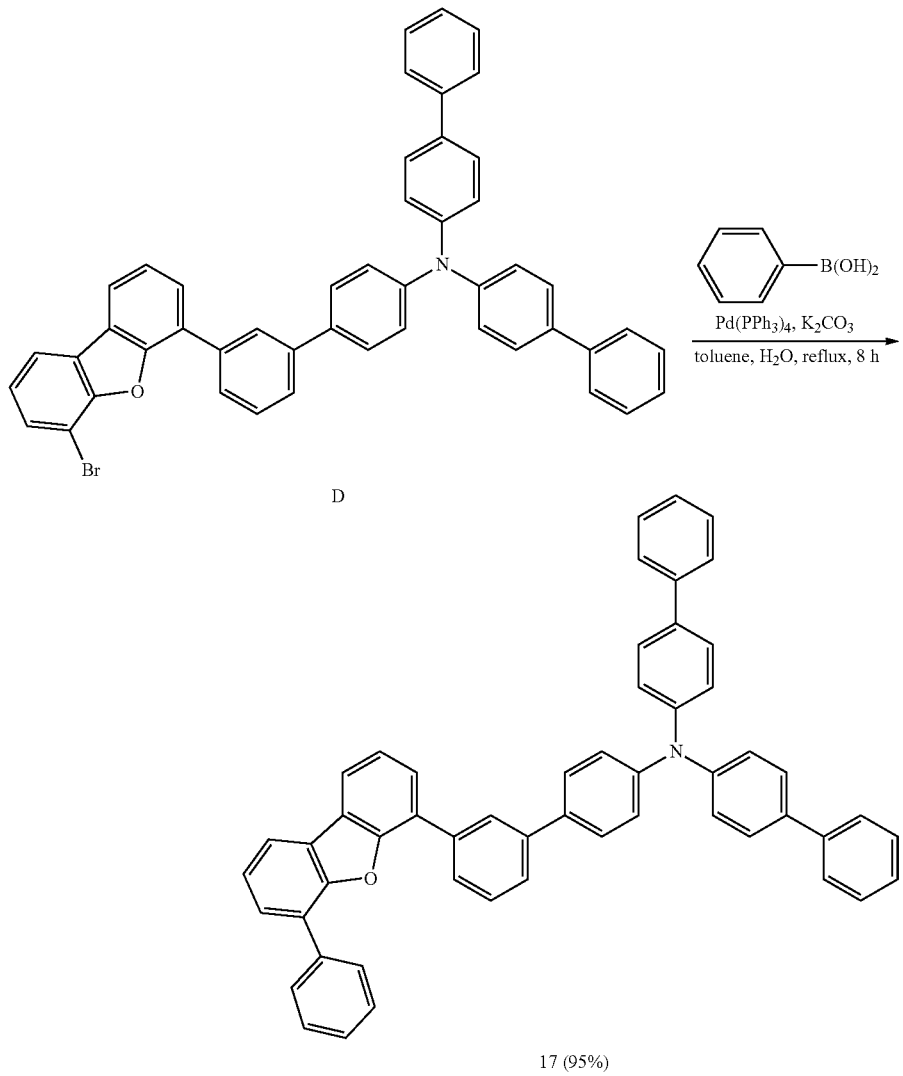

17 (95%)

The molecular weight of Compound 17 measured by FAB-MS was 715. The chemical shift values (δ) of Compound 17 measured by $^1$H-NMR (CDCl$_3$) were 7.85 (d, 2H, J=7.80 Hz), 7.81 (d, 2H, J=7.90 Hz), 7.70 (s, 1H), 7.58-7.50 (m, 19H), 7.48-7.41 (m, 7H), 6.69-6.65 (m, 6H)).

In addition, the material for an organic EL device according to an embodiment may be synthesized, for example, as follows.

Synthetic Method of Compound 5

Compound 5 was synthesized by conducting substantially the same procedure described for synthesizing Compound 17 except for utilizing 4,6-dibromodibenzothiophene instead of 4,6-dibromodibenzofuran. The molecular weight of Compound 5 measured by FAB-MS was 732. The chemical shift values (δ) of Compound 5 measured by $^1$H-NMR (CDCl$_3$) were 7.89 (d, 2H, J=7.90 Hz), 7.83 (d, 2H, J=7.70 Hz), 7.72 (s, 1H), 7.68-7.55 (m, 19H), 7.48-7.41 (m, 7H), 6.71-6.67 (m, 6H). From the results, the synthesized white solid was determined as Compound 5.

In addition, the material for an organic EL device according to an embodiment may be synthesized, for example, as follows.

Synthetic Method of Compound 77

Compound 77 was synthesized by conducting substantially the same procedure described for synthesizing Compound 17 except for utilizing 2,8-dibromodibenzothiophene instead of 4,6-dibromodibenzofuran. The molecular weight of Compound 77 measured by FAB-MS was 732. The chemical shift values (δ) of Compound 77 measured by $^1$H-NMR (CDCl$_3$) were 7.80 (d, 2H, J=7.90 Hz), 7.73 (d, 2H, J=7.70 Hz), 7.70 (d, 2H, J=7.90 Hz), 7.79 (s, 1H), 7.64-7.55 (m, 17H), 7.48-7.41 (m, 7H), 6.71-6.67 (m, 6H). From the results, the synthesized white solid was determined as Compound 77.

In addition, the material for an organic EL device according to an embodiment may be synthesized, for example, as follows.

Synthetic Method of Compound 89

Compound 89 was synthesized by conducting substantially the same procedure described for synthesizing Compound 17 except for utilizing 2,8-dibromodibenzofuran instead of 4,6-dibromodibenzofuran. The molecular weight of Compound 89 measured by FAB-MS was 715. The chemical shift values (δ) of Compound 89 measured by ¹H-NMR (CDCl₃) were 7.82 (d, 2H, J=7.84 Hz), 7.78 (d, 2H, J=7.90 Hz), 7.70 (d, 2H, J=7.88 Hz), 7.68 (s, 1H), 7.66-7.57 (m, 17H), 7.51-7.41 (m, 7H), 6.68-6.64 (m, 6H). From the results, the synthesized white solid was determined as Compound 89.

In addition, the material for an organic EL device according to an embodiment may be synthesized, for example, as follows.

Synthetic Method of Compound 141

Compound 141 was synthesized by conducting substantially the same procedure described for synthesizing Compound 17 except for utilizing 3,7-dibromodibenzofuran instead of 4,6-dibromodibenzofuran. The molecular weight of Compound 141 measured by FAB-MS was 715. The chemical shift values (δ) of Compound 141 measured by ¹H-NMR (CDCl₃) were 7.95 (d, 2H, J=7.80 Hz), 7.75 (d, 2H, J=7.70 Hz), 7.70 (s, 1H), 7.64 (d, 2H, J=7.90 Hz), 7.57-7.51 (m, 19H), 7.48-7.40 (m, 5H), 6.72-6.65 (m, 6H). From the results, the synthesized white solid was determined as Compound 141.

In addition, the material for an organic EL device according to an embodiment may be synthesized, for example, as follows.

Synthetic Method of Compound 213

Synthesis of Compound F in Formula 19

First, the following Compound F was synthesized. Under an Ar atmosphere, 30.0 g of Compound E, 16.4 g of 4-(4,4,5,5-tetramethyl-1,3,2-dioxaborolan-2-yl)aniline, 4.34 g of Pd(PPh₃)₄ and 31.8 g of K₃PO₄ were added to a 1,000 mL, three necked flask, followed by heating and stirring in a mixture solvent of 400 mL of toluene and 70 mL of water at about 80° C. for about 8 hours. After air cooling, water was added, an organic layer was separated, and the solvents were distilled. The crude product thus obtained was separated by silica gel column chromatography (utilizing a mixture solvent of dichloromethane and hexane) and recrystallized utilizing a mixture solvent of toluene and acetonitrile to produce 27.7 g of Compound F as a yellow solid (Yield 90%). The molecular weight of Compound F measured by FAB-MS was 411.

Formula 19

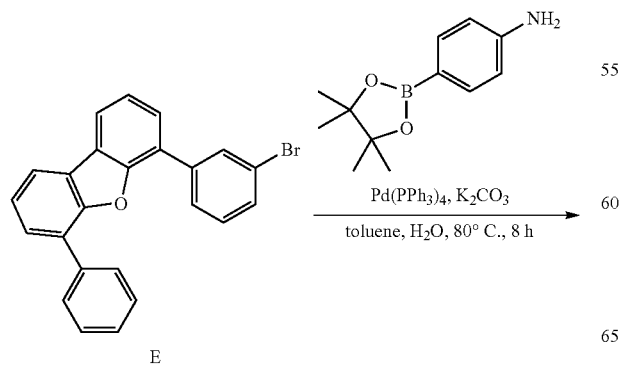

E

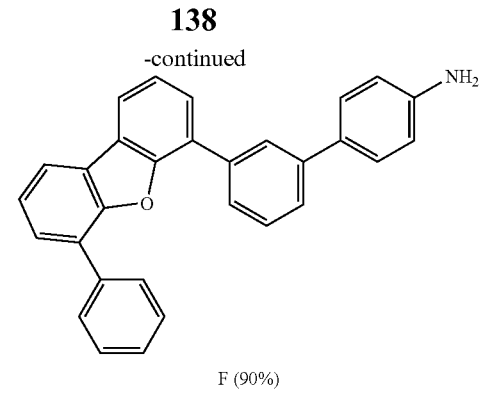

F (90%)

Synthesis of Compound G in Formula 20

The following Compound G was synthesized. Under an Ar atmosphere, 25.0 g of Compound F, 14.2 g of 4-bromobiphenyl, 1.99 g of Pd₂(dba)₃, 1.20 g of tri-tert-butylphosphine, and 8.89 g of NaOtBu were added to a 1,000 mL, three necked flask, followed by heating, refluxing and stirring in 300 mL of a mixture solvent of toluene for about 8 hours (or about 6 hours). After air cooling, water was added, an organic layer was separated, and the solvents were distilled. The crude product thus obtained was separated by silica gel column chromatography (utilizing a mixture solvent of dichloromethane and hexane) and recrystallized utilizing a mixture solvent of toluene and ethanol to produce 17.5 g of Compound G as a yellow solid (Yield 51%). The molecular weight of Compound G measured by FAB-MS was 564.

Formula 20

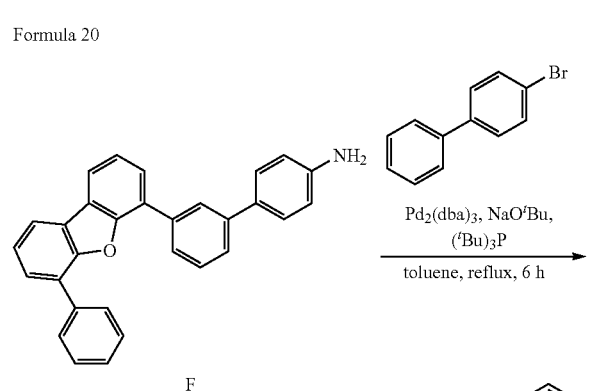

F

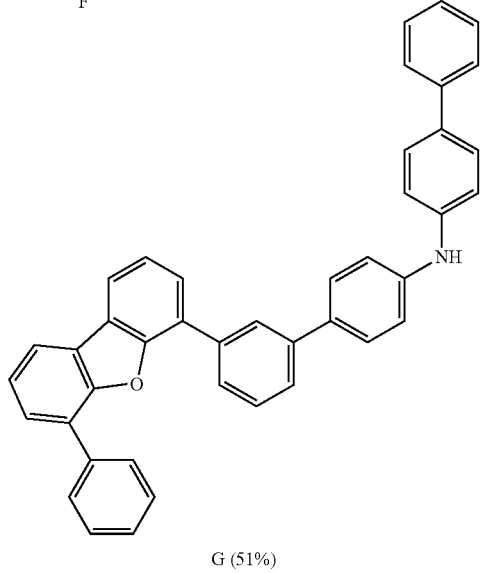

G (51%)

Synthesis of Compound 213 in Formula 21

Under an Ar atmosphere, 4.00 g of Compound G, 2.0 g of 1-(4-bromophenyl)naphthalene, 0.31 g of $Pd_2(dba)_3$, 0.52 g of tri-tert-butylphosphine and 1.09 g of NaOtBu were added to a 200 mL, three necked flask, followed by heating, refluxing and stirring in 60 mL of a mixture solvent of toluene for about 6 hours. After air cooling, water was added, an organic layer was separated, and the solvents were distilled. The crude product thus obtained was separated by silica gel column chromatography (utilizing a mixture solvent of dichloromethane and hexane) and recrystallized utilizing a mixture solvent of toluene and ethanol to produce 4.025 g of Compound 213 as a yellow solid (Yield 74%).

Formula 21

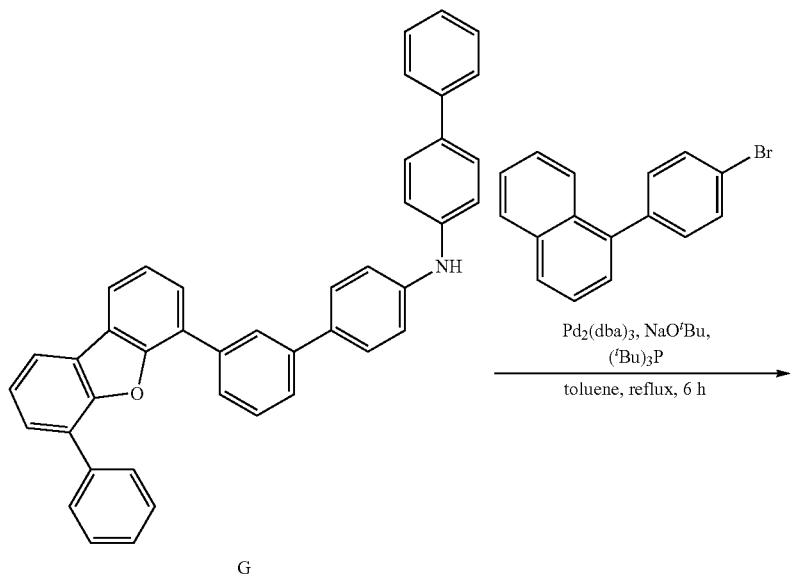

G

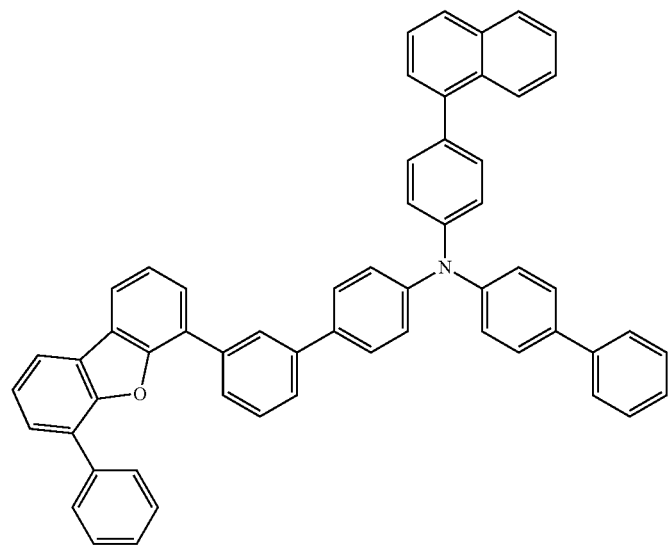

213 (74%)

The molecular weight of Compound 213 measured by FAB-MS was 766. The chemical shift values (δ) of Compound 213 measured by ¹H-NMR (CDCl₃) were 8.31 (s, 1H), 8.16 (d, 1H, J=6.10 Hz), 7.99 (d, 1H, J=7.00 Hz), 7.96 (d, 1H, J=7.20 Hz), 7.96-7.88 (m, 3H), 7.87-7.82 (m, 2H), 7.73 (d, 1H, J=7.10 Hz), 7.67-7.53 (m, 10H), 7.51-7.42 (m, 9H), 7.37-7.25 (m, 10H).

In addition, the material for an organic EL device according to an embodiment may be synthesized, for example, as follows.

Synthesis of Compound 169

In the synthesis of Compound D in the synthetic method of Compound 17 explained above, Compound A was utilized instead of Compound C to prepare an intermediate, and Compound 169 was synthesized utilizing the intermediate by conducting substantially the same procedure described for the preparation of Compound 17. The molecular weight of Compound 169 measured by FAB-MS was 640. The chemical shift values (δ) of Compound 169 measured by ¹H-NMR (CDCl₃) were 8.01-7.89 (m, 6H), 7.68-7.61 (m, 6H), 7.56-7.41 (m, 12H), 7.39-7.27 (m, 9H).

In addition, the material for an organic EL device according to an embodiment may be synthesized, for example, as follows.

Synthesis of Compound 181

Compound 181 was synthesized by conducting substantially the same procedure described for synthesizing Compound 169 except for utilizing N,N-bis([1,1'-biphenyl]-4-yl)-4'-(4,4,5,5-tetramethyl-1,3,2-dioxaborolan-2-yl)-[1,1'-biphenyl]-4-amine instead of Compound A. The molecular weight of Compound 181 measured by FAB-MS was 716. The chemical shift values (δ) of Compound 181 measured by ¹H-NMR (CDCl₃) were 8.03-7.85 (m, 6H), 7.71-7.67 (m, 8H), 7.53-7.40 (m, 14H), 7.37-7.29 (m, 9H).

In addition, the material for an organic EL device according to an embodiment may be synthesized, for example, as follows.

Synthesis of Compound 216

Compound 216 was synthesized by conducting substantially the same procedure described for synthesizing Compound 213 except for utilizing 1-iodonaphthalene instead of 1-(4-bromophenyl)naphthalene. The molecular weight of Compound 216 measured by FAB-MS was 690. The chemical shift values (δ) of Compound 216 measured by ¹H-NMR (CDCl₃) were 8.27 (s, 1H), 8.03 (d, 1H, J=7.10 Hz), 7.99-7.88 (m, 3H), 7.86-7.78 (m, 4H), 7.72 (d, 1H, J=6.80 Hz), 7.62 (d, 1H, J=6.80 Hz), 7.58-7.38 (m, 16H), 7.32-7.22 (m, 3H), 7.20-7.09 (m, 5H).

In addition, the material for an organic EL device according to an embodiment may be synthesized, for example, as follows.

Synthesis of Compound 13

Synthesis of Compound H in Formula 22

First, the following Compound H was synthesized. Under an Ar atmosphere, 29.0 g of Compound E, 13.4 g of 4-chlorophenylboronic acid, 3.14 g of Pd(PPh₃)₄, 38.8 g of K₂CO₃ were added to a 1,000 mL, three necked flask, followed by heating and stirring in a mixture solvent of 300 mL of toluene and 60 mL of water at about 80° C. for about 4 hours (or about 8 hours). After air cooling, water was added, an organic layer was separated, and the solvents were distilled. The crude product thus obtained was separated by silica gel column chromatography (utilizing a mixture solvent of dichloromethane and hexane) and recrystallized utilizing a mixture solvent of toluene and acetonitrile to produce 28.2 g of Compound H as a white solid (Yield 90%). The molecular weight of Compound H measured by FAB-MS was 430.

Formula 22

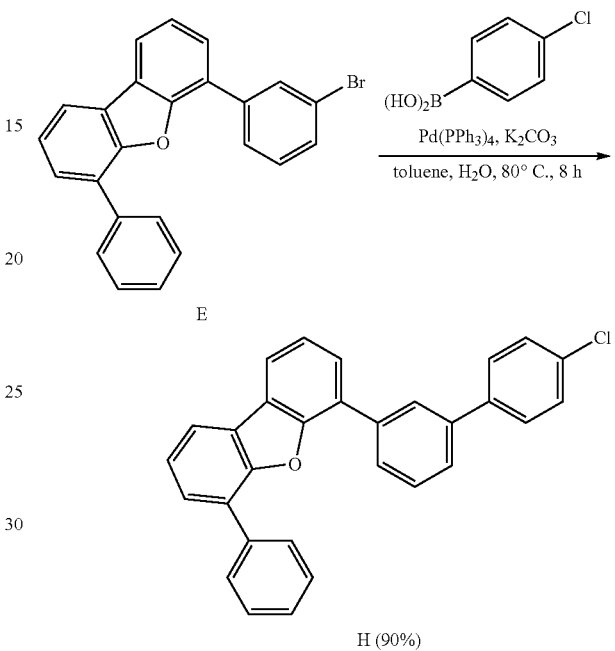

Synthesis of Compound 13

Compound 13 was synthesized by conducting substantially the same procedure described for synthesizing Compound 213 except for utilizing Compound H instead of 1-(4-bromophenyl)naphthalene and utilizing N-phenyl-1-naphthylamine instead of Compound G. The molecular weight of Compound 13 measured by FAB-MS was 614. The chemical shift values (δ) of Compound 13 measured by ¹H-NMR (CDCl₃) were 8.27-8.26 (2H, m), 8.02-7.89 (6H, m), 7.83-7.78 (2H, m), 7.72 (2H, d, J=6.0 Hz), 7.63 (2H, d, J=6.6 Hz), 7.56-7.39 (11H, m), 7.27-7.21 (3H, m), 7.14-7.09 (3H, m) 7.06 (2H, d, J=7.8 Hz), 6.97 (1H, d, J=6.0 Hz).

In addition, the material for an organic EL device according to an embodiment may be synthesized, for example, as follows.

Synthesis of Compound 23

Compound 23 was synthesized by conducting substantially the same procedure described for synthesizing Compound 213 except for utilizing 2-bromonaphthalene instead of 1-(4-bromophenyl)naphthalene. The molecular weight of Compound 23 measured by FAB-MS was 690. The chemical shift values (δ) of Compound 23 measured by ¹H-NMR (CDCl₃) were 8.25 (s, 1H), 8.00 (d, 1H, J=7.10 Hz), 7.99-7.88 (m, 3H), 7.82-7.75 (m, 4H), 7.73 (d, 1H, J=6.90 Hz), 7.62 (d, 1H, J=6.80 Hz), 7.60-7.48 (m, 16H), 7.32-7.22 (m, 3H), 7.18-7.11 (m, 5H).

In addition, the material for an organic EL device according to an embodiment may be synthesized, for example, as follows.

Synthesis of Compound 170

Synthesis of N-[4-(1-naphthalenyl)phenyl]-[1,1'-biphenyl]-4-amine

First, the following N-[4-(1-naphthalenyl)phenyl]-[1,1'-biphenyl]-4-amine was synthesized. Under an Ar atmosphere, 4.22 g of 4-bromobiphenyl, 4.05 g of 1-(4-aminophenyl)naphthalene, 0.78 g of (DPPF)PdCl$_2$, 1.60 g of DPPF and 1.77 g of NaOtBu were added to a 300 mL, three necked flask, followed by heating, refluxing and stirring in 120 mL of a mixture solvent of THF for about 3 hours. After air cooling, water was added, an organic layer was separated, and the solvents were distilled. The crude product thus obtained was separated by silica gel column chromatography (utilizing a mixture solvent of dichloromethane and hexane) and recrystallized utilizing a mixture solvent of toluene and ethanol to produce 6.31 g of a target product as a yellow solid (Yield 92%).

Formula 23

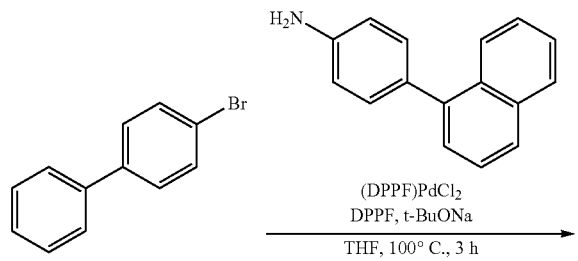

(DPPF)PdCl$_2$
DPPF, t-BuONa
THF, 100° C., 3 h

Formula 24

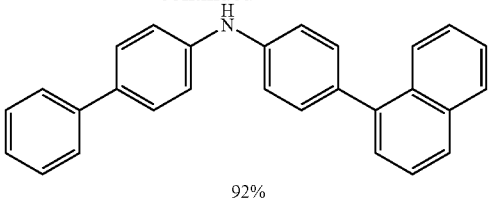

92%

Synthesis of Compound 170 in Formula 24

Under an Ar atmosphere, 3.59 g of Compound 1, 2.71 g of N-[4-(1-naphthalenyl)phenyl]-[1,1'-biphenyl]-4-amine, 0.30 g of Pd$_2$(dba)$_3$, 0.54 g of tri-tert-butylphosphine and 2.18 g of NaOtBu were added to a 200 mL, three necked flask, followed by heating, refluxing and stirring in 65 mL of a mixture solvent of toluene for about 4 hours (or about 6 hours). After air cooling, water was added, an organic layer was separated, and the solvents were distilled. The crude product thus obtained was separated by silica gel column chromatography (utilizing a mixture solvent of dichloromethane and hexane) and recrystallized utilizing a mixture solvent of toluene and ethanol to produce 4.19 g of Compound 170 as a yellow solid (Yield 81%). The molecular weight of Compound 170 measured by FAB-MS was 689. The chemical shift values (δ) of Compound 170 measured by $^1$H-NMR (CDCl$_3$) were 8.01-7.92 (m, 7H), 7.69-7.42 (m, 20H), 7.38-7.33 (m, 8H).

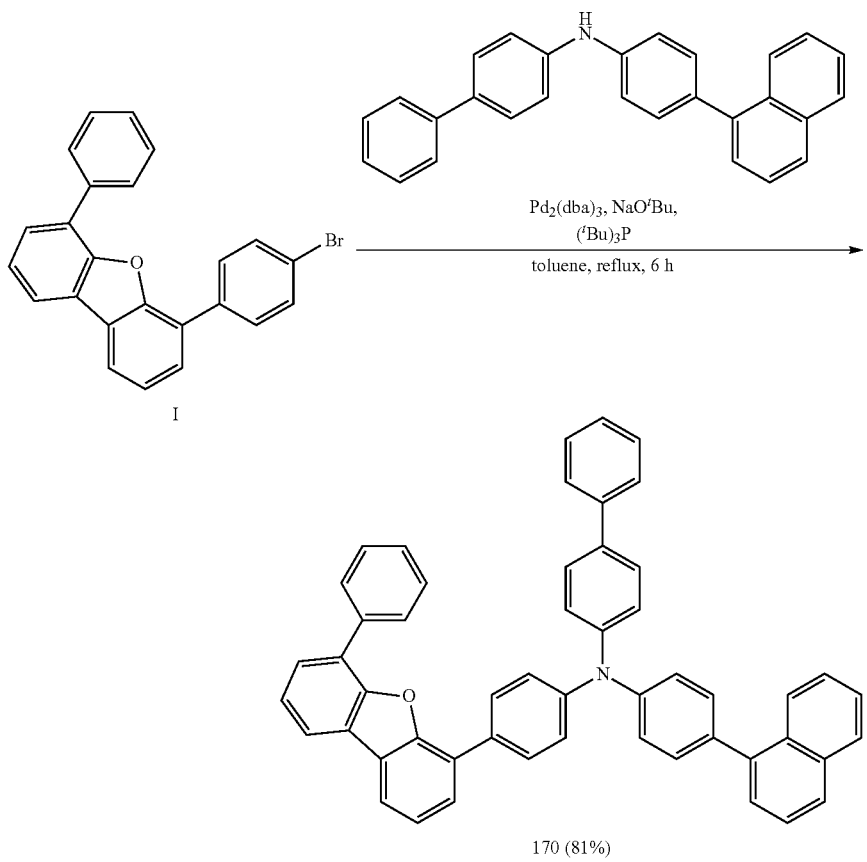

170 (81%)

In addition, the material for an organic EL device according to an embodiment may be synthesized, for example, as follows.

Synthesis of Compound 217

Compound 217 was synthesized by conducting substantially the same procedure described for synthesizing Compound 213 except for utilizing 1-iodonaphthalene instead of 1-(4-bromophenyl)naphthalene and utilizing Compound F instead of Compound G. The molecular weight of Compound 217 measured by FAB-MS was 664. The chemical shift values (δ) of Compound 217 measured by $^1$H-NMR (CDCl$_3$) were 8.24 (t, 1H, J=1.2 Hz), 8.11 (d, 2H, J=8.6 Hz), 7.98-7.84 (m, 6H), 7.78-7.69 (m, 4H), 7.63-7.31 (m, 15H), 7.20 (t, 2H, J=7.5 Hz), 6.98 (t, 1H, J=7.4 Hz), 6.72 (d, 2H, J=8.7 Hz).

In addition, the material for an organic EL device according to an embodiment may be synthesized, for example, as follows.

Synthesis of Compound 218

Synthesis of
N-[4-(1-naphthalenyl)phenyl]-phenyl-4-amine

First, the following N-[4-(1-naphthalenyl)phenyl]-phenyl-4-amine was synthesized. Substantially the same procedure described for synthesizing N-[4-(1-naphthalenyl)phenyl]-[1,1'-biphneyl]-4-amine was conducted except for utilizing dibromobenzene instead of 4-bromobiphenyl. The molecular weight measured by FAB-MS was 295.

Formula 25

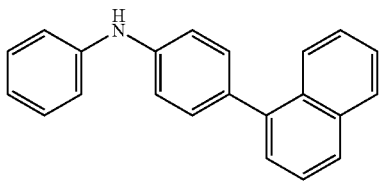

Synthesis of Compound 218

Compound 218 was synthesized by conducting substantially the same procedure described for synthesizing Compound 213 except for utilizing Compound H instead of 1-(4-bromophenyl)naphthalene and utilizing N-[4-(1-naphthalenyl)phenyl]-phenyl-4-amine instead of Compound G. The molecular weight of Compound 218 measured by FAB-MS was 690. The chemical shift values (δ) of Compound 218 measured by $^1$H-NMR (CDCl$_3$) were 8.31 (S, 1H), 8.08-8.02 (m, 1H), 7.99-7.78 (m, 7H), 7.72 (d, 1H, J=7.5 Hz), 7.64-7.21 (m, 24H), 7.09 (t, 1H, J=7.2).

In addition, the material for an organic EL device according to an embodiment may be synthesized, for example, as follows.

Synthesis of Compound 220

Synthesis of 4-(1-naphthalenyl)-N-[4-(1-naphthalenyl)phenyl]-benzenamine

First, the following 4-(1-naphthalenyl)-N-[4-(1-naphthalenyl)phenyl-benzenamine was synthesized. Substantially the same procedure described for synthesizing N-[4-(1-naphthalenyl)phenyl]-[1,1'-biphneyl]-4-amine was conducted except for utilizing 1-(4-bromophenyl)naphthalene instead of 4-bromobiphenyl. The molecular weight measured by FAB-MS was 421.

Formula 26

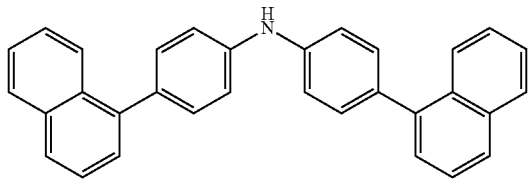

Synthesis of Compound 220

Compound 220 was synthesized by conducting substantially the same procedure described for synthesizing Compound 213 except for utilizing Compound H instead of 1-(4-bromophenyl)naphthalene and utilizing 4-(1-naphthalenyl)-N-[4-(1-naphthalenyl)phenyl]-benzenamine instead of Compound G. The molecular weight of Compound 220 measured by FAB-MS was 816. The chemical shift values (δ) of Compound 220 measured by $^1$H-NMR (CDCl$_3$) were 8.78 (d, J=7.8 Hz, 2H), 8.70 (d, J=7.8 Hz, 2H), 8.29 (d, J=8.1 Hz, 2H), 8.24 (t, J=1.5 Hz, 1H), 7.95 (d, J=7.8 Hz, 2H), 7.84 (d, J=7.8 Hz, 2H), 7.79 (d, J=8.0 Hz, 1H), 7.73-7.38 (m, 20H), 7.18 (t, J=7.5 Hz, 2H), 6.98 (t, J=7.5 Hz, 1H), 6.89 (d, J=7.8 Hz, 2H).

In addition, the material for an organic EL device according to an embodiment may be synthesized, for example, as follows.

Synthesis of Compound 222

Synthesis of
N-9-phenanthrenyl-9-phenanthrenamine

First, the following N-9-phenanthrenyl-9-phenanthrenamine was synthesized. Substantially the same procedure described for synthesizing N-[4-(1-naphthalenyl)phenyl]-[1,1'-biphneyl]-4-amine was conducted except for utilizing 9-bromophenanthrene instead of 4-bromobiphenyl and utilizing 9-aminophenanthrene instead of 1-(4-aminophenyl) naphthalene. The molecular weight measured by FAB-MS was 369.

Formula 27

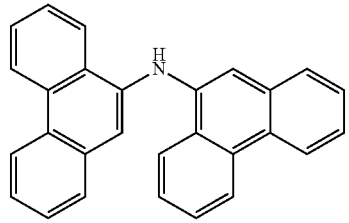

Synthesis of Compound 222

Compound 222 was synthesized by conducting substantially the same procedure described for synthesizing Compound 213 except for utilizing Compound H instead of 1-(4-bromophenyl)naphthalene and utilizing N-9-phenanthrenyl-9-phenanthrenamine instead of Compound G. The molecular weight of Compound 222 measured by FAB-MS was 764. The chemical shift values (δ) of Compound 222 measured by $^1$H-NMR (CDCl$_3$) were 8.78 (d, J=7.8 Hz, 2H), 8.70 (d, J=7.8 Hz, 2H), 8.29 (d, J=8.1 Hz, 2H), 8.24 (t, J=1.5 Hz, 1H), 7.95 (d, J=7.8 Hz, 2H), 7.84 (d, J=7.8 Hz, 2H), 7.79 (d, J=8.0 Hz, 1H), 7.73-7.38 (m, 20H), 7.18 (t, J=7.5 Hz, H), 6.98 (t, J=7.5 Hz, 1H), 6.89 (d, J=7.8 Hz, 2H).

In addition, the material for an organic EL device according to an embodiment may be synthesized, for example, as follows.

Synthesis of Compound 225

Synthesis of N-[4-(1-naphthalenyl)phenyl]-1-naphthalenamine

First, the following N-[4-(1-naphthalenyl)phenyl]-1-naphthalenamine was synthesized. Substantially the same procedure described for synthesizing N-[4-(1-naphthalenyl)phenyl]-[1,1'-biphneyl]-4-amine was conducted except for utilizing 1-iodonaphthalene instead of 4-bromobiphenyl. The molecular weight measured by FAB-MS was 345.

Formula 28

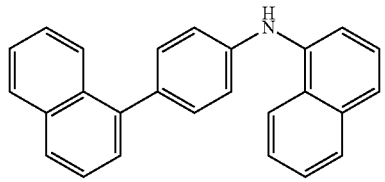

Synthesis of Compound 225

Compound 225 was synthesized by conducting substantially the same procedure described for synthesizing Compound 213 except for utilizing Compound E instead of 1-(4-bromophenyl)naphthalene and utilizing N-[4-(1-naphthalenyl)phenyl]-1-naphthalenamine instead of Compound G. The molecular weight of Compound 225 measured by FAB-MS was 664. The chemical shift values (δ) of Compound 225 measured by $^1$H-NMR (CDCl$_3$) were 8.08 (d, 1H, J=8.1 Hz), 7.98-7.84 (m, 7H), 7.83-7.75 (m, 3H), 7.64 (d, 1H, J=7.5 Hz), 7.56 (d, 1H, J=7.8 Hz), 7.54-7.43 (m, 8H), 7.43-7.33 (m, 6H), 7.25 (m, 3H), 7.16 (d, 2H, J=8.4 Hz), 7.12 (m, 1H).

In addition, the material for an organic EL device according to an embodiment may be synthesized, for example, as follows.

Synthesis of Compound 226

Compound 226 was synthesized by conducting substantially the same procedure described for synthesizing Compound 213 except for utilizing Compound E instead of 1-(4-bromophenyl)naphthalene and utilizing 4-(1-naphthalenyl)-N-[4-(1-naphthalenyl)phenyl]-benzenamine instead of Compound G. The molecular weight of Compound 226 measured by FAB-MS was 740. The chemical shift values (δ) of Compound 226 measured by $^1$H-NMR (CDCl$_3$) were 8.02 (d, 2H, J=8.4), 7.96-7.81 (m, 9H), 7.69-7.56 (m, 3H), 7.54-7.30 (m, 23H).

In addition, the material for an organic EL device according to an embodiment may be synthesized, for example, as follows.

Synthesis of Compound 229

Compound 229 was synthesized by conducting substantially the same procedure described for synthesizing Compound 213 except for utilizing Compound I instead of 1-(4-bromophenyl)naphthalene and utilizing 1,1'-dinaphthylamine instead of Compound G. The molecular weight of Compound 229 measured by FAB-MS was 588. The chemical shift values (δ) of Compound 229 measured by $^1$H-NMR (CDCl$_3$) were 8.12 (d, 2H, J=8.70 Hz), 7.95-7.86 (m, 6H), 7.77-7.73 (m, 4H), 7.65 (dd, 1H, J=1.20, 7.60 Hz), 7.58 (dd, 1H, J=1.20, 7.60 Hz), 7.52-7.47 (m, 2H), 7.46-7.28 (m, 11H), 6.81 (d, 1H, J=9.00 Hz).

In addition, the material for an organic EL device according to an embodiment may be synthesized, for example, as follows.

Synthesis of Compound 231

Compound 231 was synthesized by conducting substantially the same procedure described for synthesizing Compound 213 except for utilizing Compound I instead of 1-(4-bromophenyl)naphthalene and utilizing N-[4-(1-naphthalenyl)phenyl]-1-naphthalenamine instead of Compound G. The molecular weight of Compound 231 measured by FAB-MS was 664. The chemical shift values (δ) of Compound 231 measured by $^1$H-NMR (CDCl$_3$) were 8.09 (d, J=8.0 Hz, 1H), 8.05 (d, J=8.1 Hz, 1H), 8.00-7.81 (m, 10H), 7.66 (d, J=7.8 Hz, 1H), 7.62 (d, J=7.8 Hz, 1H), 7.60-7.33 (m, 15H), 7.29-7.2 (m, 4H).

In addition, the material for an organic EL device according to an embodiment may be synthesized, for example, as follows.

Synthesis of Compound 232

Compound 232 was synthesized by conducting substantially the same procedure described for synthesizing Compound 213 except for utilizing Compound I instead of 1-(4-bromophenyl)naphthalene and utilizing 4-(1-naphthalenyl)phenyl]-N-[4-(1-naphthalenyl)phenyl]-benzenamine instead of Compound G. The molecular weight of Compound 232 measured by FAB-MS was 740. The chemical shift values (δ) of Compound 232 measured by $^1$H-NMR (CDCl$_3$) were 8.10 (m, 2H), 7.95-8.05 (m, 7H), 7.87 (d, 2H, J=7.90 Hz), 7.70 (dd, 1H, J1=1, 20 Hz, J2=3, 70 Hz), 7.67 (dd, 1H, J1=1, 20 Hz, J2=3, 70 Hz), 7.58-7.34 (m, 21H), 7.24-7.28 (m, 2H), 7.17 (d, 1H, J=7.10 Hz).

In addition, the material for an organic EL device according to an embodiment may be synthesized, for example, as follows.

Synthesis of Compound 243

Compound 243 was synthesized by conducting substantially the same procedure described for synthesizing Compound 213 except for utilizing 1-(3-bromophenyl)naphthalene instead of 1-(4-bromophenyl)naphthalene. The molecular weight of Compound 243 measured by FAB-MS was 766. The chemical shift values (δ) of Compound 243 measured by $^1$H-NMR (CDCl$_3$) were 8.29 (t, 1H, J=1.2 Hz), 8.01-7.81 (m, 8H), 7.73 (dd, 1H, J=7.62 Hz), 7.66-7.40 (m, 18H), 7.35-7.28 (m, 8H), 7.22-7.16 (m, 3H).

In addition, the material for an organic EL device according to an embodiment may be synthesized, for example, as follows.

Synthesis of Compound 244

Synthesis of N-[1,1'-biphenyl]-4-yl-9-phenanthrenamine

First, the following N-[1,1'-biphenyl]-4-yl-9-phenanthrenamine was synthesized. Substantially the same procedure described for synthesizing N-[4-(1-naphthalenyl)phenyl]-[1,1'-biphenyl]-4-amine was conducted except for utilizing 9-aminophenanthrene instead of 1-(4-aminophenyl)naphthalene. The molecular weight measured by FAB-MS was 345.

[Formula 29]

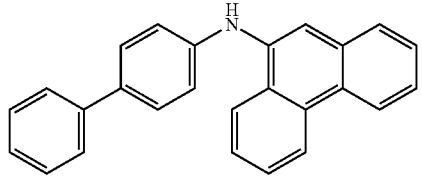

Synthesis of Compound 244

Compound 244 was synthesized by conducting substantially the same procedure described for synthesizing Compound 213 except for utilizing Compound H instead of 1-(4-bromophenyl)naphthalene and utilizing N-[1,1'-biphenyl]-4-yl-9-phenanthrenamine instead of Compound G. The molecular weight of Compound 244 measured by FAB-MS was 740. The chemical shift values (δ) of Compound 244 measured by $^1$H-NMR (CDCl$_3$) were 8.78 (d, J=8.0 Hz, 1H), 8.74 (d, J=8.0 Hz, 1H), 8.28 (t, J=1.2 Hz, 1H), 8.13 (d, J=8.0 Hz, 1H), 7.97 (d, J=8.0 Hz, 2H), 7.87 (d, J=8.1 Hz, 2H), 7.81 (d, J=8.1 Hz, 2H), 7.75-7.36 (m, 19H), 7.34-7.16 (m, 6H), 7.11 (t, J=7.5 Hz, 2H).

In addition, the material for an organic EL device according to an embodiment may be synthesized, for example, as follows.

Synthesis of Compound 245

Synthesis of N-[1,1'-biphenyl]-4-yl-2-phenanthrenamine

First, the following N-[1,1'-biphenyl]-4-yl-2-phenanthrenamine was synthesized. Substantially the same procedure described for synthesizing N-[4-(1-naphthalenyl)phenyl]-[1,1'-biphenyl]-4-amine was conducted except for utilizing 2-aminophenanthrene instead of 1-(4-aminophenyl)naphthalene. The molecular weight measured by FAB-MS was 345.

Formula 30

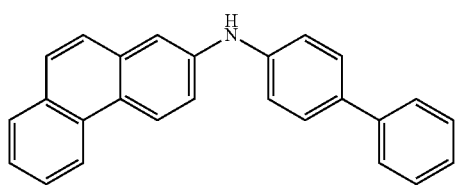

Synthesis of Compound 245

Compound 245 was synthesized by conducting substantially the same procedure described for synthesizing Compound 213 except for utilizing Compound E instead of 1-(4-bromophenyl)naphthalene and utilizing N-[1,1'-biphenyl]-4-yl-2-phenanthrenamine instead of Compound G. The molecular weight of Compound 245 measured by FAB-MS was 664. The chemical shift values (δ) of Compound 245 measured by $^1$H-NMR (CDCl$_3$) were 8.56 (d, J=7.8 Hz, 1H), 8.52 (d, J=8.0 Hz, 1H), 8.00-7.91 (m, 4H), 7.83 (d, J=8.0 Hz, 1H), 7.77 (t, J=1.5 Hz, 1H), 7.71-7.24 (m, 25H).

In addition, the material for an organic EL device according to an embodiment may be synthesized, for example, as follows.

Synthesis of Compound 246

Synthesis of Compound M in Formula 31

First, the following Compound M was synthesized. Under an Ar atmosphere, 29.0 g of Compound E, 13.4 g of 3-chlorophenylboronic acid, 3.14 g of Pd(PPh$_3$)$_4$, and 38.8 g of K$_2$CO$_3$ were added to a 1,000 mL, three necked flask, followed by heating and stirring in a mixture solvent of 300 mL of toluene and 60 ml of water at about 80° C. for about 4 hours (or about 8 hours). After air cooling, water was added, an organic layer was separated, and the solvents were distilled. The crude product thus obtained was separated utilizing silica gel column chromatography (utilizing a mixture solvent of dichloromethane and hexane) and recrystallized utilizing a mixture solvent of toluene and acetonitrile to produce 28.2 g of Compound M as a white solid (Yield 90%). The molecular weight of Compound M measured by FAB-MS was 430.

Formula 31

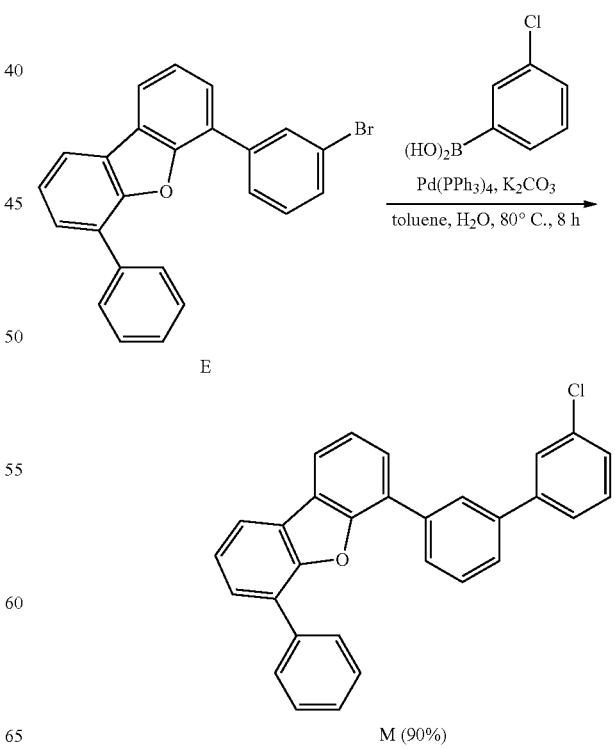

Synthesis of Compound 246

Compound 246 was synthesized by conducting substantially the same procedure described for synthesizing Compound 213 except for utilizing Compound M instead of 1-(4-bromophenyl)naphthalene and utilizing N-[4-(1-naphthalenyl)phenyl]-[1,1'-biphenyl]-4-amine instead of Compound G. The molecular weight of Compound 246 measured by FAB-MS was 766. The chemical shift values (δ) of Compound 246 measured by $^1$H-NMR (CDCl$_3$) were 8.28 (s, 1H), 8.05-7.80 (m, 8H), 7.70 (t, 2H, J=8.2 Hz), 7.62-7.25 (m, 28H).

solvent of toluene for about 5 hours (or about 6 hours). After air cooling, water was added, an organic layer was separated, and the solvents were distilled. The crude product thus obtained was separated utilizing silica gel column chromatography (utilizing a mixture solvent of dichloromethane and hexane) and recrystallized utilizing a mixture solvent of toluene and ethanol to produce 5.50 g of Compound 251 as a white solid (Yield 80%). The molecular weight of Compound 251 measured by FAB-MS was 689. The chemical shift values (δ) of Compound 251 measured by $^1$H-NMR (CDCl$_3$) were 8.00 (d, J=8.4 Hz, 1H), 7.98-7.93 (m, 4H), 7.89 (d, J=8.1 Hz, 1H), 7.83 (d, J=8.4 Hz, 1H), 7.79 (t, J=2.1 Hz, 1H), 7.68-7.65 (m, 2H), 7.62-7.53 (m, 3H), 7.52-7.26 (m, 22H).

Formula 32

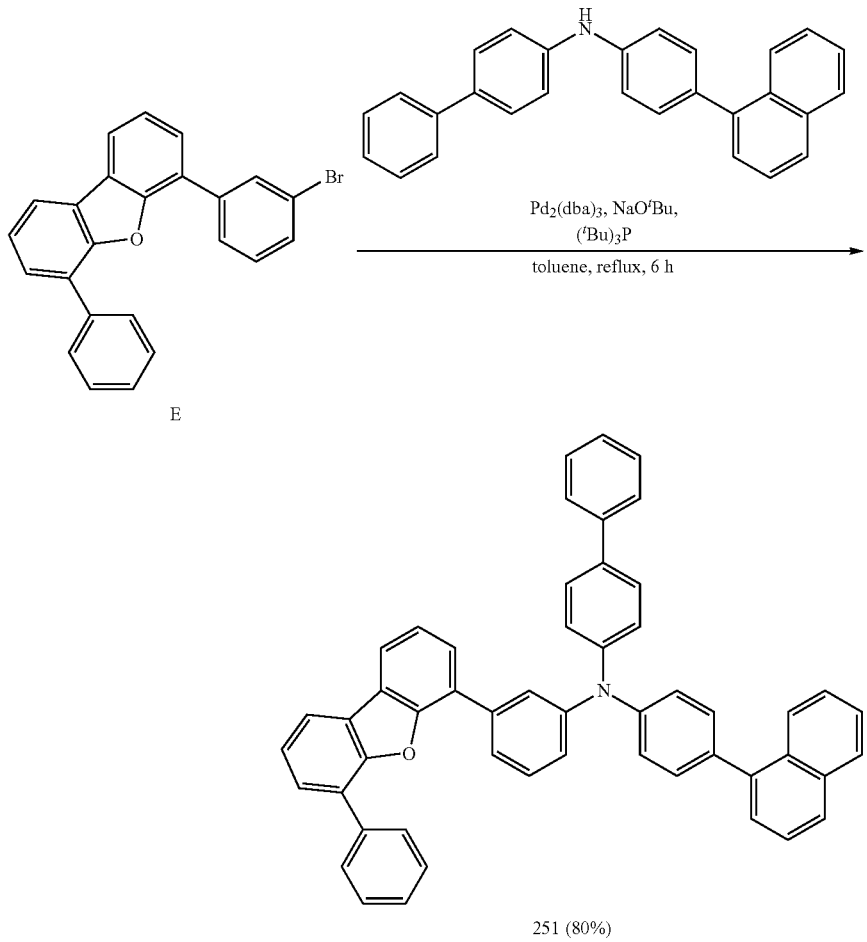

251 (80%)

In addition, the material for an organic EL device according to an embodiment may be synthesized, for example, as follows.

Synthesis of Compound 251 in Formula 32

Under an Ar atmosphere, 4.79 g of Compound E, 3.71 g of N-[4-(1-naphthalenyl)phenyl]-[1,1'-biphenyl]-4-amine, 0.40 g of Pd$_2$(dba)$_3$, 0.72 g of tri-tert-butylphosphine and 2.90 g of NaOtBu were added to a 200 mL, three necked flask, followed by heating and stirring in 87 mL of a mixture In addition, the material for an organic EL device according to an embodiment may be synthesized, for example, as follows.

Synthesis of Compound 235

Synthesis of Compound J in Formula 33

First, the following Compound J was synthesized. Under an Ar atmosphere, 27.6 g of Compound E, 12.4 g of 4-chlorophenylboronic acid, 3.10 g of Pd(PPh$_3$)$_4$, and 37.8 g of K$_2$CO$_3$ were added to a 1,000 mL, three necked flask, followed by heating and stirring in a mixture solvent of 300 mL of toluene and 60 ml of water at about 80° C. for about 4 hours (or about 8 hours). After air cooling, water was added, an organic layer was separated, and the solvents were distilled. The crude product thus obtained was separated utilizing silica gel column chromatography (utilizing a mixture solvent of dichloromethane and hexane) and recrystallized utilizing a mixture solvent of toluene and acetonitrile to produce 26.8 g of Compound J as a white solid (Yield 90%). The molecular weight of Compound J measured by FAB-MS was 430.

Formula 33

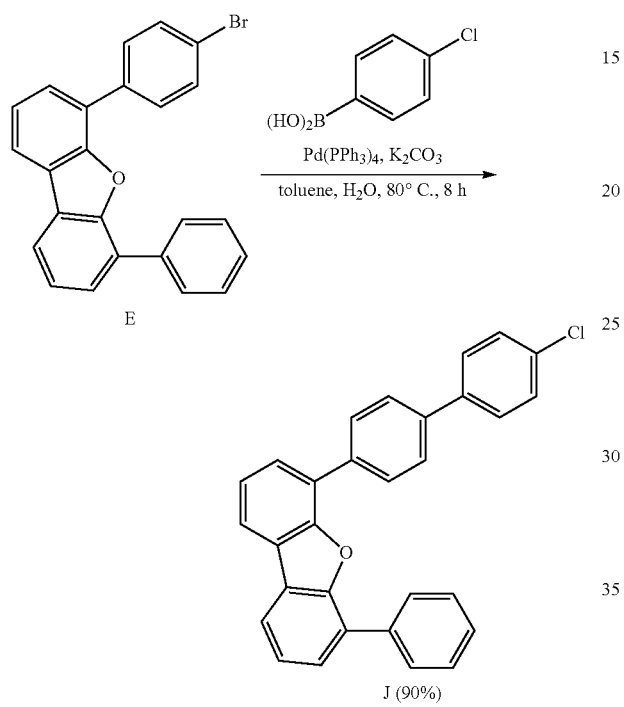

Synthesis of Compound 235

Compound 235 was synthesized by conducting substantially the same procedure described for synthesizing Compound 213 except for utilizing Compound J instead of 1-(4-bromophenyl)naphthalene and utilizing 1,1'-dinaphthylamine instead of Compound G. The molecular weight of Compound 235 measured by FAB-MS was 664. The chemical shift values (δ) of Compound 235 measured by $^1$H-NMR (CDCl$_3$) were 8.22-8.15 (4H, m), 8.07 (2H, d, J=7.80 Hz), 8.03-7.90 (4H, m), 7.81-7.69 (8H, m), 7.50-7.35 (9H, m), 7.37-7.28 (6H, m).

In addition, the material for an organic EL device according to an embodiment may be synthesized, for example, as follows.

Synthesis of Compound 242

Synthesis of Compound K in Formula 34

Under an Ar atmosphere, 8.51 g of 4-phenylphenol, 10.0 g of 3-bromo-2-fluoro-benzonitrile, and 13.8 g of potassium carbonate were added to a 200 mL, three necked flask, followed by heating and refluxing in 72 mL of a mixture solvent of DMF for about 3 hours (or about 4 hours). After air cooling, water and ethyl acetate were added, an organic layer was separated, and the solvents were distilled. To the crude product thus obtained, 20.0 g of sodium hydroxide, 140 mL of dioxane, 140 mL of ethanol and 60 mL of water were added, followed by heating and refluxing for about 20 hours (or about 24 hours). The crude product thus obtained was separated utilizing silica gel column chromatography (utilizing a mixture solvent of dichloromethane and methanol) and recrystallized utilizing a mixture solvent of toluene and ethanol to produce 14.2 g of a target product (Compound K) as a yellow solid (Yield 77%).

Formula 34

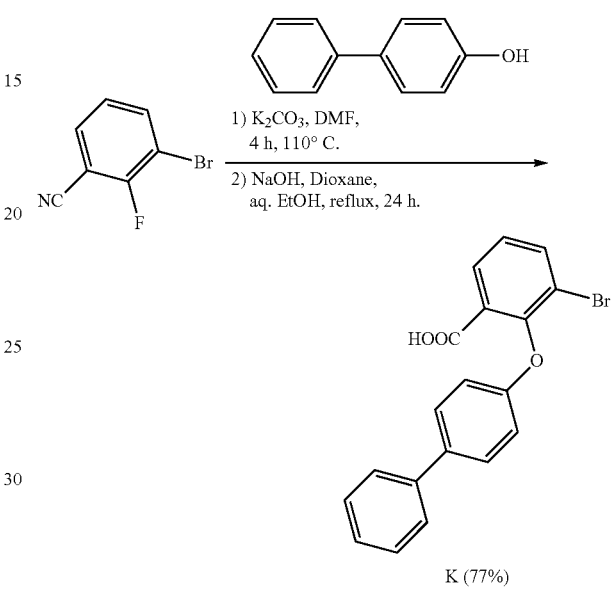

Synthesis of Compound L in Formula 35

Under an Ar atmosphere, 6.80 g of Compound K, 0.343 g of Rh(acac)(cod), and 1.53 g of potassium iodide were added to a 30 mL, two necked flask, followed by heating and stirring in 5.22 mL of a Ac$_2$O solvent at about 160° C. for about 10 hours. After air cooling, water and chloroform were added, an organic layer was separated, and the solvents were distilled. The crude product thus obtained was separated utilizing silica gel column chromatography (utilizing a mixture solvent of dichloromethane and hexane) and recrystallized utilizing a mixture solvent of toluene and hexane to produce 1.19 g of a target product (Compound L) as a yellow solid (Yield 20%).

Formula 35

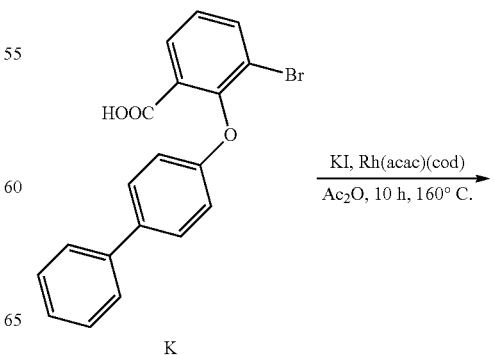

-continued

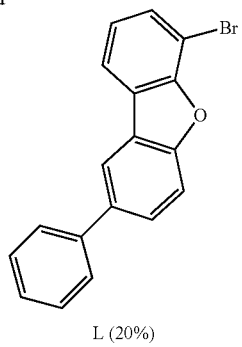

L (20%)

Synthesis of Compound 242 in Formula 36

The following Compound 242 was synthesized. Under an Ar atmosphere, 1.51 g of Compound A, 0.85 g of Compound L, 1.54 g of Pd(PPh₃)₄, and 1.65 g of K₂CO₃ were added to a 300 mL, three necked flask, followed by heating and stirring in a mixture solvent of 20 mL of toluene and 5 ml of water at about 90° C. for about 8 hours. After air cooling, water was added, an organic layer was separated, and the solvents were distilled. The crude product thus obtained was separated utilizing silica gel column chromatography (utilizing a mixture solvent of dichloromethane and hexane) and recrystallized utilizing a mixture solvent of toluene and hexane to produce 1.48 g of Compound 242 as a white solid (Yield 88%). The molecular weight of Compound 242 measured by FAB-MS was 640. The chemical shift values (δ) of Compound 242 measured by ¹H-NMR (CDCl₃) were 8.15 (d, 1H, J=1.20 Hz), 8.01 (d, 1H, J=8.10 Hz), 7.79 (d, 1H, J=0.90 Hz), 7.71-7.68 (m, 3H), 7.65-7.51 (m, 13H), 7.47 (d, 1H, J=7.80 Hz), 7.43-7.21 (m, 13H).

Formula 36

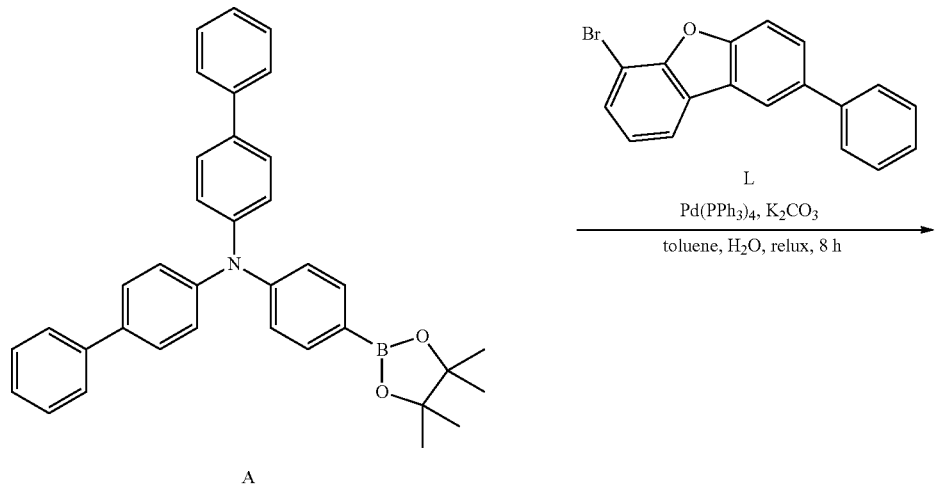

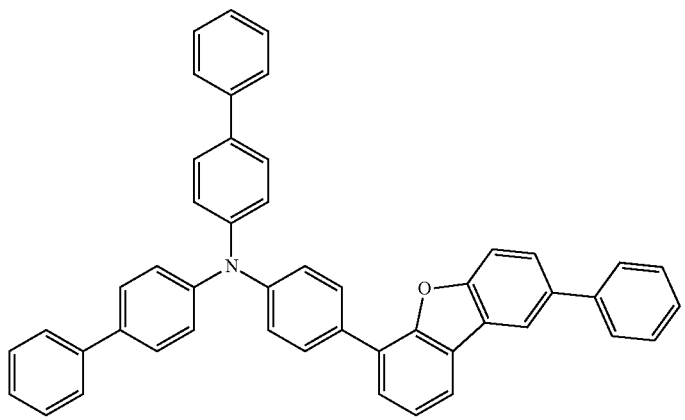

242 (88%)

Synthesis of Compound 248

Synthesis of Compound N in Formula 37

The following Compound N was synthesized. Under an Ar atmosphere, 1.02 g of biphenylboronic acid, 3.70 g of 4,6-dibromodibenzofuran, 0.24 g of Pd(PPh$_3$)$_4$, and 1.00 g of potassium carbonate were added to a 300 mL, three necked flask, followed by heating and stirring in a mixture solvent of 50 mL of toluene and 20 mL of water at about 90° C. for about 8 hours. After air cooling, water was added, an organic layer was separated, and the solvents were distilled. The crude product thus obtained was separated utilizing silica gel column chromatography (utilizing a mixture solvent of dichloromethane and hexane) and recrystallized utilizing a mixture solvent of toluene and hexane to produce 1.08 g of Compound N as a white solid (Yield 54%). The molecular weight of Compound N measured by FAB-MS was 399.

Formula 37

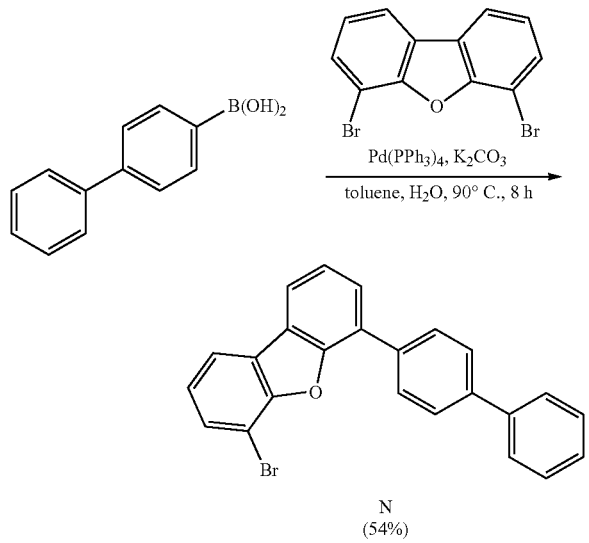

Synthesis of Compound 248

Compound 248 was synthesized by conducting substantially the same procedure described for synthesizing Compound D except for utilizing Compound N instead of 4,6-dibromodibenzofuran and utilizing Compound A instead of Compound C. The molecular weight of Compound 248 measured by FAB-MS was 716. The chemical shift values (δ) of Compound 248 measured by $^1$H-NMR (CDCl$_3$) were 8.09 (d, 2H, J=8.40 Hz), 8.01-7.89 (m, 4H), 7.74-7.72 (m, 3H), 7.68-7.42 (m, 17H), 7.37-7.21 (m, 11H). From the results, the synthesized white solid was determined as Compound 248.

In addition, the material for an organic EL device according to an embodiment may be synthesized, for example, as follows.

Synthesis of Compound 253

Synthesis of N-[4-(2-naphthalenyl)phenyl]-[1,1'-biphenyl]-4-amine

First, the following N-[4-(2-naphthalenyl)phenyl]-[1,1'-biphenyl]-4-amine was synthesized. Substantially the same procedure described for synthesizing N-[4-(1-naphthalenyl)phenyl]-[1,1'-biphenyl]-4-amine was conducted except for utilizing 2-(4-aminophenyl)naphthalene instead of 1-(4-aminophenyl)naphthalene. The molecular weight measured by FAB-MS was 371.

Formula 38

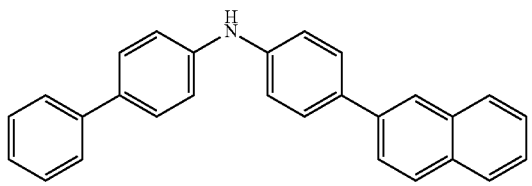

Synthesis of Compound 253

Compound 253 was synthesized by conducting substantially the same procedure described for synthesizing Compound 213 except for utilizing Compound H instead of 1-(4-bromophenyl)naphthalene and utilizing N-[4-(2-naphthalenyl)phenyl]-[1,1'-biphenyl]-4-amine instead of Compound G. The molecular weight of Compound 253 measured by FAB-MS was 766. The chemical shift values (δ) of Compound 253 measured by $^1$H-NMR (CDCl$_3$) were 8.32 (t, J=1.5 Hz, 1H), 8.05 (s, 1H), 8.02-7.97 (m, 2H), 7.96-7.82 (m, 6H), 7.78-7.73 (m, 2H), 7.72-7.53 (m, 11H), 7.52-7.41 (m, 6H), 7.37-7.24 (m, 10H).

In addition, the material for an organic EL device according to an embodiment may be synthesized, for example, as follows.

Synthesis of Compound 254

Synthesis of N-2-dibenzofuranyl-2-dibenzofuranamine

The following N-2-dibenzofuranyl-2-dibenzofuranamine was synthesized. Substantially the same procedure described for synthesizing N-[4-(1-naphthalenyl)phenyl]-[1,1'-biphenyl]-4-amine was conducted except for utilizing 3-bromodibenzofuran instead of 4-bromobiphenyl and utilizing 3-aminodibenzofuran instead of 1-(4-aminophenyl)naphthalene. The molecular weight measured by FAB-MS was 349.

Formula 39

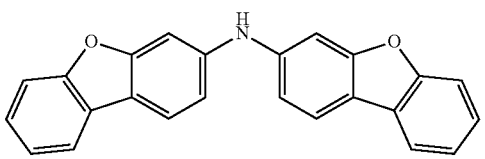

Synthesis of Compound 254

Compound 254 was synthesized by conducting substantially the same procedure described for synthesizing Compound 213 except for utilizing Compound H instead of 1-(4-bromophenyl)naphthalene and utilizing N-2-dibenzofuranyl-2-dibenzofuranamine instead of Compound G. The molecular weight of Compound 254 measured by FAB-MS was 668. The chemical shift values (δ) of Compound 254 measured by $^1$H-NMR (CDCl$_3$) were 7.99-7.95 (m, 8H), 7.83 (d, 2H, J=8.4 Hz), 7.66 (d, 2H, J=7.8 Hz), 7.54-7.29 (m, 15H), 7.23 (d, 2H, J=8.4 Hz).

In addition, the material for an organic EL device according to an embodiment may be synthesized, for example, as follows.

Synthesis of Compound 256

Synthesis of N-[1,1'-biphenyl]-4-yl-1-naphthalenamine

The following N-[1,1'-biphenyl]-4-yl-1-naphthalenamine was synthesized. Substantially the same procedure described for synthesizing N-[4-(1-naphthalenyl)phenyl]-[1,1'-biphenyl]-4-amine was conducted except for utilizing 1-aminonaphthalene instead of 1-(4-aminophenyl)naphthalene. The molecular weight measured by FAB-MS was 295.

Formula 40

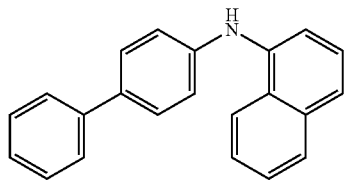

Synthesis of Compound 256

Compound 256 was synthesized by conducting substantially the same procedure described for synthesizing Compound 213 except for utilizing Compound I instead of 1-(4-bromophenyl)naphthalene and utilizing N-[1,1'-biphenyl]-4-yl-1-naphthaleneamine instead of Compound G. The molecular weight of Compound 256 measured by FAB-MS was 614. The chemical shift values (δ) of Compound 256 measured by $^1$H-NMR (CDCl$_3$) were 8.02 (d, 1H, J=8.50 Hz), 7.90-7.88 (m, 5H), 7.84-7.80 (m, 3H), 7.68-7.37 (m, 17H), 7.29 (dt, 1H, J=9.10, 2.30 Hz), 7.23-7.15 (m, 4H).

In addition, the material for an organic EL device according to an embodiment may be synthesized, for example, as follows.

Synthesis of Compound 257

Compound 257 was synthesized by conducting substantially the same procedure described for synthesizing Compound 213 except for utilizing Compound E instead of 1-(4-bromophenyl)naphthalene and utilizing N-[1,1'-biphenyl]-4-yl-[1,1'-biphenyl]-4-amine instead of Compound G. The molecular weight of Compound 257 measured by FAB-MS was 640. The chemical shift values (δ) of Compound 257 measured by $^1$H-NMR (CDCl$_3$) were 7.95 (m, 4H), 7.74 (m, 1H), 7.66 (m, 1H), 7.64 (m, 1H), 7.58 (m, 2H), 7.55 (m, 3H), 7.54-7.15 (m, 21H).

In addition, the material for an organic EL device according to an embodiment may be synthesized, for example, as follows.

Synthesis of Compound 258

Compound 258 was synthesized by conducting substantially the same procedure described for synthesizing Compound 213 except for utilizing Compound E instead of 1-(4-bromophenyl)naphthalene and utilizing N-[1,1'-biphenyl]-4-yl-1-naphthalenamine instead of Compound G. The molecular weight of Compound 258 measured by FAB-MS was 614. The chemical shift values (δ) of Compound 258 measured by $^1$H-NMR (CDCl$_3$) were 8.01 (d, 1H, J=8.44 Hz), 7.99-7.90 (m, 4H), 7.88 (d, 1H, J=8.44 Hz), 7.77 (d, 1H, J=7.92 Hz), 7.71 (t, 1H, J=1.98 Hz), 7.64 (dd, 1H, J=1.23, 7.61 Hz), 7.57-7.22 (m, 19H), 7.11 (dt, 2H, J=9.14, 2.39 Hz), 7.04 (ddd, 1H, J=8.13, 2.31, 1.00 Hz).

EXAMPLES

Organic EL devices according to Examples 1 to 9 were manufactured utilizing the hole transport materials of Compound 5, Compound 17, Compound 77, Compound 89, Compound 141, Compound 169, Compound 181, Compound 213 and Compound 216 by the above-described manufacturing method.

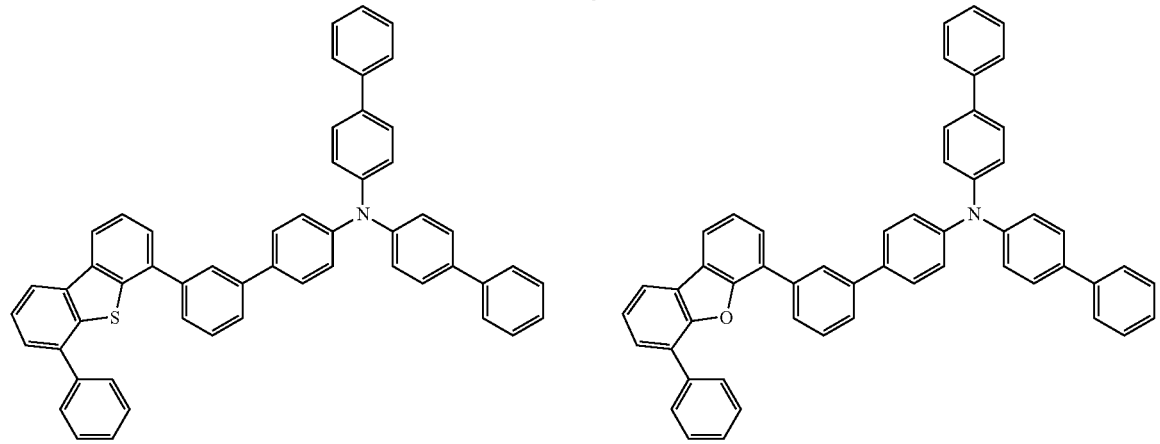

-continued
77
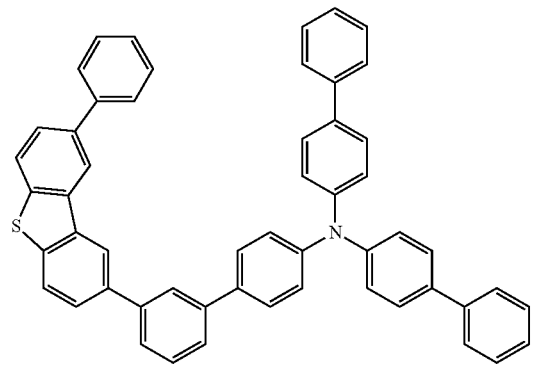
89
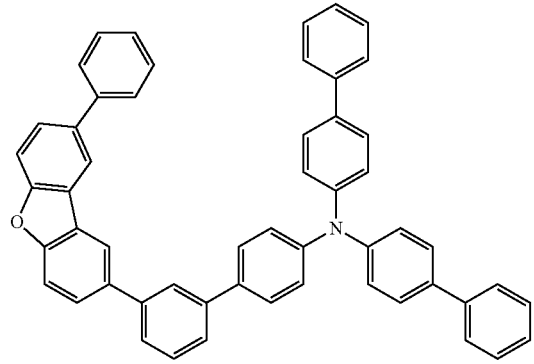
141
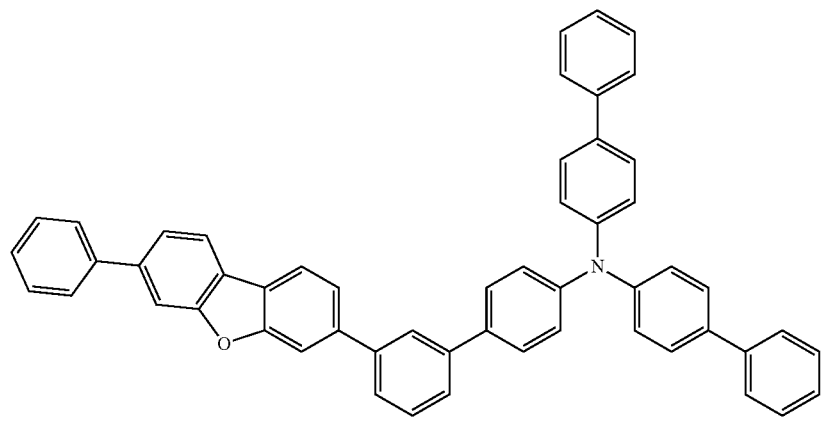
169
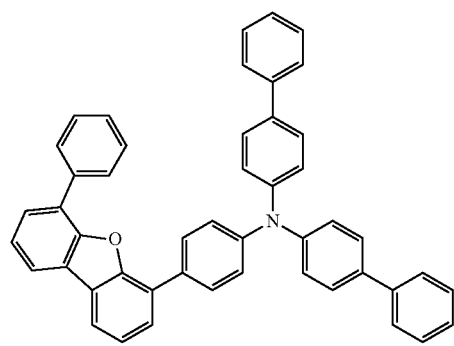
181
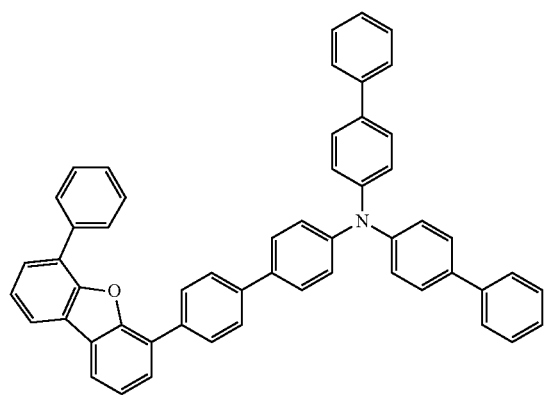

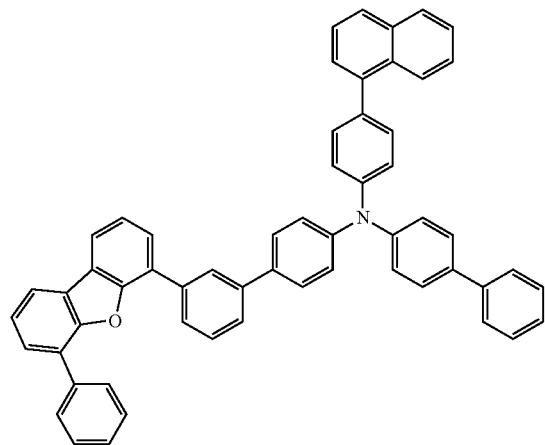
213
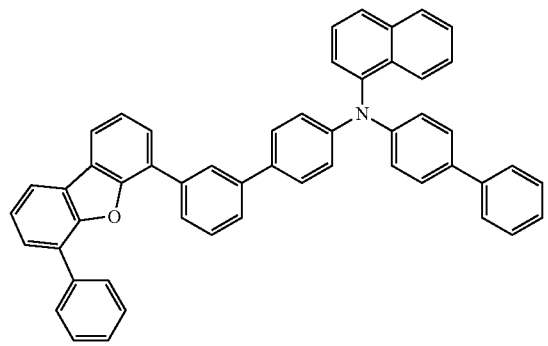
216
As Comparative Examples, organic EL devices according to Comparative Examples 1 to 5 were manufactured utilizing hole transport materials of Comparative Compounds C1 to C5.
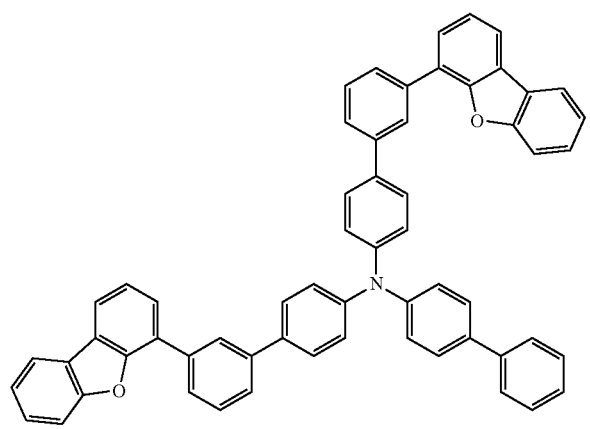
C-1
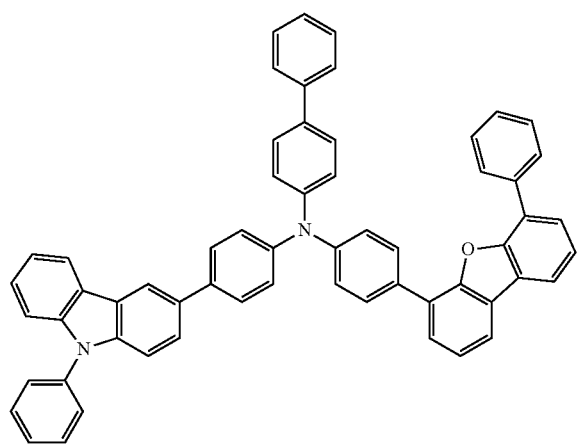
C-2
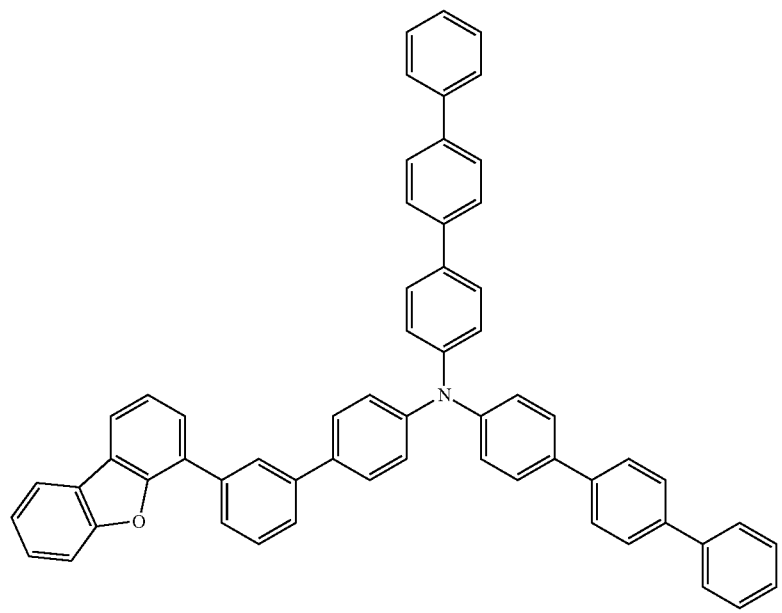
C-3

-continued

C-4

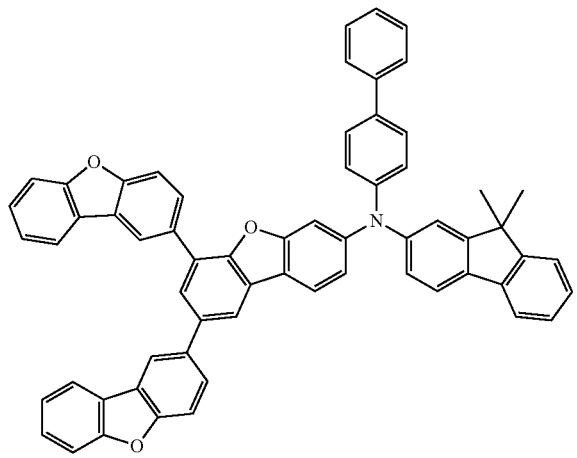

C-5

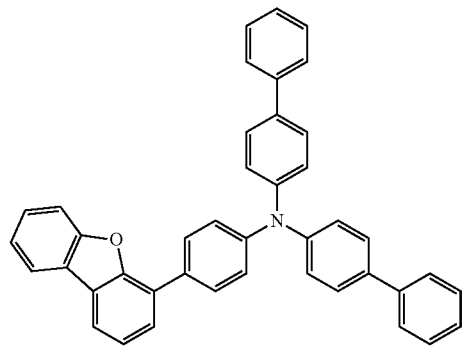

Figure 3:
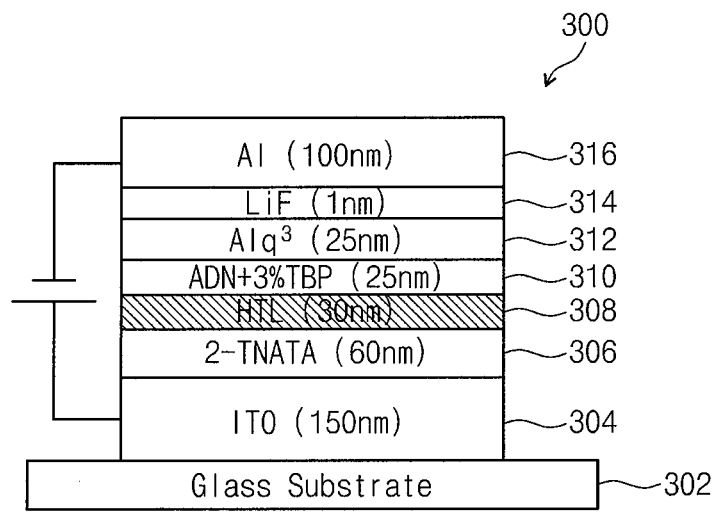
FIG. 3 is a schematic diagram illustrating an organic EL device 300 according to another embodiment.

An organic EL device 300 according to Examples 1 to 9 is shown in FIG. 3. In Examples 1 to 9, a transparent glass substrate was utilized as a substrate 302, an anode 304 was formed utilizing ITO to a layer thickness of about 150 nm, a hole injection layer 306 was formed utilizing 2-TNATA to a layer thickness of about 60 nm, a hole transport layer 308 was formed to a layer thickness of about 30 nm, an emission layer 310 was formed utilizing ADN doped with 3% TBP to a layer thickness of about 25 nm, an electron transport layer 312 was formed utilizing Alq3 to a layer thickness of about 25 nm, an electron injection layer 314 was formed utilizing LiF to a layer thickness of about 1 nm, and a cathode 316 was formed utilizing Al to a layer thickness of about 100 nm.

For the organic EL devices 300, driving voltages and half life were evaluated. The voltage and emission efficiency were obtained at current density of about 10 mA/cm², and the half life was a time period for decreasing the value of luminance to half from an initial luminance of about 1,000 cd/m². Evaluation results are shown in Table 1.

TABLE 1

| Device manufacturing example | Hole transport layer | Voltage (V) | Emission efficiency (cd/A) | Life LT50 (h) |
|---|---|---|---|---|
| Example 1 | Compound 5 | 5.6 | 6.7 | 2,200 |
| Example 2 | Compound 17 | 5.6 | 6.7 | 2,250 |
| Example 3 | Compound 77 | 5.4 | 6.8 | 2,000 |
| Example 4 | Compound 89 | 5.3 | 6.8 | 2,050 |
| Example 5 | Compound 141 | 5.5 | 6.5 | 2,000 |
| Example 6 | Compound 169 | 5.5 | 6.7 | 2,200 |
| Example 7 | Compound 181 | 5.5 | 6.7 | 2,150 |
| Example 8 | Compound 213 | 5.5 | 6.7 | 2,150 |
| Example 9 | Compound 216 | 5.5 | 6.7 | 2,100 |
| Comparative Example 1 | Comparative Compound C1 | 6.3 | 5.2 | 1,600 |
| Comparative Example 2 | Comparative Compound C2 | 6.5 | 5.0 | 1,450 |
| Comparative Example 3 | Comparative Compound C3 | 6.6 | 5.2 | 1,500 |
| Comparative Example 4 | Comparative Compound C4 | 6.6 | 5.1 | 1,600 |
| Comparative Example 5 | Comparative Compound C5 | 6.6 | 5.3 | 1,600 |

Referring to Table 1, the organic EL devices according to Examples 1 to 9 had longer life and improved emission efficiency when compared to those according to Comparative Examples 1 to 5. In Examples 1 to 9, a substituted dibenzoheterole group with high electron tolerance was introduced in an amine group, and so, the electron tolerance of the hole transport layer was improved, and the life thereof was increased. In Examples 1 to 4, molecular symmetry was broken, amorphous properties were improved, and high device efficiency was obtained by substituting an m-phenylene group in the amine group with the substituted dibenzoheterole group. In Examples 5 to 9, molecular symmetry was broken, amorphous properties were improved, and high device efficiency was obtained by substituting a p-phenylene group in the amine group with the substituted dibenzoheterole group. If an unsubstituted dibenzoheterole group was present as in Comparative Examples 1, 3, 4 and 5, a group with high electron density in the dibenzoheterole was not substituted with a substituent, and it would be suggested that a material was easily deteriorated, and the life of a device was decreased. In Comparative Examples 1, 3 and 5, Comparative Compounds C1, C3 and C5 did not include a substituent in the dibenzofuran and had insufficient amorphous properties when compared to that of Examples 1 to 9, thereby having short device life and low emission efficiency. In Comparative Example 2, a carbazole group was included, and the electron accepting properties of a hole transport layer was increased, electrons remained in the hole transport layer, and device life was deteriorated.

From the results of Table 1, long life and high efficiency were recognized if the material for an organic EL device according to an embodiment was utilized as the hole transport material in consideration of the compounds of the comparative examples. Since the material for an organic EL device according to an embodiment included the substituted dibenzoheterole group in an amine compound, the amine compound showing hole transport properties, the electron tolerance and amorphous properties of the material were improved, and high emission efficiency and long life were realized.

In addition, organic EL devices according to Examples 10 to 43 were manufactured utilizing Compound 5, Compound 13, Compound 17, Compound 23, Compound 77, Compound 89, Compound 141, Compound 169, Compound 170, Compound 181, Compound 213, Compound 216, Compound 217, Compound 218, Compound 220, Compound 222, Compound 225, Compound 226, Compound 229, Compound 231, Compound 232, Compound 235, Compound 242, Compound 243, Compound 244, Compound 245, Compound 246, Compound 248, Compound 251, Compound 253, Compound 254, Compound 256, Compound 257 and Compound 258 as the hole transport materials and by the above-described manufacturing method.

5

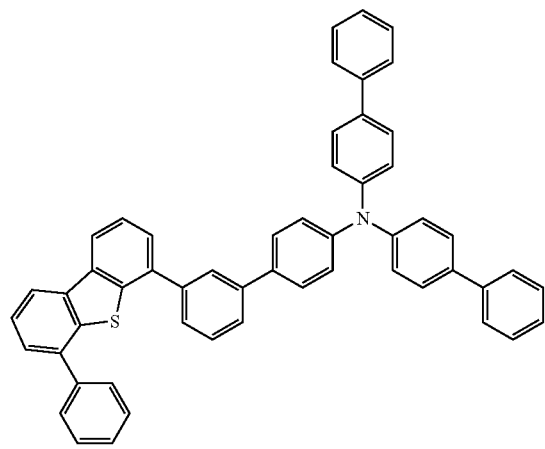

13

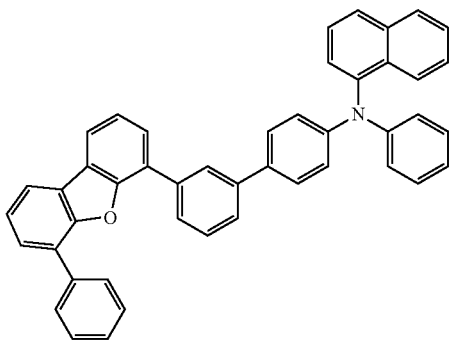

17

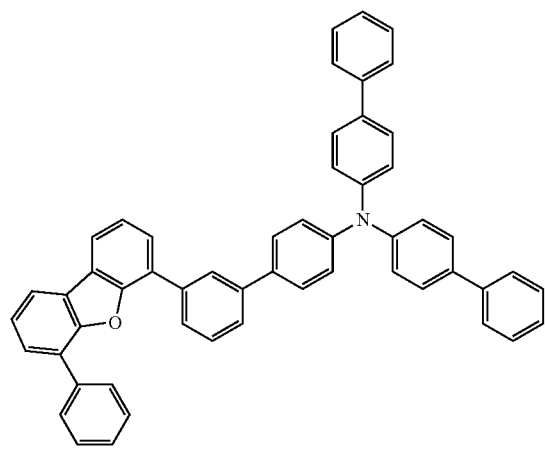

23

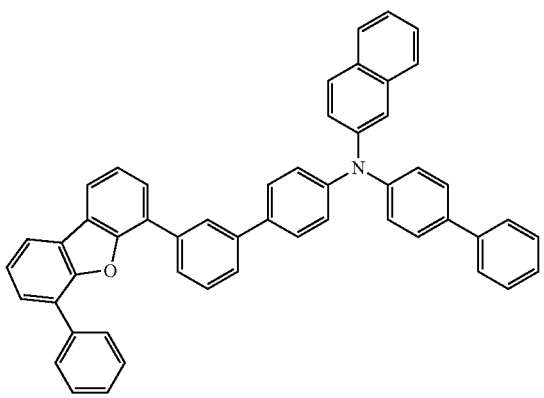

77

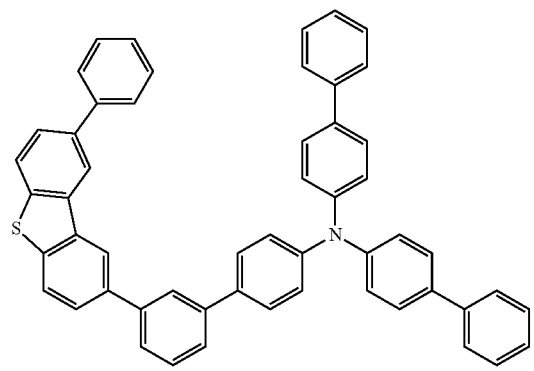

89

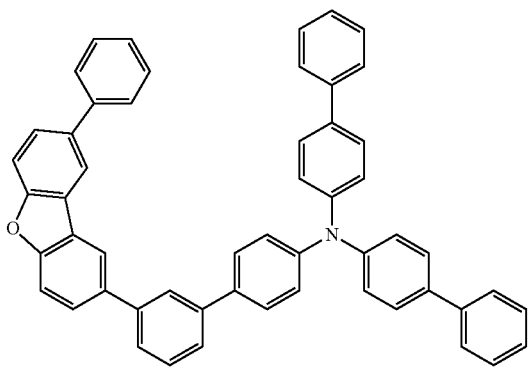

-continued
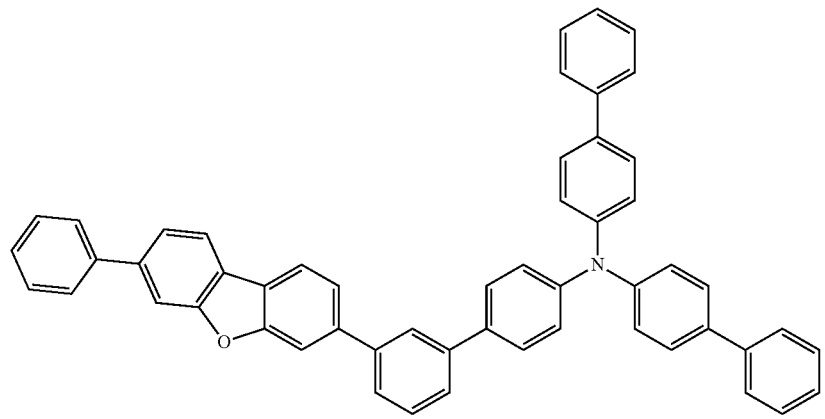
141
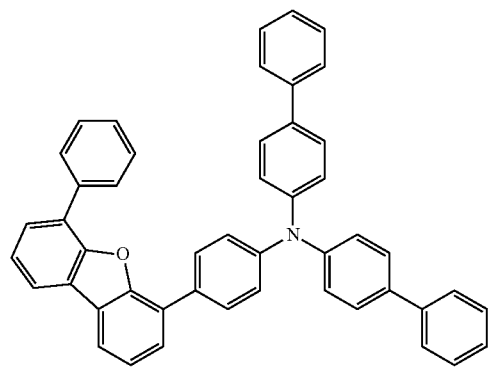
169
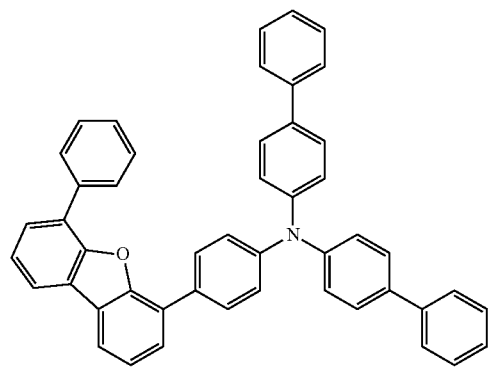
170
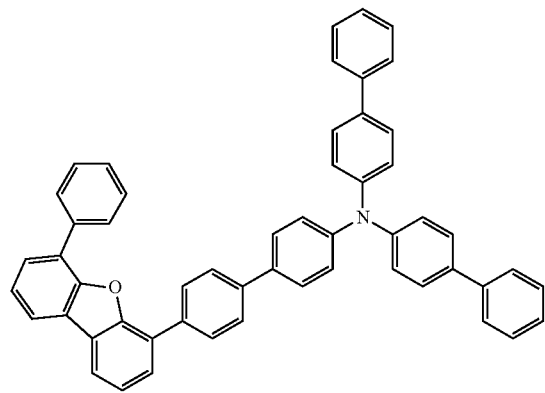
181
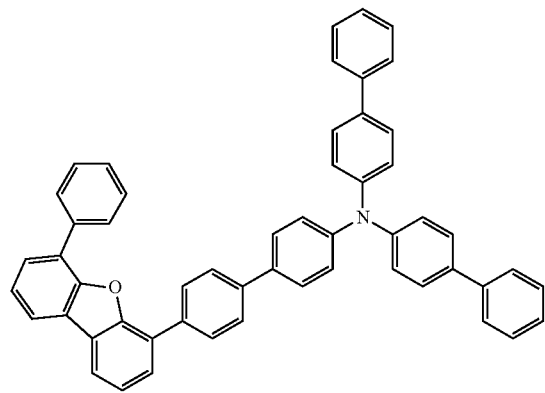
213
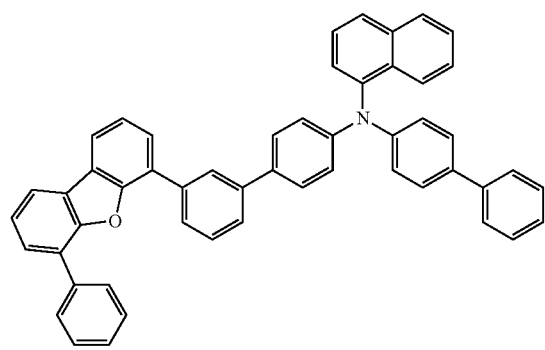
216
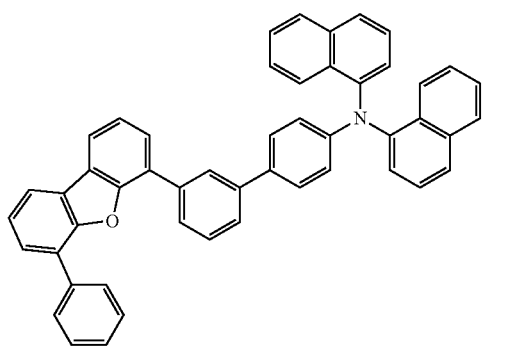
217

-continued
218
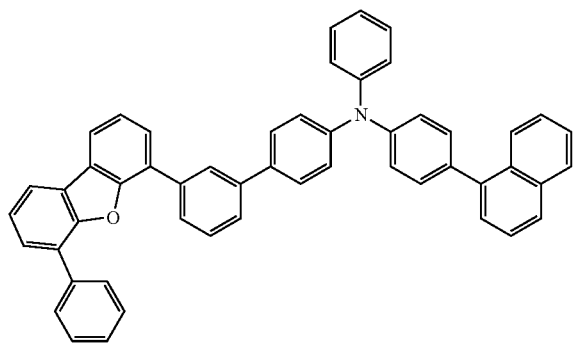
220
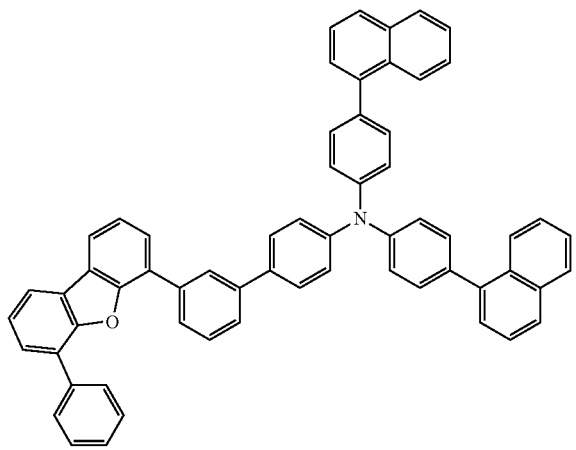
222
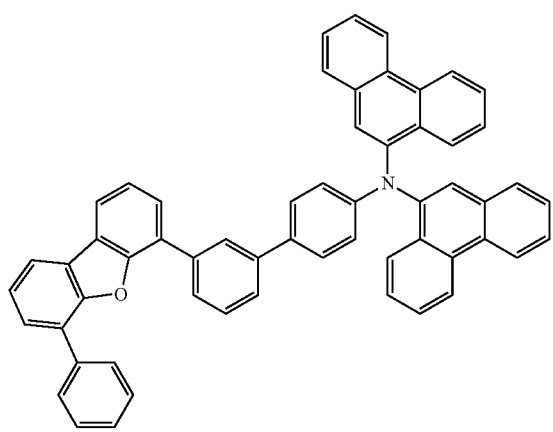
225
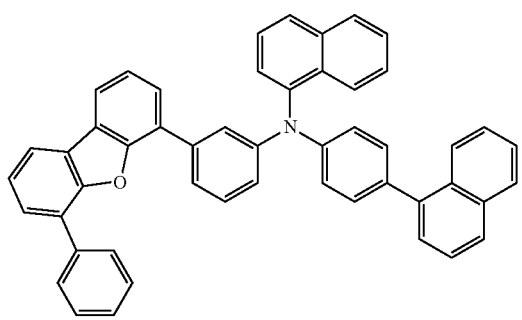
226
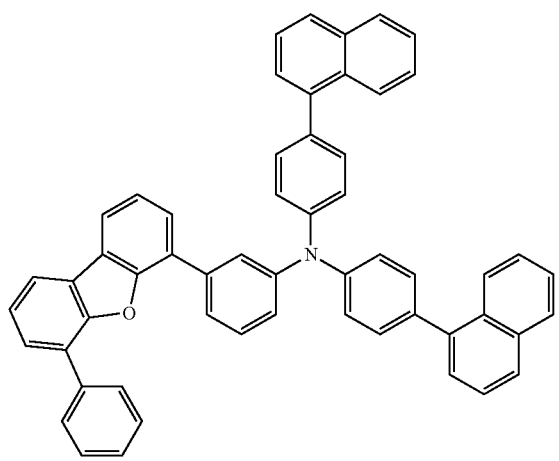
229
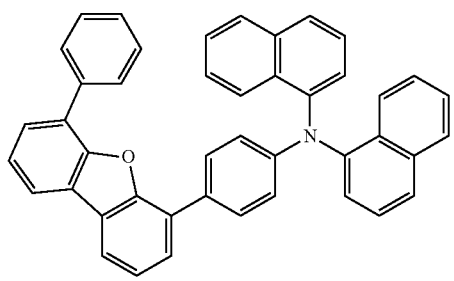

-continued
231
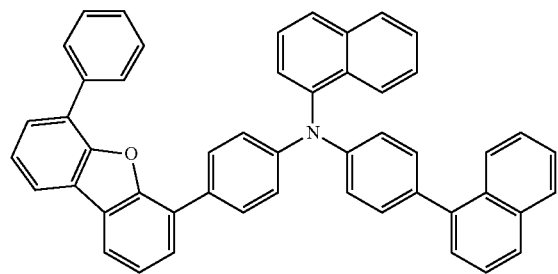
232
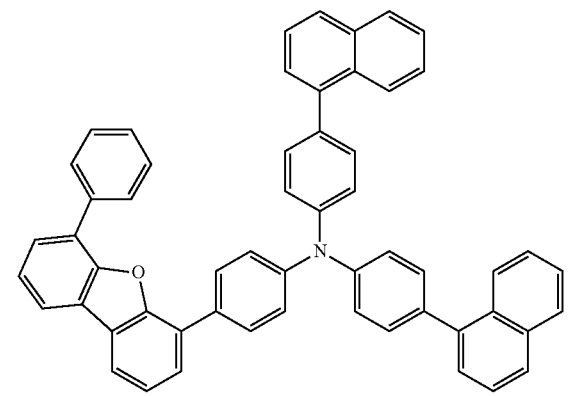
235
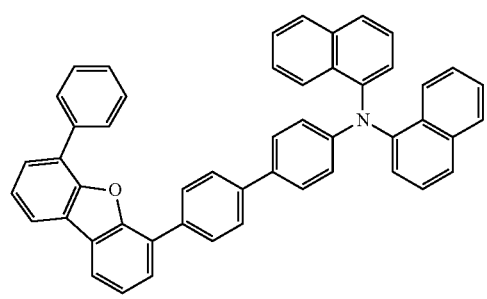
242
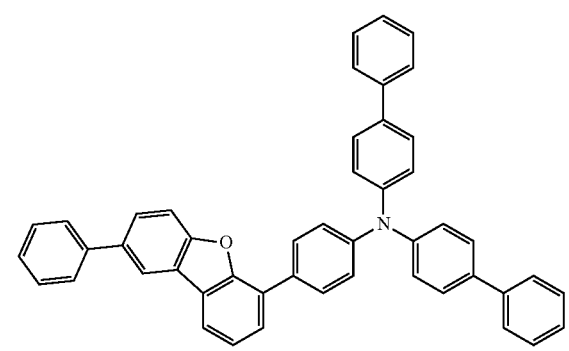
243
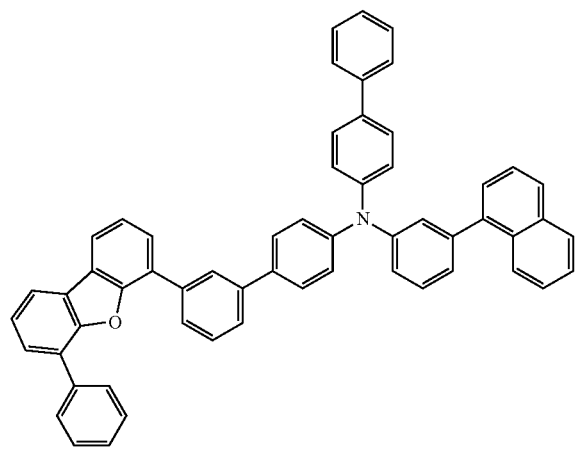
244
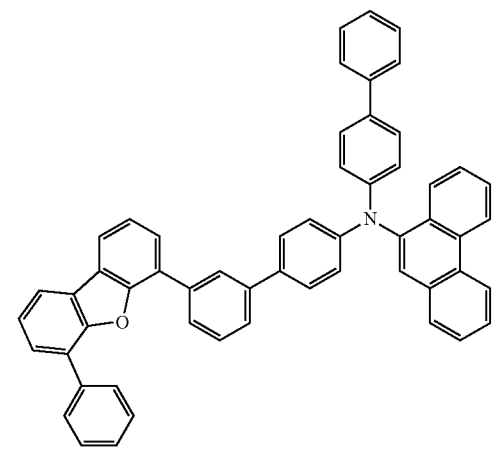
245
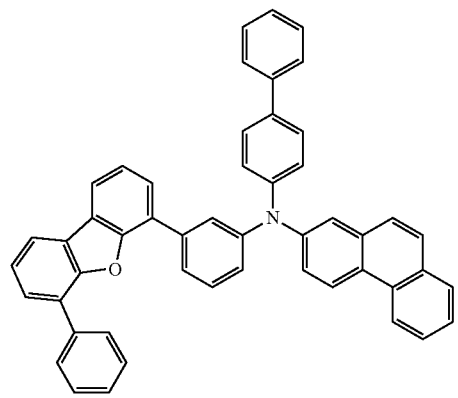
246
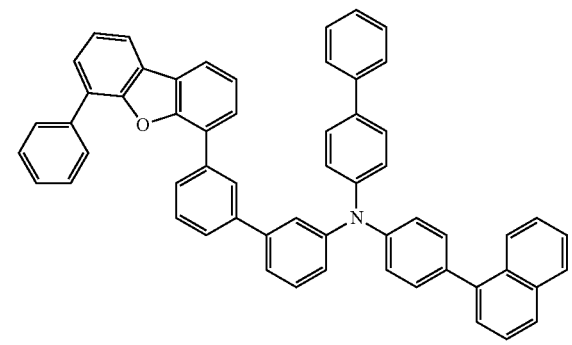

-continued
248
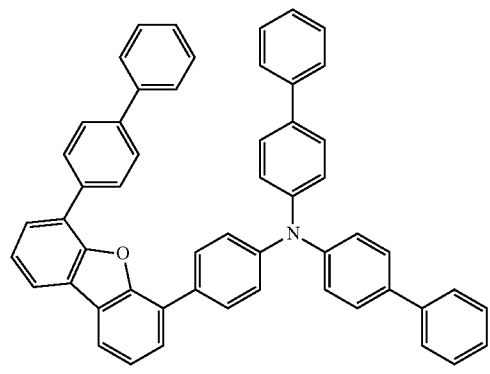
251
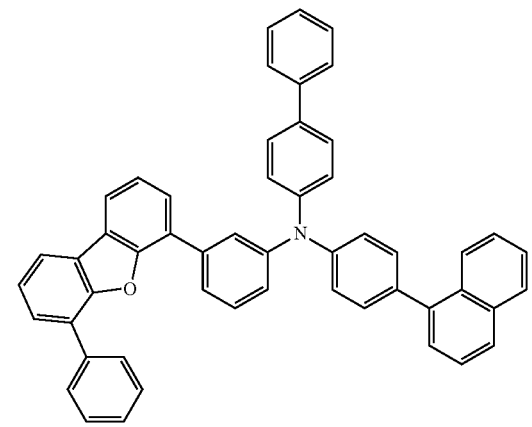
253
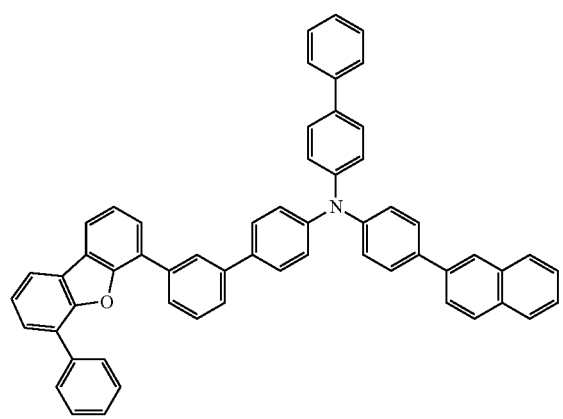
254
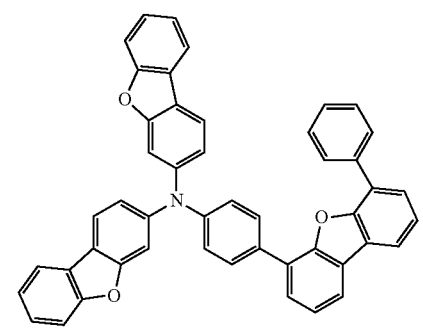
256
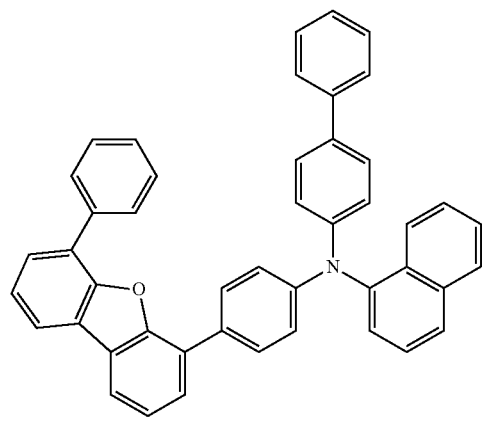
257
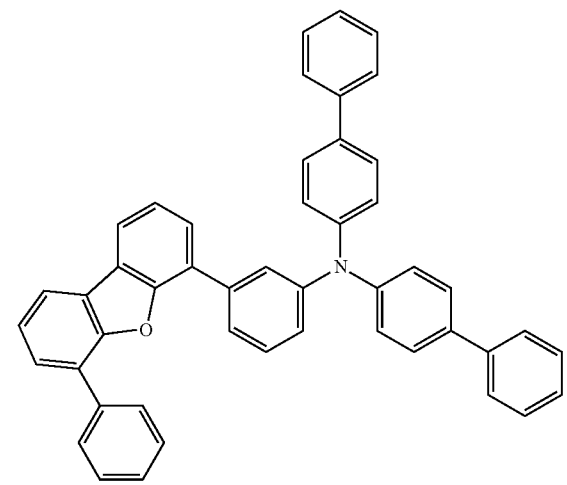

258

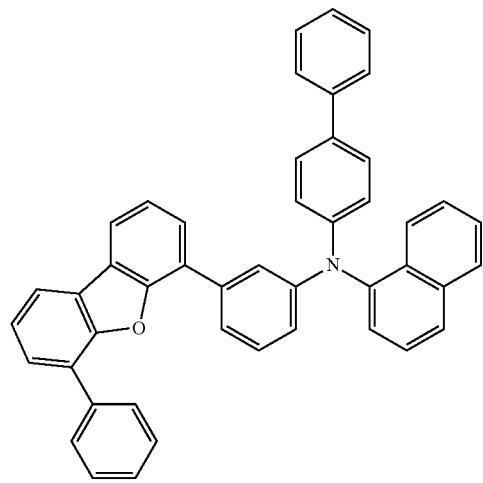

Figure 4:
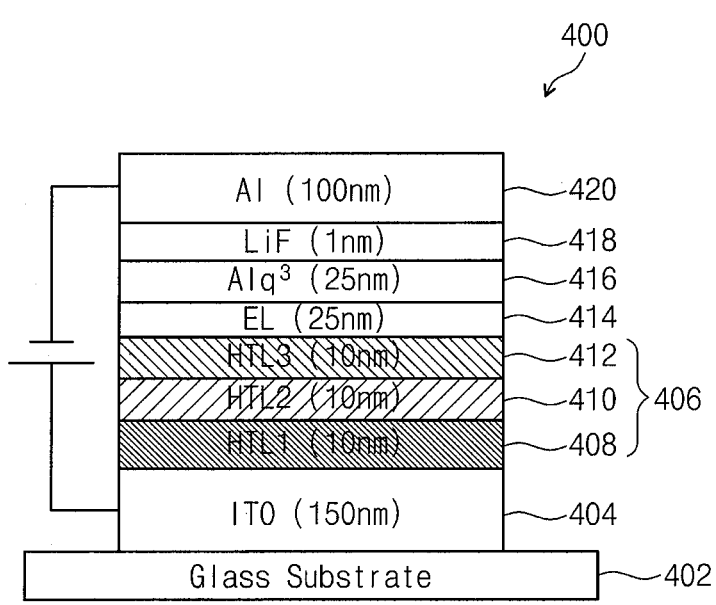
FIG. 4 is a schematic diagram illustrating an organic EL device 400 according to another embodiment.

FIG. 4 is a schematic diagram illustrating an organic EL device 400 according to Examples 10 to 43. In Examples 10 to 43, an anode 404 was formed utilizing ITO to a layer thickness of about 150 nm. On the anode 404, HTL1 was formed as a hole injection layer 408 by doping the following Compound 286 shown by Structure ac14 as an electron accepting compound to a layer thickness of about 10 nm. On the hole injection layer 408, HTL2 was formed utilizing Compound 272 to a layer thickness of about 10 nm as a first hole transport layer 410. On the first hole transport layer 410, HTL3 was formed utilizing the material for an organic EL device according to an embodiment to a layer thickness of about 10 nm as a second hole transport layer 412. Then, an emission layer 414 was formed by utilizing Compound a-7 as a host material and doping 3% of Compound 287 as a luminescent material (doping material) by co-deposition to a layer thickness of about 25 nm. An electron transport layer 416 was formed utilizing Alq3 to a layer thickness of about 25 nm, an electron injection layer 418 was formed utilizing LiF to a layer thickness of about 1 nm, and a cathode 420 was formed utilizing Al to a layer thickness of about 100 nm.

Formula 44

-continued

272

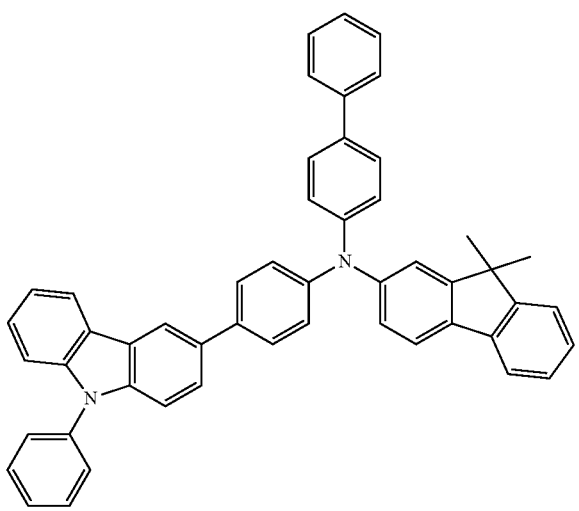

286

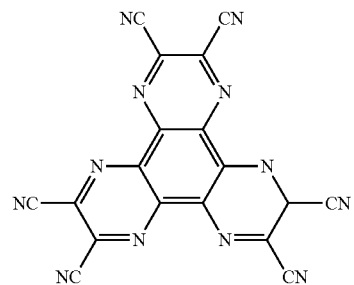

a-7

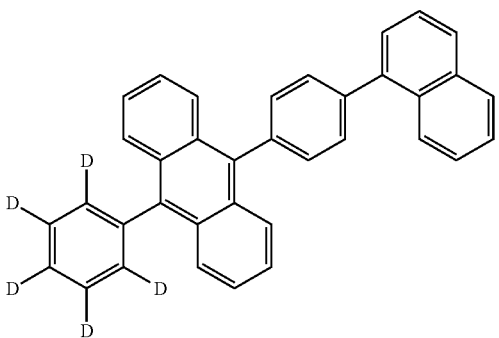

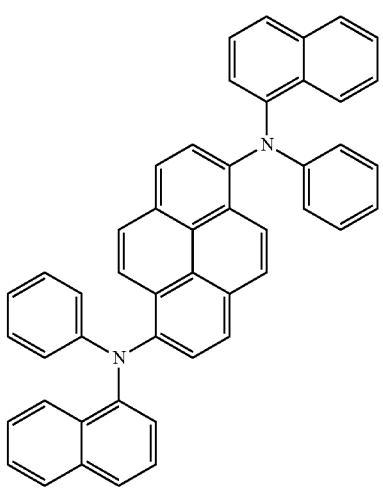

Organic EL devices according to Comparative Examples 6 to 10 were manufactured utilizing Comparative Compounds C1 to C5 as hole transport materials.

For the organic EL devices 400, driving voltages and half life were evaluated. The voltage and emission efficiency were obtained at current density of about 10 mA/cm², and the half life was a time period for decreasing the value of luminance to half from an initial luminance of about 1,000 cd/m². Evaluation results are shown in Table 2.

TABLE 2

| Device manufacturing example | Hole transport layer | Voltage (V) | Emission efficiency (cd/A) | Life LT50 (h) |
| --- | --- | --- | --- | --- |
| Example 10 | Compound 5 | 5.6 | 6.74 | 2,000 |
| Example 11 | Compound 13 | 5.5 | 6.8 | 1,900 |
| Example 12 | Compound 17 | 5.6 | 6.74 | 2,150 |
| Example 13 | Compound 23 | 5.4 | 6.7 | 2,000 |
| Example 14 | Compound 77 | 5.4 | 6.7 | 2,000 |
| Example 15 | Compound 89 | 5.2 | 6.74 | 2,000 |
| Example 16 | Compound 141 | 5.5 | 6.7 | 2.000 |
| Example 17 | Compound 169 | 5.5 | 6.5 | 2,050 |
| Example 18 | Compound 170 | 5.6 | 6.6 | 2,050 |
| Example 19 | Compound 181 | 5.5 | 6.5 | 2,050 |
| Example 20 | Compound 213 | 5.5 | 6.7 | 2,000 |
| Example 21 | Compound 216 | 5.5 | 6.8 | 1,950 |
| Example 22 | Compound 217 | 5.7 | 6.9 | 1,900 |
| Example 23 | Compound 218 | 5.5 | 6.8 | 1,950 |
| Example 24 | Compound 220 | 5.6 | 6.8 | 1,950 |
| Example 25 | Compound 222 | 5.7 | 6.7 | 1,900 |
| Example 26 | Compound 225 | 5.5 | 6.8 | 1,950 |
| Example 27 | Compound 226 | 5.6 | 6.8 | 1,950 |
| Example 28 | Compound 229 | 5.6 | 6.8 | 2,000 |
| Example 29 | Compound 231 | 5.5 | 6.6 | 2,000 |
| Example 30 | Compound 232 | 5.6 | 6.6 | 2,050 |
| Example 31 | Compound 235 | 5.6 | 6.6 | 2,050 |
| Example 32 | Compound 242 | 5.6 | 6.6 | 2,000 |
| Example 33 | Compound 243 | 5.5 | 6.8 | 1,950 |
| Example 34 | Compound 244 | 5.6 | 6.7 | 1,900 |
| Example 35 | Compound 245 | 5.6 | 6.7 | 1,950 |
| Example 36 | Compound 246 | 5.7 | 6.7 | 1,950 |
| Example 37 | Compound 248 | 5.6 | 6.5 | 2,000 |
| Example 38 | Compound 251 | 5.5 | 6.8 | 2,000 |
| Example 39 | Compound 253 | 5.5 | 6.7 | 1,950 |
| Example 40 | Compound 254 | 5.6 | 6.4 | 2,050 |
| Example 41 | Compound 256 | 5.6 | 6.6 | 2,050 |
| Example 42 | Compound 257 | 5.6 | 6.7 | 1,900 |
| Example 43 | Compound 258 | 5.4 | 6.8 | 1,950 |
| Comparative Example 6 | Comparative Compound C1 | 6.3 | 5.2 | 1,550 |
| Comparative Example 7 | Comparative Compound C2 | 6.5 | 5.0 | 1,450 |
| Comparative Example 8 | Comparative Compound C3 | 6.6 | 5.2 | 1,500 |
| Comparative Example 9 | Comparative Compound C4 | 6.6 | 5.1 | 1,550 |
| Comparative Example 10 | Comparative Compound C5 | 6.6 | 5.3 | 1,550 |

Referring to the results in Table 2, the organic EL devices according to Examples 10 to 43 showed long life and improved emission efficiency when compared to those according to Comparative Examples 6 to 10. In Examples 10 to 43, the second hole transport layer 412 formed utilizing the material for an organic EL device according to an embodiment, in which a substituted dibenzoheterole group with high electron tolerance was introduced into an amine compound, had increased electron tolerance and long life. By disposing the second hole transport layer 412 adjacent to the emission layer 414, electrons not consumed in the emission layer 414 was not diffused into the hole transport band 406 at the anode 404 side due to the second hole transport layer 412, the layers of the hole transport band 406 could be passivated, and long life could be obtained. In the material for an organic EL device according to an embodiment utilizing a compound in which an amine group and an m-phenylene group are combined, i.e., in Examples 10 to 16, 20 to 27, 33 to 36, 38, 39, 42 and 43, relatively higher device efficiency was obtained. In the material for an organic EL device according to an embodiment utilizing a compound in which an amine group and a p-phenylene group are combined, i.e., in Examples 17 to 19, 28 to 32, 37, 40 and 41, relatively longer life was obtained.

If an unsubstituted dibenzoheterole group was present as in Comparative Examples 6, 8, 9 and 10, the material was easily deteriorated, and device life was decreased, because a group with high electron density of the dibenzoheterole was not substituted with a substituent.

In Comparative Examples 6, 8 and 10, since Comparative Compounds C1, C3 and C5 did not include a substituent in the dibenzofuran, amorphous properties were insufficient, device life was short, and emission efficiency was low when compared to Examples 10 to 43. In Comparative Example 7, the amine compound included a carbazole group, and the electron accepting properties of the second hole transport layer 412 was increased, and electrons remained in the second hole transport layer 412, thereby decreasing the device life.

By introducing the substituted dibenzoheterole group into the amine compound in the material for an organic EL device according to an embodiment, the electron tolerance and amorphous properties of the material may be improved. Thus, the high emission efficiency and long life of an organic EL device may be realized. Since the material for an organic EL device according to an embodiment has a wide energy gap, application to a red emission region may be possible.

According to an embodiment, a material for an organic EL device having high emission efficiency and long life, and an organic EL device including the same may be provided. According to an embodiment, a material for an organic EL device having high emission efficiency and long life particularly within a range from a green emission region to a blue emission region, and an organic EL device including the same in at least one layer of stacking layers disposed between an emission layer and an anode may be provided. Since the material for an organic EL device according to an embodiment introduces (e.g., includes) a substituted dibenzoheterole group with high electron tolerance in an amine compound, a layer utilizing the material for an organic EL device according to an embodiment and having high efficiency and long life may be realized. Further, an organic EL device having high efficiency and long life may be manufactured.

As used herein, the term "substantially," "about," and similar terms are used as terms of approximation and not as terms of degree, and are intended to account for the inherent deviations in measured or calculated values that would be recognized by those of ordinary skill in the art. Also, any numerical range recited herein is intended to include all sub-ranges of the same numerical precision subsumed within the recited range. For example, a range of "1.0 to 10.0" is intended to include all subranges between (and including) the recited minimum value of 1.0 and the recited maximum value of 10.0, that is, having a minimum value equal to or greater than 1.0 and a maximum value equal to or less than 10.0, such as, for example, 2.4 to 7.6. Any maximum numerical limitation recited herein is intended to include all lower numerical limitations subsumed therein and any minimum numerical limitation recited in this specification is intended to include all higher numerical limitations subsumed therein. Accordingly, Applicant reserves the right to amend this specification, including the claims, to expressly recite any sub-range subsumed within the ranges expressly recited herein.

Expressions such as "at least one of," when preceding a list of elements, modify the entire list of elements and do not modify the individual elements of the list. Further, the use of "may" when describing embodiments of the disclosure refers to "one or more embodiments of the disclosure." Also, the term "exemplary" is intended to refer to an example or illustration.

The above-disclosed subject matter is to be considered illustrative and not restrictive, and the appended claims are intended to cover all such modifications, enhancements, and other embodiments, which fall within the true spirit and scope of the disclosure. Thus, to the maximum extent allowed by law, the scope of the disclosure is to be determined by the broadest permissible interpretation of the following claims and their equivalents, and shall not be restricted or limited by the foregoing detailed description.

What is claimed is:

1. A material for an organic electroluminescent (EL) device represented by Formula 5:

Formula 5

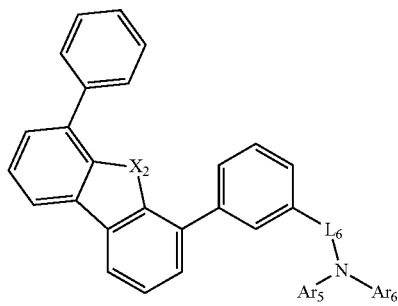

(5)

wherein in Formula 5, $X_2$ is O or S;

$Ar_5$ and $Ar_6$ are each independently a substituted or unsubstituted aryl group having 6 to 30 carbon atoms for forming a ring, a silyl group, a halogen atom, a deuterium atom, a hydrogen atom, or a substituted or unsubstituted dibenzoheterole group having 10 to 30 carbon atoms for forming a ring and including an oxygen atom or a sulfur atom;

$L_6$ is a direct linkage or a divalent group selected from a substituted or unsubstituted aryl group having 6 to 24 carbon atoms for forming a ring and a silyl group.

2. An organic electroluminescent (EL) device, comprising the material for an organic EL device of claim 1 in at least one layer of a plurality of stacking layers between an emission layer and an anode.

3. An organic EL device of claim 2, wherein the material for the organic EL device is included in a first layer adjacent to the emission layer.

4. An organic EL device of claim 3, wherein the plurality of stacking layers comprises a second layer comprising an electron accepting compound having a lowest unoccupied molecular orbital (LUMO) level within a range from about −9.0 eV to about −4.0 eV, the second layer between the anode and the first layer.

5. An organic EL device of claim 4, wherein the plurality of stacking layers comprises a third layer comprising an amine derivative represented by Formula 8, the third layer between the first layer and the second layer:

Formula 8

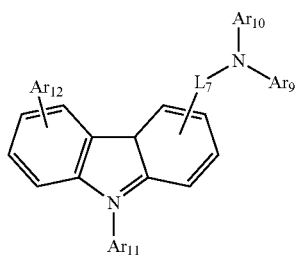

wherein in Formula 8, $Ar_9$, $Ar_{10}$ and $Ar_{11}$ are each independently a substituted or unsubstituted aryl group having 6 to 50 carbon atoms for forming a ring, or a substituted or unsubstituted heteroaryl group having 5 to 50 carbon atoms for forming a ring;

$Ar_{12}$ is a substituted or unsubstituted aryl group having 6 to 50 carbon atoms for forming a ring, a substituted or unsubstituted heteroaryl group having 5 to 50 carbon atoms for forming a ring, or a substituted or unsubstituted alkyl group having 1 to 50 carbon atoms; and $L_7$ is a direct linkage, a substituted or unsubstituted arylene group having 6 to 18 carbon atoms for forming a ring, or a substituted or unsubstituted heteroarylene group having 5 to 15 carbon atoms for forming a ring.

* * * * *